US009765135B2

(12) United States Patent
Ruike et al.

(10) Patent No.: US 9,765,135 B2
(45) Date of Patent: Sep. 19, 2017

(54) ANTI-C5 ANTIBODIES

(71) Applicant: Chugai Seiyaku Kabushiki Kaisha, Tokyo (JP)

(72) Inventors: Yoshinao Ruike, Singapore (SG); Zenjiro Sampei, Singapore (SG)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 14/974,350

(22) Filed: Dec. 18, 2015

(65) Prior Publication Data
US 2016/0176954 A1  Jun. 23, 2016

(30) Foreign Application Priority Data

Dec. 19, 2014 (JP) ................... 2014-257647

(51) Int. Cl.
| A61K 39/395 | (2006.01) |
| C07K 16/18 | (2006.01) |
| G01N 33/564 | (2006.01) |
| G01N 33/68 | (2006.01) |
| A61K 31/519 | (2006.01) |

(52) U.S. Cl.
CPC ............ *C07K 16/18* (2013.01); *A61K 31/519* (2013.01); *G01N 33/564* (2013.01); *G01N 33/6863* (2013.01); *C07K 2317/21* (2013.01); *C07K 2317/24* (2013.01); *C07K 2317/76* (2013.01); *C07K 2317/92* (2013.01); *C07K 2317/94* (2013.01); *G01N 2333/4716* (2013.01)

(58) Field of Classification Search
None
See application file for complete search history.

(56) References Cited

U.S. PATENT DOCUMENTS

| 4,801,687 | A | 1/1989 | Ngo |
| 5,322,678 | A | 6/1994 | Morgan, Jr. et al. |
| 5,639,641 | A | 6/1997 | Pedersen et al. |
| 5,795,965 | A | 8/1998 | Tsuchiya et al. |
| 5,935,935 | A | 8/1999 | Connelly et al. |
| 5,990,286 | A | 11/1999 | Khawli et al. |
| 6,329,511 | B1 | 12/2001 | Vasquez et al. |
| 6,355,245 | B1 | 3/2002 | Evans et al. |
| 6,485,943 | B2 | 11/2002 | Stevens et al. |
| 6,677,436 | B1 | 1/2004 | Sato et al. |
| 6,737,056 | B1 | 5/2004 | Presta |
| 6,884,879 | B1 | 4/2005 | Baca et al. |
| 6,913,747 | B1 | 7/2005 | Co et al. |
| 7,052,873 | B2 | 5/2006 | Tsuchiya |
| 7,276,585 | B2 | 10/2007 | Lazar et al. |
| 7,358,054 | B2 | 4/2008 | Karpusas et al. |
| 7,365,166 | B2 | 4/2008 | Baca et al. |
| 7,432,356 | B2 | 10/2008 | Fung et al. |
| 7,955,590 | B2 | 6/2011 | Gillies et al. |
| 8,062,635 | B2 | 11/2011 | Hattori et al. |
| 8,497,355 | B2 | 7/2013 | Igawa et al. |
| 8,562,991 | B2 | 10/2013 | Igawa et al. |
| 9,079,949 | B1 | 7/2015 | Andrien, Jr. et al. |
| 9,096,651 | B2 | 8/2015 | Igawa et al. |
| 9,133,269 | B2 | 9/2015 | McConnell et al. |
| 2002/0137897 | A1 | 9/2002 | Stevens et al. |
| 2002/0142374 | A1 | 10/2002 | Gallo et al. |
| 2002/0164339 | A1 | 11/2002 | Do Couto et al. |
| 2003/0059937 | A1 | 3/2003 | Ruben et al. |
| 2003/0103970 | A1 | 6/2003 | Tsuchiya |
| 2003/0129187 | A1 | 7/2003 | Fung et al. |
| 2003/0224397 | A1 | 12/2003 | Lowman et al. |
| 2004/0081651 | A1 | 4/2004 | Karpusas et al. |
| 2004/0110226 | A1* | 6/2004 | Lazar ................... C07K 16/00 435/7.1 |
| 2004/0133357 | A1 | 7/2004 | Zhong et al. |
| 2004/0236080 | A1 | 11/2004 | Aburatani et al. |

(Continued)

FOREIGN PATENT DOCUMENTS

| CA | 2647846 A1 | 10/2007 |
| CA | 2700986 A1 | 4/2009 |

(Continued)

OTHER PUBLICATIONS

Rudikoff et al., Proc Natl Acad Sci USA 79: 1979-1983 (1982).*
Colman, Research in Immunology 145: 33-36 (1994).*
Kussie et al., J. Immunol. 152: 146-152 (1994).*
Chen et al., EMBO J., 14: 2784-2794 (1995).*
Lederman et al., Molecular Immunology 28: 1171-1181 (1991).*
Li et al., PNAS 77: 3211-3214 (1980).*
Adams, C.W., et al., "Humanization of a Recombinant Monoclonal Antibody to Produce a Therapeutic Her Dimerization Inhibitor, Pertuzumab," Cancer Immunology, Immunotherapy 55(6):717-727, Springer International, Germany (2006).
Algonomics—TripoleR applications [Online] Retrieved from the Internet on Feb. 29, 2012, http://www.algonomics.com/proteinengineering/tripole_plications.php, 2 pages (Feb. 21, 2009).

(Continued)

*Primary Examiner* — Phillip Gambel
(74) *Attorney, Agent, or Firm* — Nixon & Vanderhye P.C.

(57) ABSTRACT

An objective of the invention is to provide anti-C5 antibodies and methods of using the same. The invention provides anti-C5 antibodies and methods of using the same. In some embodiments, an isolated anti-C5 antibody of the present invention binds to an epitope within the β chain of C5 with a higher affinity at neutral pH than at acidic pH. The invention also provides isolated nucleic acids encoding an anti-C5 antibody of the present invention. The invention also provides host cells comprising a nucleic acid of the present invention. The invention also provides a method of producing an antibody comprising culturing a host cell of the present invention so that the antibody is produced. The invention further provides a method of producing an anti-C5 antibody comprising immunizing an animal against a polypeptide which comprises the MG1-MG2 domain of the β chain of C5. Anti-C5 antibodies of the present invention may be for use as a medicament. Anti-C5 antibodies of the present invention may be for use in treating a complement-mediated disease or condition which involves excessive or uncontrolled activation of C5. Anti-C5 antibodies of the present invention may be for use in enhancing the clearance of C5 from plasma.

66 Claims, 23 Drawing Sheets

(56) References Cited

U.S. PATENT DOCUMENTS

| | | |
|---|---|---|
| 2005/0095243 A1 | 5/2005 | Chan et al. |
| 2005/0244403 A1 | 11/2005 | Lazar et al. |
| 2005/0260711 A1 | 11/2005 | Datta et al. |
| 2005/0261229 A1 | 11/2005 | Gillies et al. |
| 2006/0014156 A1 | 1/2006 | Rabbani et al. |
| 2006/0019342 A1 | 1/2006 | Dall'Acqua et al. |
| 2006/0063228 A1 | 3/2006 | Kasaian et al. |
| 2006/0141456 A1 | 6/2006 | Edwards et al. |
| 2006/0153860 A1 | 7/2006 | Cho et al. |
| 2007/0036785 A1 | 2/2007 | Kishimoto et al. |
| 2007/0037734 A1 | 2/2007 | Rossi et al. |
| 2007/0041978 A1 | 2/2007 | Hattori et al. |
| 2007/0059312 A1 | 3/2007 | Baca et al. |
| 2007/0148164 A1 | 6/2007 | Farrington et al. |
| 2007/0160598 A1 | 7/2007 | Dennis et al. |
| 2008/0166756 A1 | 7/2008 | Tsuchiya et al. |
| 2009/0263392 A1 | 10/2009 | Igawa et al. |
| 2009/0324589 A1 | 12/2009 | Igawa et al. |
| 2010/0216187 A1 | 8/2010 | Lasters et al. |
| 2010/0239577 A1 | 9/2010 | Igawa et al. |
| 2010/0292443 A1 | 11/2010 | Sabbadini et al. |
| 2010/0298542 A1 | 11/2010 | Igawa et al. |
| 2011/0044986 A1 | 2/2011 | Biere-Citron et al. |
| 2011/0076275 A1 | 3/2011 | Igawa et al. |
| 2011/0098450 A1 | 4/2011 | Igawa et al. |
| 2011/0111406 A1 | 5/2011 | Igawa et al. |
| 2011/0150888 A1 | 6/2011 | Foltz et al. |
| 2011/0245473 A1 | 10/2011 | Igawa et al. |
| 2013/0011866 A1 | 1/2013 | Igawa et al. |
| 2013/0303396 A1 | 11/2013 | Igawa et al. |
| 2013/0336963 A1 | 12/2013 | Igawa et al. |
| 2014/0056878 A1 | 2/2014 | McConnell et al. |
| 2014/0105889 A1 | 4/2014 | Igawa et al. |
| 2014/0234340 A1 | 8/2014 | Igawa et al. |
| 2014/0363428 A1 | 12/2014 | Igawa et al. |
| 2015/0050269 A1 | 2/2015 | Igawa et al. |
| 2015/0239966 A1 | 8/2015 | Baciu et al. |
| 2015/0247849 A1* | 9/2015 | Tamburini ............ G01N 33/564 506/9 |
| 2015/0284465 A1 | 10/2015 | Igawa et al. |
| 2015/0299313 A1 | 10/2015 | Igawa et al. |
| 2015/0315278 A1 | 11/2015 | Igawa et al. |
| 2015/0315280 A1 | 11/2015 | Hasegawa et al. |
| 2015/0353630 A1 | 12/2015 | Igawa et al. |
| 2016/0068592 A1* | 3/2016 | Chung ................... C07K 16/18 424/133.1 |

FOREIGN PATENT DOCUMENTS

| | | |
|---|---|---|
| EP | 0182495 A1 | 5/1986 |
| EP | 0783893 A1 | 7/1997 |
| EP | 1069185 A1 | 1/2001 |
| EP | 1773391 A2 | 4/2007 |
| EP | 1601697 B1 | 5/2007 |
| EP | 2006381 A1 | 12/2008 |
| EP | 2196541 A1 | 6/2010 |
| EP | 2275443 A1 | 1/2011 |
| EP | 1069185 B1 | 6/2011 |
| EP | 2 975 055 A1 | 1/2016 |
| JP | S61117457 A | 6/1986 |
| JP | S6352890 A | 3/1988 |
| JP | H0228200 A | 1/1990 |
| JP | H02163085 A | 6/1990 |
| JP | H0767688 A | 3/1995 |
| JP | 2004511426 A | 4/2004 |
| JP | 2005535341 A | 11/2005 |
| JP | 2010505436 A | 2/2010 |
| JP | 2010521194 A | 6/2010 |
| JP | 5144499 | 2/2013 |
| JP | 2013518131 A | 5/2013 |
| JP | 2013521772 A | 6/2013 |
| JP | 2013165716 A | 8/2013 |
| JP | 5334319 B2 | 11/2013 |
| RU | 2266298 C2 | 12/2005 |
| RU | 2430111 C1 | 9/2011 |
| RU | 2010116152 A | 11/2011 |
| RU | 2505603 C2 | 1/2014 |
| WO | WO-9219759 A1 | 11/1992 |
| WO | WO-9514710 A1 | 6/1995 |
| WO | WO 95/29697 | 11/1995 |
| WO | WO-9611020 A1 | 4/1996 |
| WO | WO-9612503 A1 | 5/1996 |
| WO | WO-9803546 A1 | 1/1998 |
| WO | WO-9918212 A1 | 4/1999 |
| WO | WO-9951743 A1 | 10/1999 |
| WO | WO-9958572 A1 | 11/1999 |
| WO | WO-0130854 A2 | 5/2001 |
| WO | WO-0182899 A2 | 11/2001 |
| WO | WO 02/30985 A2 | 4/2002 |
| WO | WO-03000883 A1 | 1/2003 |
| WO | WO 03/015819 A1 | 2/2003 |
| WO | WO-03020949 A2 | 3/2003 |
| WO | WO-03070760 A2 | 8/2003 |
| WO | WO-03105757 A2 | 12/2003 |
| WO | WO-03107009 A2 | 12/2003 |
| WO | WO 2004/007553 A1 | 1/2004 |
| WO | WO-2004016740 A2 | 2/2004 |
| WO | WO-2004039826 A1 | 5/2004 |
| WO | WO-2004068931 A2 | 8/2004 |
| WO | WO-2004096273 A1 | 11/2004 |
| WO | WO-2005035756 A1 | 4/2005 |
| WO | WO-2005047327 A2 | 5/2005 |
| WO | WO-2005059106 A2 | 6/2005 |
| WO | WO-2005067620 A2 | 7/2005 |
| WO | WO 2005/074607 A2 | 8/2005 |
| WO | WO-2005123126 A2 | 12/2005 |
| WO | WO-2006004663 A2 | 1/2006 |
| WO | WO-2006030200 A1 | 3/2006 |
| WO | WO-2006030220 A1 | 3/2006 |
| WO | WO-2006050491 A2 | 5/2006 |
| WO | WO-2006066598 A2 | 6/2006 |
| WO | WO-2006067913 A1 | 6/2006 |
| WO | WO-2006109592 A1 | 10/2006 |
| WO | WO-2006121852 A2 | 11/2006 |
| WO | WO-2007060411 A1 | 5/2007 |
| WO | WO-2007076524 A2 | 7/2007 |
| WO | WO 2007/106585 A1 | 9/2007 |
| WO | WO-2007114319 A1 | 10/2007 |
| WO | WO-2007114325 A1 | 10/2007 |
| WO | WO-2007142325 A1 | 12/2007 |
| WO | WO-2008043822 A2 | 4/2008 |
| WO | WO-2008060785 A2 | 5/2008 |
| WO | WO 2008/069889 A2 | 6/2008 |
| WO | WO 2008/113834 A2 | 9/2008 |
| WO | WO-2009006338 A1 | 1/2009 |
| WO | WO-2009041062 A1 | 4/2009 |
| WO | WO-2009041643 A1 | 4/2009 |
| WO | WO 2009/125825 A1 | 10/2009 |
| WO | WO-2009139822 A1 | 11/2009 |
| WO | WO 2010/015608 A1 | 2/2010 |
| WO | WO 2010/054403 A1 | 5/2010 |
| WO | WO-2011094593 A2 | 8/2011 |
| WO | WO 2011/111007 A2 | 9/2011 |
| WO | WO 2011/122011 A2 | 10/2011 |
| WO | WO 2011/137362 A1 | 11/2011 |
| WO | WO 2012/088247 A2 | 6/2012 |
| WO | WO-2012073992 A1 | 6/2012 |
| WO | WO 2013/138680 A1 | 9/2013 |
| WO | WO 2013/152001 A2 | 10/2013 |
| WO | WO 2014/028354 A1 | 2/2014 |
| WO | WO 2014/047500 A1 | 3/2014 |
| WO | WO 2014/119969 A1 | 8/2014 |
| WO | WO 2014/160958 A1 | 10/2014 |
| WO | WO 2015/127134 A2 | 8/2015 |
| WO | WO 2015/134894 A1 | 9/2015 |
| WO | WO-2016098356 A1 | 6/2016 |

OTHER PUBLICATIONS

Almagro, J.C. and Fransson, J., "Humanization of Antibodies," Frontiers in Bioscience 13:1619-1633, Frontiers in Bioscience Publications, United States (2008).

(56) References Cited

OTHER PUBLICATIONS

Amersham Biosciences: Affinity Chromatography: Principles and Methods, 2002:16-8,137.
Amersham Biosciences. Antibody Purification Handbook, Edition 18-1037-46.
"Antibody Structure and Function," in Immunology, 5th edition, Roitt, I., et al., eds., pp. 80-81.
Armour, K.L., et al., "Recombinant Human IgG Molecules Lacking Fc? Receptor I Binding and Monocyte Triggering Activities," European Journal of Immunology 29(8):2613-2624, Wiley-VCH, Germany (1999).
Bartelds, G.M., et al., "Clinical Response to Adalimumab: Relationship to Anti-adalimumab Antibodies and Serum Adalimumab Concentrations in Rheumatoid Arthritis," Annals of the Rheumatic Diseases 66(7):921-926, BMJ, England (2007).
Batra, S.K., et al., "Pharmacokinetics and Biodistribution of Genetically Engineered Antibodies," Current Opinion in Biotechnology 13(6):603-608, Current Biology, England (2002).
Bayry, J., et al., "Immuno Affinity Purification of Foot and Mouth Disease Virus Type Specific Antibodies Using Recombinant Protein Adsorbed to Polystyrene ," Journal of Virological Methods 81(1-2):21-30, North-Holland Biomedical Press, Netherlands (1999).
Beck, A., et al., "Strategies and Challenges for the Next Generation of Therapeutic Antibodies," Nature Reviews. Immunology 10(5):345-352, Nature Publishing Group, England (2010).
Bender, N.K., et al., "Immunogenicity, Efficacy and Adverse Events of Adalimumab in RA Patients," Rheumatology International 27(3):269-274, Springer International, Germany (2007).
Binz, H.K., et al., "Engineering Novel Binding Proteins from Nonimmunoglobulin Domains," Nature Biotechnology 23(10):1257-1268, Nature America Publishing, United States (2005).
Brown, M., et al., "Tolerance to Single, but Not Multiple, Amino Acid Replacements in AntibodyVH CDR2: A Means of Minimizing B Cell Wastage from Somatic Hypermutation?," Journal of Immunology 156(9):3285-3291, American Association of Immunologists, United States (1996).
Brown, N.L., "A Study of the Interactions between an IgG-Binding Domain Based on the B Domain of Staphylococcal Protein A and Rabbit IgG," Molecular Biotechnology 10(1):9-16, Humana Press, Totowa, New Jersey (1998).
Burmeister, W.P., et al., "Crystal Structure of the Complex of Rat Neonatal Fc Receptor with Fc," Nature 372(6504):379-383, Nature Publishing Group, England (1994).
Chaparro-Riggers, J., et al., "Increasing Serum Half-life and Extending Cholesterol Lowering in Vivo by Engineering Antibody With pH-sensitive Binding to PCSK9," The Journal of Biological Chemistry 287(14):11090-11097, American Society for Biochemistry and Molecular Biology, United States (2012).
Chau, L.A., et al., "HuM291(Nuvion), a Humanized Fc Receptor-Nonbinding Antibody Against CD3, Anergizes Peripheral Blood T Cells as Partial Agonist of the T Cell Receptor," Transplantation 71(7):941-950, Lippincott Williams & Wilkins, United States (2001).
Chen, C., et al., "Defective Secretion of an Immunoglobulin Caused by Mutations in the Heavy Chain Complementarity Determining Region 2," The Journal of Experimental Medicine 180(2):577-586, Rockefeller University Press, United States (1994).
Chen, C., et al., "Generation and Analysis of Random Point Mutations in an Antibody CDR2 Sequence: Many Mutated Antibodies Lose Their Ability to Bind Antigen," The Journal of Experimental Medicine 176(3):855-866, Rockefeller University Press, United States (1992).
Chen, Y., et al., "Selection and Analysis of an Optimized Anti-VEGF Antibody: Crystal Structure of an Affinity-matured Fab in Complex with Antigen," Journal of Molecular Biology 293(4):865-881, Academic Press, England (1999).
Chirino, A.J., et al., "Minimizing the Immunogenicity of Protein therapeutics," Drug Discovery Today 9(2):82-90, Elsevier Science Ltd., England (2004).

Chu, G.C., et al., "Accumulation of Succinimide in a Recombinant Monoclonal Antibody in Mildly Acidic Buffers Under Elevated Temperatures," Pharmaceutical Research 24(6):1145-1156, Kluwer Academic, United States (2007).
Cole, M.S., et al., "Human IgG2 Variants of Chimeric Anti-CD3 are Nonmitogenic to T Cells," Journal of Immunology 159(7):3613-3621, American Association of Immunologists, United States (1997).
Comper, W.D. and Glasgow, E.F., "Charge Selectivity in Kidney Ultrafiltration," Kidney International 47(5):1242-1251, Elsevier, England (1995).
Cordoba, A.J., et al., "Non-Enzymatic Hinge Region Fragmentation of Antibodies in Solution," Journal of Chromatography. B, Analytical Technologies in the Biomedical and Life Sciences 818(2):115-121, Elsevier, Netherlands (2005).
Couto, J.R., et al., "Anti-BA46 Monoclonal Antibody Mc3: Humanization Using a Novel Positional Consensus and In Vivo and In Vitro Characterization," Cancer Research 55(8):1717-1722, American Association for Cancer Research, United States (1995).
Cuatrecasas, P., and Anfinsen, C.B., "Affinity Chromatography," Methods in Enzymology 12:345-378 (1971).
Dall'Acqua, W.F., et al., "Antibody Humanization by Framework Shuffling," Methods 36(1):43-60, Academic Press, United States (2005).
Damschroder, M.M., et al., "Framework Shuffling of Antibodies to Reduce Immunogenicity and Manipulate Functional and Biophysical Properties," Molecular Immunology 44(11):3049-3060, Pergamon Press, England (2007).
De Groot, A.S., et al., "De-immunization of Therapeutic Proteins by T-cell Epitope Modification," Developments in Biologicals 122:171-194, Karger, Switzerland (2005).
Declaration of Dr. Nimish Gera, submitted in Opposition of EP Patent No. 2 275 443, filed Sep. 1, 2016, 24 pages.
Deen, W.M., et al., "Structural Determinants of Glomerular Permeability," American Journal of Physiology 281(4):F579-F596, American Physiological Society, United States (2001).
Del Rio, G., et al., "An Engineered Penicillin Acylase With Altered Surface Charge Is More Stable in Alkaline pH," Annals of the New York Academy of Sciences 799:61-64, Blackwell, United States (1996).
Devanaboyina, S.C., et al., "The Effect of pH Dependence of Antibody-antigen Interactions on Subcellular Trafficking Dynamics," mAbs 5(6):851-859, Taylor & Francis, United States. (2013).
Drake, A.W., and Papalin, G.A., "Biophysical Considerations for Development of Antibody-Based Therpeutics," 2012, Chapter 5, 95-97.
Durkee. K.H., et al., "Immunoaffinity Chromatographic Purification of Russell's Viper Venom Factor X Activator Using Elution in High Concentrations of Magnesium Chloride," Protein Expression and Purification 4(5):405-411, Academic Press, United States (1993).
Ejima D., et al., "Effective Elution of Antibodies by Arginine and Arginine Derivatives in Affinity Column Chromatography," Analytical biochemistry 345(2):250-257, Academic Press, United States (2005).
Ewert S., et al., "Stability Improvement of Antibodies for Extracellular and intracellular Applications: Cdr Grafting to Stable Frameworks and Structure-Based Framework Engineering," Molecular and cellular biology 34(2):184-199, Academic Press, United States (2004).
Feinberg, H., et al., "Mechanism of pH-dependent N-acetylgalactosamine Binding by a Functional Mimic of the Hepatocyte Asialoglycoprotein Receptor," The Journal of Biological Chemistry 275(45):35176-35184, American Society for Biochemistry and Molecular Biology, United States (2000).
Finkelman, F.D., et al., "Anti-cytokine Antibodies as Carrier Proteins. Prolongation of in Vivo Effects of Exogenous Cytokines by Injection of Cytokine-anti-cytokine Antibody Complexes," Journal of Immunology 151(3):1235-1244, American Association of Immunologists, United States (1993).
Fujii, I., et al., "Antibody Affinity Maturation by Random Mutagenesis," Methods in Molecular Biology 248:345-359, Humana Press, United States (2004).

(56) References Cited

OTHER PUBLICATIONS

GE Healthcare. Application note 28-9277-92 AA. "Highthroughput screening of elution pH for monoclonal antibodies on MabSelect SuRe using PreDictor plates".

Gerstner, R.B., et al., "Sequence Plasticity in the Antigen-binding Site of a Therapeutic Anti-HER2 Antibody," Journal of Molecular Biology 321(5):851-862, Elsevier, England (2002).

Gessner, J.E., et al., "The IgG Fc Receptor Family," Annals of Hematology 76(6):231-248, Springer International, Germany (1998).

Ghetie, V. and Ward, E.S., "FcRn: the MHC Class I-Related Receptor that is More Than an IgG Transporter," Immunology Today 18(12):592-598, Elsevier Science Publishers, England (1997).

Ghetie, V., et al., "Increasing the Serum Persistence of an IgG Fragment by Random Mutagenesis," Nature Biotechnology 15(7):637-640, Nature America Publishing, United States (1997).

Ghetie, V., et al., "Multiple Roles for the Major Histocompatibility Complex Class I-Related Receptor FcRn," Annual Review of Immunology 18:739-766, Annual Review, United States (2000).

Gobburu, J.V., et al., "Pharmacokinetics/Dynamics of 5c8, A Monoclonal Antibody to CD154 (CD40 Ligand) Suppression of an Immune Response in Monkeys," Journal of Pharmacology and Experimental Therapeutics 286(2):925-930, American Society for Pharmacology and Experimental Therapeutics, United States (1998).

Goode, N.P., et al., "The Glomerular Basement Membrane Charge-selectivity Barrier: an Oversimplified Concept?," Nephrology, Dialysis, Transplantation 11(9):1714-1716, Springer International, England (1996).

Graves, S.S., et al., "Molecular Modeling and Preclinical Evaluation of the Humanized NR-LU-13 Antibody," Clinical Cancer Research 5(4):899-908, The Association, United States (1999).

Guyre, PM et al., "Increased potency of Fc-receptor-targeted antigens," Cancer Immunology, Immunotherapy 45(3-4):146-148, Springer International, Germany (1997).

Hanson, C.V., et al., "Catalytic Antibodies and their Applications," Current Opinion in Biotechnology 16(6):631-636, Elsevier, England (2005).

He, X.Y., et al., "Humanization and Pharmacokinetics of a Monoclonal Antibody with Specificity for both E- and P-Selectin," Journal of Immunology 160(2):1029-1035, American Association of Immunologists, United States (1998).

Hinton, P.R., et al., "An Engineered Human IgG1 Antibody with Longer Serum Half-Life," Journal of Immunology 176(1):346-356, American Association of Immunologists, United States (2006).

Hinton, P.R., et al., "Engineered Human IgG Antibodies With Longer Serum Half-lives in Primates," The Journal of Biological Chemistry 279(8):6213-6216, American Society for Biochemistry and Molecular Biology, United States (2004).

Hwang, W.Y., et al., "Use of Human Germline Genes in a CDR Homology-Based Approach to Antibody Humanization," Methods 36(1):35-42, Academic Press, United States (2005).

Igawa, "Antibody Optimization Technologies for Developing Next Generation Antibody Therapeutics," Bioindustry 28(7):15-21 (2011).

Igawa, T., et al., "Antibody Recycling by Engineered Ph-dependent Antigen Binding Improves the Duration of Antigen Neutralization," Nature Biotechnology 28(11):1203-1207, Nature America Publishing, United States (2010).

Igawa, T., et al., "Engineered Monoclonal Antibody With Novel Antigen-Sweeping Activity in Vivo," PloS One 8(5):e63236, Public Library of Science, United States (2013).

Igawa, T., et al., "Engineering the Variable Region of Therapeutic IgG Antibodies," mAbs 3(3):243-252, Taylor & Francis, United States. (2011).

Igawa, T., et al., "Reduced Elimination of IgG Antibodies by Engineering the Variable Region," Protein Engineering, Design & Selection 23(5):385-392, Oxford University Press, England (2010).

Ishii-Watabe, A., et al., "FcRn, a Critical Regulator of Antibody Pharmacokinetics," Nihon Yakurigaku Zasshi 136(5):280-284, Nippon Yakuri Gakkai, (2010).

Ito, W., et al., "The His-probe Method: Effects of Histidine Residues Introduced Into the Complementarity-determining Regions of Antibodies on Antigen-antibody Interactions at Different pH Values," FEBS Letters 309(1):85-88, John Wiley & Sons, England (1992).

Johnson, K.A., et al., "Cation Exchange-HPLC and Mass Spectrometry Reveal C-Terminal Amidation of an IgG1 Heavy Chain," Analytical Biochemistry 360(1):75-83, Academic Press, United States (2007).

Jones, T.D., et al., "Identification and Removal of a Promiscuous CD4+ T Cell Epitope from the C1 Domain of Factor VIII," Journal of Thrombosis and Haemostasis 3(5):991-1000, Blackwell Pub, England (2005).

Junghans, R.P., and Anderson, C.L., "The Protection Receptor for IgG Catabolism is the beta2-Microglobulin-Containing Neonatal Intestinal Transport Receptor," Proceedings of the National Academy of Sciences 93(11):5512-5516, National Academy of Sciences, Washington, DC (1996).

Kashmiri, S.V., et al., "Generation, Characterization, and In Vivo Studies of Humanized Anticarcinoma Antibody CC49," Hybridoma 14(5):461-473, Mary Ann Liebert, United States (1995).

Katayose, Y., et al., "MUC1-Specific Targeting Immunotherapy with Bispecific Antibodies: Inhibition of Xenografted Human Bile Duct Carcinoma Growth," Cancer Research 56(18):4205-4212, American Association for Cancer Research, United States (1996).

Khawli, L.A., et al., "Improved Tumor Localization and Radioimaging with Chemically Modified Monoclonal Antibodies," Cancer Biotherapy and Radiopharmaceuticals 11(3):203-215, Liebert, United States (1996).

Kim, I., et al., "Lowering of pI by Acylation Improves the Renal Uptake of 99mTc-Labeled anti-Tac dsFv: Effect of Different Acylating Reagents," Nuclear Medicine and Biology 29(8):795-801, Elsevier, United States (2002).

Kim, I.S., et al., "Chemical Modification to Reduce Renal Uptake of Disulfide-bonded Variable Region Fragment of Anti-tac Monoclonal Antibody Labeled With 99mTc," Bioconjugate Chemistry 10(3):447-453, American Chemical Society, United States (1999).

Kim, S.J., et al., "Antibody Engineering for the Development of Therapeutic Antibodies," Molecules and cells 20(1):17-29, Korean Society for Molecular and Cellular Biology, Korea (2005).

Kobayashi, H., et al., "The Pharmacokinetic Characteristics of Glycolated Humanized Anti-tac Fabs Are Determined by their Isoelectric Points," Cancer Research 59(2):422-430, American Association for Cancer Research, United States (1999).

Kobayashi, T., et al., "A Monoclonal Antibody Specific for a Distinct Region of Hen Egg-white Lysozyme," Molecular Immunology 19(4):619-630, Pergamon Press, England (1982).

Komissarov, A.A., et al., "Site-specific Mutagenesis of a Recombinant Anti-single-stranded DNA Fab. Role of Heavy Chain Complementarity-determining Region 3 Residues in Antigen Interaction," 272(43):26864-26870, American Society for Biochemistry and Molecular Biology, United States (1997).

Laitinen, O.H., et al., "Brave New (Strept) Avidins in Biotechnology," Trends in Biotechnology 25(6):269-277, Elsevier Science Publishers, Amsterdam, Netherlands (2007).

Lee, C.V., et al., "High-affinity Human Antibodies From Phage-displayed Synthetic Fab Libraries With a Single Framework Scaffold," Journal of Molecular Biology 340(5):1073-1093, Academic Press, England (2004).

Leong, S.R., et, al., "Adapting Pharmacokinetic Properties of a Humanized Anti-Interleukin-8 Antibody for Therapeutic Applications Using Site-Specific Pegylation," Cytokine 16(3):106-119, Elsevier Science Ltd., England (2001).

Lin, Y.S., et al., "Preclinical Pharmacokinetics, Interspecies Scaling, and Tissue Distribution of a Humanized Monoclonal Antibody Against Vascular Endothelial Growth Factor," The Journal of Pharmacology and Experimental Therapeutics 288(1):371-378, American Society for Pharmacology and Experimental Therapeutics, United States (1999).

(56) References Cited

OTHER PUBLICATIONS

Linder, M., et al., "Design of a pH-Dependent Cellulose-Binding Domain," FEBS Letters 447(1):13-16, North-Holland on behalf of the Federation of European Biochemical Societies, Amsterdam (1999).

Liu, H., et al., "Heterogeneity of Monoclonal Antibodies," Journal of Pharmaceutical Sciences 97(7):2426-2447, Wiley-Liss, United States (2008).

Lobo, E.D., et al., "Antibody Pharmacokinetics and Pharmacodynamics," Journal of Pharmaceutical Sciences 93(11):2645-2668, Wiley-Liss, United States (2004).

MacCallum, R.M., et al., "Antibody-Antigen Interactions: Contact Analysis and Binding Site Topography," Journal of Molecular Biology 262(5):732-745, Elsevier, England (1996).

Maeda, K., et al., "pH-Dependent Receptor/ligand Dissociation as a Determining Factor for Intracellular Sorting of Ligands for Epidermal Growth Factor Receptors in Rat Hepatocytes," Journal of Controlled Release 82(1):71-82, Elsevier Science, Netherlands (2002).

Maini, R.N., et al, "Double-blind Randomized Controlled Clinical Trial of the Interleukin-6 Receptor Antagonist, Tocilizumab, in European Patients With Rheumatoid Arthritis Who Had an Incomplete Response to Methotrexate," 54(9):2817-2829, Wiley-Blackwell, United States (2006).

Marshall, S.A., et al., "Rational Design and Engineering of Therapeutic Proteins," Drug Discovery Today 8(5):212-221, Elsevier Science Ltd, Irvington, New Jersey (2003).

Martin, W.L., et al., "Crystal Structure at 2.8 A of an FcRn/Heterodimeric Fc Complex: Mechanism of pH-Dependent Binding," Molecular Cell 7(4):867-877, Cell Press, United States (2001).

Maxfield, F.R. and McGraw, T.E., "Endocytic Recycling," Nature Reviews 5(2):121-132, Nature Publishing Group, England (2004).

Mohan, et al CALBIOCHEM Buffers, "A guide for the preparation and use of buffers in biological systems," by chandra Mohan, Ph.D.,Copyright 2003 EMD Biosciences, Inc.,an Affliate of Merck K GaA, Darmastadt, Germany ,37pages (CALBIOCHEM Buffers Booklet, 2003).

Montero-Julian, F.A., et al., "Pharmacokinetic Study of Anti-interleukin-6 (IL-6) Therapy With Monoclonal Antibodies: Enhancement of IL-6 Clearance by Cocktails of Anti-il-6 Antibodies," Blood 85(4):917-924, American Society of Hematology, United States (1995).

Murtaugh, M.L., et al., "A Combinatorial Histidine Scanning Library Approach to Engineer Highly pH-dependent Protein Switches," Protein Science 20(9):1619-1631, Cold Spring Harbor Laboratory Press, United States (2011).

Nesterova, A., et al., "Glypican-3 as a novel target for an antibody-drug conjugate," AACR Annual Meeting Apr. 14-18, 2007, Abstract No. 656, (2007).

Nishimoto, N. and Kishimoto, T., "Interleukin 6: From Bench to Bedside," Nature Clinical Practice. Rheumatology 2(11):619-626, Nature Publishing Group, United States (2006).

Nishimoto, N., et al., "Humanized Anti-interleukin-6 Receptor Antibody Treatment of Multicentric Castleman Disease," Blood 106(8):2627-2632, American Society of Hematology, United States (2005).

Nordlund, H.R., et al., "Introduction of Histidine Residues Into Avidin Subunit Interfaces Allows pH-dependent Regulation of Quaternary Structure and Biotin Binding," FEBS Letters 555(3):449-454, John Wiley & Sons Ltd, England (2003).

Ono, K., et al., "The Humanized Anti-HM1.24 Antibody Effectively Kills Multiple Myeloma Cells by Human Effector Cell-Mediated Cytotoxicity," Molecular Immunology 36(6):387-395, Pergamon Press, England (1999).

Ozhegov, et al, Tolkovyi Slovar Russkogo iazyka: 2004, p. 292.

Pakula, A.A. and Sauer, R.T., "Genetic Analysis of Protein Stability and Function," Annual Review of Genetics 23:289-310, Annual Reviews, United States (1989).

Palladino, M.A., et al, "Anti-TNF-Alpha Therapies: the Next Generation," Nature Reviews Drug Discovery 2(9):736-746, Nature Publishing Group, England (2003).

Pardridge, W.M., et al., "Enhanced Endocytosis in Cultured Human Breast Carcinoma Cells and In Vivo Biodistribution in Rats of a Humanized Monoclonal Antibody After Cationization of the Protein," Journal of Pharmacology and Experimental Therapeutics 286(1):548-554, American Society for Pharmacology and Experimental Therapeutics, United States (1998).

Pavlinkova, G., et al., "Charge-modified Single Chain Antibody Constructs of Monoclonal Antibody CC49: Generation, Characterization, Pharmacokinetics, and Biodistribution Analysis," Nuclear Medicine and Biology 26(1):27-34, Elsevier, United States (1999).

Pavlou, A.K. and Belsey, M.J., "The Therapeutic Antibodies Market to 2008," European Journal Pharmaceutics and Biopharmaceutics 59(3):389-396, Elsevier Science, Netherlands (2005).

Poduslo, J. F. and Curran, G. L., "Polyamine Modification Increases the Permeability of Proteins at the Blood-Nerve and Blood-Brain Barriers," Journal of Neurochemistry 66(4):1599-1609, Blackwell Science, England (1996).

Pons, J., et al., "Energetic Analysis of an Antigen/Antibody Interface: Alanine Scanning Mutagenesis and Double Mutant Cycles on the HyHEL-10/lysozyme Interaction," 8(5):958-968, Cold Spring Harbor Laboratory Press, United States (1999).

Presta, L.G., "Engineering of Therapeutic Antibodies to Minimize Immunogenicity and Optimize Function," Advanced Drug Delivery Reviews 58(5-6):640-656, Elsevier Science, Netherlands (2006).

Rajpal, A., et al., "A General Method for Greatly Improving the Affinity of Antibodies by Using Combinatorial Libraries," Proceedings of the National Academy of Sciences 102(24):8466-8471, National Academy of Sciences, United States (2005).

Rathanaswami, P., et al., "Demonstration of an in Vivo Generated Sub-picomolar Affinity Fully Human Monoclonal Antibody to Interleukin-8," Biochemical and Biophysical Research Communications 334(4):1004-1013, Elsevier, United States (2005).

Reddy M.P., et al., "Elimination of Fc Receptor-Dependent Effector Functions of a Modified IgG4 Monoclonal Antibody to Human CD4," Journal of Immunology 164(4):1925-1933, American Association of Immunologists, United States (2000).

Reichert, J.M. and Valge-Archer, V.E., "Development Trends for Monoclonal Antibody Cancer Therapeutics," Nature Reviews. Drug Discovery 6(5):349-356, Nature Pub. Group, London (2007).

Reichert, J.M., et al., "Monoclonal Antibody Successes in the Clinic," Nature Biotechnology 23(9):1073-1078, Nature America Publishing, United States (2005).

Rich, R.L. and Myska, D.G., "Grading the Commercial Optical Biosensor Literature—Class of 2008: 'The Mighty Binders'," Journal of Molecular Recognition 23(1):1-64, John Wiley & Sons, England (2010).

Roitt, et al Immunology, Moscow, "Mir", 2000, pp. 110 to 111.

Rojas, J.R., et al., "Formation, Distribution, and Elimination of Infliximab and Anti-infliximab Immune Complexes in Cynomolgus Monkeys," The Journal of Pharmacology and Experimental Therapeutics 313(2):578-585, American Society for Pharmacology and Experimental Therapeutics, United States (2005).

Roopenian, D.C. and Akilesh, S., "FcRn: the Neonatal Fc Receptor Comes of Age," Nature Reviews Immunology 7(9):715-725, Nature Publishing Group, England (2007).

Rothe, A., et al., "Ribosome Display for Improved Biotherapeutic Molecules," Expert Opinion on Biological Therapy 6(2):177-187, Taylor & Francis, England (2006).

Rudikoff, S., et al., "Single Amino Acid Substitution Altering Antigen-Binding Specificity," Proceedings of the National Academy of Sciences USA 79(6):1979-1983, The National Academy of Sciences, United States (1982).

Salfeld, J.G., "Isotype Selection in Antibody Engineering," Nature Biotechnology 25(12):1369-1372, Nature America Publishing, United States (2007).

Sarkar, C.A., et al., "Rational Cytokine Design for Increased Lifetime and Enhanced Potency Using pH-activated Histidine Switching," Nature Biotechnology 20(9):908-913, Nature America Publishing, United States (2002).

(56) References Cited

OTHER PUBLICATIONS

Sato, K., et al., "Reshaping a Human Antibody to Inhibit the Interleukin 6-Dependent Tumor Cell Growth," Cancer Research 53(4):851-856, American Association for Cancer Research, United States (1993).

Schaeffer, R.C. Jr., et al., "The Rat Glomerular Filtration Barrier Does Not Show Negative Charge Selectivity," Microcirculation 9(5):329-342, Wiley-Blackwell, United States (2002).

Schmitz, U., et al., "Phage Display: a Molecular Tool for the Generation of Antibodies—a Review," Placenta 21 Suppl A:S106-S112, Elsevier, Netherlands (2000).

Schroeder, H.W., Jr., "Similarity and Divergence in the Development and Expression of the Mouse and Human Antibody Repertoires," Developmental & Comparative Immunology 30(1-2):119-135, Elsevier Science, Tarrytown New York (2006).

Shields, R.L., et al., "High Resolution Mapping of the Binding Site on Human IgG1 for Fc Gamma RI, Fc Gamma RII, Fc Gamma RIII, and FcRn and Design of IgG1 Variants with Improved Binding to the Fc Gamma R," The Journal of Biological Chemistry 276(9):6591-6604, American Society for Biochemistry and Molecular Biology, United States (2001).

Shire, S.J., et al., "Challenges in the Development of High Protein Concentration Formulations," Journal of Pharmaceutical Sciences 93(6):1390-1402, Elsevier, United States (2004).

Sigma-Aldrich®, Product Information, Monoclonal Anti-Flag® M1, Clone M1, accessed at http://www.sigmaaldrich.com/content/dam/sigmaaldrich/ does/Sigma/Datasheet/f3040dat.pdf, 1 page.

Singer, M., and Berg, P., "Genes & Genomes," Structure of Proteins 67-69 (1991).

Stearns, D.J., et al., "The Interaction of a Ca2+-dependent Monoclonal Antibody With the Protein C Activation Peptide Region. Evidence for Obligatory Ca2+ Binding to Both Antigen and Antibody," The Journal of Biological Chemistry 263(2):826-832, American Society for Biochemistry and Molecular Biology, United States (1988).

Stewart, J.D., et al., "Site-directed Mutagenesis of a Catalytic Antibody: an Arginine and a Histidine Residue Play Key Roles," Biochemistry 33(8):1994-2003, American Chemical Society, United States (1994).

Strand, V., et al., "Biologic Therapies in Rheumatology: Lessons Learned, Future Directions," Nature Reviews Drug Discovery 6(1):75-92, Nature Publishing Group, England (2007).

Tabrizi, M.A., et al., "Elimination Mechanisms of Therapeutic Monoclonal Antibodies," Drug Discovery Today 11(1-2):81-88, Virgin Mailing and Distribution, England (2006).

Tan, P.H., et al., "Engineering the Isoelectric Point of a Renal Cell Carcinoma Targeting Antibody Greatly Enhances scFV Solubility," Immunotechnology 4(2):107-114, Elsevier, Netherlands (1998).

Teeling, J.L., et al., "The Biological Activity of Human CD20 Monoclonal Antibodies is Linked to Unique Epitopes on CD20," Journal of Immunology 177(1):362-371, American Association of Immunologists, United States (2006).

Ten Kate, C.I., et al., "Effect of Isoelectric Point on Biodistribution and Inflammation: Imaging With Indium-111-labelled IgG," European Journal of Nuclear Medicine 17(6-8):305-309, Springer Verlag, Germany (1990).

Tsuchiya Credit Suisse Seminar "Therapeutic Antibody" at Fuji-Gotemba Laboratories , (2006), p. 21.

Tsurushita, N., et al., "Design of Humanized Antibodies: From Anti-Tac to Zenapax," Methods 36(1):69-83, Academic Press, United States (2005).

Vaisitti, T., et al., "Cationization of Monoclonal Antibodies: Another Step Towards The "Magic Bullet"?," Journal of Biological Regulators & Homeostatic Agents 19(3-4):105-112, Biolife, Italy (2005).

Vajdos, F.F., et al., "Comprehensive Functional Maps of the Antigen-Binding Site of an Anti-ErbB2 Antibody obtained with Shotgun Scanning Mutagenesis," Journal of Molecular Biology 320(2):415-428, Elsevier Science, United States (2002).

Van Walle, I., et al., "Immunogenicity Screening in Protein Drug Development," Expert Opinion on Biological Therapy 7(3):405-418, Taylor & Francis, Taylor & Francis (2007).

Vaughn, D.E. and Bjorkman, P.J., "Structural Basis of pH-dependent Antibody Binding by the Neonatal Fc Receptor," Structure 6(1):63-73, Cell Press, United States (1998).

Ward, S.L. and Ingham, K.C., "A Calcium-binding Monoclonal Antibody That Recognizes a Non-calcium-binding Epitope in the Short Consensus Repeat Units (SCRs) of Complement C1r," Molecular Immunology 29(1):83-93, Pergamon Press, England (1992).

Wiens, G.D., et al., "Mutation of a Single Conserved Residue in VH Complementarity-determining Region 2 Results in a Severe Ig Secretion Defect," Journal of Immunology 167(4):2179-2186, American Association of Immunologists, United States (2001).

Wiens, G.D., et al., "Somatic Mutation in VH Complementarity-determining Region 2 and Framework Region 2: Differential Effects on Antigen Binding and Ig Secretion," Journal of Immunology 159(3):1293-1302, American Association of Immunologists, United States (1997).

Wikipedia, "Chaotropic agent" [online], [retrieved on Nov. 2, 2015]. Retrieved from the Inernet: https://en.wikipedia.org/wiki/Chaotropic_agent.

Wojciak, J.M., et al., "The Crystal Structure of Sphingosine-1-phosphate in Complex With a Fab Fragment Reveals Metal Bridging of an Antibody and Its Antigen," Proceedings of the National Academy of Sciences of the USA 106(42):17717-17722, National Academy of Sciences, United States (2009).

Wu, H., et al., "Development of Motavizumab, an Ultra-potent Antibody for the Prevention of Respiratory Syncytial Virus Infection in the Upper and Lower Respiratory Tract," Journal of Molecular Biology 368(3):652-665, Academic Press, England (2007).

Xiang, J., et al., "Study of B72.3 Combining Sites by Molecular Modeling and Site-directed Mutagenesis," Protein Engineering 13(5):339-344, Oxford University Press, England (2000).

Yamamoto, T., et al., "Molecular Studies of pH-dependent Ligand Interactions With the Low-density Lipoprotein Receptor," Biochemistry 47(44):11647-11652, American Chemical Society, United States (2008).

Yamasaki, Y., et al., "Pharmacokinetic Analysis of In Vivo Disposition of Succinylated Proteins Targeted to Liver Nonparenchymal Cells Via Scavenger Receptors: Importance of Molecular Size and Negative Charge Density for In Vivo Recognition by Receptors," Journal of Pharmacology and Experimental Therapeutics 301(2):467-477, American Society for Pharmacology and Experimental Therapeutics, United States (2002).

Yang, K., et al., "Tailoring Structure-Function and Pharmacokinetic Properties of Single-chain Fv Proteins by Site-specific PEGylation," Protein Engineering 16(10):761-770, Oxford University Press, England (2003).

Yang, W.P., et al., "CDR Walking Mutagenesis for the Affinity Maturation of a Potent Human Anti-Hiv-1 Antibody into the Picomolar Range," Journal of Molecular Biology 254(3):392-403, Elsevier, England (1995).

Zalevsky, J., et al., "Enhanced Antibody Half-life Improves in Vivo Activity," Nature Biotechnology 28(2):157-159, Nature America Publishing, United States (2010).

Zhou, T., et al., "Interfacial Metal and Antibody Recognition," Proceedings of the National Academy of Sciences of the USA 102(41):14575-14580, National Academy of Sciences, United States (2005).

Zhu, X., et al, "MHC Class I-related Neonatal Fc Receptor for Igg Is Functionally Expressed in Monocytes, Intestinal Macrophages, and Dendritic Cells," Journal of Immunology 166(5):3266-3276, American Association of Immunologists, United States (2001).

Zuckier, L.S., et al., "Chimeric Human-Mouse IgG Antibodies with Shuffled Constant Region Exons Demonstrate that Multiple Domains Contribute to In Vivo Half-Life," Cancer Research 58(17):3905-3908, American Association for Cancer Research, United States (1998).

Zwick, M.B., et al., "The Long Third Complementarity-determining Region of the Heavy Chain Is Important in the Activity of the Broadly Neutralizing Anti-human Immunodeficiency Virus Type 1

(56) References Cited

OTHER PUBLICATIONS

Antibody 2F5," Journal of Virology 78(6):3155-3161, American Society for Microbiology, United States (2004).
Office Action mailed Nov. 23, 2016, in U.S. Appl. No. 13/595,139, Igawa, et al., filed Aug. 27, 2012.
Office Action mailed Nov. 25, 2016, in U.S. Appl. No. 13/889,484, Igawa, et al., filed May 8, 2013.
Office Action mailed Nov. 28, 2016, in U.S. Appl. No. 13/889,512, Igawa, et al., filed May 8, 2013.
Coloma, M.J., et al., "Position Effects of Variable Region Carbohydrate on the Affinity and in Vivo Behavior of an Anti-(1→6) Dextran Antibody," Journal of Immunology 162(4):2162-2170, American Association of Immunologists, United States (1999).
Hird, V., et al, "Tumour Localisation With a Radioactively Labelled Reshaped Human Monoclonal Antibody," British Journal of Cancer 64(5):911-914, Macmillan Press Ltd., England (1991).
Hong, G., et al., "Enhanced Cellular Uptake and Transport of Polyclonal Immunoglobulin G and Fab After Their Cationization," Journal of Drug Targeting 8(2):67-77, OPA N.V., Harwood Academic Publishers, England (2000).
Li, B., et al., "Construction and Characterization of a Humanized Anti-human CD3 Monoclonal Antibody 12F6 With Effective Immunoregulation Functions," Immunology 116(4):487-498, Blackwell Publishing Ltd., England (2005).
Pardridge, W.M., et al., "Enhanced Cellular Uptake and in Vivo Biodistribution of a Monoclonal Antibody Following Cationization," Journal of Pharmaceutical Sciences 84(8):943-948, American Chemical Society and American Pharmaceutical Association, United States (1995).
Reimann, K.A., et al., "A Humanized Form of a CD4-specific Monoclonal Antibody Exhibits Decreased Antigenicity and Prolonged Plasma Half-life in Rhesus Monkeys While Retaining Its Unique Biological and Antiviral Properties," AIDS Research and Human Retroviruses 13(11):933-943, Mary Ann Liebert, United States (1997).
Sharifi, J., et al., "Improving Monoclonal Antibody Pharmacokinetics via Chemical Modification," The Quarterly Journal of Nuclear Medicine 42(4):242-249, Minerva Medica, Italy (1998).
Verhoeyen, M., et al., "Re-Shaped Human anti-PLAP Antibodies," in Monoclonal Antibodies: Applications in Clinical Oncology, Chapter 5, Epenetos, A.A., ed., pp. 37-43, Chapman and Hall Medical, London (1991).
Verhoeyen, M.E., et al., "Construction of a Reshaped HMFG1 Antibody and Comparison of Its Fine Specificity With That of the Parent Mouse Antibody," Immunology 78(3):364-370, Blackwell Scientific, England (1993).
Office Action mailed Jul. 27, 2016, for commonly-owned U.S. Appl. No. 12/295,039.
Onda, M., et al., "Lowering the Isoelectric Point of the Fv Portion of Recombinant Immunotoxins Leads to Decreased Nonspecific Animal Toxicity without Affecting Antitumor Activity," Cancer Research, 61: 5070-5077 (Jul. 1, 2001).
Notice of Allowance mailed Aug. 9, 2016, for commonly-owned U.S. Appl. No. 13/889,512.

Schröter, C., et al., "A generic approach to engineer antibody pH-switches using combinatorial histidine scanning libraries and yeast display," mAbs, 7(1): 138-151 (Jan./Feb. 2015).
Tarditi, L., et al., "Selective high-performance liquid chromatographic purification of bispecific monoclonal antibodies," J. Chromatogr.; 599(1-2): 13-20 (1992).
Holers, V. M., "The spectrum of complement alternative pathway-mediated diseases," Immunol. Rev.; 223: 300-316 (2008).
Dmytrijuk, A., et al., "FDA Report: Eculizumab (Soliris®) for the Treatment of Patients with Paroxysmal Nocturnal Hemoglobinuria," The Oncologist; 13(9): 993-1000; doi: 10.1634/theoncologist.2008-0086 (2008).
Yeung, Y. A., et al., "Engineering Human IgG1 Affinity to Human Neonatal Fc Receptor: Impact of Affinity Improvement on Pharmacokinetics in Primates," J. Immunol.; 182(12): 7663-7671; doi: 10.4049/jimmunol.0804182 (2009).
Datta-Mannan, A., et al., "Monoclonal Antibody Clearance—Impact of Modulating the Interaction of IgG with the Neonatal Fc Receptor," J. Biol. Chem.; 282(3): 1709-1717 (2007).
Dall'Acqua, W. F., et al., "Increasing the Affinity of a Human IgG1 for the Neonatal Fc Receptor: Biological Consequences," J. Immunol.; 169: 5171-5180 (2002).
Mollnes, T. E., et al., "Identification of a Human C5 β-Chain Epitope Exposed in the Native Complement Component but Concealed in the SC5b-9 Complex," Scand. J. Immunol.; 28: 307-312 (1988).
Haviland, D. L., et al., "Complete cDNA Sequence of Human Complement Pro-C5 Evidence of Truncated Transcripts Derived from a Single Copy Gene," J. Immunol.; 146(1): 362-368 (Jan. 1, 1991).
Nishimura, J., et al.,"Genetic Variants in C5 and Poor Response to Eculizumab," N. Engl. J. Med.; 370: 632-639 (2014).
Office Action mailed Feb. 12, 2016 for commonly-owned U.S. Appl. No. 13/595,139.
Balint, R. F., et al., "Antibody engineering by parsimonious mutagenesis," Gene; 137: 109-118 (1993).
Hironiwa, N., et al., "Calcium-Dependent Antigen Binding As a Novel Modality for Antibody Recycling By Endosomal Antigen Dissociation," mAbs 8(1):65-73, Taylor & Francis, Philadelphia (2016).
Maier, J.K.X., et al., "Assessment of Fully Automated Antibody Homology Modeling Protocols In Molecular Operating Environment," Proteins 82(8):1599-1610, Wiley-Liss, New York (2014).
Amendment and Reply to Office Action dated Apr. 12, 2017 in U.S. Appl. No. 14/680,154, filed Apr. 7, 2015, 70 pages.
Amendment and Reply to Office Action dated Nov. 28, 2016 in U.S. Appl. No. 13/889,512, filed Mar. 27, 2017, 16 pages.
Igawa, T., et al., "pH-dependent Antigen-binding Antibodies as a Novel Therapeutic Modality," Biochimica et Biophysica Acta 1844(11):1943-1950, Elsevier Pub. Co., Netherlands (2014).
Ober R.J., et al., "Visualizing the Site and Dynamics of IgG Salvage by the MHC Class I-related Receptor, FcRn1," The Journal of Immunology 172(4):2021-2029, The American Association of Immunologists (2004).
Office Action mailed Jan. 13, 2017, in U.S. Appl. No. 14/680,154, Hasegawa, M., et al., filed Apr. 7, 2015, 15 pages.

* cited by examiner

Figure 27A hC5 MG1 domain (20-124)

| | 2 | | | | | | | | | | 3 | | | | | | | | | | 4 | | | | | | | | | |
|---|---|---|---|---|---|---|---|---|---|---|---|---|---|---|---|---|---|---|---|---|---|---|---|---|---|---|---|---|---|---|
| | 0 | 1 | 2 | 3 | 4 | 5 | 6 | 7 | 8 | 9 | 0 | 1 | 2 | 3 | 4 | 5 | 6 | 7 | 8 | 9 | 0 | 1 | 2 | 3 | 4 | 5 | 6 | 7 | 8 | 9 |
| | E | Q | T | Y | V | I | S | A | P | K | I | F | R | V | G | A | S | E | N | I | V | I | Q | V | Y | Y | G | Y | T | E | A |

| | 5 | | | | | | | | | | 6 | | | | | | | | | | 7 | | | | | | | | | |
|---|---|---|---|---|---|---|---|---|---|---|---|---|---|---|---|---|---|---|---|---|---|---|---|---|---|---|---|---|---|---|
| | 0 | 1 | 2 | 3 | 4 | 5 | 6 | 7 | 8 | 9 | 0 | 1 | 2 | 3 | 4 | 5 | 6 | 7 | 8 | 9 | 0 | 1 | 2 | 3 | 4 | 5 | 6 | 7 | 8 | 9 |
| | F | D | A | T | I | S | I | K | S | Y | P | D | K | K | F | S | Y | S | S | G | H | V | H | L | S | S | E | N | K | F |

| | 8 | | | | | | | | | | 9 | | | | | | | | | | 1 | 0 | | | | | | | | |
|---|---|---|---|---|---|---|---|---|---|---|---|---|---|---|---|---|---|---|---|---|---|---|---|---|---|---|---|---|---|---|
| | 0 | 1 | 2 | 3 | 4 | 5 | 6 | 7 | 8 | 9 | 0 | 1 | 2 | 3 | 4 | 5 | 6 | 7 | 8 | 9 | 0 | 1 | 2 | 3 | 4 | 5 | 6 | 7 | 8 | 9 |
| | Q | N | S | A | I | L | T | I | Q | P | K | Q | L | P | G | G | Q | N | P | V | S | Y | V | Y | L | E | V | V | S | K |

| | 1 | 1 | | | | | | | | | 1 | 2 | | | |
|---|---|---|---|---|---|---|---|---|---|---|---|---|---|---|---|
| | 0 | 1 | 2 | 3 | 4 | 5 | 6 | 7 | 8 | 9 | 0 | 1 | 2 | 3 | 4 |
| | H | F | S | K | S | K | R | M | P | I | T | Y | D | N | G |

< 3.0 Å   < 4.5 Å ature C5 protein.

SEQUENCE LISTING

```
<160> NUMBER OF SEQ ID NOS: 150

<210> SEQ ID NO 1
<211> LENGTH: 121
<212> TYPE: PRT
<213> ORGANISM: Artificial Sequence
<220> FEATURE:
<223> OTHER INFORMATION: CFA0305 VH

<400> SEQUENCE: 1

Gln Ser Leu Glu Glu Ser Gly Gly Asp Leu Val Lys Pro Gly Ala Ser
1               5                   10                  15

Leu Ala Val Thr Cys Thr Ala Ser Gly Phe Ser Ser Ser Ser Ser Tyr
            20                  25                  30

Tyr Met Cys Trp Val Arg Gln Ala Pro Gly Lys Gly Leu Glu Trp Ile
        35                  40                  45

Gly Cys Ile Tyr Thr Gly Ser Gly Ala Thr Tyr Tyr Ala Ser Trp Ala
    50                  55                  60

Lys Gly Arg Phe Thr Ile Ser Lys Thr Ser Ser Thr Val Thr Leu
65                  70                  75                  80

Gln Met Thr Ser Leu Thr Val Ala Asp Thr Ala Thr Tyr Phe Cys Ala
                85                  90                  95

Ser Asp Gly Gly Tyr Val Thr Pro Thr His Ala Met Tyr Leu Trp Gly
```

-continued

```
                100             105             110
Pro Gly Thr Leu Val Thr Val Ser Ser
        115             120

<210> SEQ ID NO 2
<211> LENGTH: 117
<212> TYPE: PRT
<213> ORGANISM: Artificial Sequence
<220> FEATURE:
<223> OTHER INFORMATION: CFA0307 VH

<400> SEQUENCE: 2

Gln Ser Leu Glu Glu Ser Gly Gly Gly Leu Val Lys Pro Gly Ala Ser
1               5                   10                  15

Leu Thr Leu Thr Cys Lys Ala Ser Gly Ile Asp Phe Ser Asn Phe Tyr
            20                  25                  30

Tyr Ile Cys Trp Val Arg Gln Ala Pro Gly Lys Gly Leu Asp Leu Ile
        35                  40                  45

Ala Cys Ile Tyr Thr Val Ser Gly Tyr Thr Tyr Tyr Ala Ser Trp Ala
    50                  55                  60

Lys Gly Arg Leu Thr Ile Ser Lys Thr Ser Thr Thr Val Thr Leu
65                  70                  75                  80

Gln Met Thr Ser Leu Thr Ala Ala Asp Thr Ala Thr Tyr Phe Cys Ala
                85                  90                  95

Arg Asp Leu His Ala Gly Ile Thr Asn Leu Trp Gly Pro Gly Thr Leu
            100                 105                 110

Val Thr Val Ser Ser
        115

<210> SEQ ID NO 3
<211> LENGTH: 122
<212> TYPE: PRT
<213> ORGANISM: Artificial Sequence
<220> FEATURE:
<223> OTHER INFORMATION: CFA0366 VH

<400> SEQUENCE: 3

Gln Ser Leu Glu Glu Ser Gly Gly Asp Leu Val Lys Pro Gly Ala Ser
1               5                   10                  15

Leu Ser Leu Thr Cys Thr Ala Ala Gly Leu Asp Phe Ser Ser Ser Tyr
            20                  25                  30

Tyr Met Cys Trp Val Arg Gln Ala Pro Gly Lys Gly Leu Glu Trp Ile
        35                  40                  45

Ala Cys Ile Tyr Ala Gly Ser Ser Gly Ile Ile Tyr Tyr Ala Asn Trp
    50                  55                  60

Ala Lys Gly Arg Phe Thr Ile Ser Arg Pro Ser Ser Thr Thr Val Thr
65                  70                  75                  80

Leu Gln Met Thr Ser Leu Thr Ala Ala Asp Thr Ala Thr Tyr Phe Cys
                85                  90                  95

Ala Thr Tyr Pro Thr Tyr Gly Asp Gly His Ala Phe Asn Leu Trp
            100                 105                 110

Gly Pro Gly Thr Leu Val Thr Val Ser Ser
        115                 120

<210> SEQ ID NO 4
<211> LENGTH: 117
<212> TYPE: PRT
<213> ORGANISM: Artificial Sequence
<220> FEATURE:
```

<223> OTHER INFORMATION: CFA0501 VH

<400> SEQUENCE: 4

Gln Ser Val Glu Glu Ser Gly Gly Arg Leu Val Thr Pro Gly Thr Pro
1               5                   10                  15

Leu Thr Leu Thr Cys Thr Ala Ser Gly Phe Ser Leu Ser Ser Tyr Tyr
            20                  25                  30

Met Asn Trp Val Arg Gln Ala Pro Gly Lys Gly Leu Glu Trp Ile Gly
        35                  40                  45

Met Ile Tyr Gly Ser Gly Ala Thr Tyr Tyr Ala Ser Trp Ala Lys Gly
    50                  55                  60

Arg Phe Thr Ile Ser Lys Thr Ser Ser Thr Thr Val Asp Leu Lys Met
65                  70                  75                  80

Thr Ser Leu Thr Thr Glu Asp Thr Ala Thr Tyr Phe Cys Ala Arg Gln
                85                  90                  95

Ile Tyr Ser Gly Asp Asn Asn Asp Asn Phe Trp Gly Pro Gly Thr Leu
            100                 105                 110

Val Thr Val Ser Ser
        115

<210> SEQ ID NO 5
<211> LENGTH: 117
<212> TYPE: PRT
<213> ORGANISM: Artificial Sequence
<220> FEATURE:
<223> OTHER INFORMATION: CFA0538 VH

<400> SEQUENCE: 5

Gln Ser Val Glu Glu Ser Gly Gly Arg Leu Val Thr Pro Gly Thr Pro
1               5                   10                  15

Leu Thr Leu Thr Cys Thr Ala Ser Gly Phe Ser Leu Ser Ser Tyr Tyr
            20                  25                  30

Met Asn Trp Val Arg Gln Ala Pro Gly Lys Gly Leu Glu Trp Ile Gly
        35                  40                  45

Met Ile Tyr Gly Ser Gly Ala Thr Tyr Tyr Ala Ser Trp Ala Lys Gly
    50                  55                  60

Arg Phe Thr Ile Ser Lys Thr Ser Ser Thr Thr Val Asp Leu Lys Met
65                  70                  75                  80

Thr Ser Leu Thr Thr Glu Asp Thr Ala Thr Tyr Phe Cys Ala Arg Gln
                85                  90                  95

Ile Tyr Ser Gly Asp Asn Asn Asp Asn Phe Trp Gly Pro Gly Thr Leu
            100                 105                 110

Val Thr Val Ser Ser
        115

<210> SEQ ID NO 6
<211> LENGTH: 117
<212> TYPE: PRT
<213> ORGANISM: Artificial Sequence
<220> FEATURE:
<223> OTHER INFORMATION: CFA0599 VH

<400> SEQUENCE: 6

Gln Ser Val Glu Glu Ser Gly Gly Arg Leu Val Thr Pro Gly Thr Pro
1               5                   10                  15

Leu Thr Leu Thr Cys Thr Val Ser Gly Leu Ser Leu Ser Asp Asn Thr
            20                  25                  30

Met Thr Trp Val Arg Gln Ala Pro Gly Lys Gly Leu Glu Trp Ile Gly

```
                35                  40                  45
Ile Ile Ser Phe Gly Gly Asp Ala Tyr Tyr Ala Ser Trp Ala Lys Gly
    50                  55                  60

Arg Phe Pro Ile Ser Lys Thr Ser Thr Thr Val Asp Leu Arg Ile Thr
 65                  70                  75                  80

Ser Pro Thr Thr Glu Asp Thr Ala Thr Tyr Phe Cys Ala Arg Val Gly
                 85                  90                  95

Ala Gly Asn Ile Phe Trp Tyr Phe Asp Leu Trp Gly Pro Gly Thr Leu
            100                 105                 110

Val Thr Val Ser Ser
            115

<210> SEQ ID NO 7
<211> LENGTH: 116
<212> TYPE: PRT
<213> ORGANISM: Artificial Sequence
<220> FEATURE:
<223> OTHER INFORMATION: CFA0666 VH

<400> SEQUENCE: 7

Gln Ser Val Glu Glu Ser Gly Gly Arg Leu Val Thr Pro Gly Thr Pro
 1               5                  10                  15

Leu Thr Leu Thr Cys Thr Val Ser Gly Phe Ser Leu Ser Thr Tyr Ala
                 20                  25                  30

Met Gly Trp Val Arg Gln Ala Pro Gly Lys Gly Leu Glu Trp Ile Gly
             35                  40                  45

Thr Ile Asp Thr Gly Asp Asn Ser Phe Tyr Ala Asn Trp Ala Lys Gly
    50                  55                  60

Arg Phe Thr Ile Ser Lys Thr Ser Thr Thr Val Asp Leu Lys Ile Thr
 65                  70                  75                  80

Ser Pro Thr Ala Glu Asp Thr Ala Thr Tyr Phe Cys Ala Arg Asn Asp
                 85                  90                  95

Gly Ser Val Tyr Asn Leu Phe Asn Leu Trp Gly Pro Gly Thr Leu Val
            100                 105                 110

Thr Val Ser Ser
            115

<210> SEQ ID NO 8
<211> LENGTH: 110
<212> TYPE: PRT
<213> ORGANISM: Artificial Sequence
<220> FEATURE:
<223> OTHER INFORMATION: CFA0672 VH

<400> SEQUENCE: 8

Gln Ser Val Glu Glu Ser Gly Gly Arg Leu Val Thr Pro Gly Thr Pro
 1               5                  10                  15

Leu Thr Leu Thr Cys Thr Ala Ser Gly Phe Ser Leu Ser Gly Asn Ala
                 20                  25                  30

Ile Asn Trp Val Arg Gln Ala Pro Gly Lys Gly Leu Glu Trp Ile Gly
             35                  40                  45

Cys Ile Tyr Thr Gly Ser Asp Thr Thr Tyr Tyr Ala Thr Trp Ala Lys
    50                  55                  60

Gly Arg Phe Thr Ile Ser Lys Thr Ser Thr Thr Val Asp Leu Lys Ile
 65                  70                  75                  80

Ala Ser Pro Thr Thr Glu Asp Thr Ala Thr Tyr Phe Cys Ala Arg Gly
                 85                  90                  95
```

Ser Gly Leu Trp Gly Pro Gly Thr Leu Val Thr Val Ser Ser
         100                 105                 110

<210> SEQ ID NO 9
<211> LENGTH: 116
<212> TYPE: PRT
<213> ORGANISM: Artificial Sequence
<220> FEATURE:
<223> OTHER INFORMATION: CFA0675 VH

<400> SEQUENCE: 9

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Thr Tyr Ala
             20                  25                  30

Met Gly Trp Val Arg Gln Ala Pro Gly Lys Gly Leu Glu Trp Ile Gly
         35                  40                  45

Thr Ile Asp Thr Gly Asp Asn Ser Phe Tyr Ala Asn Trp Ala Lys Gly
     50                  55                  60

Arg Phe Thr Ile Ser Arg Thr Ser Thr Thr Val Asp Leu Lys Ile Thr
65                  70                  75                  80

Ser Pro Thr Ala Glu Asp Thr Ala Thr Tyr Phe Cys Ala Arg Asn Asp
                 85                  90                  95

Gly Ser Val Tyr Asn Leu Phe Asn Leu Trp Gly Pro Gly Thr Leu Val
             100                 105                 110

Thr Val Ser Ser
         115

<210> SEQ ID NO 10
<211> LENGTH: 123
<212> TYPE: PRT
<213> ORGANISM: Artificial Sequence
<220> FEATURE:
<223> OTHER INFORMATION: 305L05 VH

<400> SEQUENCE: 10

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ser His Ser Ser
             20                  25                  30

Tyr Tyr Val Ala Trp Val Arg Gln Ala Pro Gly Lys Gly Leu Glu Trp
         35                  40                  45

Val Gly Ala Ile Tyr Thr Gly Ser Gly Ala Thr Tyr Lys Ala Ser Trp
     50                  55                  60

Ala Lys Gly Arg Phe Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                 85                  90                  95

Cys Ala Ser Asp Gly Gly Tyr Asp Tyr Pro Thr His Ala Met His Tyr
             100                 105                 110

Trp Gly Gln Gly Thr Leu Val Thr Val Ser Ser
         115                 120

<210> SEQ ID NO 11
<211> LENGTH: 110
<212> TYPE: PRT
<213> ORGANISM: Artificial Sequence
<220> FEATURE:
<223> OTHER INFORMATION: CFA0305 VL -continued

<400> SEQUENCE: 11

Asp Val Val Met Thr Gln Thr Pro Ala Ser Val Ser Ala Ala Val Gly
1               5                   10                  15

Gly Thr Val Thr Ile Lys Cys Gln Ala Ser Gln Asn Ile Gly Ser Asp
            20                  25                  30

Leu Ala Trp Tyr Gln Gln Lys Pro Gly Gln Pro Arg Leu Leu Ile
        35                  40                  45

Tyr Gly Ala Ser Lys Leu Ala Ser Gly Val Ser Ser Arg Phe Ser Gly
    50                  55                  60

Ser Gly Ser Gly Lys Glu Phe Thr Leu Thr Ile Ser Asp Leu Glu Cys
65                  70                  75                  80

Ala Asp Ala Val Thr Tyr Tyr Cys Gln Cys Thr Phe Val Gly Ser Ser
                85                  90                  95

Tyr Gly Asn Ala Phe Gly Gly Gly Thr Glu Val Val Val Lys
            100                 105                 110

<210> SEQ ID NO 12
<211> LENGTH: 110
<212> TYPE: PRT
<213> ORGANISM: Artificial Sequence
<220> FEATURE:
<223> OTHER INFORMATION: CFA0307 VL

<400> SEQUENCE: 12

Ala Ile Glu Met Thr Gln Thr Pro Phe Ser Val Ser Ala Ala Val Gly
1               5                   10                  15

Gly Thr Val Thr Ile Lys Cys Gln Ala Ser Gln Asn Ile Tyr Ser Asn
            20                  25                  30

Leu Ala Trp Tyr Gln Gln Lys Pro Gly Gln Arg Pro Lys Leu Leu Ile
        35                  40                  45

Tyr Gly Ala Ser Asn Leu Glu Ser Gly Val Pro Ser Arg Phe Lys Gly
    50                  55                  60

Ser Gly Ser Gly Thr Glu Tyr Thr Leu Thr Ile Ser Asp Leu Glu Cys
65                  70                  75                  80

Ala Asp Ala Ala Thr Tyr Tyr Cys Leu Gln Gly Tyr Ser Tyr Ser Asn
                85                  90                  95

Val Asp Asp Ala Phe Gly Gly Gly Thr Glu Val Val Val Lys
            100                 105                 110

<210> SEQ ID NO 13
<211> LENGTH: 112
<212> TYPE: PRT
<213> ORGANISM: Artificial Sequence
<220> FEATURE:
<223> OTHER INFORMATION: CFA0366 VL

<400> SEQUENCE: 13

Ala Gln Val Leu Thr Gln Thr Pro Ser Ser Val Ser Ala Ala Val Gly
1               5                   10                  15

Gly Thr Val Thr Ile Asn Cys Gln Ser Ser Gln Ser Val Tyr Ser Ser
            20                  25                  30

Asp Tyr Leu Ser Trp Tyr Gln Gln Lys Pro Gly Gln Pro Pro Lys Leu
        35                  40                  45

Leu Ile Tyr Glu Ala Ser Lys Leu Ala Ser Gly Val Pro Pro Arg Phe
    50                  55                  60

Ser Gly Ser Gly Ser Gly Thr Gln Phe Thr Leu Thr Ile Ser Gly Val
65                  70                  75                  80

Gln Cys Asp Asp Ala Ala Thr Tyr Tyr Cys Gln Gly Thr Tyr Tyr Ser
                85                  90                  95

Ser Gly Trp Tyr Phe Ala Phe Gly Gly Gly Thr Glu Val Val Val Lys
            100                 105                 110

<210> SEQ ID NO 14
<211> LENGTH: 110
<212> TYPE: PRT
<213> ORGANISM: Artificial Sequence
<220> FEATURE:
<223> OTHER INFORMATION: CFA0501 VL

<400> SEQUENCE: 14

Ala Tyr Asp Met Thr Gln Thr Pro Ala Ser Val Glu Val Ala Val Gly
1               5                   10                  15

Gly Thr Val Thr Ile Asn Cys Gln Ala Ser Glu Ser Ile Ser Asn Trp
            20                  25                  30

Leu Ala Trp Tyr Gln Gln Lys Pro Gly Gln Arg Pro Lys Leu Leu Ile
        35                  40                  45

Tyr Arg Ala Ser Thr Leu Ala Ser Gly Val Ser Ser Arg Phe Lys Gly
    50                  55                  60

Ser Gly Ser Gly Thr Gln Phe Thr Leu Thr Ile Ser Gly Val Glu Cys
65                  70                  75                  80

Asp Asp Ala Ala Thr Tyr Tyr Cys Gln Gln Asp Tyr Ser Ser Ser Asn
                85                  90                  95

Val Asp Asn Thr Phe Gly Gly Gly Thr Lys Val Val Val Glu
            100                 105                 110

<210> SEQ ID NO 15
<211> LENGTH: 110
<212> TYPE: PRT
<213> ORGANISM: Artificial Sequence
<220> FEATURE:
<223> OTHER INFORMATION: CFA0538 VL

<400> SEQUENCE: 15

Ala Tyr Asp Met Thr Gln Thr Pro Ala Ser Val Glu Val Ala Val Gly
1               5                   10                  15

Gly Thr Val Thr Ile Asn Cys Gln Ala Ser Glu Ser Ile Ser Asn Trp
            20                  25                  30

Leu Ala Trp Tyr Gln Gln Lys Pro Gly Gln Arg Pro Lys Leu Leu Ile
        35                  40                  45

Tyr Arg Ala Ser Thr Leu Ala Ser Gly Val Ser Ser Arg Phe Lys Gly
    50                  55                  60

Ser Gly Ser Gly Thr Gln Phe Thr Leu Thr Ile Ser Gly Val Glu Cys
65                  70                  75                  80

Asp Asp Ala Ala Thr Tyr Tyr Cys Gln Gln Asp Tyr Ser Ser Ser Asn
                85                  90                  95

Val Asp Asn Thr Phe Gly Gly Gly Thr Thr Val Val Val Glu
            100                 105                 110

<210> SEQ ID NO 16
<211> LENGTH: 110
<212> TYPE: PRT
<213> ORGANISM: Artificial Sequence
<220> FEATURE:
<223> OTHER INFORMATION: CFA0599 VL

<400> SEQUENCE: 16

Ala Tyr Asp Met Thr Gln Thr Pro Ala Ser Val Glu Val Ser Val Gly

```
            1               5                  10                 15
Gly Thr Val Thr Ile Lys Cys Gln Ala Ser Glu Ser Ile Tyr Ser Ala
                20                  25                 30

Leu Ala Trp Tyr Gln Gln Lys Pro Gly Gln Pro Lys Leu Leu Ile
        35                  40                 45

Tyr Ser Ala Ser Thr Leu Ala Ser Gly Val Pro Ser Arg Phe Lys Gly
        50                  55                 60

Ser Gly Ser Gly Thr Glu Tyr Thr Leu Thr Ile Ser Asp Leu Glu Cys
65                  70                  75                  80

Ala Asp Ala Ala Thr Tyr Tyr Cys Gln Gln Tyr Tyr Ser Ser Thr Asn
                85                  90                 95

Val His Asn Ser Phe Gly Gly Gly Thr Thr Val Val Val Glu
                100                 105                110
```

<210> SEQ ID NO 17
<211> LENGTH: 110
<212> TYPE: PRT
<213> ORGANISM: Artificial Sequence
<220> FEATURE:
<223> OTHER INFORMATION: CFA0666 VL

<400> SEQUENCE: 17

```
Asp Val Val Met Thr Gln Thr Pro Ala Ser Val Ser Ala Ala Val Gly
1               5                  10                 15

Gly Thr Val Thr Ile Lys Cys Gln Ala Ser Glu Asn Ile Tyr Ser Ala
                20                  25                 30

Leu Ser Trp Tyr Gln Gln Lys Pro Gly Leu Arg Pro Arg Leu Leu Ile
        35                  40                 45

Tyr Tyr Ala Ser Thr Leu Ala Ser Gly Val Pro Ser Arg Phe Lys Gly
        50                  55                 60

Ser Arg Ser Gly Thr Glu Phe Thr Leu Thr Ile Ser Asp Leu Glu Cys
65                  70                  75                  80

Ala Asp Ala Ala Thr Tyr Tyr Cys Gln Gln Tyr Tyr Asp Ile Asn Ser
                85                  90                 95

Val Asp Asn Thr Phe Gly Gly Gly Thr Lys Val Val Val Glu
                100                 105                110
```

<210> SEQ ID NO 18
<211> LENGTH: 111
<212> TYPE: PRT
<213> ORGANISM: Artificial Sequence
<220> FEATURE:
<223> OTHER INFORMATION: CFA0672 VL

<400> SEQUENCE: 18

```
Asp Val Val Met Thr Gln Thr Pro Ala Ser Val Ser Ala Pro Val Gly
1               5                  10                 15

Gly Thr Val Thr Ile Lys Cys Gln Ala Ser Gln Asn Ile Tyr Ser Leu
                20                  25                 30

Leu Ala Trp Tyr Gln Gln Lys Pro Gly Gln Pro Lys Leu Leu Ile
        35                  40                 45

Tyr His Thr Ser Asp Leu Ala Ser Gly Val Pro Ser Arg Phe Arg Gly
        50                  55                 60

Ser Gly Ser Gly Thr Glu Phe Thr Leu Thr Ile Ser Asp Leu Glu Cys
65                  70                  75                  80

Ala Asp Ala Ala Thr Tyr Tyr Cys Gln Cys Thr Ala Tyr Gly Ser Ser
                85                  90                 95
```

```
Asp Val Gly Gly Thr Phe Gly Gly Thr Thr Val Val Glu
            100                 105                 110

<210> SEQ ID NO 19
<211> LENGTH: 110
<212> TYPE: PRT
<213> ORGANISM: Artificial Sequence
<220> FEATURE:
<223> OTHER INFORMATION: CFA0675 VL

<400> SEQUENCE: 19

Asp Val Val Met Thr Gln Thr Pro Ala Ser Val Ser Ala Ala Val Gly
1               5                   10                  15

Gly Thr Val Thr Ile Lys Cys Gln Ala Ser Glu Asn Ile Tyr Ser Ala
            20                  25                  30

Leu Ser Trp Tyr Gln Gln Lys Pro Gly Leu Arg Pro Arg Leu Leu Ile
        35                  40                  45

Tyr Tyr Ala Ser Thr Leu Ala Ser Gly Val Pro Ser Arg Phe Lys Gly
    50                  55                  60

Ser Arg Ser Gly Thr Glu Phe Thr Leu Thr Ile Ser Asp Leu Glu Cys
65                  70                  75                  80

Ala Asp Ala Ala Ser Tyr Tyr Cys Gln Gln Tyr Tyr Asp Ile Asn Ser
                85                  90                  95

Val Asp Asn Thr Phe Gly Gly Gly Thr Lys Val Val Val Glu
            100                 105                 110

<210> SEQ ID NO 20
<211> LENGTH: 110
<212> TYPE: PRT
<213> ORGANISM: Artificial Sequence
<220> FEATURE:
<223> OTHER INFORMATION: 305L05 VL

<400> SEQUENCE: 20

Asp Val Val Met Thr Gln Ser Pro Ser Ser Leu Ser Ala Ser Val Gly
1               5                   10                  15

Asp Arg Val Thr Ile Thr Cys Gln Ala Ser Gln Asn Ile Gly Ser Ser
            20                  25                  30

Leu Ala Trp Tyr Gln Gln Lys Pro Gly Gln Ala Pro Arg Leu Leu Ile
        35                  40                  45

Tyr Gly Ala Ser Lys Thr His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Ser Thr Lys Val Gly Ser Ser
                85                  90                  95

Tyr Gly Asn His Phe Gly Gly Gly Thr Lys Val Glu Ile Lys
            100                 105                 110

<210> SEQ ID NO 21
<211> LENGTH: 117
<212> TYPE: PRT
<213> ORGANISM: Artificial Sequence
<220> FEATURE:
<223> OTHER INFORMATION: CFA0330 VH

<400> SEQUENCE: 21

Gln Ser Leu Glu Glu Ser Gly Gly Asp Leu Val Glu Pro Gly Ala Ser
1               5                   10                  15

Leu Thr Leu Thr Cys Thr Ala Ser Gly Phe Ser Trp Asn Ser Gly Tyr
```

```
            20                  25                  30
Asp Met Cys Trp Val Arg Gln Ala Pro Gly Lys Gly Leu Glu Trp Ile
        35                  40                  45

Ala Cys Ile Tyr Thr Gly Ser Ser Ala Asn Thr Ala Tyr Ala Asn Trp
    50                  55                  60

Ala Lys Gly Arg Phe Thr Ile Ser Lys Thr Ser Ser Thr Thr Val Thr
 65                 70                  75                  80

Leu Gln Met Thr Gly Leu Thr Ala Ala Asp Thr Ala Thr Tyr Phe Cys
                    85                  90                  95

Ala Arg His Asp Asp Tyr Phe Phe Asp Leu Trp Gly Pro Gly Thr Leu
                100                 105                 110

Val Thr Val Ser Ser
        115

<210> SEQ ID NO 22
<211> LENGTH: 115
<212> TYPE: PRT
<213> ORGANISM: Artificial Sequence
<220> FEATURE:
<223> OTHER INFORMATION: CFA0341 VH

<400> SEQUENCE: 22

Gln Ser Val Glu Glu Ser Gly Gly Arg Leu Val Thr Pro Gly Thr Pro
 1               5                  10                  15

Leu Thr Leu Thr Cys Thr Val Ser Gly Ile Asp Leu Ser Ser Tyr Thr
            20                  25                  30

Met Gly Trp Val Arg Gln Ala Pro Gly Lys Gly Leu Glu Cys Ile Gly
        35                  40                  45

Tyr Ile His Ser Phe Gly Ser Thr Tyr Tyr Ala Ser Trp Ala Lys Gly
    50                  55                  60

Arg Phe Thr Ile Ser Lys Thr Ser Thr Thr Val Asp Leu Glu Ile Thr
 65                 70                  75                  80

Ser Pro Thr Thr Glu Asp Thr Ala Thr Tyr Phe Cys Ala Arg Asp Val
                    85                  90                  95

Gly Gly Ser Ser Gly Trp Asp Leu Trp Gly Gln Gly Thr Leu Val Thr
                100                 105                 110

Val Ser Ser
        115

<210> SEQ ID NO 23
<211> LENGTH: 116
<212> TYPE: PRT
<213> ORGANISM: Artificial Sequence
<220> FEATURE:
<223> OTHER INFORMATION: CFA0329 VH

<400> SEQUENCE: 23

Gln Ser Leu Glu Glu Ser Gly Gly Gly Leu Val Lys Pro Gly Ala Ser
 1               5                  10                  15

Leu Thr Leu Thr Cys Thr Ala Ser Gly Phe Ser Phe Ser Ser Gly Tyr
            20                  25                  30

Tyr Met Cys Trp Val Arg Gln Ala Pro Gly Lys Gly Leu Glu Trp Ile
        35                  40                  45

Gly Cys Ile Gly Thr Ile Ser Asp Ser Thr Tyr Tyr Ala Ser Trp Ala
    50                  55                  60

Lys Gly Arg Phe Pro Ile Ser Lys Ala Ser Ser Thr Val Thr Leu
 65                 70                  75                  80
```

```
Gln Met Thr Ser Leu Thr Ala Ala Asp Thr Ala Thr Tyr Phe Cys Ala
                85                  90                  95

Arg Asp Pro Tyr Ser Tyr Gly Asp Leu Trp Gly Pro Gly Thr Leu Val
            100                 105                 110

Thr Val Ser Ser
        115

<210> SEQ ID NO 24
<211> LENGTH: 125
<212> TYPE: PRT
<213> ORGANISM: Artificial Sequence
<220> FEATURE:
<223> OTHER INFORMATION: CFA0300 VH

<400> SEQUENCE: 24

Gln Glu Gln Leu Glu Glu Ser Gly Gly Asp Leu Val Lys Pro Glu Gly
1               5                   10                  15

Ser Leu Thr Leu Thr Cys Thr Ala Ser Gly Phe Ser Phe Ser Ser Gly
            20                  25                  30

Asn Trp Ile Cys Trp Val Arg Gln Ala Pro Gly Lys Gly Leu Glu Trp
        35                  40                  45

Ile Ala Cys Ile Tyr Gly Gly Ser Val Gly Gly Thr Asp Tyr Ala Ser
    50                  55                  60

Trp Ala Lys Gly Arg Phe Thr Val Ser Lys Thr Ser Ser Thr Thr Val
65                  70                  75                  80

Thr Leu Gln Met Thr Ser Leu Thr Ala Ala Asp Thr Ala Thr Tyr Phe
                85                  90                  95

Cys Ala Arg Met Glu Asp Gly Tyr Gly Tyr Gly Tyr Asp Thr Tyr Phe
            100                 105                 110

Lys Leu Trp Gly Pro Gly Thr Leu Val Thr Val Ser Ser
        115                 120                 125

<210> SEQ ID NO 25
<211> LENGTH: 114
<212> TYPE: PRT
<213> ORGANISM: Artificial Sequence
<220> FEATURE:
<223> OTHER INFORMATION: CFA0330 VL

<400> SEQUENCE: 25

Asp Val Val Met Thr Gln Thr Pro Ala Ser Val Ser Glu Ser Val Gly
1               5                   10                  15

Gly Thr Val Thr Ile Asn Cys Gln Ala Ser Gln Ser Ile Gly Asn Asn
            20                  25                  30

Leu Ala Trp Tyr Gln Gln Lys Pro Gly Gln Pro Pro Lys Leu Leu Ile
        35                  40                  45

Tyr Asp Ala Ser Asn Leu Ala Ser Gly Val Pro Ser Arg Phe Lys Gly
    50                  55                  60

Ser Arg Ser Gly Thr Glu Pro Thr Leu Thr Asn Thr Leu Thr Ile Ser
65                  70                  75                  80

Gly Val Gln Cys Ala Asp Val Ala Thr Tyr Tyr Cys Gln Ser Gly Trp
                85                  90                  95

Tyr Gly Asn Ser Tyr Val Ala Ala Phe Gly Gly Gly Thr Glu Val Val
            100                 105                 110

Val Lys

<210> SEQ ID NO 26
<211> LENGTH: 112
```

<212> TYPE: PRT
<213> ORGANISM: Artificial Sequence
<220> FEATURE:
<223> OTHER INFORMATION: CFA0341 VL

<400> SEQUENCE: 26

Asp Val Val Met Thr Gln Thr Pro Ser Ser Val Ser Ala Ala Val Gly
1               5                   10                  15

Gly Thr Val Thr Ile Lys Cys Gln Ala Ser Glu Asn Ile Tyr Ser Asn
            20                  25                  30

Leu Ala Trp Tyr Gln Gln Lys Pro Gly Gln Pro Pro Lys Arg Leu Ile
        35                  40                  45

Tyr Asp Ala Ser Asp Leu Ala Ser Gly Val Pro Ser Arg Phe Ser Gly
    50                  55                  60

Ser Gly Tyr Gly Thr Gln Phe Thr Leu Thr Ile Ser Gly Val Gln Cys
65                  70                  75                  80

Glu Asp Ala Ala Thr Tyr Tyr Cys Gln Ala Asn Tyr Asp Ser Thr Ser
                85                  90                  95

Ser Ser Phe Gly Asn Val Phe Gly Gly Gly Thr Glu Val Val Val Lys
            100                 105                 110

<210> SEQ ID NO 27
<211> LENGTH: 110
<212> TYPE: PRT
<213> ORGANISM: Artificial Sequence
<220> FEATURE:
<223> OTHER INFORMATION: CFA0329 VL

<400> SEQUENCE: 27

Asp Leu Val Met Thr Gln Thr Pro Ala Ser Val Ser Glu Pro Val Gly
1               5                   10                  15

Gly Thr Val Thr Ile Lys Cys Gln Ala Ser Gln Ser Ile Gly Thr Tyr
            20                  25                  30

Leu Ala Trp Tyr Gln Gln Lys Pro Gly Gln Pro Pro Lys Leu Leu Ile
        35                  40                  45

Tyr Arg Ala Ser Thr Leu Ala Ser Gly Val Pro Ser Arg Phe Lys Gly
    50                  55                  60

Ser Gly Ser Gly Thr Gln Phe Thr Leu Thr Ile Ser Asp Leu Glu Cys
65                  70                  75                  80

Ala Asp Ala Ala Thr Tyr Tyr Cys Leu Gly Gly Tyr Tyr Gly Phe Ser
                85                  90                  95

Tyr Gly Asn Ala Phe Gly Gly Gly Thr Glu Val Val Val Lys
            100                 105                 110

<210> SEQ ID NO 28
<211> LENGTH: 110
<212> TYPE: PRT
<213> ORGANISM: Artificial Sequence
<220> FEATURE:
<223> OTHER INFORMATION: CFA0300 VL

<400> SEQUENCE: 28

Asp Ile Val Met Thr Gln Thr Pro Ala Ser Val Glu Ala Ala Val Gly
1               5                   10                  15

Gly Thr Val Thr Ile Lys Cys Gln Ala Ser Gln Ser Ile Thr Ser Trp
            20                  25                  30

Leu Ala Trp Tyr Gln Gln Lys Leu Gly Gln Pro Pro Lys Leu Leu Ile
        35                  40                  45

Tyr Lys Ala Ser Thr Leu Ala Ser Gly Val Ser Ser Arg Phe Lys Gly

|   |   |   |   | 50 |   |   |   |   | 55 |   |   |   |   | 60 |   |

Ser Gly Ser Gly Thr Glu Phe Thr Leu Thr Ile Ser Asp Leu Glu Cys
65                  70                  75                  80

Ala Asp Ala Ala Thr Tyr Tyr Cys Gln Gly Tyr Tyr Asp Ser Ser Thr
                85                  90                  95

Ser Ser Tyr Val Phe Gly Gly Gly Thr Glu Val Val Val Lys
                100                 105                 110

<210> SEQ ID NO 29
<211> LENGTH: 448
<212> TYPE: PRT
<213> ORGANISM: Artificial Sequence
<220> FEATURE:
<223> OTHER INFORMATION: EcuH-G2G4

<400> SEQUENCE: 29

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Ser Asn Tyr
                20                  25                  30

Trp Ile Gln Trp Val Arg Gln Ala Pro Gly Gln Gly Leu Glu Trp Met
            35                  40                  45

Gly Glu Ile Leu Pro Gly Ser Gly Ser Thr Glu Tyr Thr Glu Asn Phe
    50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Tyr Phe Phe Gly Ser Ser Pro Asn Trp Tyr Phe Asp Val Trp
                100                 105                 110

Gly Gln Gly Thr Leu Val Thr Val Ser Ser Ala Ser Thr Lys Gly Pro
            115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
                180                 185                 190

Val Pro Ser Ser Asn Phe Gly Thr Gln Thr Tyr Thr Cys Asn Val Asp
            195                 200                 205

His Lys Pro Ser Asn Thr Lys Val Asp Lys Thr Val Glu Arg Lys Cys
    210                 215                 220

Cys Val Glu Cys Pro Pro Cys Pro Ala Pro Pro Val Ala Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
                260                 265                 270

Glu Val Gln Phe Asn Trp Tyr Val Asp Gly Val Glu Val His Asn Ala
            275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr

```
            305                 310                 315                 320
Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Gln Glu Glu Met Thr Lys Asn Gln Val Ser Leu Thr Cys
                355                 360                 365

Leu Val Lys Gly Phe Tyr Pro Ser Asp Ile Ala Val Glu Trp Glu Ser
                370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
                420                 425                 430

Leu His Asn His Tyr Thr Gln Lys Ser Leu Ser Leu Ser Leu Gly Lys
                435                 440                 445

<210> SEQ ID NO 30
<211> LENGTH: 214
<212> TYPE: PRT
<213> ORGANISM: Artificial Sequence
<220> FEATURE:
<223> OTHER INFORMATION: EcuL-k0

<400> SEQUENCE: 30

Asp Ile Gln Met Thr Gln Ser Pro Ser Ser Leu Ser Ala Ser Val Gly
1               5                   10                  15

Asp Arg Val Thr Ile Thr Cys Gly Ala Ser Glu Asn Ile Tyr Gly Ala
                20                  25                  30

Leu Asn Trp Tyr Gln Gln Lys Pro Gly Lys Ala Pro Lys Leu Leu Ile
                35                  40                  45

Tyr Gly Ala Thr Asn Leu Ala Asp Gly Val Pro Ser Arg Phe Ser Gly
            50                  55                  60

Ser Gly Ser Gly Thr Asp Phe Thr Leu Thr Ile Ser Ser Leu Gln Pro
65              70                  75                  80

Glu Asp Phe Ala Thr Tyr Tyr Cys Gln Asn Val Leu Asn Thr Pro Leu
                85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
                130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
            210
```

-continued

<210> SEQ ID NO 31
<211> LENGTH: 122
<212> TYPE: PRT
<213> ORGANISM: Artificial Sequence
<220> FEATURE:
<223> OTHER INFORMATION: EcuH

<400> SEQUENCE: 31

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Ser Asn Tyr
            20                  25                  30

Trp Ile Gln Trp Val Arg Gln Ala Pro Gly Gln Gly Leu Glu Trp Met
        35                  40                  45

Gly Glu Ile Leu Pro Gly Ser Gly Ser Thr Glu Tyr Thr Glu Asn Phe
    50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Tyr Phe Phe Gly Ser Ser Pro Asn Trp Tyr Phe Asp Val Trp
            100                 105                 110

Gly Gln Gly Thr Leu Val Thr Val Ser Ser
        115                 120

<210> SEQ ID NO 32
<211> LENGTH: 107
<212> TYPE: PRT
<213> ORGANISM: Artificial Sequence
<220> FEATURE:
<223> OTHER INFORMATION: EcuL

<400> SEQUENCE: 32

Asp Ile Gln Met Thr Gln Ser Pro Ser Ser Leu Ser Ala Ser Val Gly
1               5                   10                  15

Asp Arg Val Thr Ile Thr Cys Gly Ala Ser Glu Asn Ile Tyr Gly Ala
            20                  25                  30

Leu Asn Trp Tyr Gln Gln Lys Pro Gly Lys Ala Pro Lys Leu Leu Ile
        35                  40                  45

Tyr Gly Ala Thr Asn Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Asn Val Leu Asn Thr Pro Leu
                85                  90                  95

Thr Phe Gly Gln Gly Thr Lys Val Glu Ile Lys
            100                 105

<210> SEQ ID NO 33
<211> LENGTH: 325
<212> TYPE: PRT
<213> ORGANISM: Artificial Sequence
<220> FEATURE:
<223> OTHER INFORMATION: F760G4

<400> SEQUENCE: 33

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
           35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Leu Gly Thr Lys Thr
 65                  70                  75                  80

Tyr Thr Cys Asn Val Asp His Lys Pro Ser Asn Thr Lys Val Asp Lys
                 85                  90                  95

Arg Val Glu Ser Lys Tyr Gly Pro Pro Cys Pro Pro Cys Pro Ala Pro
            100                 105                 110

Glu Phe Arg Gly Gly Pro Lys Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu
            325

<210> SEQ ID NO 34
<211> LENGTH: 325
<212> TYPE: PRT
<213> ORGANISM: Artificial Sequence
<220> FEATURE:
<223> OTHER INFORMATION: F939G4

<400> SEQUENCE: 34

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Arg Gly Gly Pro Lys Val Phe Leu Phe Pro Pro Lys Pro Lys
        115                 120                 125

Asp Thr Leu Tyr Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Tyr His Val Thr Gln Lys Ser
305                 310                 315                 320

Leu Ser Leu Ser Leu
            325

<210> SEQ ID NO 35
<211> LENGTH: 325
<212> TYPE: PRT
<213> ORGANISM: Artificial Sequence
<220> FEATURE:
<223> OTHER INFORMATION: SG402

<400> SEQUENCE: 35

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Cys Pro Ala Pro
            100                 105                 110

Glu Phe Arg Gly Gly Pro Lys Val Phe Leu Phe Pro Pro Lys Pro Lys
            115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
            210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
            275                 280                 285

Lys Leu Thr Val Asp Lys Ser Arg Trp Gln Gln Gly Asn Val Phe Ser
            290                 295                 300

Cys Ser Val Met His Glu Ala Leu His Asn His Tyr Thr Gln Lys Ser
305                 310                 315                 320

Leu Ser Leu Ser Pro
                325

<210> SEQ ID NO 36
<211> LENGTH: 107
<212> TYPE: PRT
<213> ORGANISM: Artificial Sequence
<220> FEATURE:
<223> OTHER INFORMATION: k0MTC

<400> SEQUENCE: 36

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Cys
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 37

```
<211> LENGTH: 107
<212> TYPE: PRT
<213> ORGANISM: Artificial Sequence
<220> FEATURE:
<223> OTHER INFORMATION: k0

<400> SEQUENCE: 37

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 38
<211> LENGTH: 107
<212> TYPE: PRT
<213> ORGANISM: Artificial Sequence
<220> FEATURE:
<223> OTHER INFORMATION: SK1

<400> SEQUENCE: 38

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 39
<211> LENGTH: 1676
<212> TYPE: PRT
<213> ORGANISM: Artificial Sequence
<220> FEATURE:
<223> OTHER INFORMATION: human C5

<400> SEQUENCE: 39

Met Gly Leu Leu Gly Ile Leu Cys Phe Leu Ile Phe Leu Gly Lys Thr
1               5                   10                  15

Trp Gly Gln Glu Gln Thr Tyr Val Ile Ser Ala Pro Lys Ile Phe Arg
            20                  25                  30

Val Gly Ala Ser Glu Asn Ile Val Ile Gln Val Tyr Gly Tyr Thr Glu
        35                  40                  45
```

-continued

```
Ala Phe Asp Ala Thr Ile Ser Ile Lys Ser Tyr Pro Asp Lys Lys Phe
        50                  55                  60

Ser Tyr Ser Ser Gly His Val His Leu Ser Ser Glu Asn Lys Phe Gln
65                  70                  75                  80

Asn Ser Ala Ile Leu Thr Ile Gln Pro Lys Gln Leu Pro Gly Gly Gln
                85                  90                  95

Asn Pro Val Ser Tyr Val Tyr Leu Glu Val Val Ser Lys His Phe Ser
                100                 105                 110

Lys Ser Lys Arg Met Pro Ile Thr Tyr Asp Asn Gly Phe Leu Phe Ile
            115                 120                 125

His Thr Asp Lys Pro Val Tyr Thr Pro Asp Gln Ser Val Lys Val Arg
        130                 135                 140

Val Tyr Ser Leu Asn Asp Asp Leu Lys Pro Ala Lys Arg Glu Thr Val
145                 150                 155                 160

Leu Thr Phe Ile Asp Pro Glu Gly Ser Glu Val Asp Met Val Glu Glu
                165                 170                 175

Ile Asp His Ile Gly Ile Ile Ser Phe Pro Asp Phe Lys Ile Pro Ser
            180                 185                 190

Asn Pro Arg Tyr Gly Met Trp Thr Ile Lys Ala Lys Tyr Lys Glu Asp
        195                 200                 205

Phe Ser Thr Thr Gly Thr Ala Tyr Phe Glu Val Lys Glu Tyr Val Leu
    210                 215                 220

Pro His Phe Ser Val Ser Ile Glu Pro Glu Tyr Asn Phe Ile Gly Tyr
225                 230                 235                 240

Lys Asn Phe Lys Asn Phe Glu Ile Thr Ile Lys Ala Arg Tyr Phe Tyr
                245                 250                 255

Asn Lys Val Val Thr Glu Ala Asp Val Tyr Ile Thr Phe Gly Ile Arg
                260                 265                 270

Glu Asp Leu Lys Asp Asp Gln Lys Glu Met Met Gln Thr Ala Met Gln
            275                 280                 285

Asn Thr Met Leu Ile Asn Gly Ile Ala Gln Val Thr Phe Asp Ser Glu
        290                 295                 300

Thr Ala Val Lys Glu Leu Ser Tyr Tyr Ser Leu Glu Asp Leu Asn Asn
305                 310                 315                 320

Lys Tyr Leu Tyr Ile Ala Val Thr Val Ile Glu Ser Thr Gly Gly Phe
                325                 330                 335

Ser Glu Glu Ala Glu Ile Pro Gly Ile Lys Tyr Val Leu Ser Pro Tyr
            340                 345                 350

Lys Leu Asn Leu Val Ala Thr Pro Leu Phe Leu Lys Pro Gly Ile Pro
        355                 360                 365

Tyr Pro Ile Lys Val Gln Val Lys Asp Ser Leu Asp Gln Leu Val Gly
    370                 375                 380

Gly Val Pro Val Thr Leu Asn Ala Gln Thr Ile Asp Val Asn Gln Glu
385                 390                 395                 400

Thr Ser Asp Leu Asp Pro Ser Lys Ser Val Thr Arg Val Asp Asp Gly
                405                 410                 415

Val Ala Ser Phe Val Leu Asn Leu Pro Ser Gly Val Thr Val Leu Glu
                420                 425                 430

Phe Asn Val Lys Thr Asp Ala Pro Asp Leu Pro Glu Glu Asn Gln Ala
            435                 440                 445

Arg Glu Gly Tyr Arg Ala Ile Ala Tyr Ser Ser Leu Ser Gln Ser Tyr
        450                 455                 460

Leu Tyr Ile Asp Trp Thr Asp Asn His Lys Ala Leu Leu Val Gly Glu
```

```
                465                 470                 475                 480
         His Leu Asn Ile Ile Val Thr Pro Lys Ser Pro Tyr Ile Asp Lys Ile
                             485                 490                 495

Thr His Tyr Asn Tyr Leu Ile Leu Ser Lys Gly Lys Ile Ile His Phe
                             500                 505                 510

Gly Thr Arg Glu Lys Phe Ser Asp Ala Ser Tyr Gln Ser Ile Asn Ile
                     515                 520                 525

Pro Val Thr Gln Asn Met Val Pro Ser Ser Arg Leu Leu Val Tyr Tyr
                 530                 535                 540

Ile Val Thr Gly Glu Gln Thr Ala Glu Leu Val Ser Asp Ser Val Trp
         545                 550                 555                 560

Leu Asn Ile Glu Glu Lys Cys Gly Asn Gln Leu Gln Val His Leu Ser
                         565                 570                 575

Pro Asp Ala Asp Ala Tyr Ser Pro Gly Gln Thr Val Ser Leu Asn Met
                     580                 585                 590

Ala Thr Gly Met Asp Ser Trp Val Ala Leu Ala Ala Val Asp Ser Ala
                 595                 600                 605

Val Tyr Gly Val Gln Arg Gly Ala Lys Lys Pro Leu Glu Arg Val Phe
             610                 615                 620

Gln Phe Leu Glu Lys Ser Asp Leu Gly Cys Gly Ala Gly Gly Gly Leu
         625                 630                 635                 640

Asn Asn Ala Asn Val Phe His Leu Ala Gly Leu Thr Phe Leu Thr Asn
                         645                 650                 655

Ala Asn Ala Asp Asp Ser Gln Glu Asn Asp Glu Pro Cys Lys Glu Ile
                     660                 665                 670

Leu Arg Pro Arg Arg Thr Leu Gln Lys Lys Ile Glu Glu Ile Ala Ala
                 675                 680                 685

Lys Tyr Lys His Ser Val Val Lys Lys Cys Cys Tyr Asp Gly Ala Cys
             690                 695                 700

Val Asn Asn Asp Glu Thr Cys Glu Gln Arg Ala Ala Arg Ile Ser Leu
         705                 710                 715                 720

Gly Pro Arg Cys Ile Lys Ala Phe Thr Glu Cys Cys Val Val Ala Ser
                             725                 730                 735

Gln Leu Arg Ala Asn Ile Ser His Lys Asp Met Gln Leu Gly Arg Leu
                     740                 745                 750

His Met Lys Thr Leu Leu Pro Val Ser Lys Pro Glu Ile Arg Ser Tyr
                 755                 760                 765

Phe Pro Glu Ser Trp Leu Trp Glu Val His Leu Val Pro Arg Arg Lys
             770                 775                 780

Gln Leu Gln Phe Ala Leu Pro Asp Ser Leu Thr Thr Trp Glu Ile Gln
         785                 790                 795                 800

Gly Val Gly Ile Ser Asn Thr Gly Ile Cys Val Ala Asp Thr Val Lys
                             805                 810                 815

Ala Lys Val Phe Lys Asp Val Phe Leu Glu Met Asn Ile Pro Tyr Ser
                     820                 825                 830

Val Val Arg Gly Glu Gln Ile Gln Leu Lys Gly Thr Val Tyr Asn Tyr
                 835                 840                 845

Arg Thr Ser Gly Met Gln Phe Cys Val Lys Met Ser Ala Val Glu Gly
             850                 855                 860

Ile Cys Thr Ser Glu Ser Pro Val Ile Asp His Gln Gly Thr Lys Ser
         865                 870                 875                 880

Ser Lys Cys Val Arg Gln Lys Val Glu Gly Ser Ser His Leu Val
                             885                 890                 895
```

```
Thr Phe Thr Val Leu Pro Leu Glu Ile Gly Leu His Asn Ile Asn Phe
            900                 905                 910

Ser Leu Glu Thr Trp Phe Gly Lys Glu Ile Leu Val Lys Thr Leu Arg
            915                 920                 925

Val Val Pro Glu Gly Val Lys Arg Glu Ser Tyr Ser Gly Val Thr Leu
            930                 935                 940

Asp Pro Arg Gly Ile Tyr Gly Thr Ile Ser Arg Lys Glu Phe Pro
945                 950                 955                 960

Tyr Arg Ile Pro Leu Asp Leu Pro Lys Thr Glu Ile Lys Arg Ile
                965                 970                 975

Leu Ser Val Lys Gly Leu Leu Val Gly Glu Ile Leu Ser Ala Val Leu
            980                 985                 990

Ser Gln Glu Gly Ile Asn Ile Leu Thr His Leu Pro Lys Gly Ser Ala
            995                 1000                1005

Glu Ala Glu Leu Met Ser Val Pro Val Phe Tyr Val Phe His
            1010                1015                1020

Tyr Leu Glu Thr Gly Asn His Trp Asn Ile Phe His Ser Asp Pro
            1025                1030                1035

Leu Ile Glu Lys Gln Lys Leu Lys Lys Lys Leu Lys Glu Gly Met
            1040                1045                1050

Leu Ser Ile Met Ser Tyr Arg Asn Ala Asp Tyr Ser Tyr Ser Val
            1055                1060                1065

Trp Lys Gly Gly Ser Ala Ser Thr Trp Leu Thr Ala Phe Ala Leu
            1070                1075                1080

Arg Val Leu Gly Gln Val Asn Lys Tyr Val Glu Gln Asn Gln Asn
            1085                1090                1095

Ser Ile Cys Asn Ser Leu Leu Trp Leu Val Glu Asn Tyr Gln Leu
            1100                1105                1110

Asp Asn Gly Ser Phe Lys Glu Asn Ser Gln Tyr Gln Pro Ile Lys
            1115                1120                1125

Leu Gln Gly Thr Leu Pro Val Glu Ala Arg Glu Asn Ser Leu Tyr
            1130                1135                1140

Leu Thr Ala Phe Thr Val Ile Gly Ile Arg Lys Ala Phe Asp Ile
            1145                1150                1155

Cys Pro Leu Val Lys Ile Asp Thr Ala Leu Ile Lys Ala Asp Asn
            1160                1165                1170

Phe Leu Leu Glu Asn Thr Leu Pro Ala Gln Ser Thr Phe Thr Leu
            1175                1180                1185

Ala Ile Ser Ala Tyr Ala Leu Ser Leu Gly Asp Lys Thr His Pro
            1190                1195                1200

Gln Phe Arg Ser Ile Val Ser Ala Leu Lys Arg Glu Ala Leu Val
            1205                1210                1215

Lys Gly Asn Pro Pro Ile Tyr Arg Phe Trp Lys Asp Asn Leu Gln
            1220                1225                1230

His Lys Asp Ser Ser Val Pro Asn Thr Gly Thr Ala Arg Met Val
            1235                1240                1245

Glu Thr Thr Ala Tyr Ala Leu Leu Thr Ser Leu Asn Leu Lys Asp
            1250                1255                1260

Ile Asn Tyr Val Asn Pro Val Ile Lys Trp Leu Ser Glu Glu Gln
            1265                1270                1275

Arg Tyr Gly Gly Gly Phe Tyr Ser Thr Gln Asp Thr Ile Asn Ala
            1280                1285                1290
```

```
Ile Glu Gly Leu Thr Glu Tyr Ser Leu Leu Val Lys Gln Leu Arg
1295                1300                1305

Leu Ser Met Asp Ile Asp Val Ser Tyr Lys His Lys Gly Ala Leu
1310                1315                1320

His Asn Tyr Lys Met Thr Asp Lys Asn Phe Leu Gly Arg Pro Val
1325                1330                1335

Glu Val Leu Leu Asn Asp Asp Leu Ile Val Ser Thr Gly Phe Gly
1340                1345                1350

Ser Gly Leu Ala Thr Val His Val Thr Thr Val Val His Lys Thr
1355                1360                1365

Ser Thr Ser Glu Glu Val Cys Ser Phe Tyr Leu Lys Ile Asp Thr
1370                1375                1380

Gln Asp Ile Glu Ala Ser His Tyr Arg Gly Tyr Gly Asn Ser Asp
1385                1390                1395

Tyr Lys Arg Ile Val Ala Cys Ala Ser Tyr Lys Pro Ser Arg Glu
1400                1405                1410

Glu Ser Ser Ser Gly Ser Ser His Ala Val Met Asp Ile Ser Leu
1415                1420                1425

Pro Thr Gly Ile Ser Ala Asn Glu Glu Asp Leu Lys Ala Leu Val
1430                1435                1440

Glu Gly Val Asp Gln Leu Phe Thr Asp Tyr Gln Ile Lys Asp Gly
1445                1450                1455

His Val Ile Leu Gln Leu Asn Ser Ile Pro Ser Ser Asp Phe Leu
1460                1465                1470

Cys Val Arg Phe Arg Ile Phe Glu Leu Phe Glu Val Gly Phe Leu
1475                1480                1485

Ser Pro Ala Thr Phe Thr Val Tyr Glu Tyr His Arg Pro Asp Lys
1490                1495                1500

Gln Cys Thr Met Phe Tyr Ser Thr Ser Asn Ile Lys Ile Gln Lys
1505                1510                1515

Val Cys Glu Gly Ala Ala Cys Lys Cys Val Glu Ala Asp Cys Gly
1520                1525                1530

Gln Met Gln Glu Glu Leu Asp Leu Thr Ile Ser Ala Glu Thr Arg
1535                1540                1545

Lys Gln Thr Ala Cys Lys Pro Glu Ile Ala Tyr Ala Tyr Lys Val
1550                1555                1560

Ser Ile Thr Ser Ile Thr Val Glu Asn Val Phe Val Lys Tyr Lys
1565                1570                1575

Ala Thr Leu Leu Asp Ile Tyr Lys Thr Gly Glu Ala Val Ala Glu
1580                1585                1590

Lys Asp Ser Glu Ile Thr Phe Ile Lys Lys Val Thr Cys Thr Asn
1595                1600                1605

Ala Glu Leu Val Lys Gly Arg Gln Tyr Leu Ile Met Gly Lys Glu
1610                1615                1620

Ala Leu Gln Ile Lys Tyr Asn Phe Ser Phe Arg Tyr Ile Tyr Pro
1625                1630                1635

Leu Asp Ser Leu Thr Trp Ile Glu Tyr Trp Pro Arg Asp Thr Thr
1640                1645                1650

Cys Ser Ser Cys Gln Ala Phe Leu Ala Asn Leu Asp Glu Phe Ala
1655                1660                1665

Glu Asp Ile Phe Leu Asn Gly Cys
1670                1675
```

<210> SEQ ID NO 40
<211> LENGTH: 673
<212> TYPE: PRT
<213> ORGANISM: Artificial Sequence
<220> FEATURE:
<223> OTHER INFORMATION: human C5, beta chain

<400> SEQUENCE: 40

```
Met Gly Leu Leu Gly Ile Leu Cys Phe Leu Ile Phe Leu Gly Lys Thr
1               5                   10                  15

Trp Gly Gln Glu Gln Thr Tyr Val Ile Ser Ala Pro Lys Ile Phe Arg
            20                  25                  30

Val Gly Ala Ser Glu Asn Ile Val Ile Gln Val Tyr Gly Tyr Thr Glu
        35                  40                  45

Ala Phe Asp Ala Thr Ile Ser Ile Lys Ser Tyr Pro Asp Lys Lys Phe
    50                  55                  60

Ser Tyr Ser Ser Gly His Val His Leu Ser Ser Glu Asn Lys Phe Gln
65                  70                  75                  80

Asn Ser Ala Ile Leu Thr Ile Gln Pro Lys Gln Leu Pro Gly Gly Gln
                85                  90                  95

Asn Pro Val Ser Tyr Val Tyr Leu Glu Val Val Ser Lys His Phe Ser
            100                 105                 110

Lys Ser Lys Arg Met Pro Ile Thr Tyr Asp Asn Gly Phe Leu Phe Ile
        115                 120                 125

His Thr Asp Lys Pro Val Tyr Thr Pro Asp Gln Ser Val Lys Val Arg
    130                 135                 140

Val Tyr Ser Leu Asn Asp Asp Leu Lys Pro Ala Lys Arg Glu Thr Val
145                 150                 155                 160

Leu Thr Phe Ile Asp Pro Glu Gly Ser Glu Val Asp Met Val Glu Glu
                165                 170                 175

Ile Asp His Ile Gly Ile Ile Ser Phe Pro Asp Phe Lys Ile Pro Ser
            180                 185                 190

Asn Pro Arg Tyr Gly Met Trp Thr Ile Lys Ala Lys Tyr Lys Glu Asp
        195                 200                 205

Phe Ser Thr Thr Gly Thr Ala Tyr Phe Glu Val Lys Glu Tyr Val Leu
    210                 215                 220

Pro His Phe Ser Val Ser Ile Glu Pro Glu Tyr Asn Phe Ile Gly Tyr
225                 230                 235                 240

Lys Asn Phe Lys Asn Phe Glu Ile Thr Ile Lys Ala Arg Tyr Phe Tyr
                245                 250                 255

Asn Lys Val Val Thr Glu Ala Asp Val Tyr Ile Thr Phe Gly Ile Arg
            260                 265                 270

Glu Asp Leu Lys Asp Asp Gln Lys Glu Met Met Gln Thr Ala Met Gln
        275                 280                 285

Asn Thr Met Leu Ile Asn Gly Ile Ala Gln Val Thr Phe Asp Ser Glu
    290                 295                 300

Thr Ala Val Lys Glu Leu Ser Tyr Tyr Ser Leu Glu Asp Leu Asn Asn
305                 310                 315                 320

Lys Tyr Leu Tyr Ile Ala Val Thr Val Ile Glu Ser Thr Gly Gly Phe
                325                 330                 335

Ser Glu Glu Ala Glu Ile Pro Gly Ile Lys Tyr Val Leu Ser Pro Tyr
            340                 345                 350

Lys Leu Asn Leu Val Ala Thr Pro Leu Phe Leu Lys Pro Gly Ile Pro
        355                 360                 365

Tyr Pro Ile Lys Val Gln Val Lys Asp Ser Leu Asp Gln Leu Val Gly
```

```
                    370                 375                 380
Gly Val Pro Val Thr Leu Asn Ala Gln Thr Ile Asp Val Asn Gln Glu
385                 390                 395                 400

Thr Ser Asp Leu Asp Pro Ser Lys Ser Val Thr Arg Val Asp Asp Gly
            405                 410                 415

Val Ala Ser Phe Val Leu Asn Leu Pro Ser Gly Val Thr Val Leu Glu
            420                 425                 430

Phe Asn Val Lys Thr Asp Ala Pro Asp Leu Pro Glu Glu Asn Gln Ala
            435                 440                 445

Arg Glu Gly Tyr Arg Ala Ile Ala Tyr Ser Ser Leu Ser Gln Ser Tyr
        450                 455                 460

Leu Tyr Ile Asp Trp Thr Asp Asn His Lys Ala Leu Leu Val Gly Glu
465                 470                 475                 480

His Leu Asn Ile Ile Val Thr Pro Lys Ser Pro Tyr Ile Asp Lys Ile
                485                 490                 495

Thr His Tyr Asn Tyr Leu Ile Leu Ser Lys Gly Lys Ile Ile His Phe
            500                 505                 510

Gly Thr Arg Glu Lys Phe Ser Asp Ala Ser Tyr Gln Ser Ile Asn Ile
        515                 520                 525

Pro Val Thr Gln Asn Met Val Pro Ser Ser Arg Leu Leu Val Tyr Tyr
            530                 535                 540

Ile Val Thr Gly Glu Gln Thr Ala Glu Leu Val Ser Asp Ser Val Trp
545                 550                 555                 560

Leu Asn Ile Glu Glu Lys Cys Gly Asn Gln Leu Gln Val His Leu Ser
                565                 570                 575

Pro Asp Ala Asp Ala Tyr Ser Pro Gly Gln Thr Val Ser Leu Asn Met
            580                 585                 590

Ala Thr Gly Met Asp Ser Trp Val Ala Leu Ala Ala Val Asp Ser Ala
        595                 600                 605

Val Tyr Gly Val Gln Arg Gly Ala Lys Lys Pro Leu Glu Arg Val Phe
            610                 615                 620

Gln Phe Leu Glu Lys Ser Asp Leu Gly Cys Gly Ala Gly Gly Gly Leu
625                 630                 635                 640

Asn Asn Ala Asn Val Phe His Leu Ala Gly Leu Thr Phe Leu Thr Asn
                645                 650                 655

Ala Asn Ala Asp Asp Ser Gln Glu Asn Asp Glu Pro Cys Lys Glu Ile
            660                 665                 670

Leu

<210> SEQ ID NO 41
<211> LENGTH: 105
<212> TYPE: PRT
<213> ORGANISM: Artificial Sequence
<220> FEATURE:
<223> OTHER INFORMATION: human C5, MG1

<400> SEQUENCE: 41

Glu Gln Thr Tyr Val Ile Ser Ala Pro Lys Ile Phe Arg Val Gly Ala
1               5                   10                  15

Ser Glu Asn Ile Val Ile Gln Val Tyr Gly Tyr Thr Glu Ala Phe Asp
            20                  25                  30

Ala Thr Ile Ser Ile Lys Ser Tyr Pro Asp Lys Lys Phe Ser Tyr Ser
        35                  40                  45

Ser Gly His Val His Leu Ser Ser Glu Asn Lys Phe Gln Asn Ser Ala
    50                  55                  60
```

```
Ile Leu Thr Ile Gln Pro Lys Gln Leu Pro Gly Gly Gln Asn Pro Val
 65                  70                  75                  80

Ser Tyr Val Tyr Leu Glu Val Val Ser Lys His Phe Ser Lys Ser Lys
                 85                  90                  95

Arg Met Pro Ile Thr Tyr Asp Asn Gly
                100                 105

<210> SEQ ID NO 42
<211> LENGTH: 101
<212> TYPE: PRT
<213> ORGANISM: Artificial Sequence
<220> FEATURE:
<223> OTHER INFORMATION: human C5, MG2

<400> SEQUENCE: 42

Phe Leu Phe Ile His Thr Asp Lys Pro Val Tyr Thr Pro Asp Gln Ser
  1               5                  10                  15

Val Lys Val Arg Val Tyr Ser Leu Asn Asp Asp Leu Lys Pro Ala Lys
                 20                  25                  30

Arg Glu Thr Val Leu Thr Phe Ile Asp Pro Glu Gly Ser Glu Val Asp
             35                  40                  45

Met Val Glu Glu Ile Asp His Ile Gly Ile Ile Ser Phe Pro Asp Phe
 50                  55                  60

Lys Ile Pro Ser Asn Pro Arg Tyr Gly Met Trp Thr Ile Lys Ala Lys
 65                  70                  75                  80

Tyr Lys Glu Asp Phe Ser Thr Thr Gly Thr Ala Tyr Phe Glu Val Lys
                 85                  90                  95

Glu Tyr Val Leu Pro
                100

<210> SEQ ID NO 43
<211> LENGTH: 225
<212> TYPE: PRT
<213> ORGANISM: Artificial Sequence
<220> FEATURE:
<223> OTHER INFORMATION: human C5, MG1-MG2

<400> SEQUENCE: 43

Met Gly Leu Leu Gly Ile Leu Cys Phe Leu Ile Phe Leu Gly Lys Thr
  1               5                  10                  15

Trp Gly Gln Glu Gln Thr Tyr Val Ile Ser Ala Pro Lys Ile Phe Arg
                 20                  25                  30

Val Gly Ala Ser Glu Asn Ile Val Ile Gln Val Tyr Gly Tyr Thr Glu
             35                  40                  45

Ala Phe Asp Ala Thr Ile Ser Ile Lys Ser Tyr Pro Asp Lys Lys Phe
 50                  55                  60

Ser Tyr Ser Ser Gly His Val His Leu Ser Ser Glu Asn Lys Phe Gln
 65                  70                  75                  80

Asn Ser Ala Ile Leu Thr Ile Gln Pro Lys Gln Leu Pro Gly Gly Gln
                 85                  90                  95

Asn Pro Val Ser Tyr Val Tyr Leu Glu Val Val Ser Lys His Phe Ser
                100                 105                 110

Lys Ser Lys Arg Met Pro Ile Thr Tyr Asp Asn Gly Phe Leu Phe Ile
             115                 120                 125

His Thr Asp Lys Pro Val Tyr Thr Pro Asp Gln Ser Val Lys Val Arg
130                 135                 140

Val Tyr Ser Leu Asn Asp Asp Leu Lys Pro Ala Lys Arg Glu Thr Val
```

```
145                 150                 155                 160
Leu Thr Phe Ile Asp Pro Glu Gly Ser Glu Val Asp Met Val Glu Glu
                165                 170                 175
Ile Asp His Ile Gly Ile Ile Ser Phe Pro Asp Phe Lys Ile Pro Ser
                180                 185                 190
Asn Pro Arg Tyr Gly Met Trp Thr Ile Lys Ala Lys Tyr Lys Glu Asp
                195                 200                 205
Phe Ser Thr Thr Gly Thr Ala Tyr Phe Glu Val Lys Glu Tyr Val Leu
                210                 215                 220
Pro
225

<210> SEQ ID NO 44
<211> LENGTH: 1676
<212> TYPE: PRT
<213> ORGANISM: Artificial Sequence
<220> FEATURE:
<223> OTHER INFORMATION: cynomolgus C5

<400> SEQUENCE: 44

Met Gly Leu Leu Gly Ile Leu Cys Phe Leu Ile Phe Leu Gly Lys Thr
1               5                   10                  15
Trp Gly Gln Glu Gln Thr Tyr Val Ile Ser Ala Pro Lys Ile Phe Arg
                20                  25                  30
Val Gly Ala Ser Glu Asn Ile Val Ile Gln Val Tyr Gly Tyr Thr Glu
                35                  40                  45
Ala Phe Asp Ala Thr Ile Ser Ile Lys Ser Tyr Pro Asp Lys Lys Phe
50                  55                  60
Ser Tyr Ser Ser Gly His Val His Leu Ser Ser Glu Asn Lys Phe Gln
65                  70                  75                  80
Asn Ser Ala Val Leu Thr Ile Gln Pro Lys Gln Leu Pro Gly Gly Gln
                85                  90                  95
Asn Gln Val Ser Tyr Val Tyr Leu Glu Val Val Ser Lys His Phe Ser
                100                 105                 110
Lys Ser Lys Lys Ile Pro Ile Thr Tyr Asp Asn Gly Phe Leu Phe Ile
                115                 120                 125
His Thr Asp Lys Pro Val Tyr Thr Pro Asp Gln Ser Val Lys Val Arg
                130                 135                 140
Val Tyr Ser Leu Asn Asp Asp Leu Lys Pro Ala Lys Arg Glu Thr Val
145                 150                 155                 160
Leu Thr Phe Ile Asp Pro Glu Gly Ser Glu Ile Asp Met Val Glu Glu
                165                 170                 175
Ile Asp His Ile Gly Ile Ile Ser Phe Pro Asp Phe Lys Ile Pro Ser
                180                 185                 190
Asn Pro Arg Tyr Gly Met Trp Thr Ile Gln Ala Lys Tyr Lys Glu Asp
                195                 200                 205
Phe Ser Thr Thr Gly Thr Ala Phe Phe Glu Val Lys Glu Tyr Val Leu
                210                 215                 220
Pro His Phe Ser Val Ser Val Glu Pro Glu Ser Asn Phe Ile Gly Tyr
225                 230                 235                 240
Lys Asn Phe Lys Asn Phe Glu Ile Thr Ile Lys Ala Arg Tyr Phe Tyr
                245                 250                 255
Asn Lys Val Val Thr Glu Ala Asp Val Tyr Ile Thr Phe Gly Ile Arg
                260                 265                 270
Glu Asp Leu Lys Asp Asp Gln Lys Glu Met Met Gln Thr Ala Met Gln
```

```
            275                 280                 285
Asn Thr Met Leu Ile Asn Gly Ile Ala Glu Val Thr Phe Asp Ser Glu
            290                 295                 300
Thr Ala Val Lys Glu Leu Ser Tyr Tyr Ser Leu Glu Asp Leu Asn Asn
305                 310                 315                 320
Lys Tyr Leu Tyr Ile Ala Val Thr Val Ile Glu Ser Thr Gly Gly Phe
                    325                 330                 335
Ser Glu Glu Ala Glu Ile Pro Gly Ile Lys Tyr Val Leu Ser Pro Tyr
            340                 345                 350
Lys Leu Asn Leu Val Ala Thr Pro Leu Phe Leu Lys Pro Gly Ile Pro
            355                 360                 365
Tyr Ser Ile Lys Val Gln Val Lys Asp Ala Leu Asp Gln Leu Val Gly
    370                 375                 380
Gly Val Pro Val Thr Leu Asn Ala Gln Thr Ile Asp Val Asn Gln Glu
385                 390                 395                 400
Thr Ser Asp Leu Glu Pro Arg Lys Ser Val Thr Arg Val Asp Asp Gly
                    405                 410                 415
Val Ala Ser Phe Val Val Asn Leu Pro Ser Gly Val Thr Val Leu Glu
                420                 425                 430
Phe Asn Val Lys Thr Asp Ala Pro Asp Leu Pro Asp Glu Asn Gln Ala
            435                 440                 445
Arg Glu Gly Tyr Arg Ala Ile Ala Tyr Ser Ser Leu Ser Gln Ser Tyr
    450                 455                 460
Leu Tyr Ile Asp Trp Thr Asp Asn His Lys Ala Leu Leu Val Gly Glu
465                 470                 475                 480
Tyr Leu Asn Ile Ile Val Thr Pro Lys Ser Pro Tyr Ile Asp Lys Ile
                    485                 490                 495
Thr His Tyr Asn Tyr Leu Ile Leu Ser Lys Gly Lys Ile Ile His Phe
                500                 505                 510
Gly Thr Arg Glu Lys Leu Ser Asp Ala Ser Tyr Gln Ser Ile Asn Ile
            515                 520                 525
Pro Val Thr Gln Asn Met Val Pro Ser Ser Arg Leu Leu Val Tyr Tyr
            530                 535                 540
Ile Val Thr Gly Glu Gln Thr Ala Glu Leu Val Ser Asp Ser Val Trp
545                 550                 555                 560
Leu Asn Ile Glu Glu Lys Cys Gly Asn Gln Leu Gln Val His Leu Ser
                    565                 570                 575
Pro Asp Ala Asp Thr Tyr Ser Pro Gly Gln Thr Val Ser Leu Asn Met
                580                 585                 590
Val Thr Gly Met Asp Ser Trp Val Ala Leu Thr Ala Val Asp Ser Ala
            595                 600                 605
Val Tyr Gly Val Gln Arg Arg Ala Lys Lys Pro Leu Glu Arg Val Phe
            610                 615                 620
Gln Phe Leu Glu Lys Ser Asp Leu Gly Cys Gly Ala Gly Gly Gly Leu
625                 630                 635                 640
Asn Asn Ala Asn Val Phe His Leu Ala Gly Leu Thr Phe Leu Thr Asn
                    645                 650                 655
Ala Asn Ala Asp Asp Ser Gln Glu Asn Asp Glu Pro Cys Lys Glu Ile
                660                 665                 670
Ile Arg Pro Arg Arg Met Leu Gln Glu Lys Ile Glu Glu Ile Ala Ala
            675                 680                 685
Lys Tyr Lys His Leu Val Val Lys Lys Cys Cys Tyr Asp Gly Val Arg
            690                 695                 700
```

```
Ile Asn His Asp Glu Thr Cys Glu Gln Arg Ala Ala Arg Ile Ser Val
705                 710                 715                 720

Gly Pro Arg Cys Val Lys Ala Phe Thr Glu Cys Cys Val Val Ala Ser
                725                 730                 735

Gln Leu Arg Ala Asn Asn Ser His Lys Asp Leu Gln Leu Gly Arg Leu
            740                 745                 750

His Met Lys Thr Leu Leu Pro Val Ser Lys Pro Glu Ile Arg Ser Tyr
        755                 760                 765

Phe Pro Glu Ser Trp Leu Trp Glu Val His Leu Val Pro Arg Arg Lys
770                 775                 780

Gln Leu Gln Phe Ala Leu Pro Asp Ser Val Thr Thr Trp Glu Ile Gln
785                 790                 795                 800

Gly Val Gly Ile Ser Asn Ser Gly Ile Cys Val Ala Asp Thr Ile Lys
                805                 810                 815

Ala Lys Val Phe Lys Asp Val Phe Leu Glu Met Asn Ile Pro Tyr Ser
            820                 825                 830

Val Val Arg Gly Glu Gln Val Gln Leu Lys Gly Thr Val Tyr Asn Tyr
        835                 840                 845

Arg Thr Ser Gly Met Gln Phe Cys Val Lys Met Ser Ala Val Glu Gly
    850                 855                 860

Ile Cys Thr Ser Glu Ser Pro Val Ile Asp His Gln Gly Thr Lys Ser
865                 870                 875                 880

Ser Lys Cys Val Arg Gln Lys Val Glu Gly Ser Ser Asn His Leu Val
                885                 890                 895

Thr Phe Thr Val Leu Pro Leu Glu Ile Gly Leu Gln Asn Ile Asn Phe
            900                 905                 910

Ser Leu Glu Thr Ser Phe Gly Lys Glu Ile Leu Val Lys Ser Leu Arg
        915                 920                 925

Val Val Pro Glu Gly Val Lys Arg Glu Ser Tyr Ser Gly Ile Thr Leu
    930                 935                 940

Asp Pro Arg Gly Ile Tyr Gly Thr Ile Ser Arg Arg Lys Glu Phe Pro
945                 950                 955                 960

Tyr Arg Ile Pro Leu Asp Leu Val Pro Lys Thr Glu Ile Lys Arg Ile
                965                 970                 975

Leu Ser Val Lys Gly Leu Leu Val Gly Glu Ile Leu Ser Ala Val Leu
            980                 985                 990

Ser Arg Glu Gly Ile Asn Ile Leu Thr His Leu Pro Lys Gly Ser Ala
        995                 1000                1005

Glu Ala Glu Leu Met Ser Val Val Pro Val Phe Tyr Val Phe His
    1010                1015                1020

Tyr Leu Glu Thr Gly Asn His Trp Asn Ile Phe His Ser Asp Pro
    1025                1030                1035

Leu Ile Glu Lys Arg Asn Leu Glu Lys Lys Leu Lys Glu Gly Met
    1040                1045                1050

Val Ser Ile Met Ser Tyr Arg Asn Ala Asp Tyr Ser Tyr Ser Val
    1055                1060                1065

Trp Lys Gly Gly Ser Ala Ser Thr Trp Leu Thr Ala Phe Ala Leu
    1070                1075                1080

Arg Val Leu Gly Gln Val His Lys Tyr Val Glu Gln Asn Gln Asn
    1085                1090                1095

Ser Ile Cys Asn Ser Leu Leu Trp Leu Val Glu Asn Tyr Gln Leu
    1100                1105                1110
```

```
Asp Asn Gly Ser Phe Lys Glu Asn Ser Gln Tyr Gln Pro Ile Lys
1115                1120                1125

Leu Gln Gly Thr Leu Pro Val Glu Ala Arg Glu Asn Ser Leu Tyr
1130                1135                1140

Leu Thr Ala Phe Thr Val Ile Gly Ile Arg Lys Ala Phe Asp Ile
1145                1150                1155

Cys Pro Leu Val Lys Ile Asn Thr Ala Leu Ile Lys Ala Asp Thr
1160                1165                1170

Phe Leu Leu Glu Asn Thr Leu Pro Ala Gln Ser Thr Phe Thr Leu
1175                1180                1185

Ala Ile Ser Ala Tyr Ala Leu Ser Leu Gly Asp Lys Thr His Pro
1190                1195                1200

Gln Phe Arg Ser Ile Val Ser Ala Leu Lys Arg Glu Ala Leu Val
1205                1210                1215

Lys Gly Asn Pro Pro Ile Tyr Arg Phe Trp Lys Asp Ser Leu Gln
1220                1225                1230

His Lys Asp Ser Ser Val Pro Asn Thr Gly Thr Ala Arg Met Val
1235                1240                1245

Glu Thr Thr Ala Tyr Ala Leu Leu Thr Ser Leu Asn Leu Lys Asp
1250                1255                1260

Ile Asn Tyr Val Asn Pro Ile Ile Lys Trp Leu Ser Glu Glu Gln
1265                1270                1275

Arg Tyr Gly Gly Gly Phe Tyr Ser Thr Gln Asp Thr Ile Asn Ala
1280                1285                1290

Ile Glu Gly Leu Thr Glu Tyr Ser Leu Leu Val Lys Gln Leu Arg
1295                1300                1305

Leu Asn Met Asp Ile Asp Val Ala Tyr Lys His Lys Gly Pro Leu
1310                1315                1320

His Asn Tyr Lys Met Thr Asp Lys Asn Phe Leu Gly Arg Pro Val
1325                1330                1335

Glu Val Leu Leu Asn Asp Asp Leu Val Val Ser Thr Gly Phe Gly
1340                1345                1350

Ser Gly Leu Ala Thr Val His Val Thr Thr Val Val His Lys Thr
1355                1360                1365

Ser Thr Ser Glu Glu Val Cys Ser Phe Tyr Leu Lys Ile Asp Thr
1370                1375                1380

Gln Asp Ile Glu Ala Ser His Tyr Arg Gly Tyr Gly Asn Ser Asp
1385                1390                1395

Tyr Lys Arg Ile Val Ala Cys Ala Ser Tyr Lys Pro Ser Lys Glu
1400                1405                1410

Glu Ser Ser Ser Gly Ser Ser His Ala Val Met Asp Ile Ser Leu
1415                1420                1425

Pro Thr Gly Ile Asn Ala Asn Glu Glu Asp Leu Lys Ala Leu Val
1430                1435                1440

Glu Gly Val Asp Gln Leu Phe Thr Asp Tyr Gln Ile Lys Asp Gly
1445                1450                1455

His Val Ile Leu Gln Leu Asn Ser Ile Pro Ser Ser Asp Phe Leu
1460                1465                1470

Cys Val Arg Phe Arg Ile Phe Glu Leu Phe Glu Val Gly Phe Leu
1475                1480                1485

Ser Pro Ala Thr Phe Thr Val Tyr Glu Tyr His Arg Pro Asp Lys
1490                1495                1500

Gln Cys Thr Met Phe Tyr Ser Thr Ser Asn Ile Lys Ile Gln Lys
```

```
                   1505                1510                1515
Val Cys Glu Gly Ala Thr Cys Lys Cys Ile Glu Ala Asp Cys Gly
             1520                1525                1530
Gln Met Gln Lys Glu Leu Asp Leu Thr Ile Ser Ala Glu Thr Arg
         1535                1540                1545
Lys Gln Thr Ala Cys Asn Pro Glu Ile Ala Tyr Ala Tyr Lys Val
     1550                1555                1560
Ile Ile Thr Ser Ile Thr Thr Glu Asn Val Phe Val Lys Tyr Lys
 1565                1570                1575
Ala Thr Leu Leu Asp Ile Tyr Lys Thr Gly Glu Ala Val Ala Glu
 1580                1585                1590
Lys Asp Ser Glu Ile Thr Phe Ile Lys Lys Val Thr Cys Thr Asn
 1595                1600                1605
Ala Glu Leu Val Lys Gly Arg Gln Tyr Leu Ile Met Gly Lys Glu
 1610                1615                1620
Ala Leu Gln Ile Lys Tyr Asn Phe Thr Phe Arg Tyr Ile Tyr Pro
 1625                1630                1635
Leu Asp Ser Leu Thr Trp Ile Glu Tyr Trp Pro Arg Asp Thr Thr
 1640                1645                1650
Cys Ser Ser Cys Gln Ala Phe Leu Ala Asn Leu Asp Glu Phe Ala
 1655                1660                1665
Glu Asp Ile Phe Leu Asn Gly Cys
 1670                1675

<210> SEQ ID NO 45
<211> LENGTH: 6
<212> TYPE: PRT
<213> ORGANISM: Artificial Sequence
<220> FEATURE:
<223> OTHER INFORMATION: CFA0305 HVR-H1

<400> SEQUENCE: 45

Ser Ser Tyr Tyr Met Cys
1               5

<210> SEQ ID NO 46
<211> LENGTH: 6
<212> TYPE: PRT
<213> ORGANISM: Artificial Sequence
<220> FEATURE:
<223> OTHER INFORMATION: CFA0307 HVR-H1

<400> SEQUENCE: 46

Asn Phe Tyr Tyr Ile Cys
1               5

<210> SEQ ID NO 47
<211> LENGTH: 6
<212> TYPE: PRT
<213> ORGANISM: Artificial Sequence
<220> FEATURE:
<223> OTHER INFORMATION: CFA0366 HVR-H1

<400> SEQUENCE: 47

Ser Ser Tyr Tyr Met Cys
1               5

<210> SEQ ID NO 48
<211> LENGTH: 6
<212> TYPE: PRT
<213> ORGANISM: Artificial Sequence
```

```
<220> FEATURE:
<223> OTHER INFORMATION: CFA0501 HVR-H1

<400> SEQUENCE: 48

Ser Ser Tyr Tyr Met Asn
1               5

<210> SEQ ID NO 49
<211> LENGTH: 6
<212> TYPE: PRT
<213> ORGANISM: Artificial Sequence
<220> FEATURE:
<223> OTHER INFORMATION: CFA0538 HVR-H1

<400> SEQUENCE: 49

Ser Ser Tyr Tyr Met Asn
1               5

<210> SEQ ID NO 50
<211> LENGTH: 5
<212> TYPE: PRT
<213> ORGANISM: Artificial Sequence
<220> FEATURE:
<223> OTHER INFORMATION: CFA0599 HVR-H1

<400> SEQUENCE: 50

Asp Asn Thr Met Thr
1               5

<210> SEQ ID NO 51
<211> LENGTH: 5
<212> TYPE: PRT
<213> ORGANISM: Artificial Sequence
<220> FEATURE:
<223> OTHER INFORMATION: CFA0666 HVR-H1

<400> SEQUENCE: 51

Thr Tyr Ala Met Gly
1               5

<210> SEQ ID NO 52
<211> LENGTH: 5
<212> TYPE: PRT
<213> ORGANISM: Artificial Sequence
<220> FEATURE:
<223> OTHER INFORMATION: CFA0672 HVR-H1

<400> SEQUENCE: 52

Gly Asn Ala Ile Asn
1               5

<210> SEQ ID NO 53
<211> LENGTH: 5
<212> TYPE: PRT
<213> ORGANISM: Artificial Sequence
<220> FEATURE:
<223> OTHER INFORMATION: CFA0675 HVR-H1

<400> SEQUENCE: 53

Thr Tyr Ala Met Gly
1               5

<210> SEQ ID NO 54
<211> LENGTH: 6
<212> TYPE: PRT
<213> ORGANISM: Artificial Sequence
<220> FEATURE:
```

<223> OTHER INFORMATION: 305L05 HVR-H1

<400> SEQUENCE: 54

Ser Ser Tyr Tyr Val Ala
1               5

<210> SEQ ID NO 55
<211> LENGTH: 17
<212> TYPE: PRT
<213> ORGANISM: Artificial Sequence
<220> FEATURE:
<223> OTHER INFORMATION: CFA0305 HVR-H2

<400> SEQUENCE: 55

Cys Ile Tyr Thr Gly Ser Gly Ala Thr Tyr Tyr Ala Ser Trp Ala Lys
1               5                   10                  15

Gly

<210> SEQ ID NO 56
<211> LENGTH: 17
<212> TYPE: PRT
<213> ORGANISM: Artificial Sequence
<220> FEATURE:
<223> OTHER INFORMATION: CFA0307 HVR-H2

<400> SEQUENCE: 56

Cys Ile Tyr Thr Val Ser Gly Tyr Thr Tyr Tyr Ala Ser Trp Ala Lys
1               5                   10                  15

Gly

<210> SEQ ID NO 57
<211> LENGTH: 18
<212> TYPE: PRT
<213> ORGANISM: Artificial Sequence
<220> FEATURE:
<223> OTHER INFORMATION: CFA0366 HVR-H2

<400> SEQUENCE: 57

Cys Ile Tyr Ala Gly Ser Ser Gly Ile Ile Tyr Tyr Ala Asn Trp Ala
1               5                   10                  15

Lys Gly

<210> SEQ ID NO 58
<211> LENGTH: 16
<212> TYPE: PRT
<213> ORGANISM: Artificial Sequence
<220> FEATURE:
<223> OTHER INFORMATION: CFA0501 HVR-H2

<400> SEQUENCE: 58

Met Ile Tyr Gly Ser Gly Ala Thr Tyr Tyr Ala Ser Trp Ala Lys Gly
1               5                   10                  15

<210> SEQ ID NO 59
<211> LENGTH: 16
<212> TYPE: PRT
<213> ORGANISM: Artificial Sequence
<220> FEATURE:
<223> OTHER INFORMATION: CFA0538 HVR-H2

<400> SEQUENCE: 59

Met Ile Tyr Gly Ser Gly Ala Thr Tyr Tyr Ala Ser Trp Ala Lys Gly
1               5                   10                  15

-continued

```
<210> SEQ ID NO 60
<211> LENGTH: 16
<212> TYPE: PRT
<213> ORGANISM: Artificial Sequence
<220> FEATURE:
<223> OTHER INFORMATION: CFA0599 HVR-H2

<400> SEQUENCE: 60

Ile Ile Ser Phe Gly Gly Asp Ala Tyr Tyr Ala Ser Trp Ala Lys Gly
1               5                   10                  15

<210> SEQ ID NO 61
<211> LENGTH: 16
<212> TYPE: PRT
<213> ORGANISM: Artificial Sequence
<220> FEATURE:
<223> OTHER INFORMATION: CFA0666 HVR-H2

<400> SEQUENCE: 61

Thr Ile Asp Thr Gly Asp Asn Ser Phe Tyr Ala Asn Trp Ala Lys Gly
1               5                   10                  15

<210> SEQ ID NO 62
<211> LENGTH: 17
<212> TYPE: PRT
<213> ORGANISM: Artificial Sequence
<220> FEATURE:
<223> OTHER INFORMATION: CFA0672 HVR-H2

<400> SEQUENCE: 62

Cys Ile Tyr Thr Gly Ser Asp Thr Thr Tyr Tyr Ala Thr Trp Ala Lys
1               5                   10                  15

Gly

<210> SEQ ID NO 63
<211> LENGTH: 16
<212> TYPE: PRT
<213> ORGANISM: Artificial Sequence
<220> FEATURE:
<223> OTHER INFORMATION: CFA0675 HVR-H2

<400> SEQUENCE: 63

Thr Ile Asp Thr Gly Asp Asn Ser Phe Tyr Ala Asn Trp Ala Lys Gly
1               5                   10                  15

<210> SEQ ID NO 64
<211> LENGTH: 17
<212> TYPE: PRT
<213> ORGANISM: Artificial Sequence
<220> FEATURE:
<223> OTHER INFORMATION: 305L05 HVR-H2

<400> SEQUENCE: 64

Ala Ile Tyr Thr Gly Ser Gly Ala Thr Tyr Lys Ala Ser Trp Ala Lys
1               5                   10                  15

Gly

<210> SEQ ID NO 65
<211> LENGTH: 13
<212> TYPE: PRT
<213> ORGANISM: Artificial Sequence
<220> FEATURE:
<223> OTHER INFORMATION: CFA0305 HVR-H3

<400> SEQUENCE: 65

Asp Gly Gly Tyr Val Thr Pro Thr His Ala Met Tyr Leu
```

<210> SEQ ID NO 66
<211> LENGTH: 9
<212> TYPE: PRT
<213> ORGANISM: Artificial Sequence
<220> FEATURE:
<223> OTHER INFORMATION: CFA0307 HVR-H3

<400> SEQUENCE: 66

Asp Leu His Ala Gly Ile Thr Asn Leu
1               5

<210> SEQ ID NO 67
<211> LENGTH: 13
<212> TYPE: PRT
<213> ORGANISM: Artificial Sequence
<220> FEATURE:
<223> OTHER INFORMATION: CFA0366 HVR-H3

<400> SEQUENCE: 67

Tyr Pro Thr Tyr Gly Asp Gly Gly His Ala Phe Asn Leu
1               5                   10

<210> SEQ ID NO 68
<211> LENGTH: 11
<212> TYPE: PRT
<213> ORGANISM: Artificial Sequence
<220> FEATURE:
<223> OTHER INFORMATION: CFA0501 HVR-H3

<400> SEQUENCE: 68

Gln Ile Tyr Ser Gly Asp Asn Asn Asp Asn Phe
1               5                   10

<210> SEQ ID NO 69
<211> LENGTH: 11
<212> TYPE: PRT
<213> ORGANISM: Artificial Sequence
<220> FEATURE:
<223> OTHER INFORMATION: CFA0538 HVR-H3

<400> SEQUENCE: 69

Gln Ile Tyr Ser Gly Asp Asn Asn Asp Asn Phe
1               5                   10

<210> SEQ ID NO 70
<211> LENGTH: 12
<212> TYPE: PRT
<213> ORGANISM: Artificial Sequence
<220> FEATURE:
<223> OTHER INFORMATION: CFA0599 HVR-H3

<400> SEQUENCE: 70

Val Gly Ala Gly Asn Ile Phe Trp Tyr Phe Asp Leu
1               5                   10

<210> SEQ ID NO 71
<211> LENGTH: 11
<212> TYPE: PRT
<213> ORGANISM: Artificial Sequence
<220> FEATURE:
<223> OTHER INFORMATION: CFA0666 HVR-H3

<400> SEQUENCE: 71

Asn Asp Gly Ser Val Tyr Asn Leu Phe Asn Leu
1               5                   10

```
<210> SEQ ID NO 72
<211> LENGTH: 4
<212> TYPE: PRT
<213> ORGANISM: Artificial Sequence
<220> FEATURE:
<223> OTHER INFORMATION: CFA0672 HVR-H3

<400> SEQUENCE: 72

Gly Ser Gly Leu
1

<210> SEQ ID NO 73
<211> LENGTH: 11
<212> TYPE: PRT
<213> ORGANISM: Artificial Sequence
<220> FEATURE:
<223> OTHER INFORMATION: CFA0675 HVR-H3

<400> SEQUENCE: 73

Asn Asp Gly Ser Val Tyr Asn Leu Phe Asn Leu
1               5                   10

<210> SEQ ID NO 74
<211> LENGTH: 13
<212> TYPE: PRT
<213> ORGANISM: Artificial Sequence
<220> FEATURE:
<223> OTHER INFORMATION: 305L05 HVR-H3

<400> SEQUENCE: 74

Asp Gly Gly Tyr Asp Tyr Pro Thr His Ala Met His Tyr
1               5                   10

<210> SEQ ID NO 75
<211> LENGTH: 11
<212> TYPE: PRT
<213> ORGANISM: Artificial Sequence
<220> FEATURE:
<223> OTHER INFORMATION: CFA0305 HVR-L1

<400> SEQUENCE: 75

Gln Ala Ser Gln Asn Ile Gly Ser Asp Leu Ala
1               5                   10

<210> SEQ ID NO 76
<211> LENGTH: 11
<212> TYPE: PRT
<213> ORGANISM: Artificial Sequence
<220> FEATURE:
<223> OTHER INFORMATION: CFA0307 HVR-L1

<400> SEQUENCE: 76

Gln Ala Ser Gln Asn Ile Tyr Ser Asn Leu Ala
1               5                   10

<210> SEQ ID NO 77
<211> LENGTH: 13
<212> TYPE: PRT
<213> ORGANISM: Artificial Sequence
<220> FEATURE:
<223> OTHER INFORMATION: CFA0366 HVR-L1

<400> SEQUENCE: 77

Gln Ser Ser Gln Ser Val Tyr Ser Ser Asp Tyr Leu Ser
1               5                   10
```

<210> SEQ ID NO 78
<211> LENGTH: 11
<212> TYPE: PRT
<213> ORGANISM: Artificial Sequence
<220> FEATURE:
<223> OTHER INFORMATION: CFA0501 HVR-L1

<400> SEQUENCE: 78

Gln Ala Ser Glu Ser Ile Ser Asn Trp Leu Ala
1               5                   10

<210> SEQ ID NO 79
<211> LENGTH: 11
<212> TYPE: PRT
<213> ORGANISM: Artificial Sequence
<220> FEATURE:
<223> OTHER INFORMATION: CFA0538 HVR-L1

<400> SEQUENCE: 79

Gln Ala Ser Glu Ser Ile Ser Asn Trp Leu Ala
1               5                   10

<210> SEQ ID NO 80
<211> LENGTH: 11
<212> TYPE: PRT
<213> ORGANISM: Artificial Sequence
<220> FEATURE:
<223> OTHER INFORMATION: CFA0599 HVR-L1

<400> SEQUENCE: 80

Gln Ala Ser Glu Ser Ile Tyr Ser Ala Leu Ala
1               5                   10

<210> SEQ ID NO 81
<211> LENGTH: 11
<212> TYPE: PRT
<213> ORGANISM: Artificial Sequence
<220> FEATURE:
<223> OTHER INFORMATION: CFA0666 HVR-L1

<400> SEQUENCE: 81

Gln Ala Ser Glu Asn Ile Tyr Ser Ala Leu Ser
1               5                   10

<210> SEQ ID NO 82
<211> LENGTH: 11
<212> TYPE: PRT
<213> ORGANISM: Artificial Sequence
<220> FEATURE:
<223> OTHER INFORMATION: CFA0672 HVR-L1

<400> SEQUENCE: 82

Gln Ala Ser Gln Asn Ile Tyr Ser Leu Leu Ala
1               5                   10

<210> SEQ ID NO 83
<211> LENGTH: 11
<212> TYPE: PRT
<213> ORGANISM: Artificial Sequence
<220> FEATURE:
<223> OTHER INFORMATION: CFA0675 HVR-L1

<400> SEQUENCE: 83

Gln Ala Ser Glu Asn Ile Tyr Ser Ala Leu Ser
1               5                   10

```
<210> SEQ ID NO 84
<211> LENGTH: 11
<212> TYPE: PRT
<213> ORGANISM: Artificial Sequence
<220> FEATURE:
<223> OTHER INFORMATION: 305L05 HVR-L1

<400> SEQUENCE: 84

Gln Ala Ser Gln Asn Ile Gly Ser Ser Leu Ala
1               5                   10

<210> SEQ ID NO 85
<211> LENGTH: 7
<212> TYPE: PRT
<213> ORGANISM: Artificial Sequence
<220> FEATURE:
<223> OTHER INFORMATION: CFA0305 HVR-L2

<400> SEQUENCE: 85

Gly Ala Ser Lys Leu Ala Ser
1               5

<210> SEQ ID NO 86
<211> LENGTH: 7
<212> TYPE: PRT
<213> ORGANISM: Artificial Sequence
<220> FEATURE:
<223> OTHER INFORMATION: CFA0307 HVR-L2

<400> SEQUENCE: 86

Gly Ala Ser Asn Leu Glu Ser
1               5

<210> SEQ ID NO 87
<211> LENGTH: 7
<212> TYPE: PRT
<213> ORGANISM: Artificial Sequence
<220> FEATURE:
<223> OTHER INFORMATION: CFA0366 HVR-L2

<400> SEQUENCE: 87

Glu Ala Ser Lys Leu Ala Ser
1               5

<210> SEQ ID NO 88
<211> LENGTH: 7
<212> TYPE: PRT
<213> ORGANISM: Artificial Sequence
<220> FEATURE:
<223> OTHER INFORMATION: CFA0501 HVR-L2

<400> SEQUENCE: 88

Arg Ala Ser Thr Leu Ala Ser
1               5

<210> SEQ ID NO 89
<211> LENGTH: 7
<212> TYPE: PRT
<213> ORGANISM: Artificial Sequence
<220> FEATURE:
<223> OTHER INFORMATION: CFA0538 HVR-L2

<400> SEQUENCE: 89

Arg Ala Ser Thr Leu Ala Ser
1               5

<210> SEQ ID NO 90
```

```
<211> LENGTH: 7
<212> TYPE: PRT
<213> ORGANISM: Artificial Sequence
<220> FEATURE:
<223> OTHER INFORMATION: CFA0599 HVR-L2

<400> SEQUENCE: 90

Ser Ala Ser Thr Leu Ala Ser
1               5

<210> SEQ ID NO 91
<211> LENGTH: 7
<212> TYPE: PRT
<213> ORGANISM: Artificial Sequence
<220> FEATURE:
<223> OTHER INFORMATION: CFA0666 HVR-L2

<400> SEQUENCE: 91

Tyr Ala Ser Thr Leu Ala Ser
1               5

<210> SEQ ID NO 92
<211> LENGTH: 7
<212> TYPE: PRT
<213> ORGANISM: Artificial Sequence
<220> FEATURE:
<223> OTHER INFORMATION: CFA0672 HVR-L2

<400> SEQUENCE: 92

His Thr Ser Asp Leu Ala Ser
1               5

<210> SEQ ID NO 93
<211> LENGTH: 7
<212> TYPE: PRT
<213> ORGANISM: Artificial Sequence
<220> FEATURE:
<223> OTHER INFORMATION: CFA0675 HVR-L2

<400> SEQUENCE: 93

Tyr Ala Ser Thr Leu Ala Ser
1               5

<210> SEQ ID NO 94
<211> LENGTH: 7
<212> TYPE: PRT
<213> ORGANISM: Artificial Sequence
<220> FEATURE:
<223> OTHER INFORMATION: 305L05 HVR-L2

<400> SEQUENCE: 94

Gly Ala Ser Lys Thr His Ser
1               5

<210> SEQ ID NO 95
<211> LENGTH: 12
<212> TYPE: PRT
<213> ORGANISM: Artificial Sequence
<220> FEATURE:
<223> OTHER INFORMATION: CFA0305 HVR-L3

<400> SEQUENCE: 95

Gln Cys Thr Phe Val Gly Ser Ser Tyr Gly Asn Ala
1               5                   10

<210> SEQ ID NO 96
<211> LENGTH: 12
```

```
<212> TYPE: PRT
<213> ORGANISM: Artificial Sequence
<220> FEATURE:
<223> OTHER INFORMATION: CFA0307 HVR-L3

<400> SEQUENCE: 96

Leu Gln Gly Tyr Ser Tyr Ser Asn Val Asp Asp Ala
1               5                   10

<210> SEQ ID NO 97
<211> LENGTH: 12
<212> TYPE: PRT
<213> ORGANISM: Artificial Sequence
<220> FEATURE:
<223> OTHER INFORMATION: CFA0366 HVR-L3

<400> SEQUENCE: 97

Gln Gly Thr Tyr Tyr Ser Ser Gly Trp Tyr Phe Ala
1               5                   10

<210> SEQ ID NO 98
<211> LENGTH: 12
<212> TYPE: PRT
<213> ORGANISM: Artificial Sequence
<220> FEATURE:
<223> OTHER INFORMATION: CFA0501 HVR-L3

<400> SEQUENCE: 98

Gln Gln Asp Tyr Ser Ser Ser Asn Val Asp Asn Thr
1               5                   10

<210> SEQ ID NO 99
<211> LENGTH: 12
<212> TYPE: PRT
<213> ORGANISM: Artificial Sequence
<220> FEATURE:
<223> OTHER INFORMATION: CFA0538 HVR-L3

<400> SEQUENCE: 99

Gln Gln Asp Tyr Ser Ser Ser Asn Val Asp Asn Thr
1               5                   10

<210> SEQ ID NO 100
<211> LENGTH: 12
<212> TYPE: PRT
<213> ORGANISM: Artificial Sequence
<220> FEATURE:
<223> OTHER INFORMATION: CFA0599 HVR-L3

<400> SEQUENCE: 100

Gln Gln Tyr Tyr Ser Ser Thr Asn Val His Asn Ser
1               5                   10

<210> SEQ ID NO 101
<211> LENGTH: 12
<212> TYPE: PRT
<213> ORGANISM: Artificial Sequence
<220> FEATURE:
<223> OTHER INFORMATION: CFA0666 HVR-L3

<400> SEQUENCE: 101

Gln Gln Tyr Tyr Asp Ile Asn Ser Val Asp Asn Thr
1               5                   10

<210> SEQ ID NO 102
<211> LENGTH: 13
<212> TYPE: PRT
```

-continued

<213> ORGANISM: Artificial Sequence
<220> FEATURE:
<223> OTHER INFORMATION: CFA0672 HVR-L3

<400> SEQUENCE: 102

Gln Cys Thr Ala Tyr Gly Ser Ser Asp Val Gly Gly Thr
1               5                   10

<210> SEQ ID NO 103
<211> LENGTH: 12
<212> TYPE: PRT
<213> ORGANISM: Artificial Sequence
<220> FEATURE:
<223> OTHER INFORMATION: CFA0675 HVR-L3

<400> SEQUENCE: 103

Gln Gln Tyr Tyr Asp Ile Asn Ser Val Asp Asn Thr
1               5                   10

<210> SEQ ID NO 104
<211> LENGTH: 12
<212> TYPE: PRT
<213> ORGANISM: Artificial Sequence
<220> FEATURE:
<223> OTHER INFORMATION: 305L05 HVR-L3

<400> SEQUENCE: 104

Gln Ser Thr Lys Val Gly Ser Ser Tyr Gly Asn His
1               5                   10

<210> SEQ ID NO 105
<211> LENGTH: 1680
<212> TYPE: PRT
<213> ORGANISM: Artificial Sequence
<220> FEATURE:
<223> OTHER INFORMATION: mouse C5

<400> SEQUENCE: 105

Met Gly Leu Trp Gly Ile Leu Cys Leu Leu Ile Phe Leu Asp Lys Thr
1               5                   10                  15

Trp Gly Gln Glu Gln Thr Tyr Val Ile Ser Ala Pro Lys Ile Leu Arg
            20                  25                  30

Val Gly Ser Ser Glu Asn Val Val Ile Gln Val His Gly Tyr Thr Glu
        35                  40                  45

Ala Phe Asp Ala Thr Leu Ser Leu Lys Ser Tyr Pro Asp Lys Lys Val
    50                  55                  60

Thr Phe Ser Ser Gly Tyr Val Asn Leu Ser Pro Glu Asn Lys Phe Gln
65                  70                  75                  80

Asn Ala Ala Leu Leu Thr Leu Gln Pro Asn Gln Val Pro Arg Glu Glu
                85                  90                  95

Ser Pro Val Ser His Val Tyr Leu Glu Val Val Ser Lys His Phe Ser
            100                 105                 110

Lys Ser Lys Lys Ile Pro Ile Thr Tyr Asn Asn Gly Ile Leu Phe Ile
        115                 120                 125

His Thr Asp Lys Pro Val Tyr Thr Pro Asp Gln Ser Val Lys Ile Arg
    130                 135                 140

Val Tyr Ser Leu Gly Asp Asp Leu Lys Pro Ala Lys Arg Glu Thr Val
145                 150                 155                 160

Leu Thr Phe Ile Asp Pro Glu Gly Ser Glu Val Asp Ile Val Glu Glu
                165                 170                 175

Asn Asp Tyr Thr Gly Ile Ile Ser Phe Pro Asp Phe Lys Ile Pro Ser

```
            180                 185                 190
Asn Pro Lys Tyr Gly Val Trp Thr Ile Lys Ala Asn Tyr Lys Lys Asp
            195                 200                 205

Phe Thr Thr Thr Gly Thr Ala Tyr Phe Glu Ile Lys Glu Tyr Val Leu
210                 215                 220

Pro Arg Phe Ser Val Ser Ile Glu Leu Glu Arg Thr Phe Ile Gly Tyr
225                 230                 235                 240

Lys Asn Phe Lys Asn Phe Glu Ile Thr Val Lys Ala Arg Tyr Phe Tyr
                245                 250                 255

Asn Lys Val Val Pro Asp Ala Glu Val Tyr Ala Phe Phe Gly Leu Arg
                260                 265                 270

Glu Asp Ile Lys Asp Glu Glu Lys Gln Met Met His Lys Ala Thr Gln
            275                 280                 285

Ala Ala Lys Leu Val Asp Gly Val Ala Gln Ile Ser Phe Asp Ser Glu
            290                 295                 300

Thr Ala Val Lys Glu Leu Ser Tyr Asn Ser Leu Glu Asp Leu Asn Asn
305                 310                 315                 320

Lys Tyr Leu Tyr Ile Ala Val Thr Val Thr Glu Ser Ser Gly Gly Phe
                325                 330                 335

Ser Glu Glu Ala Glu Ile Pro Gly Val Lys Tyr Val Leu Ser Pro Tyr
                340                 345                 350

Thr Leu Asn Leu Val Ala Thr Pro Leu Phe Val Lys Pro Gly Ile Pro
            355                 360                 365

Phe Ser Ile Lys Ala Gln Val Lys Asp Ser Leu Glu Gln Ala Val Gly
            370                 375                 380

Gly Val Pro Val Thr Leu Met Ala Gln Thr Val Asp Val Asn Gln Glu
385                 390                 395                 400

Thr Ser Asp Leu Glu Thr Lys Arg Ser Ile Thr His Asp Thr Asp Gly
                405                 410                 415

Val Ala Val Phe Val Leu Asn Leu Pro Ser Asn Val Thr Val Leu Lys
                420                 425                 430

Phe Glu Ile Arg Thr Asp Asp Pro Glu Leu Pro Glu Glu Asn Gln Ala
            435                 440                 445

Ser Lys Glu Tyr Glu Ala Val Ala Tyr Ser Ser Leu Ser Gln Ser Tyr
            450                 455                 460

Ile Tyr Ile Ala Trp Thr Glu Asn Tyr Lys Pro Met Leu Val Gly Glu
465                 470                 475                 480

Tyr Leu Asn Ile Met Val Thr Pro Lys Ser Pro Tyr Ile Asp Lys Ile
                485                 490                 495

Thr His Tyr Asn Tyr Leu Ile Leu Ser Lys Gly Lys Ile Val Gln Tyr
                500                 505                 510

Gly Thr Arg Glu Lys Leu Phe Ser Ser Thr Tyr Gln Asn Ile Asn Ile
            515                 520                 525

Pro Val Thr Gln Asn Met Val Pro Ser Ala Arg Leu Leu Val Tyr Tyr
            530                 535                 540

Ile Val Thr Gly Glu Gln Thr Ala Glu Leu Val Ala Asp Ala Val Trp
545                 550                 555                 560

Ile Asn Ile Glu Glu Lys Cys Gly Asn Gln Leu Gln Val His Leu Ser
                565                 570                 575

Pro Asp Glu Tyr Val Tyr Ser Pro Gly Gln Thr Val Ser Leu Asp Met
                580                 585                 590

Val Thr Glu Ala Asp Ser Trp Val Ala Leu Ser Ala Val Asp Arg Ala
            595                 600                 605
```

```
Val Tyr Lys Val Gln Gly Asn Ala Lys Arg Ala Met Gln Arg Val Phe
    610                 615                 620

Gln Ala Leu Asp Glu Lys Ser Asp Leu Gly Cys Gly Ala Gly Gly Gly
625                 630                 635                 640

His Asp Asn Ala Asp Val Phe His Leu Ala Gly Leu Thr Phe Leu Thr
                645                 650                 655

Asn Ala Asn Ala Asp Asp Ser His Tyr Arg Asp Asp Ser Cys Lys Glu
            660                 665                 670

Ile Leu Arg Ser Lys Arg Asn Leu His Leu Leu Arg Gln Lys Ile Glu
    675                 680                 685

Glu Gln Ala Ala Lys Tyr Lys His Ser Val Pro Lys Cys Cys Tyr
690                 695                 700

Asp Gly Ala Arg Val Asn Phe Tyr Glu Thr Cys Glu Glu Arg Val Ala
705                 710                 715                 720

Arg Val Thr Ile Gly Pro Leu Cys Ile Arg Ala Phe Asn Glu Cys Cys
                725                 730                 735

Thr Ile Ala Asn Lys Ile Arg Lys Glu Ser Pro His Lys Pro Val Gln
            740                 745                 750

Leu Gly Arg Ile His Ile Lys Thr Leu Leu Pro Val Met Lys Ala Asp
    755                 760                 765

Ile Arg Ser Tyr Phe Pro Glu Ser Trp Leu Trp Glu Ile His Arg Val
770                 775                 780

Pro Lys Arg Lys Gln Leu Gln Val Thr Leu Pro Asp Ser Leu Thr Thr
785                 790                 795                 800

Trp Glu Ile Gln Gly Ile Gly Ile Ser Asp Asn Gly Ile Cys Val Ala
                805                 810                 815

Asp Thr Leu Lys Ala Lys Val Phe Lys Glu Val Phe Leu Glu Met Asn
            820                 825                 830

Ile Pro Tyr Ser Val Val Arg Gly Glu Gln Ile Gln Leu Lys Gly Thr
    835                 840                 845

Val Tyr Asn Tyr Met Thr Ser Gly Thr Lys Phe Cys Val Lys Met Ser
850                 855                 860

Ala Val Glu Gly Ile Cys Thr Ser Gly Ser Ser Ala Ala Ser Leu His
865                 870                 875                 880

Thr Ser Arg Pro Ser Arg Cys Val Phe Gln Arg Ile Glu Gly Ser Ser
                885                 890                 895

Ser His Leu Val Thr Phe Thr Leu Leu Pro Leu Glu Ile Gly Leu His
            900                 905                 910

Ser Ile Asn Phe Ser Leu Glu Thr Ser Phe Gly Lys Asp Ile Leu Val
    915                 920                 925

Lys Thr Leu Arg Val Val Pro Glu Gly Val Lys Arg Glu Ser Tyr Ala
930                 935                 940

Gly Val Ile Leu Asp Pro Lys Gly Ile Arg Gly Ile Val Asn Arg Arg
945                 950                 955                 960

Lys Glu Phe Pro Tyr Arg Ile Pro Leu Asp Leu Val Pro Lys Thr Lys
                965                 970                 975

Val Glu Arg Ile Leu Ser Val Lys Gly Leu Leu Val Gly Glu Phe Leu
            980                 985                 990

Ser Thr Val Leu Ser Lys Glu Gly Ile Asn Ile Leu Thr His Leu Pro
    995                 1000                1005

Lys Gly Ser Ala Glu Ala Glu  Leu Met Ser Ile Ala  Pro Val Phe
    1010                1015                 1020
```

-continued

| | | | | | | | | | | | | |
|---|---|---|---|---|---|---|---|---|---|---|---|---|
|Tyr|Val|Phe|His|Tyr|Leu|Glu|Ala|Gly|Asn|His|Trp|Asn Ile Phe|
|1025| | | | |1030| | | | |1035| | |
|Tyr|Pro|Asp|Thr|Leu|Ser|Lys|Arg|Gln|Ser|Leu|Glu|Lys Lys Ile|
|1040| | | | |1045| | | | |1050| | |
|Lys|Gln|Gly|Val|Val|Ser|Val|Met|Ser|Tyr|Arg|Asn|Ala Asp Tyr|
|1055| | | | |1060| | | | |1065| | |
|Ser|Tyr|Ser|Met|Trp|Lys|Gly|Ala|Ser|Ala|Ser|Thr|Trp Leu Thr|
|1070| | | | |1075| | | | |1080| | |
|Ala|Phe|Ala|Leu|Arg|Val|Leu|Gly|Gln|Val|Ala|Lys|Tyr Val Lys|
|1085| | | | |1090| | | | |1095| | |
|Gln|Asp|Glu|Asn|Ser|Ile|Cys|Asn|Ser|Leu|Leu|Trp|Leu Val Glu|
|1100| | | | |1105| | | | |1110| | |
|Lys|Cys|Gln|Leu|Glu|Asn|Gly|Ser|Phe|Lys|Glu|Asn|Ser Gln Tyr|
|1115| | | | |1120| | | | |1125| | |
|Leu|Pro|Ile|Lys|Leu|Gln|Gly|Thr|Leu|Pro|Ala|Glu|Ala Gln Glu|
|1130| | | | |1135| | | | |1140| | |
|Lys|Thr|Leu|Tyr|Leu|Thr|Ala|Phe|Ser|Val|Ile|Gly|Ile Arg Lys|
|1145| | | | |1150| | | | |1155| | |
|Ala|Val|Asp|Ile|Cys|Pro|Thr|Met|Lys|Ile|His|Thr|Ala Leu Asp|
|1160| | | | |1165| | | | |1170| | |
|Lys|Ala|Asp|Ser|Phe|Leu|Leu|Glu|Asn|Thr|Leu|Pro|Ser Lys Ser|
|1175| | | | |1180| | | | |1185| | |
|Thr|Phe|Thr|Leu|Ala|Ile|Val|Ala|Tyr|Ala|Leu|Ser|Leu Gly Asp|
|1190| | | | |1195| | | | |1200| | |
|Arg|Thr|His|Pro|Arg|Phe|Arg|Leu|Ile|Val|Ser|Ala|Leu Arg Lys|
|1205| | | | |1210| | | | |1215| | |
|Glu|Ala|Phe|Val|Lys|Gly|Asp|Pro|Pro|Ile|Tyr|Arg|Tyr Trp Arg|
|1220| | | | |1225| | | | |1230| | |
|Asp|Thr|Leu|Lys|Arg|Pro|Asp|Ser|Ser|Val|Pro|Ser|Ser Gly Thr|
|1235| | | | |1240| | | | |1245| | |
|Ala|Gly|Met|Val|Glu|Thr|Thr|Ala|Tyr|Ala|Leu|Leu|Ala Ser Leu|
|1250| | | | |1255| | | | |1260| | |
|Lys|Leu|Lys|Asp|Met|Asn|Tyr|Ala|Asn|Pro|Ile|Ile|Lys Trp Leu|
|1265| | | | |1270| | | | |1275| | |
|Ser|Glu|Glu|Gln|Arg|Tyr|Gly|Gly|Phe|Tyr|Ser|Thr|Gln Asp|
|1280| | | | |1285| | | | |1290| | |
|Thr|Ile|Asn|Ala|Ile|Glu|Gly|Leu|Thr|Glu|Tyr|Ser|Leu Leu Leu|
|1295| | | | |1300| | | | |1305| | |
|Lys|Gln|Ile|His|Leu|Asp|Met|Asp|Ile|Asn|Val|Ala|Tyr Lys His|
|1310| | | | |1315| | | | |1320| | |
|Glu|Gly|Asp|Phe|His|Lys|Tyr|Lys|Val|Thr|Glu|Lys|His Phe Leu|
|1325| | | | |1330| | | | |1335| | |
|Gly|Arg|Pro|Val|Glu|Val|Ser|Leu|Asn|Asp|Asp|Leu|Val Val Ser|
|1340| | | | |1345| | | | |1350| | |
|Thr|Gly|Tyr|Ser|Ser|Gly|Leu|Ala|Thr|Val|Tyr|Val|Lys Thr Val|
|1355| | | | |1360| | | | |1365| | |
|Val|His|Lys|Ile|Ser|Val|Ser|Glu|Glu|Phe|Cys|Ser|Phe Tyr Leu|
|1370| | | | |1375| | | | |1380| | |
|Lys|Ile|Asp|Thr|Gln|Asp|Ile|Glu|Ala|Ser|Ser|His|Phe Arg Leu|
|1385| | | | |1390| | | | |1395| | |
|Ser|Asp|Ser|Gly|Phe|Lys|Arg|Ile|Ile|Ala|Cys|Ala|Ser Tyr Lys|
|1400| | | | |1405| | | | |1410| | |
|Pro|Ser|Lys|Glu|Glu|Ser|Thr|Ser|Gly|Ser|Ser|His|Ala Val Met|

```
                    1415                1420                1425

Asp Ile Ser Leu Pro Thr Gly Ile Gly Ala Asn Glu Glu Asp Leu
                    1430                1435                1440

Arg Ala Leu Val Glu Gly Val Asp Gln Leu Leu Thr Asp Tyr Gln
                    1445                1450                1455

Ile Lys Asp Gly His Val Ile Leu Gln Leu Asn Ser Ile Pro Ser
                    1460                1465                1470

Arg Asp Phe Leu Cys Val Arg Phe Arg Ile Phe Glu Leu Phe Gln
                    1475                1480                1485

Val Gly Phe Leu Asn Pro Ala Thr Phe Thr Val Tyr Glu Tyr His
                    1490                1495                1500

Arg Pro Asp Lys Gln Cys Thr Met Ile Tyr Ser Ile Ser Asp Thr
                    1505                1510                1515

Arg Leu Gln Lys Val Cys Gly Ala Ala Cys Thr Cys Val Glu
                    1520                1525                1530

Ala Asp Cys Ala Gln Leu Gln Ala Glu Val Asp Leu Ala Ile Ser
                    1535                1540                1545

Ala Asp Ser Arg Lys Glu Lys Ala Cys Lys Pro Glu Thr Ala Tyr
                    1550                1555                1560

Ala Tyr Lys Val Arg Ile Thr Ser Ala Thr Glu Glu Asn Val Phe
                    1565                1570                1575

Val Lys Tyr Thr Ala Thr Leu Leu Val Thr Tyr Lys Thr Gly Glu
                    1580                1585                1590

Ala Ala Asp Glu Asn Ser Glu Val Thr Phe Ile Lys Lys Met Ser
                    1595                1600                1605

Cys Thr Asn Ala Asn Leu Val Lys Gly Lys Gln Tyr Leu Ile Met
                    1610                1615                1620

Gly Lys Glu Val Leu Gln Ile Lys His Asn Phe Ser Phe Lys Tyr
                    1625                1630                1635

Ile Tyr Pro Leu Asp Ser Ser Thr Trp Ile Glu Tyr Trp Pro Thr
                    1640                1645                1650

Asp Thr Thr Cys Pro Ser Cys Gln Ala Phe Val Glu Asn Leu Asn
                    1655                1660                1665

Asn Phe Ala Glu Asp Leu Phe Leu Asn Ser Cys Glu
                    1670                1675                1680

<210> SEQ ID NO 106
<211> LENGTH: 123
<212> TYPE: PRT
<213> ORGANISM: Artificial Sequence
<220> FEATURE:
<223> OTHER INFORMATION: 305LO15 VH

<400> SEQUENCE: 106

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Val His Ser Ser
            20                  25                  30

Tyr Tyr Met Ala Trp Val Arg Gln Ala Pro Gly Lys Gly Leu Glu Trp
        35                  40                  45

Val Gly Ala Ile Phe Thr Gly Ser Gly Ala Glu Tyr Lys Ala Glu Trp
    50                  55                  60

Ala Lys Gly Arg Val Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
```

-continued

```
                85                  90                  95
Cys Ala Ser Asp Ala Gly Tyr Asp Tyr Pro Thr His Ala Met His Tyr
            100                 105                 110
Trp Gly Gln Gly Thr Leu Val Thr Val Ser Ser
        115                 120

<210> SEQ ID NO 107
<211> LENGTH: 123
<212> TYPE: PRT
<213> ORGANISM: Artificial Sequence
<220> FEATURE:
<223> OTHER INFORMATION: 305LO16 VH

<400> SEQUENCE: 107

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Val His Ser Ser
            20                  25                  30

Tyr Tyr Met Ala Trp Val Arg Gln Ala Pro Gly Lys Gly Leu Glu Trp
        35                  40                  45

Val Gly Ala Ile Phe Thr Gly Ser Gly Ala Glu Tyr Lys Ala Glu Trp
    50                  55                  60

Val Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Ser Asp Ala Gly Tyr Asp Tyr Pro Thr His Ala Met His Tyr
            100                 105                 110

Trp Gly Arg Gly Thr Leu Val Thr Val Ser Ser
        115                 120

<210> SEQ ID NO 108
<211> LENGTH: 123
<212> TYPE: PRT
<213> ORGANISM: Artificial Sequence
<220> FEATURE:
<223> OTHER INFORMATION: 305LO18 VH

<400> SEQUENCE: 108

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Val His Ser Ser
            20                  25                  30

Tyr Tyr Met Ala Trp Val Arg Gln Ala Pro Gly Lys Gly Leu Glu Trp
        35                  40                  45

Val Gly Ala Ile Phe Thr Gly Ser Gly Ala Glu Tyr Lys Ala Glu Trp
    50                  55                  60

Ala Lys Gly Arg Val Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Ser Asp Ala Gly Tyr Asp Tyr Pro Thr His Ala Met His Tyr
            100                 105                 110

Trp Gly Arg Gly Thr Leu Val Thr Val Ser Ser
        115                 120

<210> SEQ ID NO 109
<211> LENGTH: 123
```

```
<212> TYPE: PRT
<213> ORGANISM: Artificial Sequence
<220> FEATURE:
<223> OTHER INFORMATION: 305LO19, 20, 22 VH

<400> SEQUENCE: 109

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val His Ser Ser
            20                  25                  30

Tyr Tyr Met Ala Trp Val Arg Gln Ala Pro Gly Lys Gly Leu Glu Trp
        35                  40                  45

Val Gly Ala Ile Phe Thr Gly Ser Gly Ala Glu Tyr Lys Ala Glu Trp
    50                  55                  60

Ala Lys Gly Arg Val Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Ser Asp Ala Gly Tyr Asp Tyr Pro Thr His Ala Met His Tyr
            100                 105                 110

Trp Gly Gln Gly Thr Leu Val Thr Val Ser Ser
        115                 120

<210> SEQ ID NO 110
<211> LENGTH: 123
<212> TYPE: PRT
<213> ORGANISM: Artificial Sequence
<220> FEATURE:
<223> OTHER INFORMATION: 305LO23 VH

<400> SEQUENCE: 110

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val His Ser Ser
            20                  25                  30

Tyr Tyr Met Ala Trp Val Arg Gln Ala Pro Gly Lys Gly Leu Glu Trp
        35                  40                  45

Val Ser Gly Ile Phe Thr Gly Ser Gly Ala Thr Tyr Lys Ala Glu Trp
    50                  55                  60

Ala Lys Gly Arg Val Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Ser Asp Ala Gly Tyr Asp Tyr Pro Thr His Ala Met His Tyr
            100                 105                 110

Trp Gly Gln Gly Thr Leu Val Thr Val Ser Ser
        115                 120

<210> SEQ ID NO 111
<211> LENGTH: 110
<212> TYPE: PRT
<213> ORGANISM: Artificial Sequence
<220> FEATURE:
<223> OTHER INFORMATION: 305LO15, 16, 18, 19 VL

<400> SEQUENCE: 111

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ser
```

```
                    20                  25                  30

Leu Ala Trp Tyr Gln Gln Lys Pro Gly Lys Ala Pro Lys Leu Leu Ile
            35                  40                  45

Tyr Gly Ala Ser Glu Thr Glu Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Asn Thr Lys Val Gly Ser Ser
                85                  90                  95

Tyr Gly Asn Thr Phe Gly Gly Gly Thr Lys Val Glu Ile Lys
            100                 105                 110

<210> SEQ ID NO 112
<211> LENGTH: 110
<212> TYPE: PRT
<213> ORGANISM: Artificial Sequence
<220> FEATURE:
<223> OTHER INFORMATION: 305LO20 VL

<400> SEQUENCE: 112

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ser
            20                  25                  30

Leu Ala Trp Tyr Gln Gln Lys Pro Gly Gln Ala Pro Arg Leu Leu Ile
            35                  40                  45

Tyr Gly Ala Ser Glu Thr Glu Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Asn Thr Lys Val Gly Ser Ser
                85                  90                  95

Tyr Gly Asn Thr Phe Gly Gly Gly Thr Lys Val Glu Ile Lys
            100                 105                 110

<210> SEQ ID NO 113
<211> LENGTH: 110
<212> TYPE: PRT
<213> ORGANISM: Artificial Sequence
<220> FEATURE:
<223> OTHER INFORMATION: 305LO22, 23 VL

<400> SEQUENCE: 113

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ser
            20                  25                  30

Leu Ala Trp Tyr Gln Gln Lys Pro Gly Gln Ala Pro Arg Leu Leu Ile
            35                  40                  45

Tyr Gly Ala Ser Thr Thr Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Asn Thr Lys Val Gly Ser Ser
                85                  90                  95

Tyr Gly Asn Thr Phe Gly Gly Gly Thr Lys Val Glu Ile Lys
            100                 105                 110
```

```
<210> SEQ ID NO 114
<211> LENGTH: 328
<212> TYPE: PRT
<213> ORGANISM: Artificial Sequence
<220> FEATURE:
<223> OTHER INFORMATION: SG115

<400> SEQUENCE: 114

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Arg Arg Gly Pro Lys Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Gly Leu Pro Ser Ser Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Leu His Glu Ala Leu His Ala His Tyr Thr
305                 310                 315                 320

Arg Lys Glu Leu Ser Leu Ser Pro
                325

<210> SEQ ID NO 115
<211> LENGTH: 325
<212> TYPE: PRT
<213> ORGANISM: Artificial Sequence
<220> FEATURE:
```

<223> OTHER INFORMATION: SG422

<400> SEQUENCE: 115

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Arg Arg Gly Pro Lys Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser His Glu Asp Pro Glu Val Lys Phe Asn Trp Tyr Val Asp
145                 150                 155                 160

Gly Val Glu Val His Asn Ala Lys Thr Lys Pro Arg Glu Glu Gln Tyr
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Arg Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Lys Leu Thr Val Asp Lys Ser Arg Trp Gln Gln Gly Asn Val Phe Ser
    290                 295                 300

Cys Ser Val Leu His Glu Ala Leu His Ala His Tyr Thr Arg Lys Glu
305                 310                 315                 320

Leu Ser Leu Ser Pro
                325

<210> SEQ ID NO 116
<211> LENGTH: 325
<212> TYPE: PRT
<213> ORGANISM: Artificial Sequence
<220> FEATURE:
<223> OTHER INFORMATION: SG429

<400> SEQUENCE: 116

Ala Ser Thr Lys Gly Pro Ser Val Phe Pro Leu Ala Pro Cys Ser Arg
1               5                   10                  15

```
Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Arg Arg Gly Pro Lys Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser His Glu Asp Pro Glu Val Lys Phe Asn Trp Tyr Val Asp
145                 150                 155                 160

Gly Val Glu Val His Asn Ala Lys Thr Lys Pro Arg Glu Glu Gln Tyr
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Arg Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Gln Gly Asn Val Phe Ser
    290                 295                 300

Cys Ser Val Leu His Glu Ala Leu His Ala His Tyr Thr Arg Lys Glu
305                 310                 315                 320

Leu Ser Leu Ser Pro
                325

<210> SEQ ID NO 117
<211> LENGTH: 6
<212> TYPE: PRT
<213> ORGANISM: Artificial Sequence
<220> FEATURE:
<223> OTHER INFORMATION: 305LO15, 16, 18, 19, 20, 22, 23 HVR-H1

<400> SEQUENCE: 117

Ser Ser Tyr Tyr Met Ala
1               5

<210> SEQ ID NO 118
<211> LENGTH: 17
<212> TYPE: PRT
<213> ORGANISM: Artificial Sequence
```

```
<220> FEATURE:
<223> OTHER INFORMATION: 305LO15, 18, 19, 20, 22 HVR-H2

<400> SEQUENCE: 118

Ala Ile Phe Thr Gly Ser Gly Ala Glu Tyr Lys Ala Glu Trp Ala Lys
1               5                   10                  15

Gly

<210> SEQ ID NO 119
<211> LENGTH: 17
<212> TYPE: PRT
<213> ORGANISM: Artificial Sequence
<220> FEATURE:
<223> OTHER INFORMATION: 305LO16 HVR-H2

<400> SEQUENCE: 119

Ala Ile Phe Thr Gly Ser Gly Ala Glu Tyr Lys Ala Glu Trp Val Lys
1               5                   10                  15

Gly

<210> SEQ ID NO 120
<211> LENGTH: 17
<212> TYPE: PRT
<213> ORGANISM: Artificial Sequence
<220> FEATURE:
<223> OTHER INFORMATION: 305LO23 HVR-H2

<400> SEQUENCE: 120

Gly Ile Phe Thr Gly Ser Gly Ala Thr Tyr Lys Ala Glu Trp Ala Lys
1               5                   10                  15

Gly

<210> SEQ ID NO 121
<211> LENGTH: 13
<212> TYPE: PRT
<213> ORGANISM: Artificial Sequence
<220> FEATURE:
<223> OTHER INFORMATION: 305LO15, 16, 18, 19, 20, 22, 23 HVR-H3

<400> SEQUENCE: 121

Asp Ala Gly Tyr Asp Tyr Pro Thr His Ala Met His Tyr
1               5                   10

<210> SEQ ID NO 122
<211> LENGTH: 11
<212> TYPE: PRT
<213> ORGANISM: Artificial Sequence
<220> FEATURE:
<223> OTHER INFORMATION: 305LO15, 16, 18, 19, 20, 22, 23 HVR-L1

<400> SEQUENCE: 122

Arg Ala Ser Gln Gly Ile Ser Ser Ser Leu Ala
1               5                   10

<210> SEQ ID NO 123
<211> LENGTH: 7
<212> TYPE: PRT
<213> ORGANISM: Artificial Sequence
<220> FEATURE:
<223> OTHER INFORMATION: 305LO15, 16, 18, 19, 20 HVR-L2

<400> SEQUENCE: 123

Gly Ala Ser Glu Thr Glu Ser
1               5
```

```
<210> SEQ ID NO 124
<211> LENGTH: 7
<212> TYPE: PRT
<213> ORGANISM: Artificial Sequence
<220> FEATURE:
<223> OTHER INFORMATION: 305LO22, 23 HVR-L2

<400> SEQUENCE: 124

Gly Ala Ser Thr Thr Gln Ser
1               5

<210> SEQ ID NO 125
<211> LENGTH: 12
<212> TYPE: PRT
<213> ORGANISM: Artificial Sequence
<220> FEATURE:
<223> OTHER INFORMATION: 305LO15, 16, 18, 19, 20, 22, 23 HVR-L3

<400> SEQUENCE: 125

Gln Asn Thr Lys Val Gly Ser Ser Tyr Gly Asn Thr
1               5                   10

<210> SEQ ID NO 126
<211> LENGTH: 6
<212> TYPE: PRT
<213> ORGANISM: Artificial Sequence
<220> FEATURE:
<223> OTHER INFORMATION: 305LOxx HVR-H1
<220> FEATURE:
<221> NAME/KEY: MISC_FEATURE
<222> LOCATION: (5)..(5)
<223> OTHER INFORMATION: Xaa can be Methionine or Valine
<220> FEATURE:
<221> NAME/KEY: MISC_FEATURE
<222> LOCATION: (6)..(6)
<223> OTHER INFORMATION: Xaa can be Cysteine or Alanine

<400> SEQUENCE: 126

Ser Ser Tyr Tyr Xaa Xaa
1               5

<210> SEQ ID NO 127
<211> LENGTH: 17
<212> TYPE: PRT
<213> ORGANISM: Artificial Sequence
<220> FEATURE:
<223> OTHER INFORMATION: 305LOxx HVR-H2
<220> FEATURE:
<221> NAME/KEY: MISC_FEATURE
<222> LOCATION: (1)..(1)
<223> OTHER INFORMATION: Xaa can be Cysteine, Alanine, or Glycine
<220> FEATURE:
<221> NAME/KEY: MISC_FEATURE
<222> LOCATION: (3)..(3)
<223> OTHER INFORMATION: Xaa can be Tyrosine or Phenylalanine
<220> FEATURE:
<221> NAME/KEY: MISC_FEATURE
<222> LOCATION: (9)..(9)
<223> OTHER INFORMATION: Xaa can be Threonine, Aspartic Acid, or
     Glutamic Acid
<220> FEATURE:
<221> NAME/KEY: MISC_FEATURE
<222> LOCATION: (11)..(11)
<223> OTHER INFORMATION: Xaa can be Tyrosine, Lysine, or Glutamine
<220> FEATURE:
<221> NAME/KEY: MISC_FEATURE
<222> LOCATION: (13)..(13)
<223> OTHER INFORMATION: Xaa can be Serine, Aspartic Acid, or Glutamic
     Acid
<220> FEATURE:
<221> NAME/KEY: MISC_FEATURE
<222> LOCATION: (15)..(15)
```

<223> OTHER INFORMATION: Xaa can be Alanine or Valine

<400> SEQUENCE: 127

Xaa Ile Xaa Thr Gly Ser Gly Ala Xaa Tyr Xaa Ala Xaa Trp Xaa Lys
1               5                   10                  15

Gly

<210> SEQ ID NO 128
<211> LENGTH: 13
<212> TYPE: PRT
<213> ORGANISM: Artificial Sequence
<220> FEATURE:
<223> OTHER INFORMATION: 305LOxx HVR-H3
<220> FEATURE:
<221> NAME/KEY: MISC_FEATURE
<222> LOCATION: (2)..(2)
<223> OTHER INFORMATION: Xaa can be Glycine or Alanine
<220> FEATURE:
<221> NAME/KEY: MISC_FEATURE
<222> LOCATION: (5)..(5)
<223> OTHER INFORMATION: Xaa can be Valine, Glutamine or Aspartic Acid
<220> FEATURE:
<221> NAME/KEY: MISC_FEATURE
<222> LOCATION: (6)..(6)
<223> OTHER INFORMATION: Xaa can be Threonine or Tyrosine
<220> FEATURE:
<221> NAME/KEY: MISC_FEATURE
<222> LOCATION: (12)..(12)
<223> OTHER INFORMATION: Xaa can be Tyrosine or Histidine
<220> FEATURE:
<221> NAME/KEY: MISC_FEATURE
<222> LOCATION: (13)..(13)
<223> OTHER INFORMATION: Xaa can be Leucine or Tyrosine

<400> SEQUENCE: 128

Asp Xaa Gly Tyr Xaa Xaa Pro Thr His Ala Met Xaa Xaa
1               5                   10

<210> SEQ ID NO 129
<211> LENGTH: 11
<212> TYPE: PRT
<213> ORGANISM: Artificial Sequence
<220> FEATURE:
<223> OTHER INFORMATION: 305LOxx HVR-L1
<220> FEATURE:
<221> NAME/KEY: MISC_FEATURE
<222> LOCATION: (1)..(1)
<223> OTHER INFORMATION: Xaa can be Glutamine or Arginine
<220> FEATURE:
<221> NAME/KEY: MISC_FEATURE
<222> LOCATION: (5)..(5)
<223> OTHER INFORMATION: Xaa can be Asparagine, Glutamine or Glycine
<220> FEATURE:
<221> NAME/KEY: MISC_FEATURE
<222> LOCATION: (7)..(7)
<223> OTHER INFORMATION: Xaa can be Glycine or Serine
<220> FEATURE:
<221> NAME/KEY: MISC_FEATURE
<222> LOCATION: (9)..(9)
<223> OTHER INFORMATION: Xaa can be Aspartic Acid, Lysine or Serine

<400> SEQUENCE: 129

Xaa Ala Ser Gln Xaa Ile Xaa Ser Xaa Leu Ala
1               5                   10

<210> SEQ ID NO 130
<211> LENGTH: 7
<212> TYPE: PRT
<213> ORGANISM: Artificial Sequence
<220> FEATURE:
<223> OTHER INFORMATION: 305LOxx HVR-L2
<220> FEATURE:

```
<221> NAME/KEY: MISC_FEATURE
<222> LOCATION: (4)..(4)
<223> OTHER INFORMATION: Xaa can be Lysine, Glutamic Acid or Threonine
<220> FEATURE:
<221> NAME/KEY: MISC_FEATURE
<222> LOCATION: (5)..(5)
<223> OTHER INFORMATION: Xaa can be Leucine or Threonine
<220> FEATURE:
<221> NAME/KEY: MISC_FEATURE
<222> LOCATION: (6)..(6)
<223> OTHER INFORMATION: Xaa can be Alanine, Histidine, Glutamic Acid
      or Glutamine

<400> SEQUENCE: 130

Gly Ala Ser Xaa Xaa Xaa Ser
1               5

<210> SEQ ID NO 131
<211> LENGTH: 12
<212> TYPE: PRT
<213> ORGANISM: Artificial Sequence
<220> FEATURE:
<223> OTHER INFORMATION: 305LOxx HVR-L3
<220> FEATURE:
<221> NAME/KEY: MISC_FEATURE
<222> LOCATION: (2)..(2)
<223> OTHER INFORMATION: Xaa can be Serine, Cysteine, Asparagine or
      Threonine
<220> FEATURE:
<221> NAME/KEY: MISC_FEATURE
<222> LOCATION: (4)..(4)
<223> OTHER INFORMATION: Xaa can be Phenylalanine or Lysine
<220> FEATURE:
<221> NAME/KEY: MISC_FEATURE
<222> LOCATION: (12)..(12)
<223> OTHER INFORMATION: Xaa can be Alanine, Threonine or Histidine

<400> SEQUENCE: 131

Gln Xaa Thr Xaa Val Gly Ser Ser Tyr Gly Asn Xaa
1               5                   10

<210> SEQ ID NO 132
<211> LENGTH: 30
<212> TYPE: PRT
<213> ORGANISM: Artificial Sequence
<220> FEATURE:
<223> OTHER INFORMATION: 305LO5 H-FR1

<400> SEQUENCE: 132

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ser His
            20                  25                  30

<210> SEQ ID NO 133
<211> LENGTH: 30
<212> TYPE: PRT
<213> ORGANISM: Artificial Sequence
<220> FEATURE:
<223> OTHER INFORMATION: 305LO15, 16, 18 H-FR1

<400> SEQUENCE: 133

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Val His
            20                  25                  30

<210> SEQ ID NO 134
<211> LENGTH: 30
```

```
<212> TYPE: PRT
<213> ORGANISM: Artificial Sequence
<220> FEATURE:
<223> OTHER INFORMATION: 305LO19, 20, 22, 23 H-FR1

<400> SEQUENCE: 134

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val His
            20                  25                  30

<210> SEQ ID NO 135
<211> LENGTH: 14
<212> TYPE: PRT
<213> ORGANISM: Artificial Sequence
<220> FEATURE:
<223> OTHER INFORMATION: 305LO5, 15, 16, 18, 19, 20, 22 H-FR2

<400> SEQUENCE: 135

Trp Val Arg Gln Ala Pro Gly Lys Gly Leu Glu Trp Val Gly
1               5                   10

<210> SEQ ID NO 136
<211> LENGTH: 14
<212> TYPE: PRT
<213> ORGANISM: Artificial Sequence
<220> FEATURE:
<223> OTHER INFORMATION: 305LO23 H-FR2

<400> SEQUENCE: 136

Trp Val Arg Gln Ala Pro Gly Lys Gly Leu Glu Trp Val Ser
1               5                   10

<210> SEQ ID NO 137
<211> LENGTH: 32
<212> TYPE: PRT
<213> ORGANISM: Artificial Sequence
<220> FEATURE:
<223> OTHER INFORMATION: 305LO5 H-FR3

<400> SEQUENCE: 137

Arg Phe Thr Ile Ser Lys Asp Thr Ser Lys Asn Gln Val Val Leu Thr
1               5                   10                  15

Met Thr Asn Met Asp Pro Val Asp Thr Ala Thr Tyr Tyr Cys Ala Ser
            20                  25                  30

<210> SEQ ID NO 138
<211> LENGTH: 32
<212> TYPE: PRT
<213> ORGANISM: Artificial Sequence
<220> FEATURE:
<223> OTHER INFORMATION: 305LO15, 18, 19, 20, 22, 23 H-FR3

<400> SEQUENCE: 138

Arg Val Thr Ile Ser Lys Asp Thr Ser Lys Asn Gln Val Val Leu Thr
1               5                   10                  15

Met Thr Asn Met Asp Pro Val Asp Thr Ala Thr Tyr Tyr Cys Ala Ser
            20                  25                  30

<210> SEQ ID NO 139
<211> LENGTH: 32
<212> TYPE: PRT
<213> ORGANISM: Artificial Sequence
<220> FEATURE:
<223> OTHER INFORMATION: 305LO16 H-FR3
```

```
<400> SEQUENCE: 139

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Ser
                20                  25                  30

<210> SEQ ID NO 140
<211> LENGTH: 11
<212> TYPE: PRT
<213> ORGANISM: Artificial Sequence
<220> FEATURE:
<223> OTHER INFORMATION: 305LO5, 15, 19, 20, 22, 23 H-FR4

<400> SEQUENCE: 140

Trp Gly Gln Gly Thr Leu Val Thr Val Ser Ser
1               5                   10

<210> SEQ ID NO 141
<211> LENGTH: 11
<212> TYPE: PRT
<213> ORGANISM: Artificial Sequence
<220> FEATURE:
<223> OTHER INFORMATION: 305LO16, 18 H-FR4

<400> SEQUENCE: 141

Trp Gly Arg Gly Thr Leu Val Thr Val Ser Ser
1               5                   10

<210> SEQ ID NO 142
<211> LENGTH: 23
<212> TYPE: PRT
<213> ORGANISM: Artificial Sequence
<220> FEATURE:
<223> OTHER INFORMATION: 305LO5 L-FR1

<400> SEQUENCE: 142

Asp Val Val Met Thr Gln Ser Pro Ser Ser Leu Ser Ala Ser Val Gly
1               5                   10                  15

Asp Arg Val Thr Ile Thr Cys
                20

<210> SEQ ID NO 143
<211> LENGTH: 23
<212> TYPE: PRT
<213> ORGANISM: Artificial Sequence
<220> FEATURE:
<223> OTHER INFORMATION: 305LO15, 16, 18, 19, 20, 22, 23 L-FR1

<400> SEQUENCE: 143

Asp Ile Gln Met Thr Gln Ser Pro Ser Ser Leu Ser Ala Ser Val Gly
1               5                   10                  15

Asp Arg Val Thr Ile Thr Cys
                20

<210> SEQ ID NO 144
<211> LENGTH: 15
<212> TYPE: PRT
<213> ORGANISM: Artificial Sequence
<220> FEATURE:
<223> OTHER INFORMATION: 305LO5, 20, 22, 23 L-FR2

<400> SEQUENCE: 144

Trp Tyr Gln Gln Lys Pro Gly Gln Ala Pro Arg Leu Leu Ile Tyr
1               5                   10                  15
```

```
<210> SEQ ID NO 145
<211> LENGTH: 15
<212> TYPE: PRT
<213> ORGANISM: Artificial Sequence
<220> FEATURE:
<223> OTHER INFORMATION: 305LO15, 16, 18, 19, L-FR2

<400> SEQUENCE: 145

Trp Tyr Gln Gln Lys Pro Gly Lys Ala Pro Lys Leu Leu Ile Tyr
1               5                   10                  15

<210> SEQ ID NO 146
<211> LENGTH: 32
<212> TYPE: PRT
<213> ORGANISM: Artificial Sequence
<220> FEATURE:
<223> OTHER INFORMATION: 305LO5 L-FR3

<400> SEQUENCE: 146

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Val Ala Thr Tyr Tyr Cys
            20                  25                  30

<210> SEQ ID NO 147
<211> LENGTH: 32
<212> TYPE: PRT
<213> ORGANISM: Artificial Sequence
<220> FEATURE:
<223> OTHER INFORMATION: 305LO15, 16, 18, 19, 20, 22, 23 L-FR3

<400> SEQUENCE: 147

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 148
<211> LENGTH: 10
<212> TYPE: PRT
<213> ORGANISM: Artificial Sequence
<220> FEATURE:
<223> OTHER INFORMATION: 305LO5, 15, 16, 18, 19, 20, 22, 23 L-FR4

<400> SEQUENCE: 148

Phe Gly Gly Gly Thr Lys Val Glu Ile Lys
1               5                   10

<210> SEQ ID NO 149
<211> LENGTH: 448
<212> TYPE: PRT
<213> ORGANISM: Artificial Sequence
<220> FEATURE:
<223> OTHER INFORMATION: BNJ441H

<400> SEQUENCE: 149

Gln Val Gln Leu Val Gln Ser Gly Ala Glu Val Lys Lys Pro Gly Ala
1               5                   10                  15

Ser Val Lys Val Ser Cys Lys Ala Ser Gly His Ile Phe Ser Asn Tyr
            20                  25                  30

Trp Ile Gln Trp Val Arg Gln Ala Pro Gly Gln Gly Leu Glu Trp Met
        35                  40                  45

Gly Glu Ile Leu Pro Gly Ser Gly His Thr Glu Tyr Thr Glu Asn Phe
    50                  55                  60
```

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
            85                  90                  95

Ala Arg Tyr Phe Phe Gly Ser Ser Pro Asn Trp Tyr Phe Asp Val Trp
            100                 105                 110

Gly Gln Gly Thr Leu Val Thr Val Ser Ser Ala Ser Thr Lys Gly Pro
            115                 120                 125

Ser Val Phe Pro Leu Ala Pro Cys Ser Arg Ser Thr Ser Glu Ser Thr
            130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
            165                 170                 175

Ala Val Leu Gln Ser Ser Gly Leu Tyr Ser Leu Ser Ser Val Val Thr
            180                 185                 190

Val Pro Ser Ser Asn Phe Gly Thr Gln Thr Tyr Thr Cys Asn Val Asp
            195                 200                 205

His Lys Pro Ser Asn Thr Lys Val Asp Lys Thr Val Glu Arg Lys Cys
            210                 215                 220

Cys Val Glu Cys Pro Pro Cys Pro Ala Pro Pro Val Ala Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
            275                 280                 285

Lys Thr Lys Pro Arg Glu Glu Gln Phe Asn Ser Thr Tyr Arg Val Val
            290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
            325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
            405                 410                 415

Arg Trp Gln Glu Gly Asn Val Phe Ser Cys Ser Val Leu His Glu Ala
            420                 425                 430

Leu His Ser His Tyr Thr Gln Lys Ser Leu Ser Leu Ser Leu Gly Lys
            435                 440                 445

<210> SEQ ID NO 150
<211> LENGTH: 214
<212> TYPE: PRT
<213> ORGANISM: Artificial Sequence
<220> FEATURE:

```
<223> OTHER INFORMATION: BNJ441L

<400> SEQUENCE: 150

Asp Ile Gln Met Thr Gln Ser Pro Ser Ser Leu Ser Ala Ser Val Gly
1               5                   10                  15

Asp Arg Val Thr Ile Thr Cys Gly Ala Ser Glu Asn Ile Tyr Gly Ala
            20                  25                  30

Leu Asn Trp Tyr Gln Gln Lys Pro Gly Lys Ala Pro Lys Leu Leu Ile
        35                  40                  45

Tyr Gly Ala Thr Asn Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Asn Val Leu Asn Thr Pro Leu
                85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

ANTI-C5 ANTIBODIES

REFERENCE TO SEQUENCE LISTING SUBMITTED ELECTRONICALLY

The content of the electronically submitted sequence listing in ASCII text file NAME_SeqList.txt (3467_0130000 SL_ST25.txt; Size: 146 KB; and Date of Creation: Dec. 16, 2015) filed with the application is herein incorporated by reference in its entirety.

BACKGROUND

The present invention relates to anti-C5 antibodies and methods of using the same. The complement system plays a central role in the clearance of immune complexes and in immune responses to infectious agents, foreign antigens, virus-infected cells and tumor cells. There are about 25-30 complement proteins, which are found as a complex collection of plasma proteins and membrane cofactors. Complement components achieve their immune defensive functions by interacting in a series of intricate enzymatic cleavages and membrane binding events. The resulting complement cascades lead to the production of products with opsonic, immunoregulatory, and lytic functions.

Currently, it is widely accepted that the complement system can be activated through three distinct pathways: the classical pathway, the lectin pathway, and the alternative pathway. These pathways share many components, and while they differ in their initial steps, they converge and share the same terminal complement components (C5 through C9) responsible for the activation and destruction of target cells.

The classical pathway is normally activated by the formation of antigen-antibody complexes. Independently, the first step in activation of the lectin pathway is the binding of specific lectins such as mannan-binding lectin (MBL), H-ficolin, M-ficolin, L-ficolin and C-type lectin CL-11. In contrast, the alternative pathway spontaneously undergoes a low level of turnover activation, which can be readily amplified on foreign or other abnormal surfaces (bacteria, yeast, virally infected cells, or damaged tissue). These pathways converge at a point where complement component C3 is cleaved by an active protease to yield C3a and C3b.

C3a is an anaphylatoxin. C3b binds to bacterial and other cells, as well as to certain viruses and immune complexes, and tags them for removal from the circulation (the role known as opsonin). C3b also forms a complex with other components to form C5 convertase, which cleaves C5 into C5a and C5b.

C5 is a 190 kDa protein found in normal serum at approximately 80 µg/ml (0.4 µM). C5 is glycosylated with about 1.5-3% of its mass attributed to carbohydrate. Mature C5 is a heterodimer of 115 kDa α chain that is disulfide linked to 75 kDa β chain. C5 is synthesized as a single chain precursor protein (pro-C5 precursor) of 1676 amino acids (see, e.g., U.S. Pat. Nos. 6,355,245 and 7,432,356). The pro-C5 precursor is cleaved to yield the β chain as an amino terminal fragment and the α chain as a carboxyl terminal fragment. The alpha chain and the beta chain polypeptide fragments are connected to each other via a disulfide bond and constitute the mature C5 protein.

Mature C5 is cleaved into the C5a and C5b fragments during activation of the complement pathways. C5a is cleaved from the α chain of C5 by C5 convertase as a amino terminal fragment comprising the first 74 amino acids of the α chain. The remaining portion of mature C5 is fragment C5b, which contains the rest of the α chain disulfide bonded to the β chain. Approximately 20% of the 11 kDa mass of C5a is attributed to carbohydrate.

C5a is another anaphylatoxin. C5b combines with C6, C7, C8 and C9 to form the membrane attack complex (MAC, C5b-9, terminal complement complex (TCC)) at the surface of the target cell. When sufficient numbers of MACs are inserted into target cell membranes, MAC pores are formed to mediate rapid osmotic lysis of the target cells.

As mentioned above, C3a and C5a are anaphylatoxins. They can trigger mast cell degranulation, which releases histamine and other mediators of inflammation, resulting in smooth muscle contraction, increased vascular permeability, leukocyte activation, and other inflammatory phenomena including cellular proliferation resulting in hypercellularity. C5a also functions as a chemotactic peptide that serves to attract granulocytes such as neutrophils, eosinophils, basophils and monocytes to the site of complement activation.

The activity of C5a is regulated by the plasma enzyme carboxypeptidase N that removes the carboxy-terminal arginine from C5a forming C5a-des-Arg derivative. C5a-des-Arg exhibits only 1% of the anaphylactic activity and polymorphonuclear chemotactic activity of unmodified C5a.

While a properly functioning complement system provides a robust defense against infecting microbes, inappropriate regulation or activation of complement has been implicated in the pathogenesis of a variety of disorders including, e.g., rheumatoid arthritis (RA); lupus nephritis; ischemia-reperfusion injury; paroxysmal nocturnal hemoglobinuria (PNH); atypical hemolytic uremic syndrome (aHUS); dense deposit disease (DDD); macular degeneration (e.g., age-related macular degeneration (AMD)); hemolysis, elevated liver enzymes, and low platelets (HELLP) syndrome; thrombotic thrombocytopenic purpura (TTP); spontaneous fetal loss; Pauci-immune vasculitis; epidermolysis bullosa; recurrent fetal loss; multiple sclerosis (MS); traumatic brain injury; and injury resulting from myocardial infarction, cardiopulmonary bypass and hemodialysis (see, e.g., Holers et al., *Immunol. Rev.* 223:300-316 (2008)). Therefore, inhibition of excessive or uncontrolled activations of the complement cascade can provide clinical benefits to patients with such disorders.

Paroxysmal nocturnal hemoglobinuria (PNH) is an uncommon blood disorder, wherein red blood cells are compromised and are thus destroyed more rapidly than normal red blood cells. PNH results from the clonal expansion of hematopoietic stem cells with somatic mutations in the PIG-A (phosphatidylinositol glycan class A) gene which is located on the X chromosome. Mutations in PIG-A lead to an early block in the synthesis of glycosylphosphatidylinositol (GPI), a molecule which is required for the anchor of many proteins to cell surfaces. Consequently, PNH blood cells are deficient in GPI-anchored proteins, which include complement-regulatory proteins CD55 and CD59. Under normal circumstances, these complement-regulatory proteins block the formation of MAC on cell surfaces, thereby preventing erythrocyte lysis. The absence of the GPI-anchored proteins causes complement-mediated hemolysis in PNH.

PNH is characterized by hemolytic anemia (a decreased number of red blood cells), hemoglobinuria (the presence of hemoglobin in urine, particularly evident after sleeping), and hemoglobinemia (the presence of hemoglobin in the bloodstream). PNH-afflicted individuals are known to have paroxysms, which are defined here as incidences of dark-colored urine. Hemolytic anemia is due to intravascular destruction of red blood cells by complement components.

Other known symptoms include dysphasia, fatigue, erectile dysfunction, thrombosis and recurrent abdominal pain.

Eculizumab is a humanized monoclonal antibody directed against the complement protein C5, and the first therapy approved for the treatment of paroxysmal nocturnal hemoglobinuria (PNH) and atypical hemolytic uremic syndrome (aHUS) (see, e.g., Dmytrijuk et al., *The Oncologist* 13(9): 993-1000 (2008)). Eculizumab inhibits the cleavage of C5 into C5a and C5b by C5 convertase, which prevents the generation of the terminal complement complex C5b-9. Both C5a and C5b-9 cause the terminal complement-mediated events that are characteristic of PNH and aHUS (see also, WO 2005/074607, WO 2007/106585, WO 2008/069889, and WO 2010/054403).

Several reports have described anti-C5 antibodies. For example, WO 95/29697 described an anti-C5 antibody which binds to the α chain of C5 but does not bind to C5a, and blocks the activation of C5, while WO 2002/30985 described an anti-C5 monoclonal antibody which inhibits C5a formation. On the other hand, WO 2004/007553 described an anti-C5 antibody which recognizes the proteolytic site for C5 convertase on the α chain of C5, and inhibits the conversion of C5 to C5a and C5b. WO 2010/015608 described an anti-C5 antibody which has an affinity constant of at least $1 \times 10^7$ $M^{-1}$.

Antibodies (IgGs) bind to neonatal Fc receptor (FcRn), and have long plasma retention times. The binding of IgGs to FcRn is typically observed under acidic conditions (e.g., pH 6.0), and it is rarely observed under neutral conditions (e.g., pH 7.4). Typically, IgGs are nonspecifically incorporated into cells via endocytosis, and return to the cell surfaces by binding to endosomal FcRn under the acidic conditions in the endosomes. Then, IgGs dissociate from FcRn under the neutral conditions in plasma. IgGs that have failed to bind to FcRn are degraded in lysosomes. When the FcRn binding ability of an IgG under acidic conditions is eliminated by introducing mutations into its Fc region, the IgG is not recycled from the endosomes into the plasma, leading to marked impairment of the plasma retention of the IgG. To improve the plasma retention of IgGs, a method that enhances their FcRn binding under acidic conditions has been reported. When the FcRn binding of an IgG under acidic conditions is improved by introducing an amino acid substitution into its Fc region, the IgG is more efficiently recycled from the endosomes to the plasma, and thereby shows improved plasma retention. Meanwhile, it has also been reported that an IgG with enhanced FcRn binding under neutral conditions does not dissociate from FcRn under the neutral conditions in plasma even when it returns to the cell surface via its binding to FcRn under the acidic conditions in the endosomes, and consequently its plasma retention remains unaltered, or rather, is worsened (see, e.g., Yeung et al., *J Immunol.* 182(12): 7663-7671 (2009); Datta-Mannan et al., *J Biol. Chem.* 282(3):1709-1717 (2007); Dall'Acqua et al., *J. Immunol.* 169(9):5171-5180 (2002)).

Recently, antibodies that bind to antigens in a pH-dependent manner have been reported (see, e.g., WO 2009/125825 and WO 2011/122011). These antibodies strongly bind to antigens under the plasma neutral conditions and dissociate from the antigens under the endosomal acidic conditions. After dissociating from the antigens, the antibodies become capable once again of binding to antigens when recycled to the plasma via FcRn. Thus, a single antibody molecule can repeatedly bind to multiple antigen molecules. In general, the plasma retention of an antigen is much shorter than that of an antibody that has the above-mentioned FcRn-mediated recycling mechanism. Therefore, when an antigen is bound to an antibody, the antigen normally shows prolonged plasma retention, resulting in an increase of the plasma concentration of the antigen. On the other hand, it has been reported that the above-described antibodies, which bind to antigens in a pH-dependent manner, eliminate antigens from plasma more rapidly than typical antibodies because they dissociate from the antigens within the endosomes during the FcRn-mediated recycling process. WO 2011/111007 also described computer modeling analysis showing that an antibody with pH-dependent binding directed against C5 could extend antigen knockdown.

BRIEF SUMMARY

The invention provides anti-C5 antibodies and methods of using the same.

In some embodiments, an isolated anti-C5 antibody of the present invention binds to an epitope within the β chain of C5. In some embodiments, an isolated anti-C5 antibody of the present invention binds to an epitope within the MG1-MG2 domain of the β chain of C5. In some embodiments, an isolated anti-C5 antibody of the present invention binds to an epitope within a fragment consisting of amino acids 33-124 of the β chain (SEQ ID NO: 40) of C5. In some embodiments, an isolated anti-C5 antibody of the present invention binds to an epitope within the β chain (SEQ ID NO: 40) of C5 which comprises at least one fragment selected from the group consisting of amino acids 47-57, 70-76, and 107-110. In some embodiments, an isolated anti-C5 antibody of the present invention binds to an epitope within a fragment of the β chain (SEQ ID NO: 40) of C5 which comprises at least one amino acid residue selected from the group consisting of Glu48, Asp51, His70, His72, Lys109, and His110 of SEQ ID NO: 40. In further embodiments, the antibody binds to C5 with a higher affinity at neutral pH than at acidic pH. In further embodiments, the antibody binds to C5 with a higher affinity at pH7.4 than at pH5.8. In another embodiment, an isolated anti-C5 antibody of the present invention binds to the same epitope as an antibody described in Table 2. In further embodiments, the antibody binds to the same epitope as an antibody described in Table 2 with a higher affinity at pH7.4 than at pH5.8. In a further embodiment, the anti-C5 antibody of the present invention binds to the same epitope as an antibody described in Tables 7 or 8. In further embodiments, the antibody binds to the same epitope as an antibody described in Tables 7 or 8 with a higher affinity at pH7.4 than at pH5.8.

In certain embodiments, an anti-C5 antibody of the present invention competes for binding C5 with an antibody comprising a VH and VL pair selected from: (a) a VH of SEQ ID NO:1 and a VL of SEQ ID NO:11; (b) a VH of SEQ ID NO: 5 and a VL of SEQ ID NO:15; (c) a VH of SEQ ID NO:4 and a VL of SEQ ID NO:14; (d) a VH of SEQ ID NO: 6 and a VL of SEQ ID NO: 16; (e) a VH of SEQ ID NO:2 and a VL of SEQ ID NO:12; (f) a VH of SEQ ID NO: 3 and a VL of SEQ ID NO: 13; (g) a VH of SEQ ID NO:9 and a VL of SEQ ID NO:19; (h) a VH of SEQ ID NO:7 and a VL of SEQ ID NO: 17; (i) aVH of SEQ ID NO:8 and a VL of SEQ ID NO:18; and (j) a VH of SEQ ID NO:10 and a VL of SEQ ID NO:20. In further embodiments, the anti-C5 antibody binds to C5 with a higher affinity at neutral pH than at acidic pH. In further embodiments, the anti-C5 antibody binds to C5 with a higher affinity at pH7.4 than at pH5.8.

In some embodiments, an isolated anti-C5 antibody of the present invention has a characteristic selected from the group consisting of: (a) the antibody contacts amino acids D51 and K109 of C5 (SEQ ID NO:39); (b) the affinity of the antibody for C5 (SEQ ID NO:39) is greater than the affinity of the antibody for a C5 mutant consisting of an E48A substitution of SEQ ID NO:39; or (c) the antibody binds to a C5 protein consisting of the amino acid sequence of SEQ ID NO:39 at pH7.4, but does not bind to a C5 protein consisting of the amino acid sequence of SEQ ID NO:39 with a H72Y substitution at pH7.4. In further embodiments, the antibody binds to C5 with a higher affinity at neutral pH than at acidic pH. In further embodiments, the antibody binds to C5 with a higher affinity at pH7.4 than at pH5.8.

In some embodiments, an isolated anti-C5 antibody of the present invention inhibits activation of C5. In some embodiments, an isolated anti-C5 antibody of the present invention inhibits activation of C5 variant R885H. In some embodiments, an isolated anti-C5 antibody of the present invention is a monoclonal antibody. In some embodiments, an isolated anti-C5 antibody of the present invention is a human, humanized, or chimeric antibody. In some embodiments, an isolated anti-C5 antibody of the present invention is an antibody fragment that binds to C5. In some embodiments, an isolated anti-C5 antibody of the present invention is a full length IgG1 or IgG4 antibody.

In some embodiments, an anti-C5 antibody of the present invention competes for binding C5 with an antibody comprising a VH and VL pair selected from: (a) a VH of SEQ ID NO:1 and a VL of SEQ ID NO:11; (b) a VH of SEQ ID NO: 22 and a VL of SEQ ID NO:26; (c) a VH of SEQ ID NO:21 and a VL of SEQ ID NO:25; (d) a VH of SEQ ID NO:5 and a VL of SEQ ID NO:15; (e) a VH of SEQ ID NO:4 and a VL of SEQ ID NO:14; (f) a VH of SEQ ID NO: 6 and a VL of SEQ ID NO: 16; (g) a VH of SEQ ID NO:2 and a VL of SEQ ID NO:12; (h) a VH of SEQ ID NO: 3 and a VL of SEQ ID NO: 13; (i) a VH of SEQ ID NO:9 and a VL of SEQ ID NO:19; (j) a VH of SEQ ID NO:7 and a VL of SEQ ID NO: 17; (k) aVH of SEQ ID NO:8 and a VL of SEQ ID NO:18; (1) a VH of SEQ ID NO: 23 and a VL of SEQ ID NO:27; and (m) a VH of SEQ ID NO: 10 and a VL of SEQ ID NO:20.

In some embodiments, an anti-C5 antibody of the present invention binds C5 and contacts amino acid Asp51 (D51) of SEQ ID NO:39. In additional embodiments, an anti-C5 antibody of the present invention binds C55 and contacts amino acid Lys109 (K109) of SEQ ID NO:39. In a further embodiment, an anti-C5 antibody of the present invention binds C5 and contacts amino acid Asp51 (D51) and amino acid Lys109 (K109) of SEQ ID NO:39.

In some embodiments, an isolated anti-C5 antibody of the present invention comprises (a) a HVR-H3 comprising the amino acid sequence $DX_1GYX_2X_3PTHAMX_4X_5$, wherein $X_1$ is G or A, $X_2$ is V, Q or D, $X_3$ is T or Y, $X_4$ is Y or H, $X_5$ is L or Y (SEQ ID NO: 128), (b) a HVR-L3 comprising the amino acid sequence $QX_1TX_2VGSSYGNX_3$, wherein $X_1$ is S, C, N or T, $X_2$ is F or K, $X_3$ is A, T or H (SEQ ID NO: 131), and (c) a HVR-H2 comprising the amino acid sequence $X_1IX_2TGSGAX_3YX_4AX_5WX_6KG$, wherein $X_1$ is C, A or G, $X_2$ is Y or F, $X_3$ is T, D or E, $X_4$ is Y, K or Q, $X_5$ is S, D or E, $X_6$ is A or V (SEQ ID NO: 127).

In some embodiments, an isolated anti-C5 antibody of the present invention comprises (a) a HVR-H1 comprising the amino acid sequence $SSYYX_1X_2$, wherein $X_1$ is M or V, $X_2$ is C or A (SEQ ID NO: 126), (b) a HVR-H2 comprising the amino acid sequence $X_1IX_2TGSGAX_3YX_4AX_5WX_6KG$, wherein $X_1$ is C, A or G, $X_2$ is Y or F, $X_3$ is T, D or E, $X_4$ is Y, K or Q, $X_5$ is S, D or E, $X_6$ is A or V (SEQ ID NO: 127), and (c) a HVR-H3 comprising the amino acid sequence $DX_1GYX_2X_3PTHAMX_4X_5$, wherein $X_1$ is G or A, $X_2$ is V, Q or D, $X_3$ is T or Y, $X_4$ is Y or H, $X_5$ is L or Y (SEQ ID NO: 128). In further embodiments, the antibody comprises (a) a HVR-L1 comprising the amino acid sequence $X_1ASQX_2IX_3SX_4LA$, wherein $X_1$ is Q or R, $X_2$ is N, Q or G, $X_3$ is G or S, $X_4$ is D, K or S (SEQ ID NO: 129); (b) a HVR-L2 comprising the amino acid sequence $GASX_1X_2X_3S$, wherein $X_1$ is K, E or T, $X_2$ is L or T, $X_3$ is A, H, E or Q (SEQ ID NO: 130); and (c) a HVR-L3 comprising the amino acid sequence $QX_1TX_2VGSSYGNX_3$, wherein $X_1$ is S, C, N or T, $X_2$ is F or K, $X_3$ is A, T or H (SEQ ID NO: 131).

In some embodiments, an isolated anti-C5 antibody of the present invention comprises (a) a HVR-L1 comprising the amino acid sequence $X_1ASQX_2IX_3SX_4LA$, wherein $X_1$ is Q or R, $X_2$ is N, Q or G, $X_3$ is G or S, $X_4$ is D, K or S (SEQ ID NO: 129); (b) a HVR-L2 comprising the amino acid sequence $GASX_1X_2X_3S$, wherein $X_1$ is K, E or T, $X_2$ is L or T, $X_3$ is A, H, E or Q (SEQ ID NO: 130); and (c) a HVR-L3 comprising the amino acid sequence $QX_1TX_2VGSSYGNX_3$, wherein $X_1$ is S, C, N or T, $X_2$ is F or K, $X_3$ is A, T or H (SEQ ID NO: 131).

In some embodiments, an isolated anti-C5 antibody of the present invention comprises a heavy chain variable domain framework FR1 comprising the amino acid sequence of SEQ ID NO: 132, 133, or 134; FR2 comprising the amino acid sequence of SEQ ID NO: 135 or 136; FR3 comprising the amino acid sequence of SEQ ID NO: 137, 138, or 139; and FR4 comprising the amino acid sequence of SEQ ID NO: 140 or 141. In some embodiments, an isolated anti-C5 antibody of the present invention comprises a light chain variable domain framework FR1 comprising the amino acid sequence of SEQ ID NO: 142 or 143; FR2 comprising the amino acid sequence of SEQ ID NO: 144 or 145; FR3 comprising the amino acid sequence of SEQ ID NO: 146 or 147; and FR4 comprising the amino acid sequence of SEQ ID NO: 148.

In some embodiments, an isolated anti-C5 antibody of the present invention comprises (a) a VH sequence having at least 95% sequence identity to the amino acid sequence of SEQ ID NO: 10, 106, 107, 108, 109, or 110; (b) a VL sequence having at least 95% sequence identity to the amino acid sequence of SEQ ID NO: 20, 111, 112, or 113; or (c) a VH sequence as in (a) and a VL sequence as in (b). In further embodiments, the antibody comprises a VH sequence of SEQ ID NO: 10, 106, 107, 108, 109, or 110. In further embodiments, the antibody comprises a VL sequence of SEQ ID NO: 20, 111, 112, or 113.

The invention provides an antibody comprising a VH sequence of SEQ ID NO: 10, 106, 107, 108, 109, or 110 and a VL sequence of SEQ ID NO: 20, 111, 112, or 113.

The invention also provides isolated nucleic acids encoding an anti-C5 antibody of the present invention. The invention also provides host cells comprising a nucleic acid of the present invention. The invention also provides a method of producing an antibody comprising culturing a host cell of the present invention so that the antibody is produced.

The invention further provides a method of producing an anti-C5 antibody. In some embodiments, the method comprises immunizing an animal against a polypeptide which comprises the MG1-MG2 domain (SEQ ID NO: 43) of the β chain of C5. In some embodiments, the method comprises immunizing an animal against a polypeptide which comprises the region corresponding to amino acids at positions 33 to 124 of the β chain (SEQ ID NO: 40) of C5. In some embodiments, the method comprises immunizing an animal against a polypeptide which comprises at least one fragment selected from amino acids 47-57, 70-76, and 107-110 of the β chain (SEQ ID NO: 40) of C5. In some embodiments, the method comprises immunizing an animal against a polypeptide which comprises a fragment of the β chain (SEQ ID NO: 40) of C5, which comprises at least one amino acid selected from Glu48, Asp51, His70, His72, Lys109, and His110.

In some embodiments, an anti-C5 antibody provided herein is used in a method for detecting the presence of C5 in a biological sample. In other embodiments, an anti-C5 antibody is used in a method of neutralizing C5 in a biological sample that comprises contacting a biological sample containing C5 with the antibody under conditions permissive for binding of the antibody to the C5, and, and inhibiting the activation of C5. In some embodiments, an anti-C5 antibody is used in a method of neutralizing C5 in a biological sample that comprises contacting a biological sample containing C5 with the antibody at a neutral pH (e.g., pH7.4) under conditions permissive for binding of the antibody to the C5, and, and inhibiting the activation of C5. In additional embodiments, an anti-C5 antibody provided herein is used in a method of reducing the concentration of C5 in a biological sample that comprises contacting the biological sample containing C5 with the antibody under conditions permissive for binding of the antibody to the C5, and removing the complex formed between the antibody and the C5. In additional embodiments, an anti-C5 antibody provided herein is used in a method of reducing the concentration of C5 in a biological sample that comprises contacting the biological sample containing C5 with the antibody at a neutral pH (e.g., pH7.4) under conditions permissive for binding of the antibody to the C5, and removing the complex formed between the antibody and the C5. In some embodiments, one or more of the above methods is performed in vitro. In some embodiments, one or more of the above methods is performed in vivo.

The invention also provides a pharmaceutical formulation comprising an anti-C5 antibody of the present invention and a pharmaceutically acceptable carrier.

Anti-C5 antibodies of the present invention may be for use as a medicament. Anti-C5 antibodies of the present invention may be used in treating a complement-mediated disease or condition which involves excessive or uncontrolled activation of C5. In additional embodiments, anti-C5 antibodies of the present invention may be used in treating diseases or disorders that include but are not limited to, paroxysmal nocturnal hemoglobinuria (PNH), age-related macular degeneration, a myocardial infarction, rheumatoid arthritis, osteoporosis, osteoarthritis, and inflammation. Anti-C5 antibodies of the present invention may also be used to enhance the clearance of C5 from plasma.

Anti-C5 antibodies of the present invention may be used in the manufacture of a medicament. In some embodiments, the medicament is for treatment of a complement-mediated disease or condition which involves excessive or uncontrolled activation of C5. In some embodiments, the medicament is for enhancing the clearance of C5 from plasma.

The invention also provides a method of treating an individual having a complement-mediated disease or condition which involves excessive or uncontrolled activation of C5. In some embodiments, the method comprises administering to the individual an effective amount of an anti-C5 antibody of the present invention. The invention also provides a method of enhancing the clearance of C5 from plasma in an individual. In some embodiments, the method comprises administering to the individual an effective amount of an anti-C5 antibody of the present invention to enhance the clearance of C5 from plasma.

BRIEF DESCRIPTION OF THE DRAWINGS/FIGURES

Figure 3:
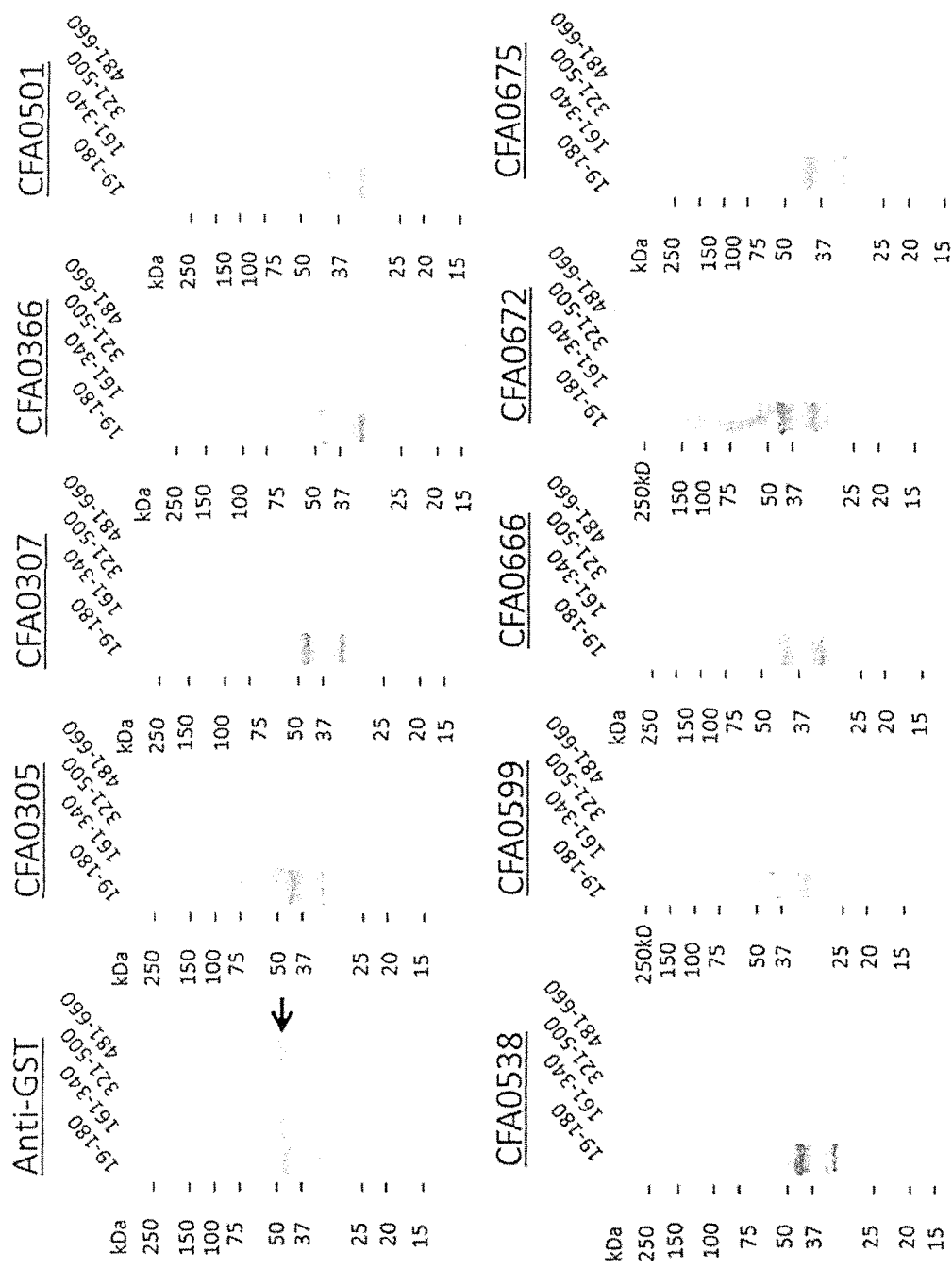

FIG. 3 illustrates Western Blot analysis against C5 β-chain-derived fragments (amino acids 19-180, 161-340, 321-500, and 481-660 of SEQ ID NO:40) fused to GST-tag, as described in Example 4.1. CFA0305, CFA0307, CFA0366, CFA0501, CFA0538, CFA0599, CFA0666, CFA0672, and CFA0675 are antibodies grouped into epitope C. Anti-GST antibody is a positive control. The position of the GST-fused C5 fragments (46-49 kDa) is marked with an arrow.

Figure 4:
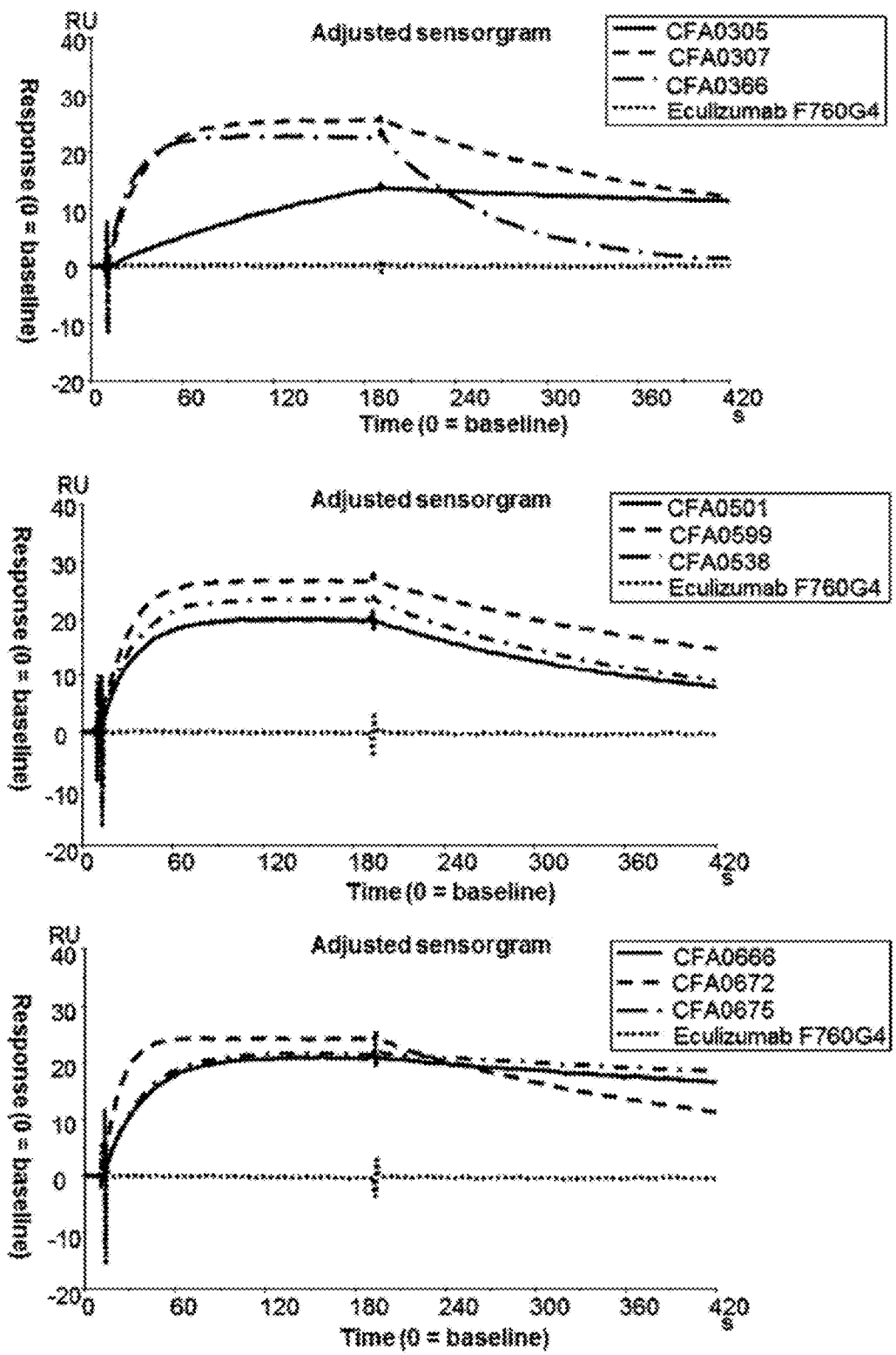

FIG. 4 illustrates BIACORE® sensorgrams of anti-C5 antibodies towards MG1-MG2 domain of C5 β-chain, as described in Example 4.3. The upper panel shows the results of CFA0305 (solid line), CFA0307 (dashed line), CFA0366 (dash-dot line), and eculizumab (dotted line). The middle panel shows the results of CFA0501 (solid line), CFA0599 (dashed line), CFA0538 (dash-dot line), and eculizumab (dotted line). The lower panel shows the results of CFA0666 (solid line), CFA0672 (dashed line), CFA0675 (dash-dot line), and eculizumab (dotted line). CFA0305, CFA0307, CFA0366, CFA0501, CFA0538, CFA0599, CFA0666, CFA0672, and CFA0675 are antibodies grouped into epitope C. Eculizumab is a control anti-C5 antibody.

Figure 5A:
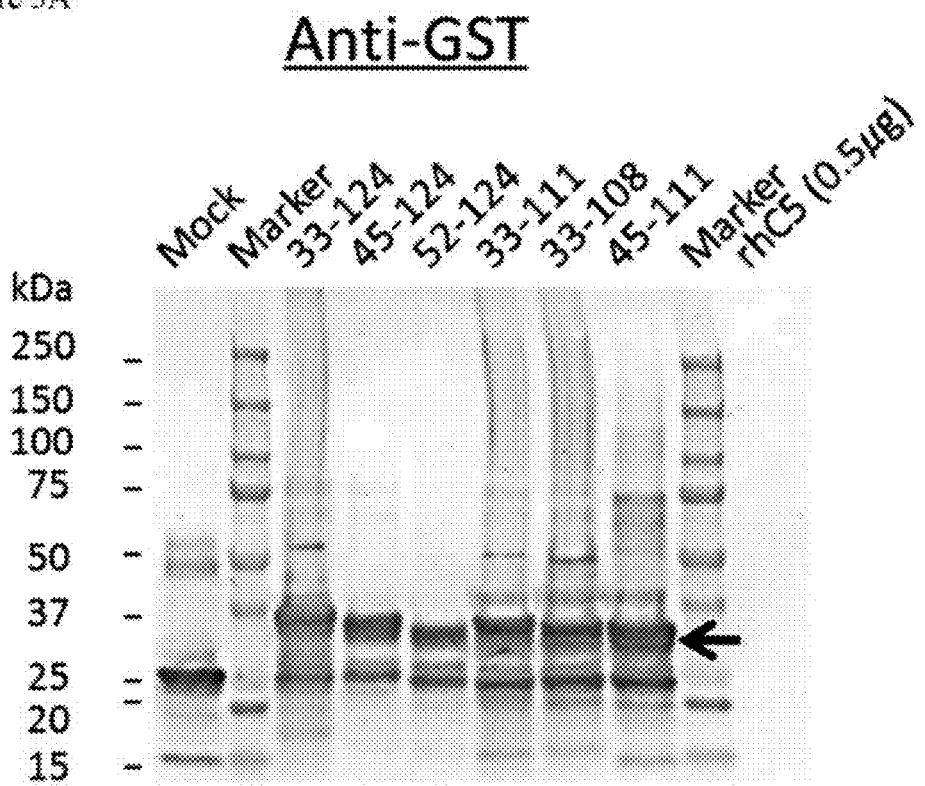

FIG. 5A illustrates Western Blot analysis against MG1-MG2 domain-derived peptide fragments (amino acids 33-124, 45-124, 52-124, 33-111, 33-108, and 45-111 of SEQ ID NO:40) fused to GST-tag, as described in Example 4.4. Anti-GST antibody is used as an antibody for reaction. The position of the GST-fused C5 fragments (35-37 kDa) is marked with an arrow.

Figure 5B:
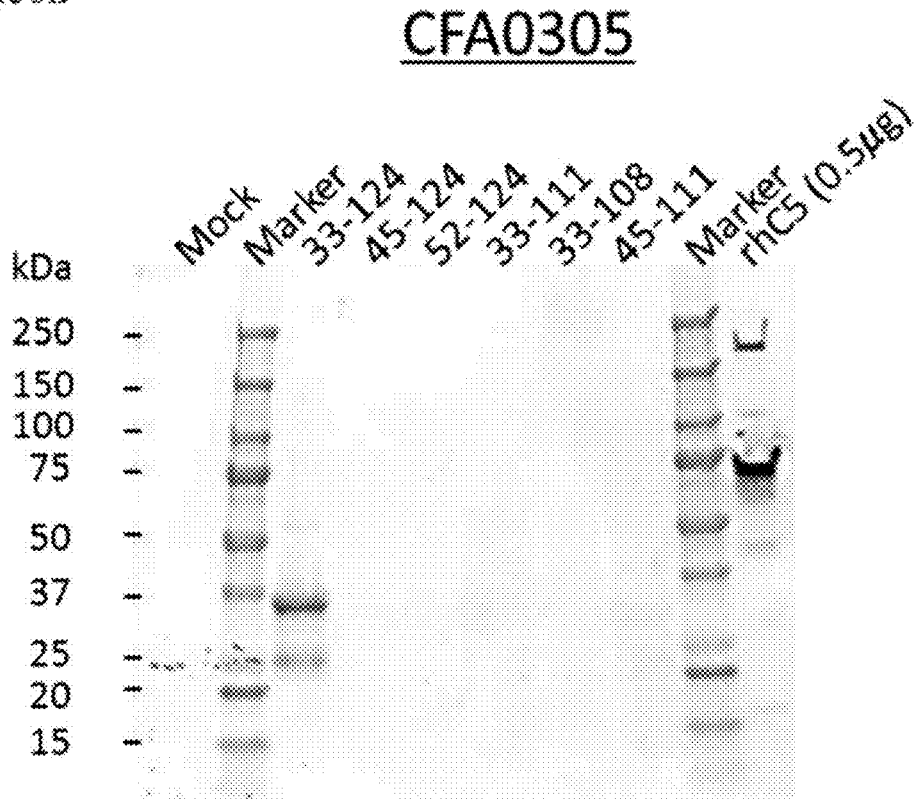

FIG. 5B illustrates Western Blot analysis against MG1-MG2 domain-derived peptide fragments (amino acids 33-124, 45-124, 52-124, 33-111, 33-108, and 45-111 of SEQ ID NO:40) fused to GST-tag, as described in Example 4.4. CFA0305 is used as an antibody for reaction.

Figure 5C:
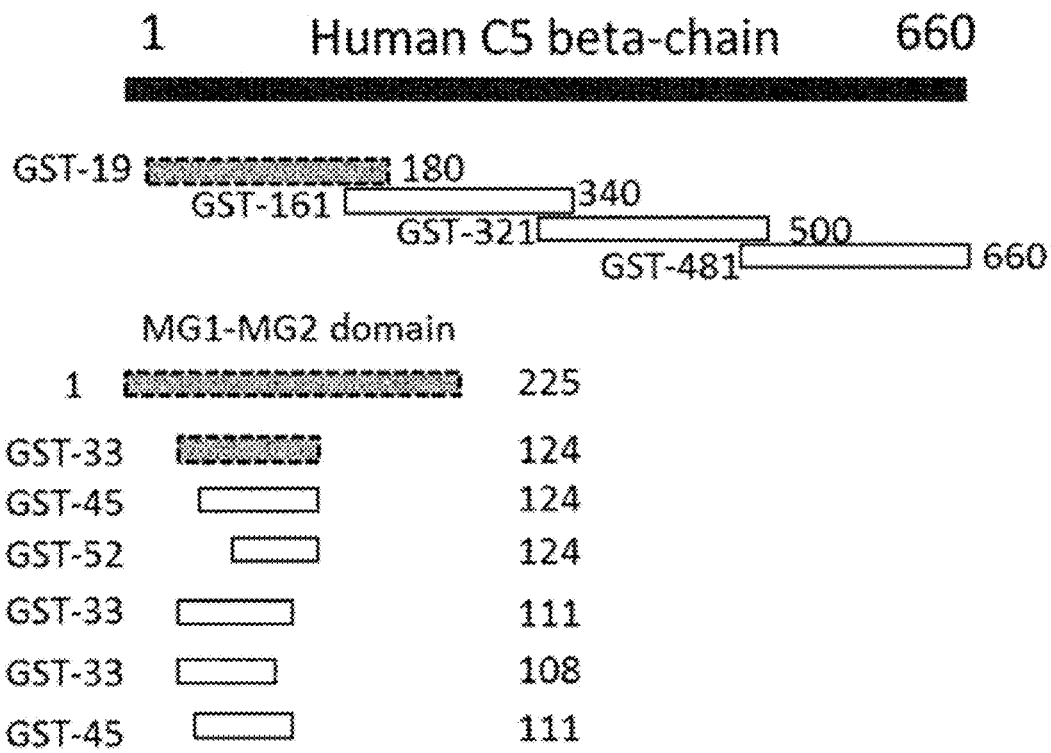

FIG. 5C summarizes binding reactions of anti-C5 antibodies to C5 β-chain-derived fragments, as described in Example 4.4. The fragments to which the anti-C5 antibodies grouped into epitope C (CFA0305, CFA0307, CFA0366, CFA0501, CFA0538, CFA0599, CFA0666, CFA0672, and CFA0675) bind are shown in gray, and the fragments to which they don't bind are shown in white.

Figure 6:
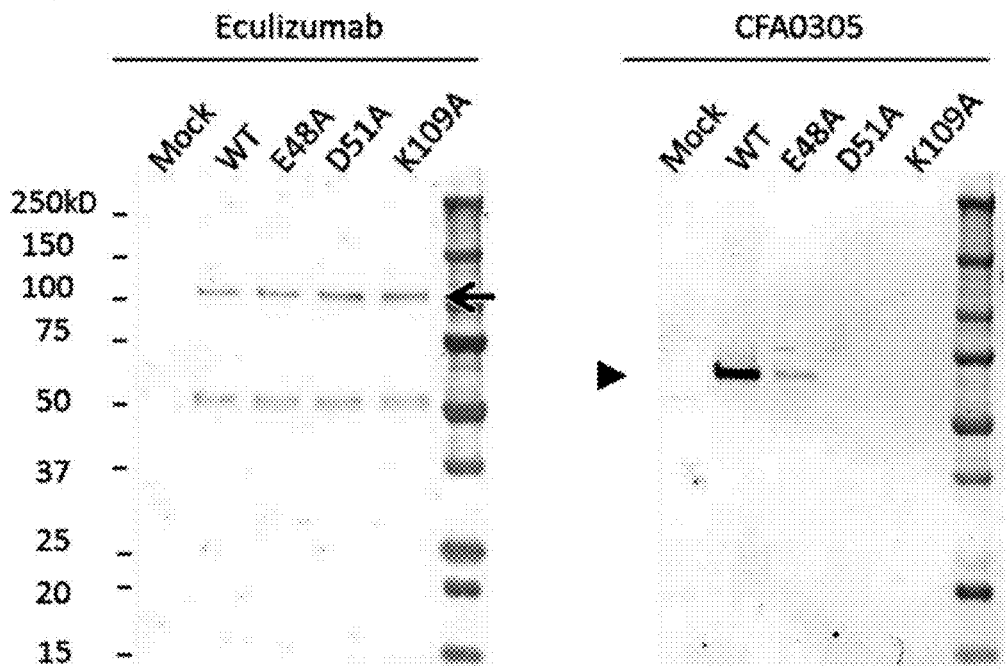

FIG. 6 illustrates Western Blot analysis against C5 point mutants in which E48, D51, and K109 of the β-chain is substituted with alanine (E48A, D51A, and K109A, respectively), as described in Example 4.5. In the left panel, eculizumab (anti-C5 antibody, α-chain binder) is used as an antibody for reaction and the position of the α-chain of C5

(approx. 113 kDa) is marked with an arrow. In the right panel, CFA0305 (grouped into epitope C, β-chain binder) is used as an antibody for reaction and the position of the β-chain of C5 (approx. 74 kDa) is marked with an arrowhead.

Figure 7:
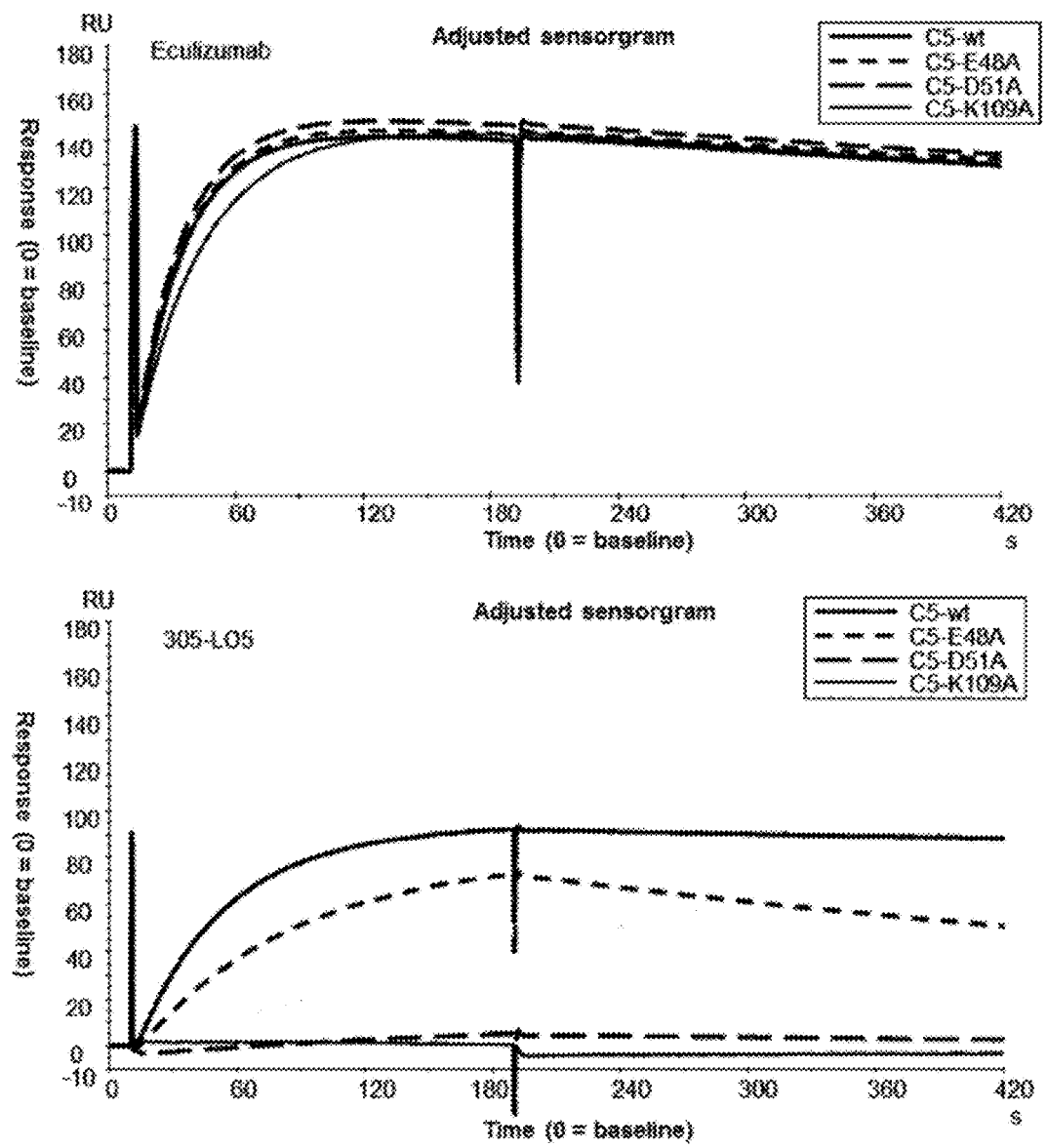

FIG. 7 presents BIACORE® sensorgrams showing the interaction of eculizumab-F760G4 (upper panel) or 305LO5 (lower panel) with C5 mutants, as described in Example 4.6. Sensorgrams were obtained by injection of C5-wt (thick solid curve), C5-E48A (short-dashed curve), C5-D51A (long-dashed curve), and C5-K109A (thin solid curve), respectively, over sensor surface immobilized with eculizumab-F760G4 or 305LO5. Eculizumab is a control anti-C5 antibody. 305LO5 is a humanized antibody of CFA0305 (grouped into epitope C), as described in Example 2.3.

Figure 8:
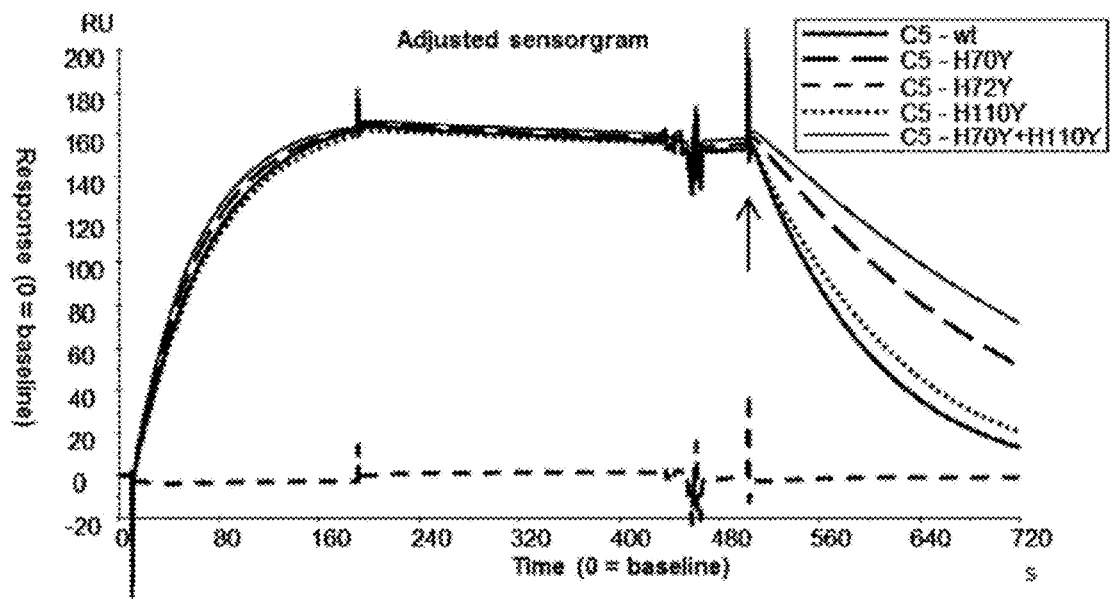

FIG. 8 presents BIACORE® sensorgrams showing the interaction of 305LO5 with C5 His mutants to assess pH-dependency, as described in Example 4.7. Sensorgrams were obtained by injection of C5-wt (thick solid curve), C5-H70Y (long-dashed curve), C5-H72Y (short-dashed curve), C5-H110Y (dotted curve), and C5-H70Y+H110Y (thin solid curve), respectively, over sensor surface immobilized with 305LO5. The antibody/antigen complexes were allowed to dissociate at pH7.4, followed by additional dissociation at pH5.8 (pointed by an arrow) to assess the pH-dependent interactions.

Figure 9A:
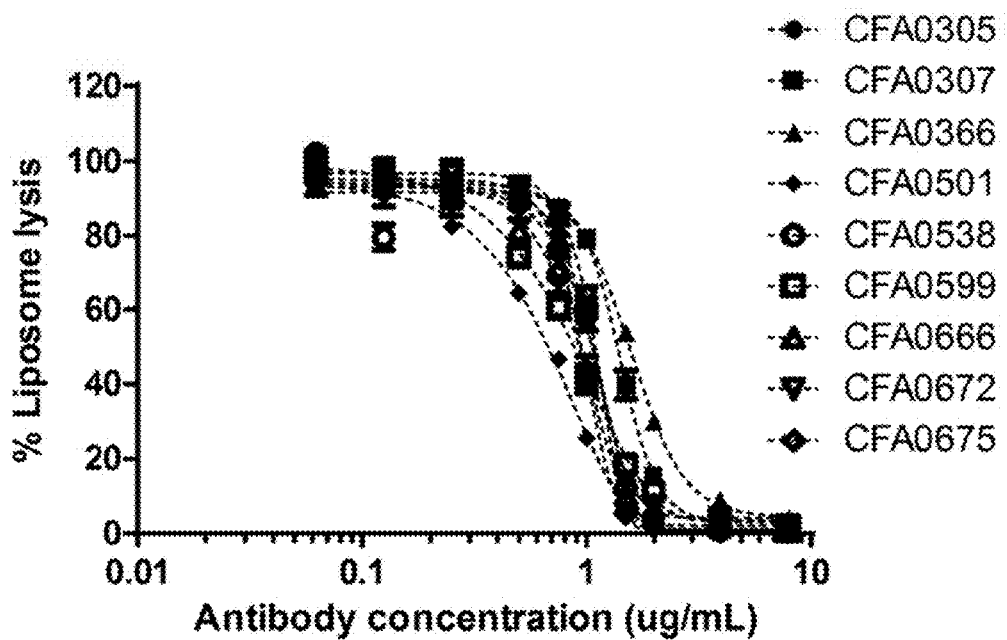

FIG. 9A illustrates inhibition of complement-activated liposome lysis by anti-C5 antibodies, as described in Example 5.1. The results of CFA0305, CFA0307, CFA0366, CFA0501, CFA0538, CFA0599, CFA0666, CFA0672, and CFA0675 grouped into epitope C, as described in Example 2.2, are shown.

Figure 9B:
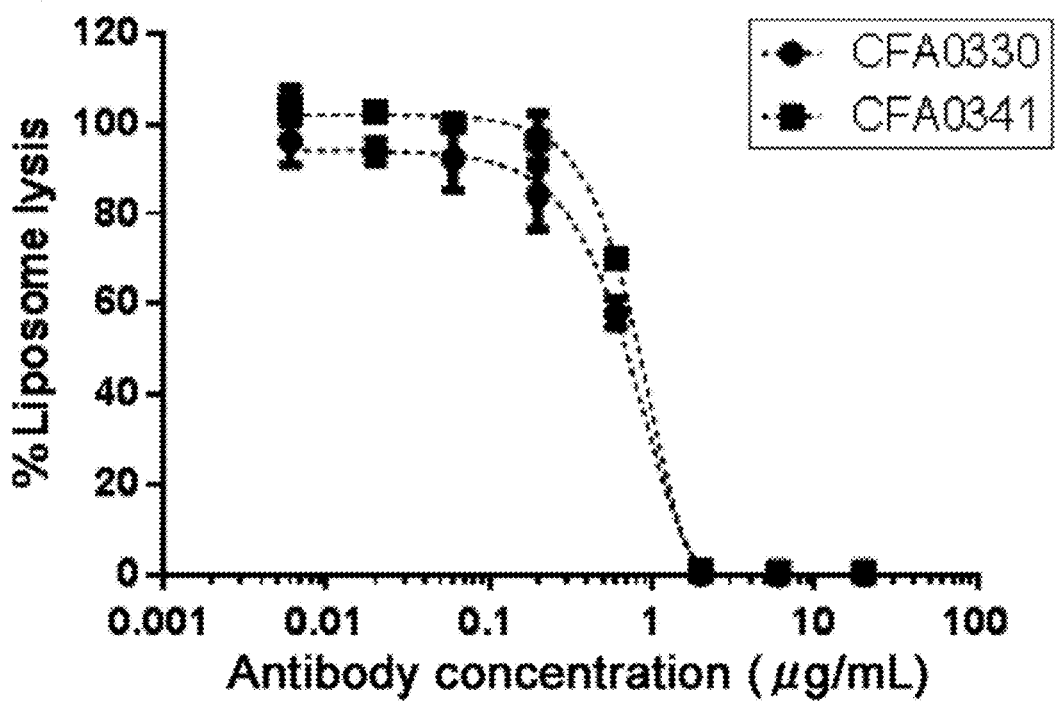

FIG. 9B illustrates inhibition of complement-activated liposome lysis by anti-C5 antibodies, as described in Example 5.1. The results of antibodies CFA0330 and CFA0341 grouped into epitope B, as described in Example 2.2, are shown.

Figure 10A:
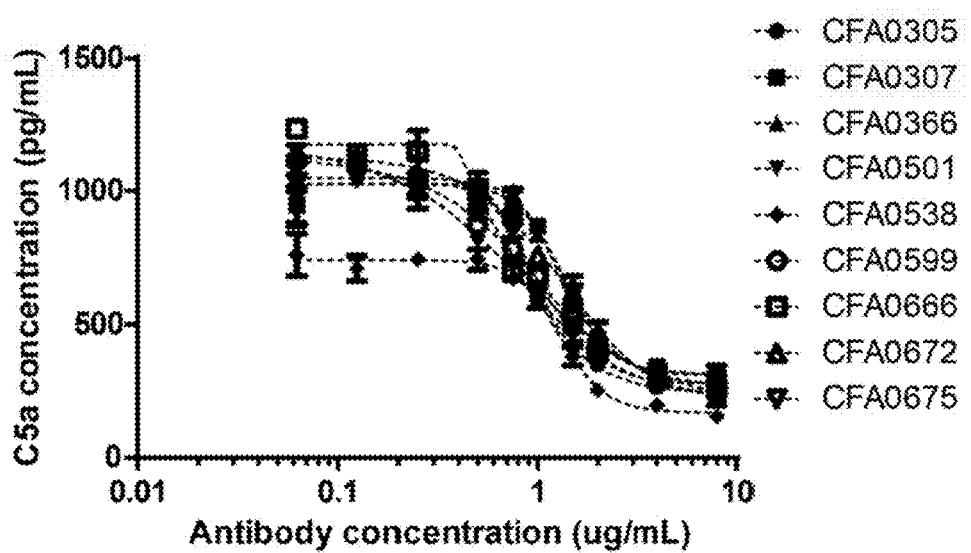

FIG. 10A illustrates inhibition of C5a generation by anti-C5 antibodies, as described in Example 5.2. C5a concentrations were quantified in the supernatants obtained during the liposome lysis assay described in FIG. 9A.

Figure 10B:
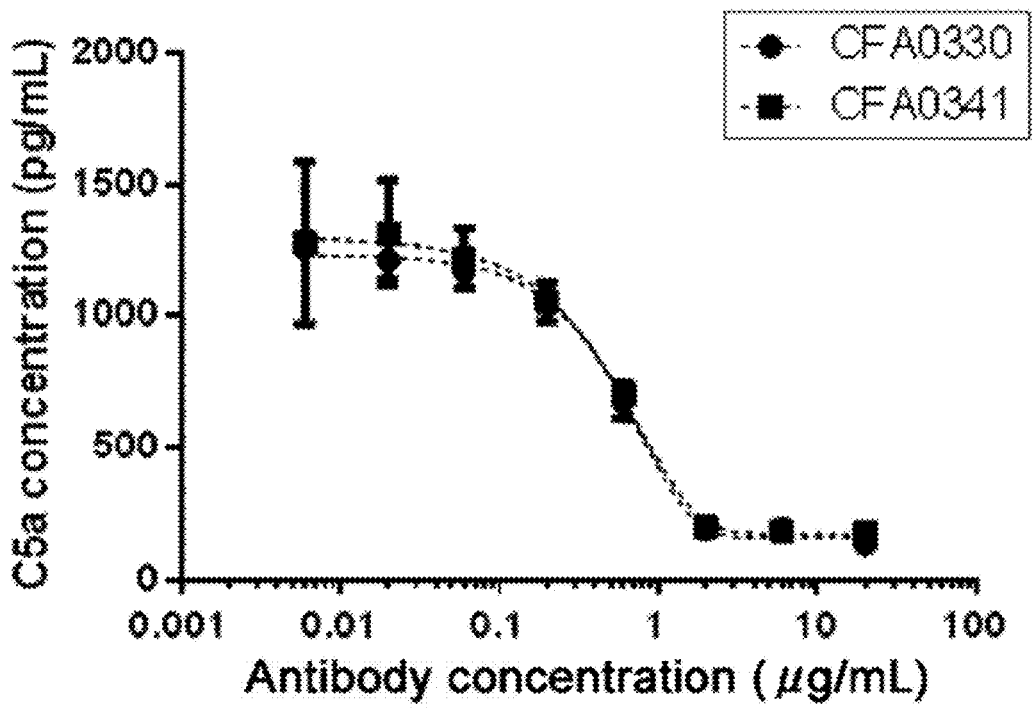

FIG. 10B illustrates inhibition of C5a generation by anti-C5 antibodies, as described in Example 5.2. C5a concentrations were quantified in the supernatants obtained during the liposome lysis assay described in FIG. 9B.

Figure 11:
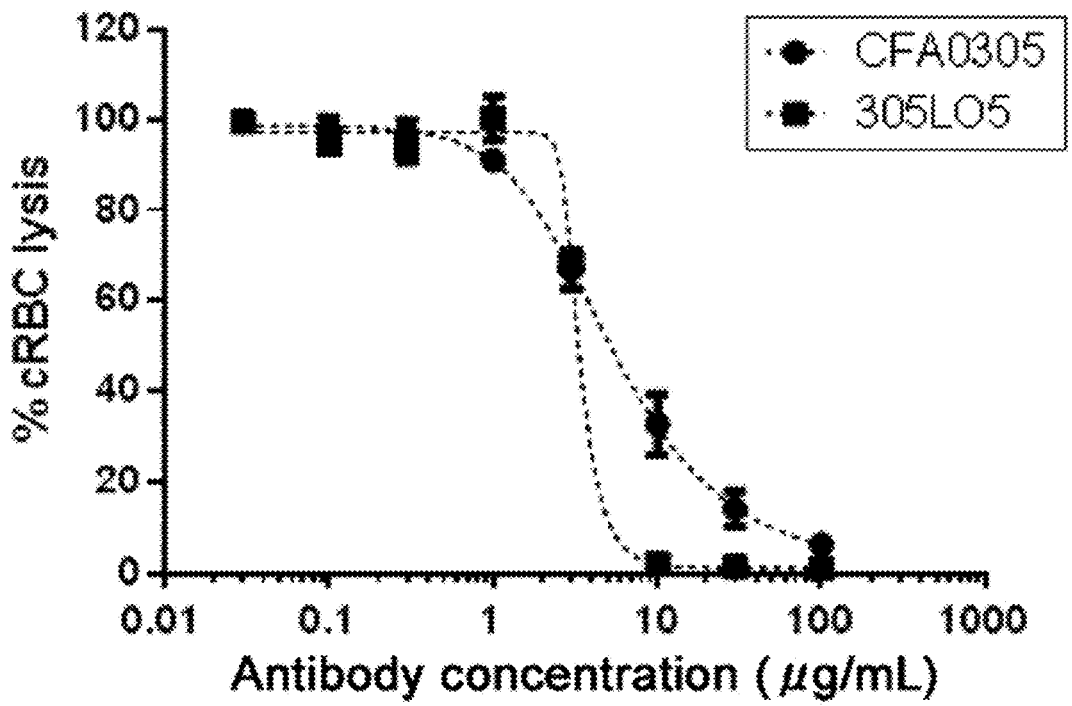

FIG. 11 illustrates inhibition of complement-activated hemolysis by anti-C5 antibodies, as described in Example 5.3. Complements were activated via the classical pathway.

Figure 12:
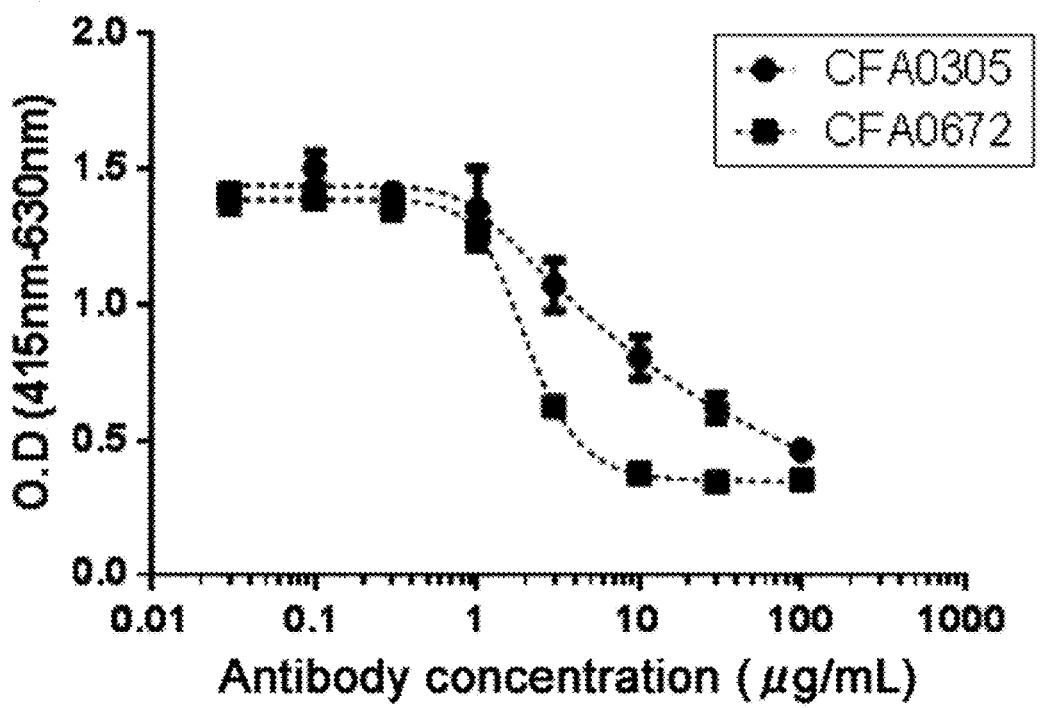

FIG. 12 illustrates inhibition of complement-activated hemolysis by anti-C5 antibodies, as described in Example 5.4. Complements were activated via the alternative pathway.

Figure 13:
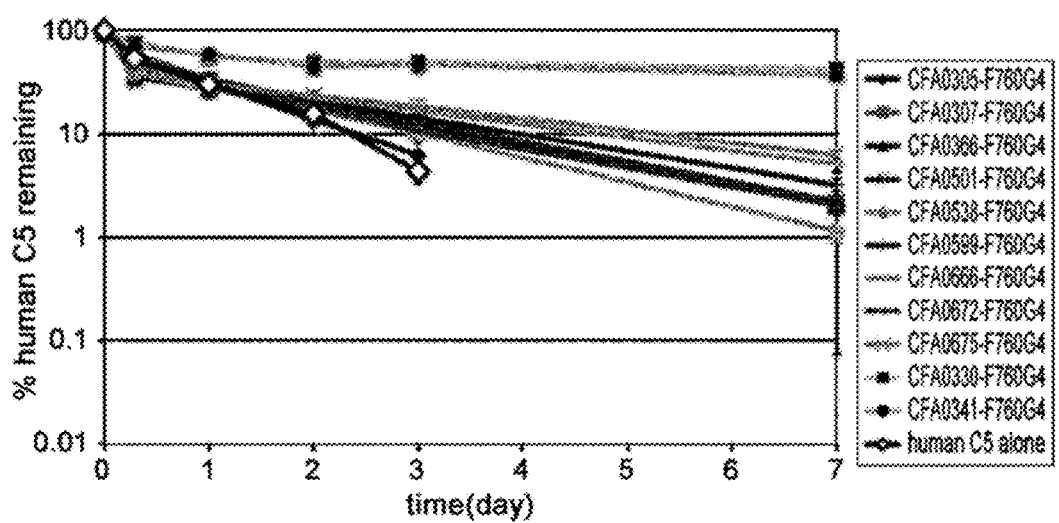

FIG. 13 illustrates the time course of plasma human C5 concentration after intravenous administration of human C5 alone or human C5 and an anti-human C5 antibody in mice assessing C5 clearance, as described in Example 6.2. CFA0305, CFA0307, CFA0366, CFA0501, CFA0538, CFA0599, CFA0666, CFA0672, and CFA0675 are antibodies grouped into epitope C and CFA0330 and CFA0341 are antibodies grouped into epitope B, as described in Example 2.2.

Figure 14:
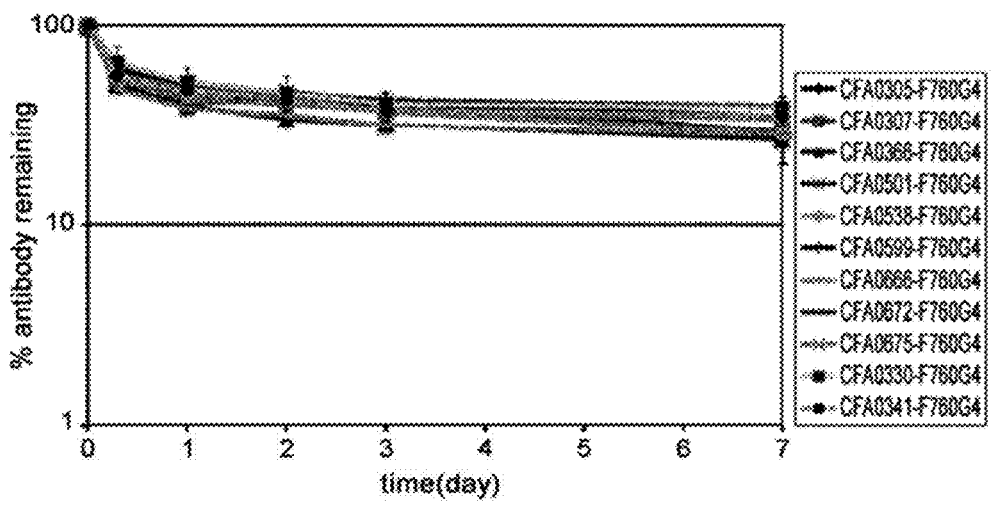

FIG. 14 illustrates the time course of plasma anti-human C5 antibody concentration after intravenous administration of human C5 and an anti-human C5 antibody in mice assessing antibody pharmacokinetics, as described in Example 6.3. CFA0305, CFA0307, CFA0366, CFA0501, CFA0538, CFA0599, CFA0666, CFA0672, and CFA0675 are antibodies grouped into epitope C and CFA0330 and CFA0341 are antibodies grouped into epitope B, as described in Example 2.2.

Figure 15:
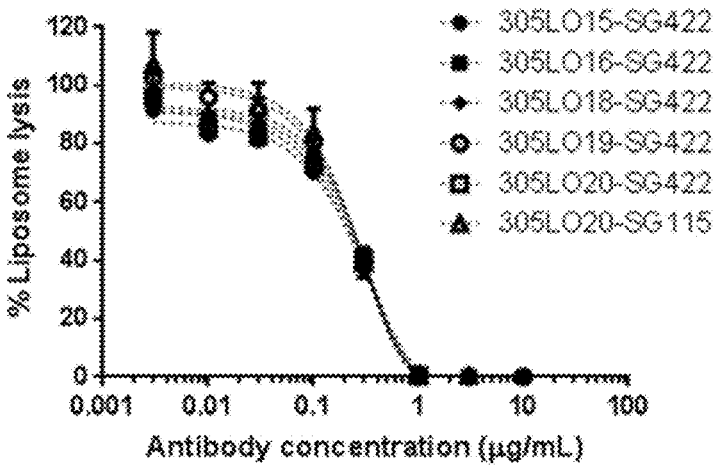

FIG. 15 illustrates inhibition of complement-activated liposome lysis by anti-C5 antibodies, as described in Example 9.1. The results of antibodies 305LO15-SG422, 305LO16-SG422, 305LO18-SG422, 305LO19-SG422, 305LO20-SG422, and 305LO20-SG115 are shown.

Figure 16:
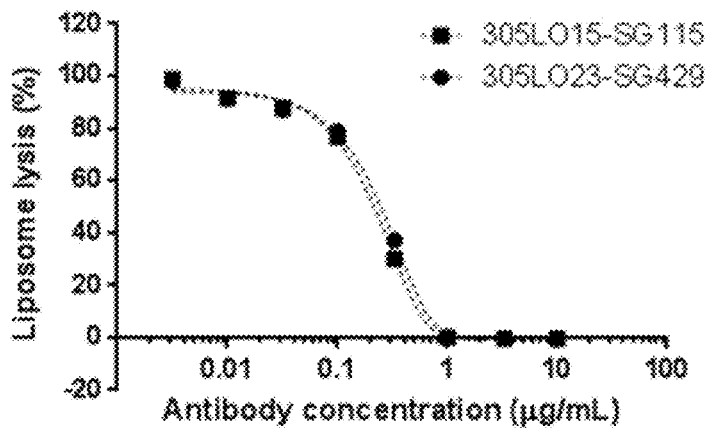

FIG. 16 illustrates inhibition of complement-activated liposome lysis by anti-C5 antibodies, as described in Example 9.1. The results of antibodies 305LO15-SG115 and 305LO23-SG429 are shown.

Figure 17:
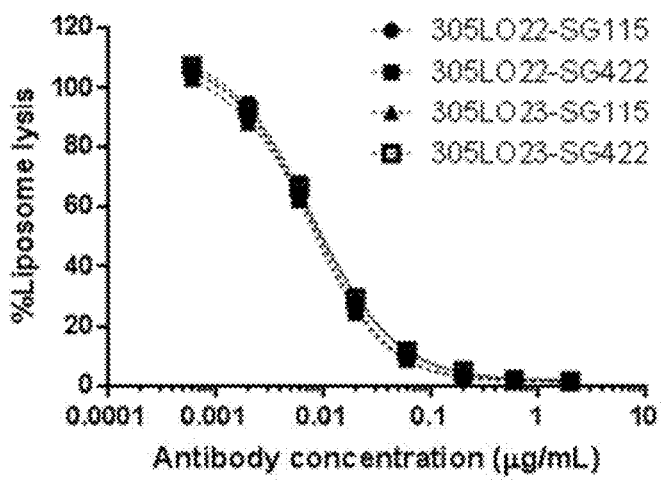

FIG. 17 illustrates inhibition of complement-activated liposome lysis by anti-C5 antibodies, as described in Example 9.1. The results of antibodies 305LO22-SG115, 305LO22-SG422, 305LO23-SG115, and 305LO23-SG422 are shown.

Figure 18:
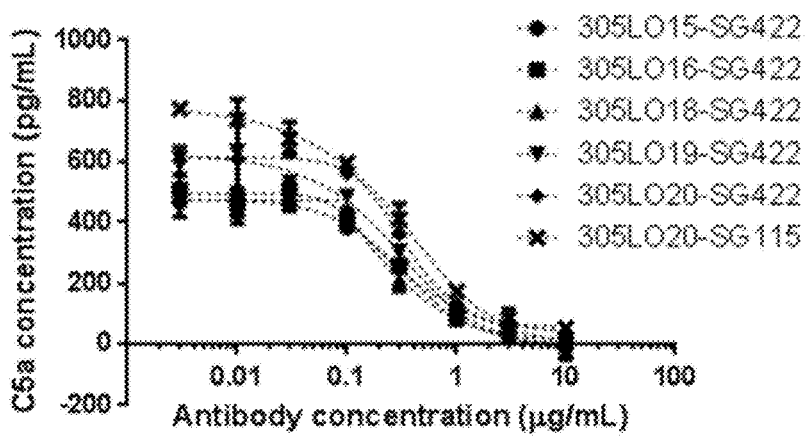

FIG. 18 illustrates inhibition of C5a generation by anti-C5 antibodies, as described in Example 9.2. C5a concentrations were quantified in the supernatants obtained during the liposome lysis assay described in FIG. 15.

Figure 19:
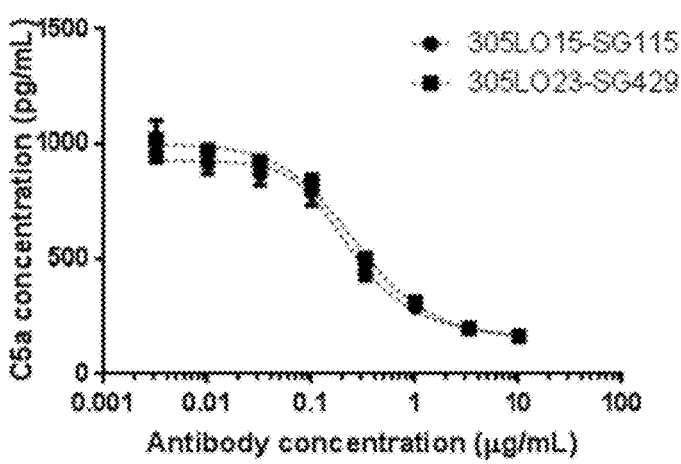

FIG. 19 illustrates inhibition of C5a generation by anti-C5 antibodies, as described in Example 9.2. C5a concentrations were quantified in the supernatants obtained during the liposome lysis assay described in FIG. 16.

Figure 20:
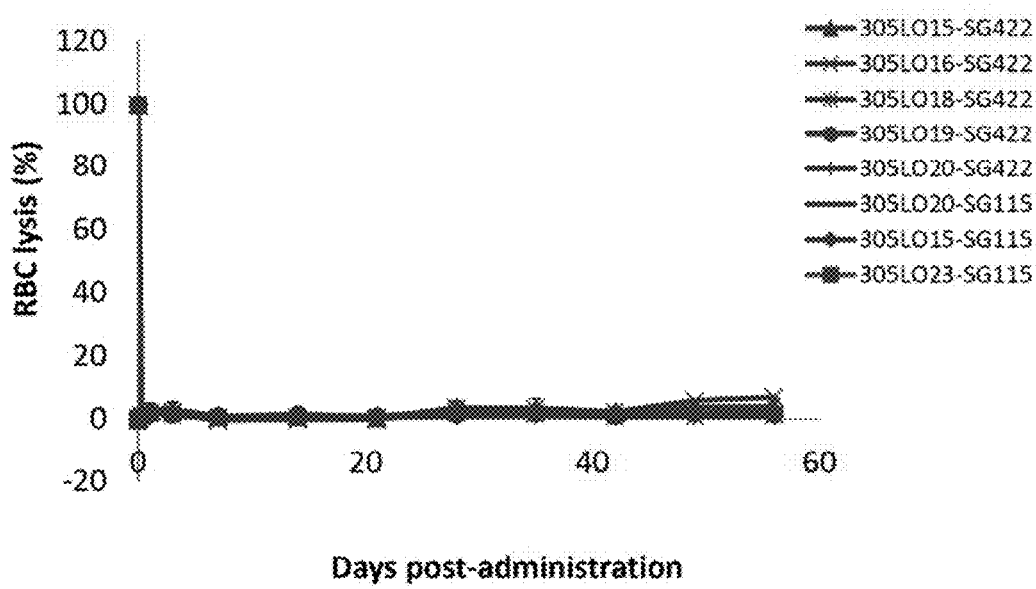

FIG. 20 illustrates inhibition of complement activity in monkey plasma by anti-C5 antibodies, as described in Example 9.3. Anti-C5 antibodies were administered into cynomolgus monkeys, and complement activities in plasma of the monkeys were measured in hemolysis assay.

Figure 21:
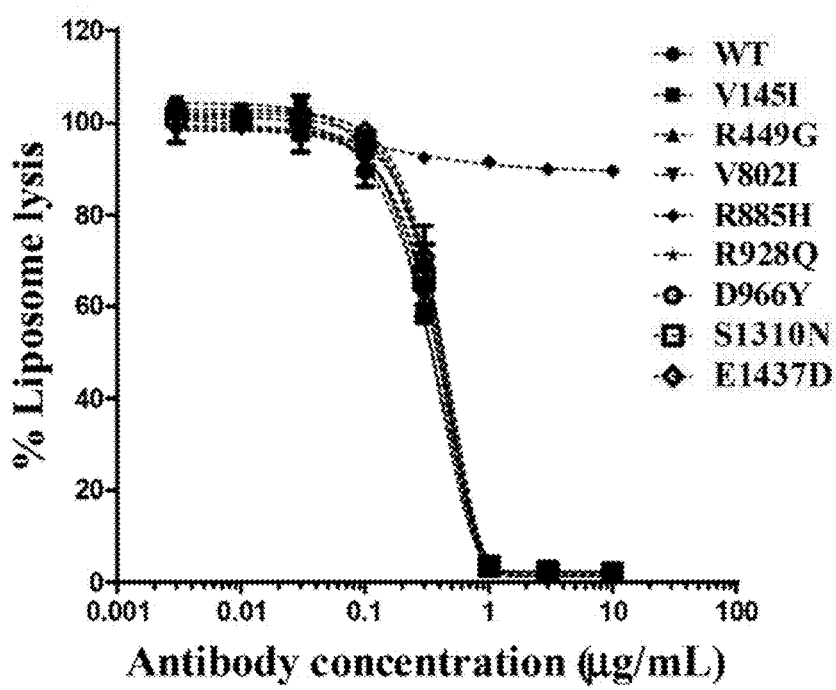

FIG. 21 illustrates inhibition of biological activity of wild type C5 (WT) and C5 variants (V145I, R449G, V802I, R885H, R928Q, D966Y, S1310N, and E1437D) by an anti-C5 antibody (eculizumab), as described in Example 9.4.

Figure 22:
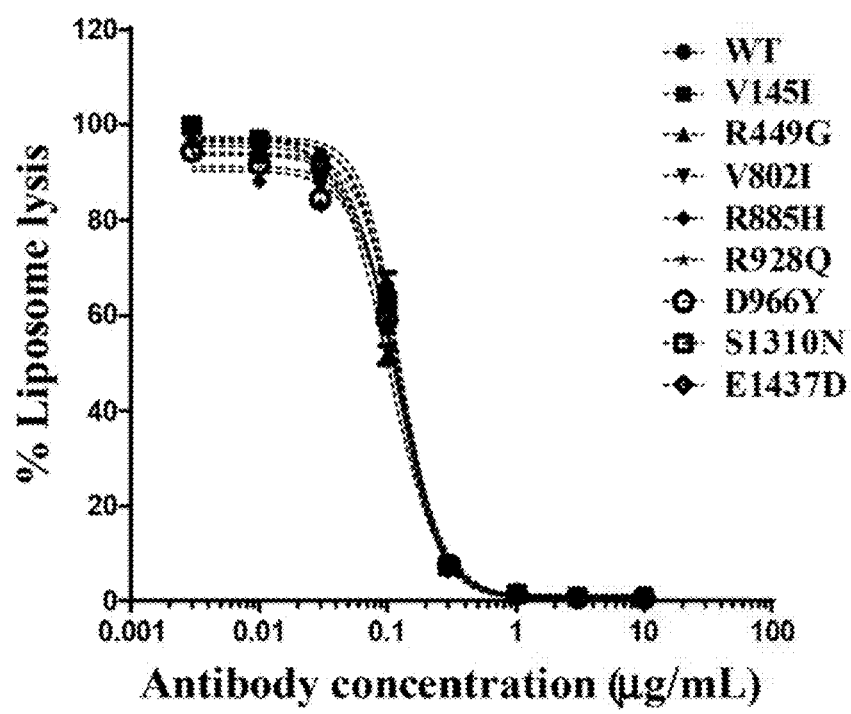

FIG. 22 illustrates inhibition of biological activity of wild type C5 (WT) and C5 variants (V145I, R449G, V802I, R885H, R928Q, D966Y, S1310N, and E1437D) by anti-C5 antibody (a 305 variant), as described in Example 9.4.

Figure 23:
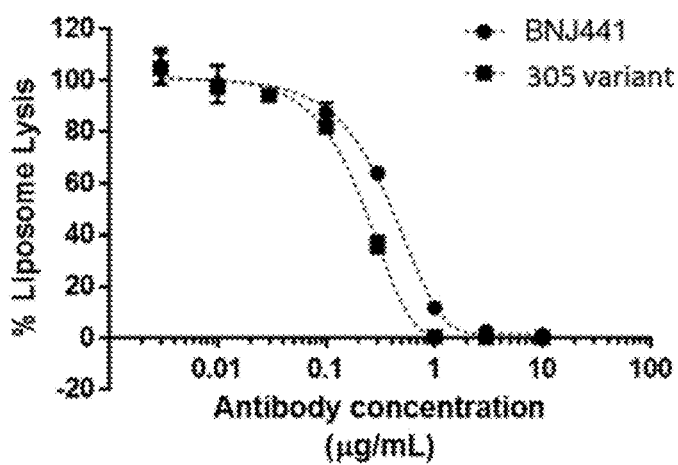

FIG. 23 illustrates inhibition of complement-activated liposome lysis by anti-C5 antibodies (BNJ441 and a 305 variant), as described in Example 9.5.

Figure 24:
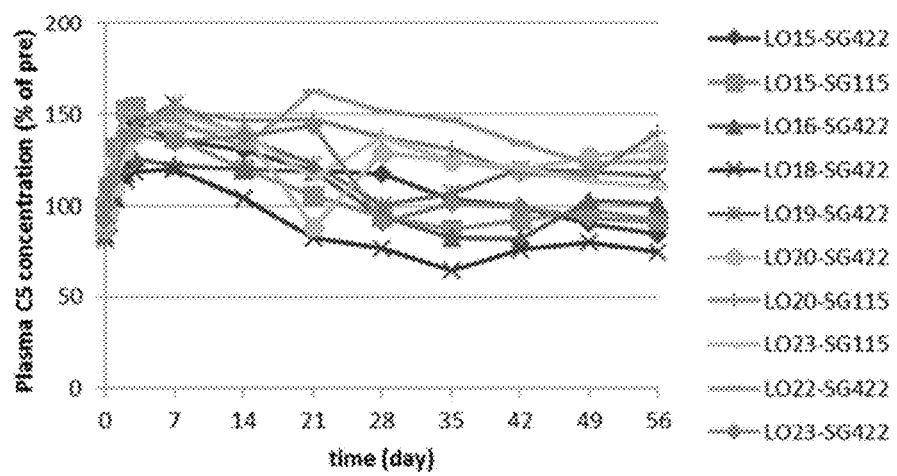

FIG. 24 illustrates the time course of plasma cynomolgus C5 concentration after intravenous administration of an anti-human C5 antibody in cynomolgus monkeys assessing C5 clearance, as described in Example 10.2.

Figure 25:
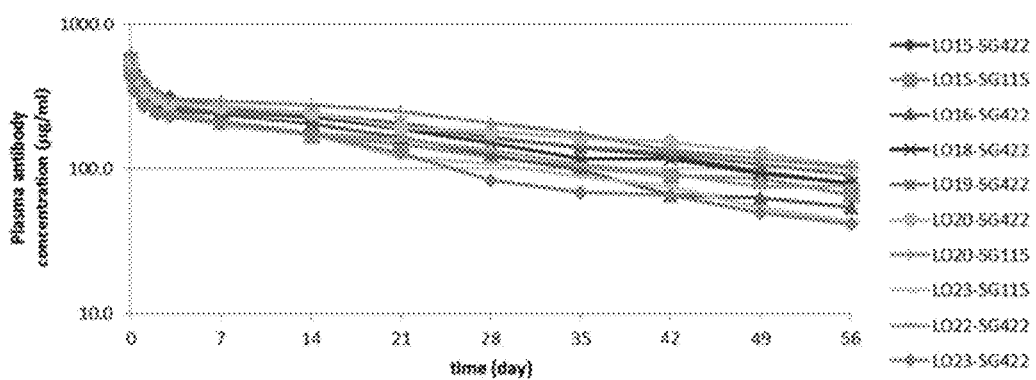

FIG. 25 illustrates the time course of plasma anti-human C5 antibody concentration after intravenous administration of an anti-human C5 antibody in cynomolgus monkeys assessing antibody pharmacokinetics, as described in Example 10.3.

Figure 26A:
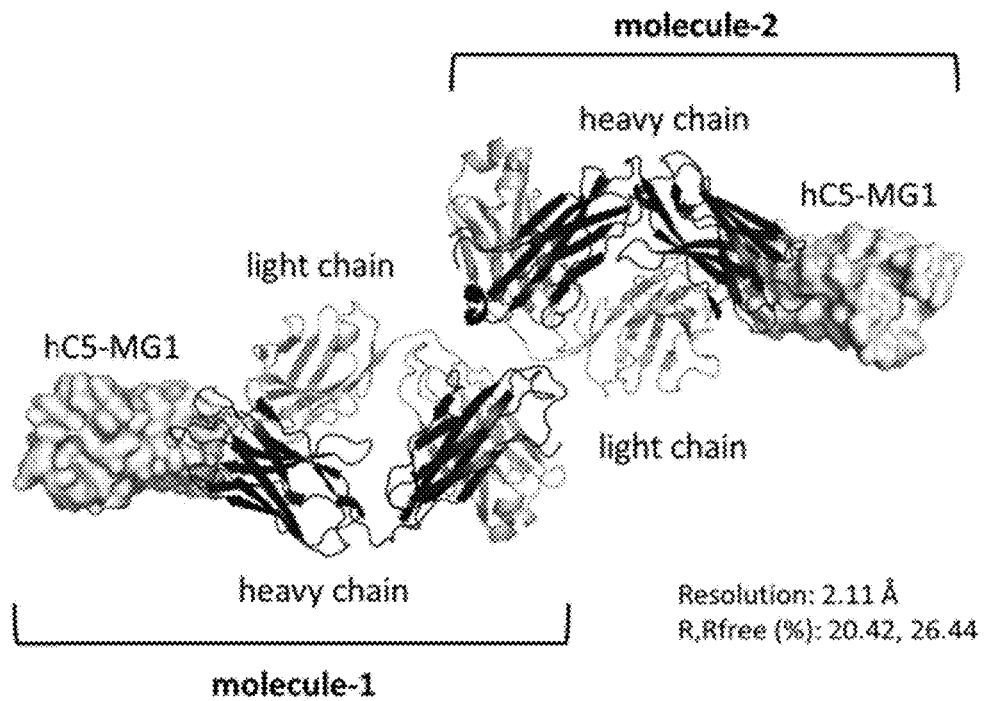
Figure 26B:
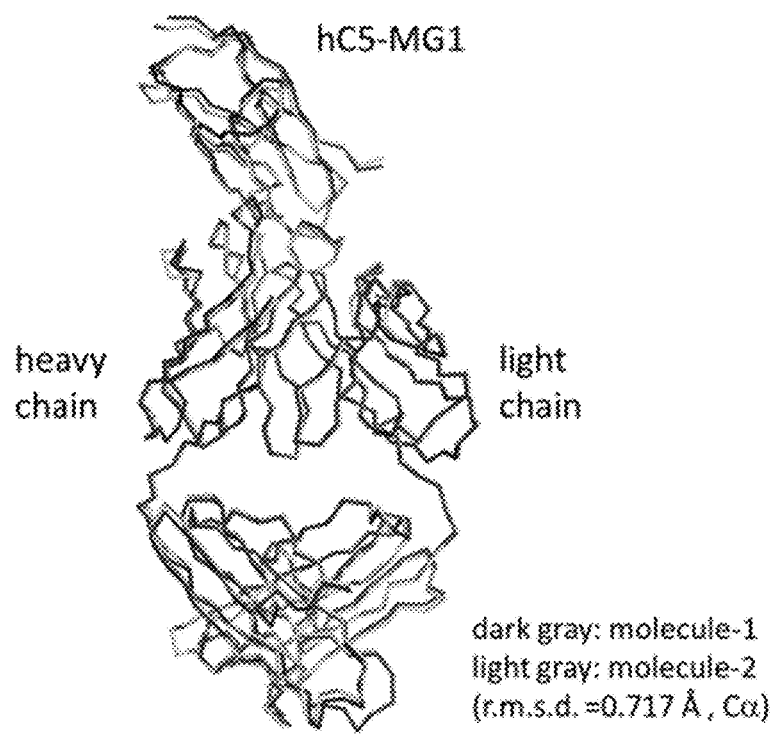

FIGS. 26A and 26B illustrate the crystal structure of the 305 Fab bound to the human C5 (hC5)-MG1 domain, as described in Example 11.6. FIG. 26A illustrates an asymmetric unit. MG1 is shown in surface representation and the 305 Fab is shown as ribbons (dark gray: heavy chain, light gray: light chain). FIG. 26B illustrates molecules 1 and 2 superimposed (dark gray: molecule 1, light gray: molecule 2).

Figure 27B:
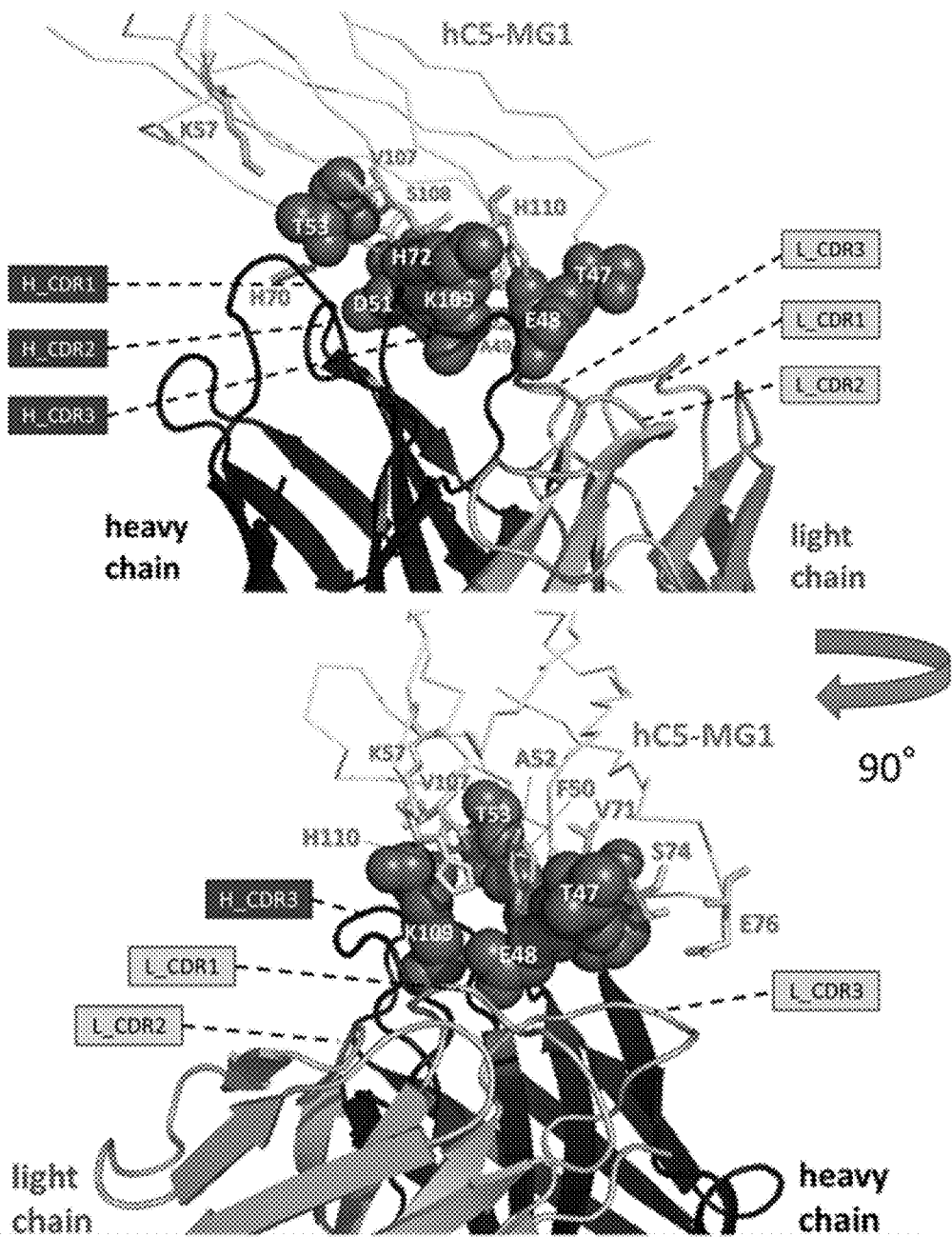

FIGS. 27A and 27B illustrate the epitope of the 305 Fab contact region on the MG1 domain, as described in Example 11.6. FIG. 27A illustrates epitope mapping in the MG1 amino acid sequence (dark gray: closer than 3.0 Å, light gray: closer than 4.5 Å). FIG. 27B illustrates epitope mapping in the crystal structure (dark gray spheres: closer than 3.0 Å, light gray sticks: closer than 4.5 Å).

Figure 28A:
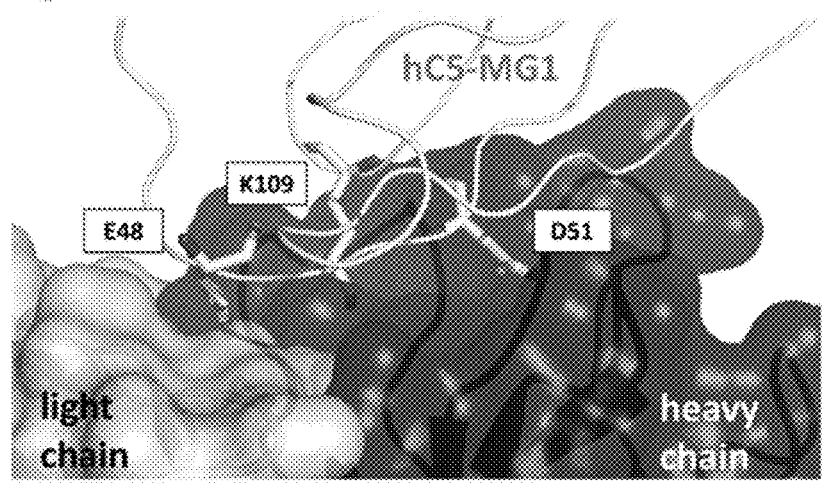

FIG. 28A illustrates a close-up view of the interactions E48, D51, and K109 (stick representation) with the 305 Fab (surface representation), as described in Example 11.7.

Figure 28B:
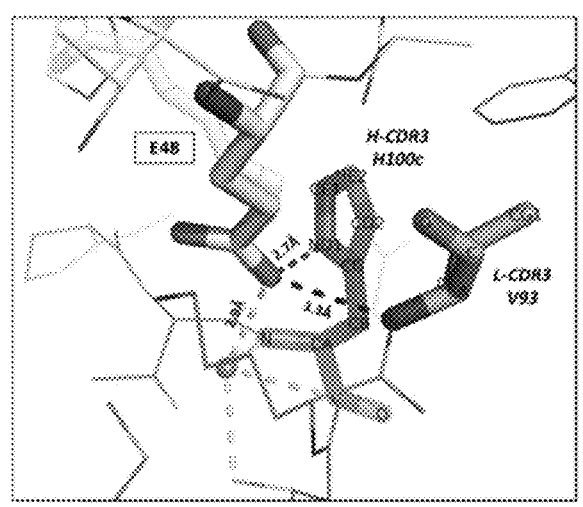

FIG. 28B illustrates interactions between E48 and its environment (dark gray dotted line: hydrogen bond with the Fab, light gray dotted line: water-mediated hydrogen bond), as described in Example 11.7.

Figure 28C:
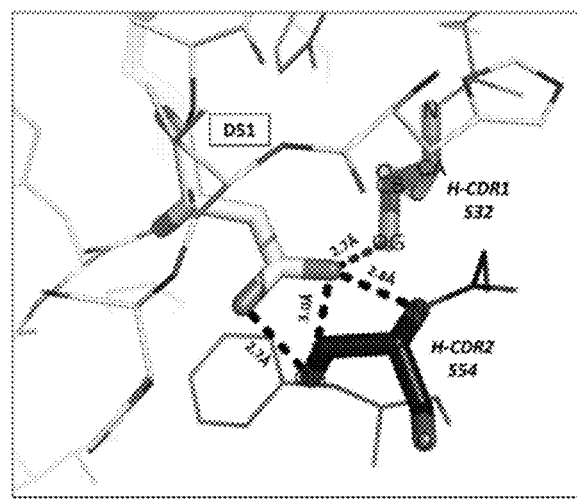

FIG. 28C illustrates interactions between D51 and its environment (dark gray dotted line: hydrogen bond with the Fab), as described in Example 11.7.

Figure 28D:
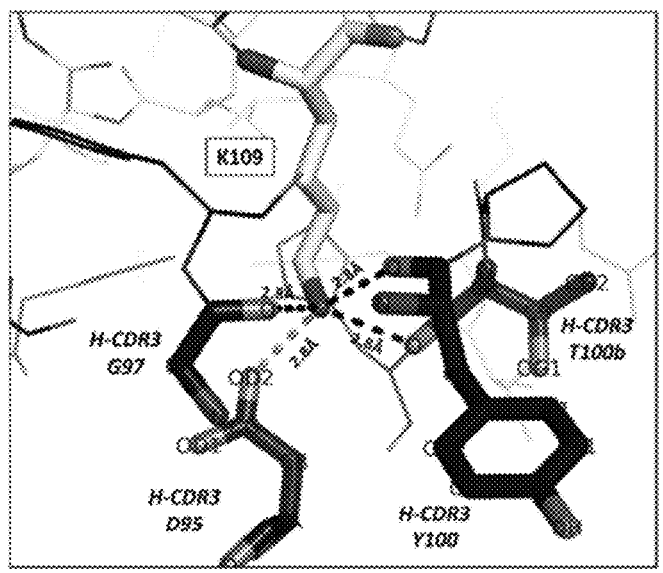

FIG. 28D illustrates interactions between K109 and its environment (dark gray dotted line: hydrogen bond with the Fab, light gray dotted line: salt bridge with H-CDR3_D95), as described in Example 11.7.

Figure 29A:
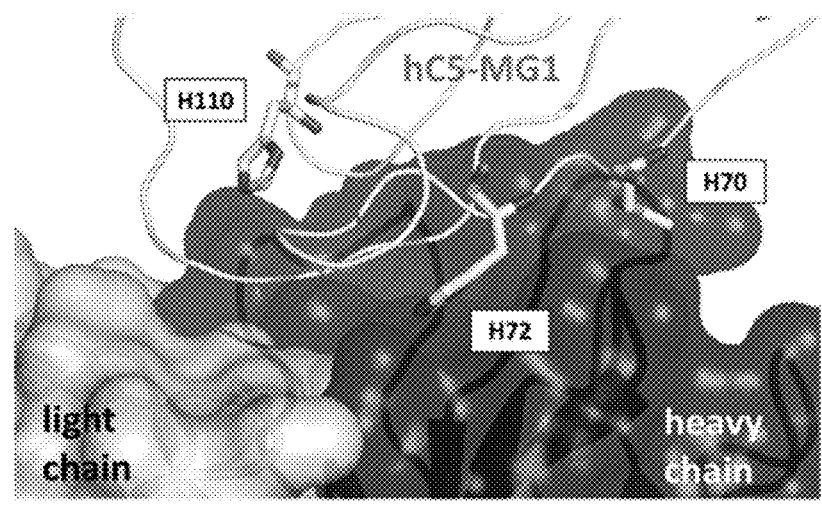

FIG. 29A illustrates a close-up view of the interactions of H70, H72, and H110 (stick representation) with the 305 Fab (surface representation), as described in Example 11.8, in the same orientation as FIG. 28A.

Figure 29B:
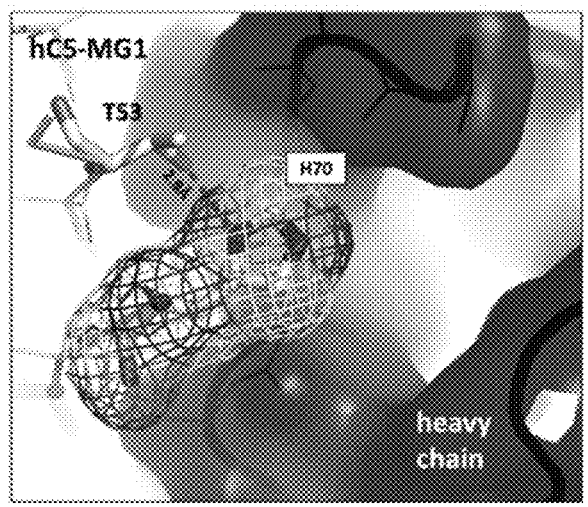
Figure 29C:
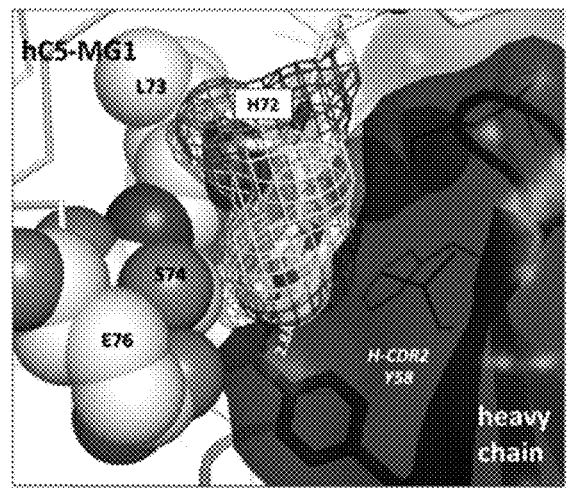
Figure 29D:
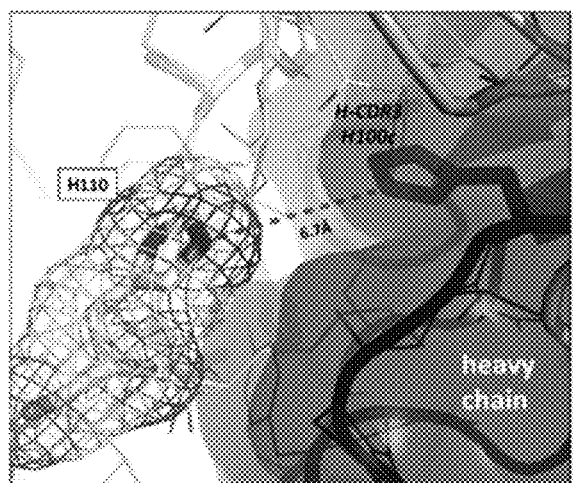

FIGS. 29B, 29C, and 29D illustrate interactions between each histidine residue (H70, H72, and H110, respectively) and its environment, as described in Example 11.8. These histidine residues are indicated is stick and mesh representation. Hydrogen bonds are indicated by dotted lines in FIGS. 29B and 29C. The distance between H110 and H-CDR3_H100c is shown in FIG. 29D (dotted line).

DETAILED DESCRIPTION

The techniques and procedures described or referenced herein are generally well understood and commonly employed using conventional methodology by those skilled in the art, such as, for example, the widely utilized methodologies described in Sambrook et al., Molecular Cloning: A Laboratory Manual 3d edition (2001) Cold Spring Harbor Laboratory Press, Cold Spring Harbor, N.Y.; Current Protocols in Molecular Biology (F. M. Ausubel, et al. eds., (2003)); the series Methods in Enzymology (Academic Press, Inc.): PCR 2: A Practical Approach (M. J. MacPherson, B. D. Hames and G. R. Taylor eds. (1995)), Harlow and Lane, eds. (1988) Antibodies, A Laboratory Manual, and Animal Cell Culture (R. I. Freshney, ed. (1987)); Oligonucleotide Synthesis (M. J. Gait, ed., 1984); Methods in Molecular Biology, Humans Press; Cell Biology: A Laboratory Notebook (J. E. Cellis, ed., 1998) Academic Press; Animal Cell Culture (R. I. Freshney), ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-8) J. Wiley and Sons; Handbook of Experimental Immunology (D. M. Weir and C. C. Blackwell, eds.); Gene Transfer Vectors for Mammalian Cells (J. M. Miller and M. P. Calos, eds., 1987); PCR: The Polymerase Chain Reaction, (Mullis et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: A Practical Approach (D. Catty., ed., IRL Press, 1988-1989); Monoclonal Antibodies: A Practical Approach (P. Shepherd and C. Dean, eds., Oxford University Press, 2000); Using Antibodies: A Laboratory Manual (E. Harlow and D. Lane (Cold Spring Harbor Laboratory Press, 1999); The Antibodies (M. Zanetti and J. D. Capra, eds., Harwood Academic Publishers, 1995); and Cancer: Principles and Practice of Oncology (V. T. DeVita et al., eds., J. B. Lippincott Company, 1993).

I. Definitions

Unless defined otherwise, technical and scientific terms used herein have the same meaning as commonly understood by one of ordinary skill in the art to which this invention belongs. Singleton et al., Dictionary of Microbiology and Molecular Biology 2nd ed., J. Wiley & Sons (N.Y., N.Y. 1994), and March, Advanced Organic Chemistry Reactions, Mechanisms and Structure 4th ed., John Wiley & Sons (New York, N.Y. 1992), provide one skilled in the art with a general guide to many of the terms used in the present application. All references cited herein, including patent applications and publications, are incorporated by reference in their entirety. In particular, the disclosure of Japanese Pat. Appl. No. 2014-257647, filed Dec. 19, 2014, is herein incorporated by reference in its entirety.

For purposes of interpreting this specification, the following definitions will apply and whenever appropriate, terms used in the singular will also include the plural and vice versa. It is to be understood that the terminology used herein is for the purpose of describing particular embodiments only, and is not intended to be limiting. In the event that any definition set forth below conflicts with any document incorporated herein by reference, the definition set forth below shall control.

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Specific illustrative and exemplary embodiments for measuring binding affinity are described in the following.

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

The terms "anti-C5 antibody" and "an antibody that binds to C5" refer to an antibody that is capable of binding C5 with sufficient affinity such that the antibody is useful as a diagnostic and/or therapeutic agent in targeting C5. In one embodiment, the extent of binding of an anti-C5 antibody to an unrelated, non-C5 protein is less than about 10% of the binding of the antibody to C5 as measured, e.g., by a radioimmunoassay (RIA). In certain embodiments, an antibody that binds to C5 has a dissociation constant (Kd) of ≤1 μM, ≤100 nM, ≤10 nM, ≤1 nM, ≤0.1 nM, ≤0.01 nM, or ≤0.001 nM (e.g., $10^{-8}$ M or less, e.g., from $10^{-8}$ M to $10^{-13}$ M, e.g., from $10^{-9}$ M to $10^{-13}$ M). In certain embodiments, an anti-C5 antibody binds to an epitope of C5 that is conserved among C5 from different species.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g., scFv); and multispecific antibodies formed from antibody fragments.

An "antibody that binds to the same epitope" as a reference antibody refers to an antibody that blocks binding of the reference antibody to its antigen in a competition assay, and/or conversely, the reference antibody blocks binding of the antibody to its antigen in a competition assay. An exemplary competition assay is provided herein.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG$_1$, IgG$_2$, IgG$_3$, IgG$_4$, IgA$_1$, and IgA$_2$. The heavy chain constant domains that correspond to the different classes of immunoglobulins are called $\alpha$, $\delta$, $\epsilon$, $\gamma$, and $\mu$, respectively.

The term "cytotoxic agent" as used herein refers to a substance that inhibits or prevents a cellular function and/or causes cell death or destruction. Cytotoxic agents include, but are not limited to, radioactive isotopes (e.g., At$^{211}$, I$^{131}$, I$^{125}$, Y$^{90}$, Re$^{186}$, Re$^{188}$, Sm$^{153}$, Bi$^{212}$, P$^{32}$, Pb$^{212}$ and radioactive isotopes of Lu); chemotherapeutic agents or drugs (e.g., methotrexate, adriamycin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anticancer agents disclosed below.

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g., B cell receptor); and B cell activation.

An "effective amount" of an agent, e.g., a pharmaceutical formulation, refers to an amount effective, at dosages and for periods of time necessary, to achieve the desired therapeutic or prophylactic result.

The term "epitope" includes any determinant capable of being bound by an antibody. An epitope is a region of an antigen that is bound by an antibody that targets that antigen, and includes specific amino acids that directly contact the antibody. Epitope determinants can include chemically active surface groupings of molecules such as amino acids, sugar side chains, phosphoryl or sulfonyl groups, and can have specific three dimensional structural characteristics, and/or specific charge characteristics. Generally, antibodies specific for a particular target antigen will preferentially recognize an epitope on the target antigen in a complex mixture of proteins and/or macromolecules.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., *Sequences of Proteins of Immunological Interest*, 5th Ed. Public Health Service, National Institutes of Health, Bethesda, Md., 1991.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The terms "full length antibody," "intact antibody," and "whole antibody" are used herein interchangeably to refer to an antibody having a structure substantially similar to a native antibody structure or having heavy chains that contain an Fc region as defined herein.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest*, Fifth Edition, NIH Publication 91-3242, Bethesda Md. (1991), vols. 1-3, which is herein incorporated by reference in its entirety. In one embodiment, for the VL, the subgroup is subgroup kappa 1 as in Kabat et al., supra. In one embodiment, for the VH, the subgroup is subgroup III as in Kabat et al., supra.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR" as used herein refers to each of the regions of an antibody variable domain which are hypervariable in sequence ("complementarity determining regions" or "CDRs") and/or form structurally defined loops ("hypervariable loops") and/or contain the antigen-contacting residues ("antigen contacts"). Generally, antibodies comprise six HVRs: three in the VH (H1, H2, H3), and three in the VL (L1, L2, L3). Exemplary HVRs herein include: (a) hypervariable loops occurring at amino acid residues 26-32 (L1), 50-52 (L2), 91-96 (L3), 26-32 (H1), 53-55 (H2), and 96-101 (H3) (Chothia, J. Mol. Biol. 196:901-917 (1987)); (b) CDRs occurring at amino acid residues 24-34 (L1), 50-56 (L2), 89-97 (L3), 31-35b (H1), 50-65 (H2), and 95-102 (H3) (Kabat et al., Sequences of Proteins of Immunological Interest, 5th Ed. Public Health Service, NIH, Bethesda, Md. (1991)); (c) antigen contacts occurring at amino acid residues 27c-36 (L1), 46-55 (L2), 89-96 (L3), 30-35b (H1), 47-58 (H2), and 93-101 (H3) (MacCallum et al. J. Mol. Biol. 262:732-745 (1996)); and (d) combinations of (a), (b), and/or (c), including HVR amino acid residues 46-56 (L2), 47-56 (L2), 48-56 (L2), 49-56 (L2), 26-35 (H1), 26-35b (H1), 49-65 (H2), 93-102 (H3), and 94-102 (H3).

Unless otherwise indicated, HVR residues and other residues in the variable domain (e.g., FR residues) are numbered herein according to Kabat et al., supra.

An "immunoconjugate" is an antibody conjugated to one or more heterologous molecule(s), including but not limited to a cytotoxic agent.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC) methods. For review of methods for assessment of antibody purity, see, e.g., Flatman et al., J. Chromatogr. B 848:79-87 (2007).

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an anti-C5 antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

A "naked antibody" refers to an antibody that is not conjugated to a heterologous moiety (e.g., a cytotoxic moiety) or radiolabel. The naked antibody may be present in a pharmaceutical formulation.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

The term "package insert" is used to refer to instructions customarily included in commercial packages of therapeutic products, that contain information about the indications, usage, dosage, administration, combination therapy, contraindications and/or warnings concerning the use of such therapeutic products.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the US Copyright Office, Washington D.C., 20559, where it is registered under US Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y, where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

The term "C5", as used herein, encompasses any native C5 from any vertebrate source, including mammals such as primates (e.g., humans and monkeys) and rodents (e.g., mice and rats). Unless otherwise indicated, the term "C5" refers to a human C5 protein having the amino acid sequence shown in SEQ ID NO: 39 and containing the β chain sequence shown in SEQ ID NO: 40. The term encompasses "full-length," unprocessed C5 as well as any form of C5 that results from processing in the cell. The term also encompasses naturally occurring variants of C5, e.g., splice variants or allelic variants. The amino acid sequence of an exemplary human C5 is shown in SEQ ID NO: 39 ("wild-type" or "WT" C5). The amino acid sequence of an exemplary β chain of human C5 is shown in SEQ ID NO: 40. The amino acid sequences of exemplary MG1, MG2 and MG1-MG2 domains of the β chain of human C5 are shown in SEQ ID NO: 41, 42, and 43, respectively. The amino acid sequences of exemplary cynomolgus monkey and murine C5 are shown in SEQ ID NO: 44 and 105, respectively. Amino acid residues 1-19 of SEQ ID NOs: 39, 40, 43, 44, and 105 correspond to a signal sequence that is removed during processing in the cell and is thus missing from the corresponding exemplary amino acid sequence.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. Kuby Immunology, $6^{th}$ ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., J. Immunol. 150:880-887 (1993); Clarkson et al., Nature 352:624-628 (1991).

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors".

II. Compositions and Methods

In one aspect, the invention is based, in part, on anti-C5 antibodies and uses thereof. In certain embodiments, antibodies that bind to C5 are provided. Antibodies of the invention are useful, e.g., for the diagnosis or treatment of a complement-mediated disease or condition which involves excessive or uncontrolled activation of C5.

A. Exemplary Anti-C5 Antibodies

In one aspect, the invention provides isolated antibodies that bind to C5. In certain embodiments, an anti-C5 antibody of the present invention binds to an epitope within the β chain of C5. In certain embodiments, the anti-C5 antibody binds to an epitope within the MG1-MG2 domain of the β chain of C5. In certain embodiments, the anti-C5 antibody binds to an epitope within a fragment consisting of amino acids 19-180 of the β chain of C5. In certain embodiments, the anti-C5 antibody binds to an epitope within the MG1 domain (amino acids 20-124 of SEQ ID NO: 40 (SEQ ID NO: 41)) of the β chain of C5. In certain embodiments, the anti-C5 antibody binds to an epitope within a fragment consisting of amino acids 33-124 of the β chain of C5 (SEQ ID NO: 40). In another embodiment, the antibody does not bind to a fragment shorter than the fragment consisting of amino acids 33-124 of the β chain of C5, e.g., a fragment consisting of amino acids 45-124, 52-124, 33-111, 33-108, or 45-111 of the β chain of C5 (SEQ ID NO: 40).

In another aspect, the invention provides anti-C5 antibodies that exhibit pH-dependent binding characteristics. As used herein, the expression "pH-dependent binding" means that the antibody exhibits "reduced binding to C5 at acidic pH as compared to its binding at neutral pH" (for purposes of the present disclosure, both expressions may be used interchangeably). For example, antibodies "with pH-dependent binding characteristics" include antibodies that bind to C5 with higher affinity at neutral pH than at acidic pH. In certain embodiments, the antibodies of the present invention bind to C5 with at least 2, 3, 5, 10, 15, 20, 25, 30, 35, 40, 45, 50, 55, 60, 65, 70, 75, 80, 85, 90, 95, 100, 200, 400, 1000, 10000, or more times higher affinity at neutral pH than at acidic pH. In some embodiments, the antibodies bind to C5 with higher affinity at pH7.4 than at pH5.8. In further embodiments, the antibodies of the present invention bind to C5 with at least 2, 3, 5, 10, 15, 20, 25, 30, 35, 40, 45, 50, 55, 60, 65, 70, 75, 80, 85, 90, 95, 100, 200, 400, 1000, 10000, or more times higher affinity at pH7.4 than at pH5.8.

The "affinity" of an antibody for C55, for purposes of the present disclosure, is expressed in terms of the KD of the antibody. The KD of an antibody refers to the equilibrium dissociation constant of an antibody-antigen interaction. The greater the KD value is for an antibody binding to its antigen, the weaker its binding affinity is for that particular antigen. Accordingly, as used herein, the expression "higher affinity at neutral pH than at acidic pH" (or the equivalent expression "pH-dependent binding") means that the KD for the antibody binding to C5 at acidic pH is greater than the KD for the antibody binding to C5 at neutral pH. For example, in the context of the present invention, an antibody is considered to bind to C5 with a higher affinity at neutral pH than at acidic pH if the KD of the antibody binding to C5 at acidic pH is at least 2 times greater than the KD of the antibody binding to C5 at neutral pH. Thus, the present invention includes antibodies that bind to C5 at acidic pH with a KD that is at least 2, 3, 5, 10, 15, 20, 25, 30, 35, 40, 45, 50, 55, 60, 65, 70, 75, 80, 85, 90, 95, 100, 200, 400, 1000, 10000, or more times greater than the KD of the antibody binding to C5 at neutral pH. In another embodiment, the KD value of the antibody at neutral pH can be $10^{-7}$ M, $10^{-8}$ M, $10^{-9}$ M, $10^{-10}$ M, $10^{-11}$ M, $10^{-12}$ M, or less. In another embodiment, the KD value of the antibody at acidic pH can be $10^{-9}$ M, $10^{-8}$ M, $10^{-7}$ M, $10^{-6}$ M, or greater.

In further embodiments an antibody is considered to bind to C5 with a higher affinity at neutral pH than at acidic pH if the KD of the antibody binding to C5 at pH5.8 is at least 2 times greater than the KD of the antibody binding to C5 at pH7.4. In some embodiments the provided antibodies bind to C5 at pH5.8 with a KD that is at least 3, 5, 10, 15, 20, 25, 30, 35, 40, 45, 50, 55, 60, 65, 70, 75, 80, 85, 90, 95, 100, 200, 400, 1000, 10000, or more times greater than the KD of the antibody binding to C5 at pH7.4. In another embodiment, the KD value of the antibody at pH7.4 can be $10^{-7}$ M, $10^{-8}$ M, $10^{-9}$ M, $10^{-10}$ M, $10^{-11}$ M, $10^{-12}$ M, or less. In another embodiment, the KD value of the antibody at pH5.8 can be $10^{-9}$ M, $10^{-8}$ M, $10^{-7}$ M, $10^{-6}$ M, or greater.

The binding properties of an antibody for a particular antigen may also be expressed in terms of the kd of the antibody. The kd of an antibody refers to the dissociation rate constant of the antibody with respect to a particular antigen and is expressed in terms of reciprocal seconds (i.e., $\sec^{-1}$). An increase in kd value signifies weaker binding of an antibody to its antigen. The present invention therefore includes antibodies that bind to C5 with a higher kd value at acidic pH than at neutral pH. The present invention includes antibodies that bind to C5 at acidic pH with a kd that is at least 2, 3, 5, 10, 15, 20, 25, 30, 35, 40, 45, 50, 55, 60, 65, 70, 75, 80, 85, 90, 95, 100, 200, 400, 1000, 10000, or more times greater than the kd of the antibody binding to C5 at neutral pH. In another embodiment, the kd value of the antibody at neutral pH can be $10^{-2}$ 1/s, $10^{-3}$ 1/s, $10^{-4}$ 1/s, $10^{-5}$ 1/s, $10^{-6}$ 1/s, or less. In another embodiment, the kd value of the antibody at acidic pH can be $10^{-3}$ 1/s, $10^{-2}$ 1/s, $10^{-1}$ 1/s, or greater. The invention also includes antibodies that bind to C5 with a higher kd value at pH5.8 than at pH7.4. The present invention includes antibodies that bind to C5 at pH5.8 with a kd that is at least 3, 5, 10, 15, 20, 25, 30, 35, 40, 45, 50, 55, 60, 65, 70, 75, 80, 85, 90, 95, 100, 200, 400, 1000, 10000, or more times greater than the kd of the antibody binding to C5 at pH7.4. In another embodiment, the kd value of the antibody at pH7.4 can be $10^{-2}$ 1/s, $10^{-3}$ 1/s, $10^{-4}$ 1/s, $10^{-5}$ 1/s, $10^{-6}$ 1/s, or less. In another embodiment, the kd value of the antibody at pH5.8 can be $10^{-3}$ 1/s, $10^{-2}$ 1/s, $10^{-1}$ 1/s, or greater.

In certain instances, a "reduced binding to C5 at acidic pH as compared to its binding at neutral pH" is expressed in terms of the ratio of the KD value of the antibody binding to C5 at acidic pH to the KD value of the antibody binding to C5 at neutral pH (or vice versa). For example, an antibody may be regarded as exhibiting "reduced binding to C5 at acidic pH as compared to its binding at neutral pH", for purposes of the present invention, if the antibody exhibits an acidic/neutral KD ratio of 2 or greater. In certain exemplary embodiments, the pH5.8/pH7.4 KD ratio for an antibody of the present invention is 2 or greater. In certain exemplary embodiments, the acidic/neutral KD ratio for an antibody of the present invention can be 2, 3, 5, 10, 15, 20, 25, 30, 35, 40, 45, 50, 55, 60, 65, 70, 75, 80, 85, 90, 95, 100, 200, 400, 1000, 10000, or greater. In another embodiment, the KD value of the antibody at neutral pH can be $10^{-7}$ M, $10^{-8}$ M, $10^{-9}$ M, $10^{-10}$ M, $10^{-11}$ M, $10^{-12}$ M, or less. In another embodiment, the KD value of the antibody at acidic pH can be $10^{-9}$ M, $10^{-8}$ M, $10^{-7}$ M, $10^{-6}$ M, or greater. In further instances an antibody may be regarded as exhibiting "reduced binding to C5 at acidic pH as compared to its binding at neutral pH", for purposes of the present invention, if the antibody exhibits an pH5.8/pH7.4 KD ratio of 2 or greater. In certain exemplary embodiments, the pH5.8/pH7.4 KD ratio for an antibody of the present invention can be 3, 5, 10, 15, 20, 25, 30, 35, 40, 45, 50, 55, 60, 65, 70, 75, 80, 85, 90, 95, 100, 200, 400, 1000, 10000, or greater. In another embodiment, the KD value of the antibody at pH7.4 can be $10^{-7}$ M, $10^{-8}$ M, $10^{-9}$ M, $10^{-10}$ M, $10^{-11}$ M, $10^{-12}$ M, or less. In another embodiment, the KD value of the antibody at pH5.8 can be $10^{-9}$ M, $10^{-8}$ M, $10^{-7}$ M, $10^{-6}$ M, or greater.

In certain instances, a "reduced binding to C5 at acidic pH as compared to its binding at neutral pH" is expressed in terms of the ratio of the kd value of the antibody binding to C5 at acidic pH to the kd value of the antibody binding to C5 at neutral pH (or vice versa). For example, an antibody may be regarded as exhibiting "reduced binding to C5 at acidic pH as compared to its binding at neutral pH", for purposes of the present invention, if the antibody exhibits an acidic/neutral kd ratio of 2 or greater. In certain exemplary embodiments, the pH5.8/pH7.4 kd ratio for an antibody of the present invention is 2 or greater. In certain exemplary embodiments, the acidic/neutral kd ratio for an antibody of the present invention can be 2, 3, 5, 10, 15, 20, 25, 30, 35, 40, 45, 50, 55, 60, 65, 70, 75, 80, 85, 90, 95, 100, 200, 400, 1000, 10000, or greater. In further exemplary embodiments, the pH 5.8/pH 7.4 kd ratio for an antibody of the present invention can be 2, 3, 5, 10, 15, 20, 25, 30, 35, 40, 45, 50, 55, 60, 65, 70, 75, 80, 85, 90, 95, 100, 200, 400, 1000, 10000, or greater. In another embodiment, the kd value of the antibody at neutral pH can be $10^{-2}$ 1/s, $10^{-3}$ 1/s, $10^{-4}$ 1/s, $10^{-5}$ 1/s, $10^{-6}$ 1/s, or less. In a further embodiment, the kd value of the antibody at pH 7.4 can be $10^{-2}$ l/s, $10^{-3}$ l/s, $10^{-4}$ l/s, $10^{-5}$ l/s, $10^{-6}$ l/s, or less. In another embodiment, the kd value of the antibody at acidic pH can be $10^{-3}$ l/s, $10^{-2}$ l/s, $10^{-1}$ l/s, or greater. In a further embodiment, the kd value of the antibody at pH5.8 can be $10^{-3}$ l/s, $10^{-2}$ l/s, $10^{-1}$ l/s, or greater.

As used herein, the expression "acidic pH" means a pH of 4.0 to 6.5. The expression "acidic pH" includes pH values of any one of 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, and 6.5. In particular aspects, the "acidic pH" is 5.8.

As used herein, the expression "neutral pH" means a pH of 6.7 to about 10.0. The expression "neutral pH" includes pH values of any one of 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, and 10.0. In particular aspects, the "neutral pH" is 7.4.

KD values, and kd values, as expressed herein, may be determined using a surface plasmon resonance-based biosensor to characterize antibody-antigen interactions. (See, e.g., Example 3, herein). KD values, and kd values can be determined at 25° C. or 37° C.

In certain embodiments, an anti-C5 antibody of the present invention binds to an epitope within the β chain of C5 which consists of the MG1 domain (SEQ ID NO:41). In certain embodiments, an anti-C5 antibody of the present invention binds to an epitope within the β chain (SEQ ID NO: 40) of C5 which comprises at least one fragment selected from the group consisting of amino acids 47-57, 70-76, and 107-110. In certain embodiments, an anti-C5 antibody of the present invention binds to an epitope within a fragment of the β chain (SEQ ID NO: 40) of C5 which comprises at least one amino acid selected from the group consisting of Thr47, Glu48, Ala49, Phe50, Asp51, Ala52, Thr53, Lys57, His70, Val71, His72, Ser74, Glu76, Val107, Ser108, Lys109, and His110. In certain embodiments, an anti-C5 antibody of the present invention binds to an epitope within a fragment of the β chain (SEQ ID NO: 40) of C5 which comprises at least one amino acid selected from the group consisting of Glu48, Asp51, His70, His72, Lys109, and His110. In certain embodiments, binding of an anti-C5 antibody of the present invention to a C5 mutant is reduced compared to its binding to wild type C5, wherein the C5 mutant has at least one amino acid substitution at a position selected from the group consisting of Glu48, Asp51, His72, and Lys109. In another embodiment, pH-dependent binding of an anti-C5 antibody of the present invention to a C5 mutant is reduced compared to its pH-dependent binding to wild type C5, wherein the C5 mutant has at least one amino acid substitution at a position selected from the group consisting of His70, His72, and His110. In a further embodiment, an amino acid at a position selected from Glu48, Asp51, and Lys109 is substituted with alanine, and an amino acid at a position selected from His70, His72, and His110 is substituted with tyrosine in the C5 mutant.

In certain embodiments, an anti-C5 antibody of the present invention competes for binding C5 with an antibody comprising a VH and VL pair selected from: (a) a VH of SEQ ID NO:1 and a VL of SEQ ID NO:11; (b) a VH of SEQ ID NO: 22 and a VL of SEQ ID NO:26; (c) a VH of SEQ ID NO:21 and a VL of SEQ ID NO:25; (d) a VH of SEQ ID NO: 5 and a VL of SEQ ID NO:15; (e) a VH of SEQ ID NO:4 and a VL of SEQ ID NO: 14; (f) a VH of SEQ ID NO: 6 and a VL of SEQ ID NO: 16; (g) a VH of SEQ ID NO:2 and a VL of SEQ ID NO: 12; (h) a VH of SEQ ID NO: 3 and a VL of SEQ ID NO: 13; (i) a VH of SEQ ID NO:9 and a VL of SEQ ID NO:19; (j) a VH of SEQ ID NO:7 and a VL of SEQ ID NO: 17; (k) aVH of SEQ ID NO:8 and a VL of SEQ ID NO:18; (l) a VH of SEQ ID NO: 23 and a VL of SEQ ID NO:27; and (m) a VH of SEQ ID NO: 10 and a VL of SEQ ID NO:20. In further embodiments, the anti-C5 antibody binds to the same epitope as one of the above VH and VL pairs.

In certain embodiments, an anti-C5 antibody of the present invention binds C55 and contacts amino acid Asp51 (D51) of SEQ ID NO:39. In additional embodiments, an anti-C5 antibody of the present invention binds C5 and contacts amino acid Lys109 (K109) of SEQ ID NO:39. In a further embodiment, an anti-C5 antibody of the present invention binds C5 and contacts amino acid Asp51 (D51) and amino acid Lys109 (K109) of SEQ ID NO:39.

In certain embodiments, binding of an anti-C5 antibody of the present invention to a C5 mutant is reduced compared to its binding to wild type C5, wherein the C5 mutant has a Glu48Ala (E48A) substitution of SEQ ID NO:39. In another embodiment, pH-dependent binding of an anti-C5 antibody of the present invention to a C5 mutant is reduced compared to its pH-dependent binding to wild type C5, wherein the C5 mutant has a Glu48Ala (E48A) substitution of SEQ ID NO:39.

In a further embodiment, an anti-C5 antibody binds to a C5 protein consisting of the amino acid sequence of SEQ ID NO:39, but does not bind to a C5 protein consisting of the amino acid sequence of SEQ ID NO:39 with a H72Y substitution, wherein the C5 protein and the H72Y substituted C5 protein are prepared and screened under the same conditions. In a further embodiment, the anti-C5 antibody binds to a C5 protein consisting of the amino acid sequence of SEQ ID NO:39 at pH7.4, but does not bind to the H72Y substituted C5 protein at pH7.4.

Without being restricted to a particular theory, it can be speculated that the binding of an anti-C5 antibody to C5 is reduced (or almost lost) when an amino acid residue on C5 is substituted with another amino acid, which means that the amino acid residue on C5 is critical for the interactions between the anti-C5 antibody and C5, and that the antibody may recognize an epitope around the amino acid residue on C5.

It has been discovered in the present invention that a group of anti-C5 antibodies that compete with one another or bind to the same epitope can exhibit pH-dependent binding characteristics. Among amino acids, histidine, with a pKa value of approximately 6.0 to 6.5, can have different proton dissociation states between neutral and acidic pH. Therefore, a histidine residue on C5 can contribute to the pH-dependent interactions between an anti-C5 antibody and C5. Without being restricted to a particular theory, it can be speculated that an anti-C5 antibody may recognize a conformational structure around a histidine residue on C5, which is variable depending on pH. That speculation can be consistent with the experimental results described below: that the pH-dependency of an anti-C5 antibody is reduced (or almost lost) when a histidine residue on C5 is substituted with another amino acid (i.e., an anti-C5 antibody with pH-dependent binding characteristics binds to a histidine mutant of C5 with similar affinity to wild type C5 at neutral pH, while the same antibody binds to the histidine mutant of C5 with higher affinity than wild type C5 at acidic pH).

In certain embodiments, an anti-C5 antibody of the present invention binds to C5 from more than one species. In further embodiments, the anti-C5 antibody binds to C5 from human and a non-human animal. In further embodiments, the anti-C5 antibody binds to C5 from human and monkey (e.g., cynomolgus, rhesus macaque, marmoset, chimpanzee, or baboon).

In one aspect, the invention provides anti-C5 antibodies that inhibit activation of C5. In certain embodiments, anti-C5 antibodies are provided which prevent the cleavage of C5 to form C5a and C5b, thus preventing the generation of anaphylatoxic activity associated with C5a, as well as preventing the assembly of the C5b-9 membrane attack complex (MAC) associated with C5b. In certain embodiments, anti-C5 antibodies are provided which block the conversion of C5 into C5a and C5b by C5 convertase. In certain embodiments, anti-C5 antibodies are provided which block access of the C5 convertase to the cleavage site on C5. In certain embodiments, anti-C5 antibodies are provided which block hemolytic activity caused by the activation of C5. In further embodiments, anti-C5 antibodies of the present invention inhibit the activation of C5 via classical pathway and/or alternative pathway.

In one aspect, the invention provides anti-C5 antibodies that inhibit activation of a C5 variant. A C5 variant means a genetic variant of C5 which is due to genetic variation such as a mutation, polymorphism or allelic variation. A genetic variation may comprise a deletion, substitution or insertion of one or more nucleotides. A C5 variant may comprise one or more genetic variations in C5. In certain embodiments, the C5 variant has biological activity similar to wild type C5. Such C5 variant may comprise at least one variation selected from the group consisting of V145I, R449G, V802I, R885H, R928Q, D966Y, S1310N, and E1437D. Herein, R885H, for example, means a genetic variation where arginine at position 885 is substituted by histidine. In certain embodiments, an anti-C5 antibody of the present invention inhibits activation of both wild type C5 and at least one C5 variant selected from the group consisting of V145I, R449G, V802I, R885H, R928Q, D966Y, S1310N, and E1437D.

In one aspect, the invention provides an anti-C5 antibody comprising at least one, two, three, four, five, or six hypervariable regions (HVRs) selected from (a) a HVR-H1 comprising the amino acid sequence of SEQ ID NO: 45-53, or 54; (b) a HVR-H2 comprising the amino acid sequence of SEQ ID NO: 55-63, or 64; (c) a HVR-H3 comprising the amino acid sequence of SEQ ID NO: 65-73, or 74; (d) a HVR-L1 comprising the amino acid sequence of SEQ ID NO: 75-83, or 84; (e) a HVR-L2 comprising the amino acid sequence of SEQ ID NO: 85-93, or 94; and (f) a HVR-L3 comprising the amino acid sequence of SEQ ID NO: 95-103, or 104.

In one aspect, the invention provides an antibody comprising at least one, at least two, or all three VH HVR sequences selected from (a) a HVR-H1 comprising the amino acid sequence of SEQ ID NO: 45-53, or 54; (b) a HVR-H2 comprising the amino acid sequence of SEQ ID NO: 55-63, or 64; and (c) a HVR-H3 comprising the amino acid sequence of SEQ ID NO: 65-73, or 74. In one embodiment, the antibody comprises a HVR-H3 comprising the amino acid sequence of SEQ ID NO: 65-73, or 74. In another embodiment, the antibody comprises a HVR-H3 comprising the amino acid sequence of SEQ ID NO: 65-73, or 74 and a HVR-L3 comprising the amino acid sequence of SEQ ID NO: 95-103, or 104. In a further embodiment, the antibody comprises a HVR-H3 comprising the amino acid sequence of SEQ ID NO: 65-73, or 74, a HVR-L3 comprising the amino acid sequence of SEQ ID NO: 95-103, or 104, and a HVR-H2 comprising the amino acid sequence of SEQ ID NO: 55-63, or 64. In a further embodiment, the antibody comprises (a) a HVR-H1 comprising the amino acid sequence of SEQ ID NO: 45-53, or 54; (b) a HVR-H2 comprising the amino acid sequence of SEQ ID NO: 55-63, or 64; and (c) a HVR-H3 comprising the amino acid sequence of SEQ ID NO: 65-73, or 74.

In another aspect, the invention provides an antibody comprising at least one, at least two, or all three VL HVR sequences selected from (a) a HVR-L1 comprising the amino acid sequence of SEQ ID NO: 75-83, or 84; (b) a HVR-L2 comprising the amino acid sequence of SEQ ID NO: 85-93, or 94; and (c) a HVR-L3 comprising the amino acid sequence of SEQ ID NO: 95-103, or 104. In one embodiment, the antibody comprises (a) a HVR-L1 comprising the amino acid sequence of SEQ ID NO: 75-83, or 84; (b) a HVR-L2 comprising the amino acid sequence of SEQ ID NO: 85-93, or 94; and (c) a HVR-L3 comprising the amino acid sequence of SEQ ID NO: 95-103, or 104.

In another aspect, an antibody of the invention comprises (a) a VH domain comprising at least one, at least two, or all three VH HVR sequences selected from (i) a HVR-H1 comprising the amino acid sequence of SEQ ID NO: 45-53, or 54, (ii) a HVR-H2 comprising the amino acid sequence of SEQ ID NO: 55-63, or 64, and (iii) a HVR-H3 comprising the amino acid sequence of SEQ ID NO: 65-73, or 74; and (b) a VL domain comprising at least one, at least two, or all three VL HVR sequences selected from (i) a HVR-L1 comprising the amino acid sequence of SEQ ID NO: 75-83, or 84, (ii) a HVR-L2 comprising the amino acid sequence of SEQ ID NO: 85-93, or 94, and (c) a HVR-L3 comprising the amino acid sequence of SEQ ID NO: 95-103, or 104.

In another aspect, the invention provides an antibody comprising (a) a HVR-H1 comprising the amino acid sequence of SEQ ID NO: 45-53, or 54; (b) a HVR-H2 comprising the amino acid sequence of SEQ ID NO: 55-63, or 64; (c) a HVR-H3 comprising the amino acid sequence of SEQ ID NO: 65-73, or 74; (d) a HVR-L1 comprising the amino acid sequence of SEQ ID NO: 75-83, or 84; (e) a HVR-L2 comprising the amino acid sequence of SEQ ID NO: 85-93, or 94; and (f) a HVR-L3 comprising the amino acid sequence of SEQ ID NO: 95-103, or 104.

In one aspect, the invention provides an anti-C5S antibody comprising at least one, two, three, four, five, or six HVRs selected from (a) a HVR-H1 comprising the amino acid sequence of SEQ ID NO: 45, 54, 117, or 126; (b) a HVR-H2 comprising the amino acid sequence of SEQ ID NO: 55, 64, 118-120, or 127; (c) a HVR-H3 comprising the amino acid sequence of SEQ ID NO:65, 74, 121, or 128; (d) a HVR-L1 comprising the amino acid sequence of SEQ ID NO: 75, 84, 122, or 129; (e) a HVR-L2 comprising the amino acid sequence of SEQ ID NO: 85, 94, 123, 124, or 130; and (f) a HVR-L3 comprising the amino acid sequence of SEQ ID NO: 95, 104, 125, or 131.

In one aspect, the invention provides an antibody comprising at least one, at least two, or all three VH HVR sequences selected from (a) a HVR-H1 comprising the amino acid sequence of SEQ ID NO: 45, 54, 117, or 126; (b) a HVR-H2 comprising the amino acid sequence of SEQ ID NO: 55, 64, 118-120, or 127; and (c) a HVR-H3 comprising the amino acid sequence of SEQ ID NO:65, 74, 121, or 128. In one embodiment, the antibody comprises HVR-H3 comprising the amino acid sequence of SEQ ID NO:65, 74, 121, or 128. In another embodiment, the antibody comprises a HVR-H3 comprising the amino acid sequence of SEQ ID NO:65, 74, 121, or 128 and a HVR-L3 comprising the amino acid sequence of SEQ ID NO: 95, 104, 125, or 131. In a further embodiment, the antibody comprises a HVR-H3 comprising the amino acid sequence of SEQ ID NO:65, 74, 121, or 128, a HVR-L3 comprising the amino acid sequence of SEQ ID NO: 95, 104, 125, or 131, and a HVR-H2 comprising the amino acid sequence of SEQ ID NO: 55, 64, 118-120, or 127. In a further embodiment, the antibody comprises (a) a HVR-H1 comprising the amino acid sequence of SEQ ID NO: 45, 54, 117, or 126; (b) a HVR-H2 comprising the amino acid sequence of SEQ ID NO: 55, 64, 118-120, or 127; and (c) a HVR-H3 comprising the amino acid sequence of SEQ ID NO:65, 74, 121, or 128.

In another aspect, the invention provides an antibody comprising at least one, at least two, or all three VL HVR sequences selected from (a) a HVR-L1 comprising the amino acid sequence of SEQ ID NO: 75, 84, 122, or 129; (b) a HVR-L2 comprising the amino acid sequence of SEQ ID NO: 85, 94, 123, 124, or 130; and (c) a HVR-L3 comprising the amino acid sequence of SEQ ID NO: 95, 104, 125, or 131. In one embodiment, the antibody comprises (a) a HVR-L1 comprising the amino acid sequence of SEQ ID NO: 75, 84, 122, or 129; (b) a HVR-L2 comprising the amino acid sequence of SEQ ID NO: 85, 94, 123, 124, or 130; and (c) a HVR-L3 comprising the amino acid sequence of SEQ ID NO: 95, 104, 125, or 131.

In another aspect, an antibody of the invention comprises (a) a VH domain comprising at least one, at least two, or all three VH HVR sequences selected from (i) a HVR-H1 comprising the amino acid sequence of SEQ ID NO: 45, 54, 117, or 126, (ii) a HVR-H2 comprising the amino acid sequence of SEQ ID NO: 55, 64, 118-120, or 127, and (iii) a HVR-H3 comprising the amino acid sequence of SEQ ID NO:65, 74, 121, or 128; and (b) a VL domain comprising at least one, at least two, or all three VL HVR sequences selected from (i) a HVR-L1 comprising the amino acid sequence of SEQ ID NO: 75, 84, 122, or 129, (ii) a HVR-L2 comprising the amino acid sequence of SEQ ID NO: 85, 94, 123, 124, or 130, and (c) a HVR-L3 comprising the amino acid sequence of SEQ ID NO: 95, 104, 125, or 131.

In another aspect, the invention provides an antibody comprising (a) a HVR-H1 comprising the amino acid sequence of SEQ ID NO: 45, 54, 117, or 126; (b) a HVR-H2 comprising the amino acid sequence of SEQ ID NO: 55, 64, 118-120, or 127; (c) a HVR-H3 comprising the amino acid sequence of SEQ ID NO:65, 74, 121, or 128; (d) a HVR-L1 comprising the amino acid sequence of SEQ ID NO: 75, 84, 122, or 129; (e) a HVR-L2 comprising the amino acid sequence of SEQ ID NO: 85, 94, 123, 124, or 130; and (f) a HVR-L3 comprising the amino acid sequence of SEQ ID NO: 95, 104, 125, or 131.

In certain embodiments, any one or more amino acids of an anti-C5 antibody as provided above are substituted at the following HVR positions: (a) in HVR-H1 (SEQ ID NO: 45), at positions 5, and 6; (b) in HVR-H2 (SEQ ID NO: 55), at positions 1, 3, 9, 11, 13, and 15; (c) in HVR-H3 (SEQ ID NO: 65), at positions 2, 5, 6, 12, and 13; (d) in HVR-L1 (SEQ ID NO: 75), at positions 1, 5, 7, and 9; (e) in HVR-L2 (SEQ ID NO: 85), at positions 4, 5, and 6; and (f) in HVR-L3 (SEQ ID NO: 95), at positions 2, 4, and 12.

In certain embodiments, the substitutions are conservative substitutions, as provided herein. In certain embodiments, any one or more of the following substitutions may be made in any combination: (a) in HVR-H1 (SEQ ID NO: 45), M5V or C6A; (b) in HVR-H2 (SEQ ID NO: 55), C1A or G, Y3F, T9D or E, Y11K or Q, S13D or E, or A15V; (c) in HVR-H3 (SEQ ID NO: 65), G2A, V5Q or D, T6Y, Y12H, or L13Y; (d) in HVR-L1 (SEQ ID NO: 75), Q1R, N5Q or G, G7S, D9K or S; (e) in HVR-L2 (SEQ ID NO: 85), K4T or E, L5T, or A6H, A6 E, or A6Q; (f) in HVR-L3 (SEQ ID NO: 95) C2S, C2N, or C2T, F4K; or A12T or A12H.

All possible combinations of the above substitutions are encompassed by the consensus sequences of SEQ ID NOs: 126, 127, 128, 129, 130, and 131 for HVR-H1, HVR-H2, HVR-H3, HVR-L1, HVR-L2, and HVR-L3, respectively.

In any of the above embodiments, an anti-C5 antibody is humanized. In one embodiment, an anti-C5 antibody comprises HVRs as in any of the above embodiments, and further comprises an acceptor human framework, e.g., a human immunoglobulin framework or a human consensus framework. In another embodiment, an anti-C5 antibody comprises HVRs as in any of the above embodiments, and further comprises a VH or VL comprising an FR sequence, wherein the FR sequences are as follows. For the heavy chain variable domain, the FR1 comprises the amino acid sequence of SEQ ID NO: 132, 133, or 134, FR2 comprises the amino acid sequence of SEQ ID NO: 135 or 136, FR3 comprises the amino acid sequence of SEQ ID NO: 137, 138, or 139, FR4 comprises the amino acid sequence of SEQ ID NO: 140 or 141. For the light chain variable domain, FR1 comprises the amino acid sequence of SEQ ID NO: 142 or 143, FR2 comprises the amino acid sequence of SEQ ID NO: 144 or 145, FR3 comprises the amino acid sequence of SEQ ID NO: 146 or 147, FR4 comprises the amino acid sequence of SEQ ID NO: 148.

In another aspect, an anti-C5 antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 1-9, or 10. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-C5 antibody comprising that sequence retains the ability to bind to C5. In certain embodiments, a total of 1 to 10 amino acids have been substituted, inserted and/or deleted in SEQ ID NO: 1-9, or 10. In certain embodiments, substitutions, insertions, or deletions occur in regions outside the HVRs (i.e., in the FRs). Optionally, the anti-C5 antibody comprises the VH sequence in SEQ ID NO: 1-9, or 10, including post-translational modifications of that sequence. In a particular embodiment, the VH comprises one, two or three HVRs selected from: (a) HVR-H1 comprising the amino acid sequence of SEQ ID NO: 45-53, or 54, (b) HVR-H2 comprising the amino acid sequence of SEQ ID NO: 55-63, or 64, and (c) HVR-H3 comprising the amino acid sequence of SEQ ID NO: 65-73, or 74.

In another aspect, an anti-C5 antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 11-19, or 20. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-C5 antibody comprising that sequence retains the ability to bind to C5. In certain embodiments, a total of 1 to 10 amino acids have been substituted, inserted and/or deleted in SEQ ID NO: 11-19, or 20. In certain embodiments, the substitutions, insertions, or deletions occur in regions outside the HVRs (i.e., in the FRs). Optionally, the anti-C5 antibody comprises the VL sequence in SEQ ID NO: 11-19, or 20, including post-translational modifications of that sequence. In a particular embodiment, the VL comprises one, two or three HVRs selected from (a) HVR-L1 comprising the amino acid sequence of SEQ ID NO: 75-83, or 84; (b) HVR-L2 comprising the amino acid sequence of SEQ ID NO: 85-93, or 94; and (c) HVR-L3 comprising the amino acid sequence of SEQ ID NO: 95-103, or 104.

In another aspect, an anti-C5 antibody is provided, wherein the antibody comprises a VH as in any of the embodiments provided above, and a VL as in any of the embodiments provided above. In one embodiment, the antibody comprises the VH and VL sequences in SEQ ID NO: 1-9, or 10, and SEQ ID NO: 11-19, or 20, respectively, including post-translational modifications of those sequences.

In another aspect, an anti-C5 antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 10, 106, 107, 108, 109, or 110. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-C5 antibody comprising that sequence retains the ability to bind to C5. In certain embodiments, a total of 1 to 10 amino acids have been substituted, inserted and/or deleted in SEQ ID NO: 10, 106-109, or 110. In certain embodiments, substitutions, insertions, or deletions occur in regions outside the HVRs (i.e., in the FRs). Optionally, the anti-C5 antibody comprises the VH sequence in SEQ ID NO: 10, 106-109, or 110, including post-translational modifications of that sequence. In a particular embodiment, the VH comprises one, two or three HVRs selected from: (a) a HVR-H1 comprising the amino acid sequence of SEQ ID NO: 45, 54, 117, or 126, (b) a HVR-H2 comprising the amino acid sequence of SEQ ID NO: 55, 64, 118-120, or 127, and (c) a HVR-H3 comprising the amino acid sequence of SEQ ID NO:65, 74, 121, or 128.

In another aspect, an anti-C5 antibody comprises a VH sequence having at least 90%, 91%, 92%, 93%, 94%, 95%, 96%, 97%, 98%, 99%, or 100% sequence identity to the amino acid sequence of SEQ ID NO: 10, 106, 107, 108, 109, or 110. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-C5 antibody comprising that sequence retains the ability to bind to C5. In certain embodiments, a total of 1 to 10 amino acids have been substituted, inserted and/or deleted in SEQ ID NO: 10, 106-109, or 110. In certain embodiments, substitutions, insertions, or deletions occur in regions outside the HVRs (i.e., in the FRs). Optionally, the anti-C5 antibody comprises the VH sequence in SEQ ID NO: 10, 106-109, or 110, including post-translational modifications of that sequence. In a particular embodiment, the VH comprises one, two or three HVRs selected from: (a) a HVR-H1 comprising the amino acid sequence of SEQ ID NO: 45, 54, 117, or 126, (b) a HVR-H2 comprising the amino acid sequence of SEQ ID NO: 55, 64, 118-120, or 127, and (c) a HVR-H3 comprising the amino acid sequence of SEQ ID NO:65, 74, 121, or 128.

In another aspect, an anti-C5 antibody comprises a VH sequence having at least 90%, 91%, 92%, 93%, 94%, 95%, 96%, 97%, 98%, 99%, or 100% sequence identity to the amino acid sequence of SEQ ID NO:10. In certain embodiments, the VH sequence is the amino acid sequence of SEQ ID NO:10. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-C5 antibody comprising that sequence retains the ability to bind to C5. In certain embodiments, a total of 1 to 10 amino acids have been substituted, inserted and/or deleted in SEQ ID NO: 10. In certain embodiments, substitutions, insertions, or deletions occur in regions outside the HVRs (i.e., in the FRs). Optionally, the anti-C5 antibody comprises the VH sequence in SEQ ID NO: 10 including post-translational modifications of that sequence. In a particular embodiment, the VH comprises one, two or three HVRs selected from: (a) a HVR-H1 comprising the amino acid sequence of SEQ ID NO: 54, (b) a HVR-H2 comprising the amino acid sequence of SEQ ID NO: 64, and (c) a HVR-H3 comprising the amino acid sequence of SEQ ID NO: 74.

In another aspect, an anti-C5 antibody comprises a VH sequence having at least 90%, 91%, 92%, 93%, 94%, 95%, 96%, 97%, 98%, 99%, or 100% sequence identity to the amino acid sequence of SEQ ID NO: 106. In certain embodiments, the VH sequence is the amino acid sequence of SEQ ID NO:106. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-C5 antibody comprising that sequence retains the ability to bind to C5. In certain embodiments, a total of 1 to 10 amino acids have been substituted, inserted and/or deleted in SEQ ID NO: 106. In certain embodiments, substitutions, insertions, or deletions occur in regions outside the HVRs (i.e., in the FRs). Optionally, the anti-C5 antibody comprises the VH sequence in SEQ ID NO: 106, including post-translational modifications of that sequence. In a particular embodiment, the VH comprises one, two or three HVRs selected from: (a) a HVR-H1 comprising the amino acid sequence of SEQ ID NO: 117, (b) a HVR-H2 comprising the amino acid sequence of SEQ ID NO: 118, and (c) a HVR-H3 comprising the amino acid sequence of SEQ ID NO: 121.

In another aspect, an anti-C5 antibody comprises a VH sequence having at least 90%, 91%, 92%, 93%, 94%, 95%, 96%, 97%, 98%, 99%, or 100% sequence identity to the amino acid sequence of SEQ ID NO: 107. In certain embodiments, the VH sequence is the amino acid sequence of SEQ ID NO:107. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-C5 antibody comprising that sequence retains the ability to bind to C5. In certain embodiments, a total of 1 to 10 amino acids have been substituted, inserted and/or deleted in SEQ ID NO: 107. In certain embodiments, substitutions, insertions, or deletions occur in regions outside the HVRs (i.e., in the FRs). Optionally, the anti-C5 antibody comprises the VH sequence in SEQ ID NO: 107, including post-translational modifications of that sequence. In a particular embodiment, the VH comprises one, two or three HVRs selected from: (a) a HVR-H1 comprising the amino acid sequence of SEQ ID NO: 117 (b) a HVR-H2 comprising the amino acid sequence of SEQ ID NO: 119, and (c) a HVR-H3 comprising the amino acid sequence of SEQ ID NO: 121.

In another aspect, an anti-C5 antibody comprises a VH sequence having at least 90%, 91%, 92%, 93%, 94%, 95%, 96%, 97%, 98%, 99%, or 100% sequence identity to the amino acid sequence of SEQ ID NO: 108. In certain embodiments, the VH sequence is the amino acid sequence of SEQ ID NO:108. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-C5 antibody comprising that sequence retains the ability to bind to C5. In certain embodiments, a total of 1 to 10 amino acids have been substituted, inserted and/or deleted in SEQ ID NO: 108. In certain embodiments, substitutions, insertions, or deletions occur in regions outside the HVRs (i.e., in the FRs). Optionally, the anti-C5 antibody comprises the VH sequence in SEQ ID NO: 108, including post-translational modifications of that sequence. In a particular embodiment, the VH comprises one, two or three HVRs selected from: (a) a HVR-H1 comprising the amino acid sequence of SEQ ID NO: 117 (b) a HVR-H2 comprising the amino acid sequence of SEQ ID NO: 118, and (c) a HVR-H3 comprising the amino acid sequence of SEQ ID NO: 121.

In another aspect, an anti-C5 antibody comprises a VH sequence having at least 90%, 91%, 92%, 93%, 94%, 95%, 96%, 97%, 98%, 99%, or 100% sequence identity to the amino acid sequence of SEQ ID NO: 109. In certain embodiments, the VH sequence is the amino acid sequence of SEQ ID NO:109. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-C5 antibody comprising that sequence retains the ability to bind to C5. In certain embodiments, a total of 1 to 10 amino acids have been substituted, inserted and/or deleted in SEQ ID NO: 109. In certain embodiments, substitutions, insertions, or deletions occur in regions outside the HVRs (i.e., in the FRs). Optionally, the anti-C5 antibody comprises the VH sequence in SEQ ID NO: 109, including post-translational modifications of that sequence. In a particular embodiment, the VH comprises one, two or three HVRs selected from: (a) a HVR-H1 comprising the amino acid sequence of SEQ ID NO: 117 (b) a HVR-H2 comprising the amino acid sequence of SEQ ID NO: 118, and (c) a HVR-H3 comprising the amino acid sequence of SEQ ID NO: 121.

In another aspect, an anti-C5 antibody comprises a VH sequence having at least 90%, 91%, 92%, 93%, 94%, 95%, 96%, 97%, 98%, 99%, or 100% sequence identity to the amino acid sequence of SEQ ID NO: 110. In certain embodiments, the VH sequence is the amino acid sequence of SEQ ID NO:110. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-C5 antibody comprising that sequence retains the ability to bind to C5. In certain embodiments, a total of 1 to 10 amino acids have been substituted, inserted and/or deleted in SEQ ID NO: 110. In certain embodiments, substitutions, insertions, or deletions occur in regions outside the HVRs (i.e., in the FRs). Optionally, the anti-C5 antibody comprises the VH sequence in SEQ ID NO: 110, including post-translational modifications of that sequence. In a particular embodiment, the VH comprises one, two or three HVRs selected from: (a) a HVR-H1 comprising the amino acid sequence of SEQ ID NO: 117 (b) a HVR-H2 comprising the amino acid sequence of SEQ ID NO: 120, and (c) a HVR-H3 comprising the amino acid sequence of SEQ ID NO: 121.

In another aspect, an anti-C5 antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 20, 111, 112, or 113. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-C5 antibody comprising that sequence retains the ability to bind to C55. In certain embodiments, a total of 1 to 10 amino acids have been substituted, inserted and/or deleted in SEQ ID NO: 20, 111, 112, or 113. In certain embodiments, the substitutions, insertions, or deletions occur in regions outside the HVRs (i.e., in the FRs). Optionally, the anti-C5 antibody comprises the VL sequence in SEQ ID NO: 20, 111, 112, or 113, including post-translational modifications of that sequence. In a particular embodiment, the VL comprises one, two or three HVRs selected from (a) a HVR-L1 comprising the amino acid sequence of SEQ ID NO: 75, 84, 122, or 129; (b) a HVR-L2 comprising the amino acid sequence of SEQ ID NO: 85, 94, 123, 124, or 130; and (c) a HVR-L3 comprising the amino acid sequence of SEQ ID NO: 95, 104, 125, or 131.

In another aspect, an anti-C5 antibody is provided, wherein the antibody comprises a VL having at least 90%, 91%, 92%, 93%, 94%, 95%, 96%, 97%, 98%, 99%, or 100% sequence identity to the amino acid sequence of SEQ ID NO: 20. In certain embodiments, the VL sequence is the amino acid sequence of SEQ ID NO:20. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-C5 antibody comprising that sequence retains the ability to bind to C5. In certain embodiments, a total of 1 to 10 amino acids have been substituted, inserted and/or deleted in SEQ ID NO: 20. In certain embodiments, the substitutions, insertions, or deletions occur in regions outside the HVRs (i.e., in the FRs). Optionally, the anti-C5 antibody comprises the VL sequence in SEQ ID NO: 20, including post-translational modifications of that sequence. In a particular embodiment, the VL comprises one, two or three HVRs selected from (a) a HVR-L1 comprising the amino acid sequence of SEQ ID NO: 84; (b) a HVR-L2 comprising the amino acid sequence of SEQ ID NO: 94; and (c) a HVR-L3 comprising the amino acid sequence of SEQ ID NO: 104.

In another aspect, an anti-C5 antibody is provided, wherein the antibody comprises a VL having at least 90%, 91%, 92%, 93%, 94%, 95%, 96%, 97%, 98%, 99%, or 100% sequence identity to the amino acid sequence of SEQ ID NO: 111. In certain embodiments, the VL sequence is the amino acid sequence of SEQ ID NO:111. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-C5 antibody comprising that sequence retains the ability to bind to C5. In certain embodiments, a total of 1 to 10 amino acids have been substituted, inserted and/or deleted in SEQ ID NO: 111. In certain embodiments, the substitutions, insertions, or deletions occur in regions outside the HVRs (i.e., in the FRs). Optionally, the anti-C5 antibody comprises the VL sequence in SEQ ID NO: 111, including post-translational modifications of that sequence. In a particular embodiment, the VL comprises one, two or three HVRs selected from (a) a HVR-L1 comprising the amino acid sequence of SEQ ID NO: 122; (b) a HVR-L2 comprising the amino acid sequence of SEQ ID NO: 123; and (c) a HVR-L3 comprising the amino acid sequence of SEQ ID NO: 125.

In another aspect, an anti-C5 antibody is provided, wherein the antibody comprises a VL having at least 90%, 91%, 92%, 93%, 94%, 95%, 96%, 97%, 98%, 99%, or 100% sequence identity to the amino acid sequence of SEQ ID NO: 112. In certain embodiments, the VL sequence is the amino acid sequence of SEQ ID NO:112. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-C5 antibody comprising that sequence retains the ability to bind to C5. In certain embodiments, a total of 1 to 10 amino acids have been substituted, inserted and/or deleted in SEQ ID NO: 112. In certain embodiments, the substitutions, insertions, or deletions occur in regions outside the HVRs (i.e., in the FRs). Optionally, the anti-C5 antibody comprises the VL sequence in SEQ ID NO: 112, including post-translational modifications of that sequence. In a particular embodiment, the VL comprises one, two or three HVRs selected from (a) a HVR-L1 comprising the amino acid sequence of SEQ ID NO: 122; (b) a HVR-L2 comprising the amino acid sequence of SEQ ID NO: 123; and (c) a HVR-L3 comprising the amino acid sequence of SEQ ID NO: 125.

In another aspect, an anti-C5 antibody is provided, wherein the antibody comprises a VL having at least 90%, 91%, 92%, 93%, 94%, 95%, 96%, 97%, 98%, 99%, or 100% sequence identity to the amino acid sequence of SEQ ID NO: 113. In certain embodiments, the VL sequence is the amino acid sequence of SEQ ID NO:113. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-C5 antibody comprising that sequence retains the ability to bind to C5. In certain embodiments, a total of 1 to 10 amino acids have been substituted, inserted and/or deleted in SEQ ID NO: 113. In certain embodiments, the substitutions, insertions, or deletions occur in regions outside the HVRs (i.e., in the FRs). Optionally, the anti-C5 antibody comprises the VL sequence in SEQ ID NO: 113, including post-translational modifications of that sequence. In a particular embodiment, the VL comprises one, two or three HVRs selected from (a) a HVR-L1 comprising the amino acid sequence of SEQ ID NO: 122; (b) a HVR-L2 comprising the amino acid sequence of SEQ ID NO: 124; and (c) a HVR-L3 comprising the amino acid sequence of SEQ ID NO: 125.

In another aspect, an anti-C5 antibody is provided wherein the antibody comprises a VH as in any of the embodiments provided above, and a VL as in any of the embodiments provided above. In one embodiment, the antibody comprises the VH and VL sequences in SEQ ID NO: 10, 106-109, or 110 and SEQ ID NO: 20, 111, 112, or 113, respectively, including post-translational modifications of those sequences. In one embodiment, the antibody comprises a VH sequence of SEQ ID NO:10 and a VL sequence of SEQ ID NO: 20. In one embodiment, the antibody comprises a VH sequence of SEQ ID NO:106 and a VL sequence of SEQ ID NO: 111. In another embodiment, the antibody comprises a VH sequence of SEQ ID NO:107 and a VL sequence of SEQ ID NO: 111. In an additional embodiment, the antibody comprises a VH sequence of SEQ ID NO:108 and a VL sequence of SEQ ID NO 111. In another embodiment, the antibody comprises a VH sequence of SEQ ID NO:109 and a VL sequence of SEQ ID NO: 111. In another embodiment, the antibody comprises a VH sequence of SEQ ID NO:109 and a VL sequence of SEQ ID NO: 112. In another embodiment, the antibody comprises a VH sequence of SEQ ID NO:109 and a VL sequence of SEQ ID NO: 113. In another embodiment, the antibody comprises a VH sequence of SEQ ID NO:110 and a VL sequence of SEQ ID NO: 113.

In one aspect, an anti-C5 antibody is provided wherein the antibody comprises a VH sequence containing (a) a HVR-H1 comprising the amino acid sequence of SEQ ID NO: 54, (b) a HVR-H2 comprising the amino acid sequence of SEQ ID NO: 64, and (c) a HVR-H3 comprising the amino acid sequence of SEQ ID NO: 74, and a VL sequence containing (a) a HVR-L1 comprising the amino acid sequence of SEQ ID NO: 84; (b) a HVR-L2 comprising the amino acid sequence of SEQ ID NO: 94; and (c) a HVR-L3 comprising the amino acid sequence of SEQ ID NO: 104.

In another aspect, an anti-C5 antibody is provided wherein the antibody comprises a VH sequence containing (a) a HVR-H1 comprising the amino acid sequence of SEQ ID NO: 117, (b) a HVR-H2 comprising the amino acid sequence of SEQ ID NO: 118, and (c) a HVR-H3 comprising the amino acid sequence of SEQ ID NO: 121, and a VL sequence containing (a) a HVR-L1 comprising the amino acid sequence of SEQ ID NO: 122; (b) a HVR-L2 comprising the amino acid sequence of SEQ ID NO: 123; and (c) a HVR-L3 comprising the amino acid sequence of SEQ ID NO: 125.

In another aspect, an anti-C5 antibody is provided wherein the antibody comprises a VH sequence containing (a) a HVR-H1 comprising the amino acid sequence of SEQ ID NO: 117, (b) a HVR-H2 comprising the amino acid sequence of SEQ ID NO: 119, and (c) a HVR-H3 comprising the amino acid sequence of SEQ ID NO: 121, and a VL sequence containing (a) a HVR-L1 comprising the amino acid sequence of SEQ ID NO: 122; (b) a HVR-L2 comprising the amino acid sequence of SEQ ID NO: 123; and (c) a HVR-L3 comprising the amino acid sequence of SEQ ID NO: 125.

In another aspect, an anti-C5 antibody is provided wherein the antibody comprises a VH sequence containing (a) a HVR-H1 comprising the amino acid sequence of SEQ ID NO: 117, (b) a HVR-H2 comprising the amino acid sequence of SEQ ID NO: 118, and (c) a HVR-H3 comprising the amino acid sequence of SEQ ID NO: 121, and a VL sequence containing (a) a HVR-L1 comprising the amino acid sequence of SEQ ID NO: 122; (b) a HVR-L2 comprising the amino acid sequence of SEQ ID NO: 124; and (c) a HVR-L3 comprising the amino acid sequence of SEQ ID NO: 125.

In another aspect, an anti-C5 antibody is provided wherein the antibody comprises a VH sequence containing (a) a HVR-H1 comprising the amino acid sequence of SEQ ID NO: 117, (b) a HVR-H2 comprising the amino acid sequence of SEQ ID NO: 120, and (c) a HVR-H3 comprising the amino acid sequence of SEQ ID NO: 121, and a VL sequence containing (a) a HVR-L1 comprising the amino acid sequence of SEQ ID NO: 122; (b) a HVR-L2 comprising the amino acid sequence of SEQ ID NO: 124; and (c) a HVR-L3 comprising the amino acid sequence of SEQ ID NO: 125.

In certain embodiments, an anti-C5 antibody of the present invention comprises a VH as in any of the embodiments provided above and a heavy chain constant region comprising the amino acid sequence of SEQ ID NO: 33, 34, 35, 114, or 115, and 116. In certain embodiments, an anti-C5 antibody of the present invention comprises a VL as in any of the embodiments provided above and a light chain constant region comprising the amino acid sequence of SEQ ID NO: 36, 37, or 38.

In another aspect, the invention provides an antibody that binds to the same epitope as an anti-C5 antibody provided herein. For example, in certain embodiments, an antibody is provided that binds to the same epitope as an antibody described in Table 2. As demonstrated by the working examples below, all the anti-C5 antibodies described in Table 2 are grouped into the same epitope bin of C5 and exhibit pH-dependent binding characteristics.

In an additional aspect, the invention provides an antibody that binds to the same epitope as an antibody provided herein. In a further aspect, the invention provides an antibody that binds to the same epitope as an antibody described in Tables 7 or 8. In certain embodiments, an antibody is provided that binds to an epitope within a fragment consisting of amino acids 33-124 of the β chain of C5 (SEQ ID NO: 40). In certain embodiments, an antibody is provided that binds to an epitope within the β chain of C5 (SEQ ID NO: 40) which comprises at least one fragment selected from the group consisting of amino acids 47-57, 70-76, and 107-110. In certain embodiments, an antibody is provided that binds to an epitope within a fragment of the β chain of C5 (SEQ ID NO: 40) which comprises at least one amino acid selected from the group consisting of Thr47, Glu48, Ala49, Phe50, Asp51, Ala52, Thr53, Lys57, His70, Val71, His72, Ser74, Glu76, Val107, Ser108, Lys109, and His110. In another embodiment, an epitope of an anti-C5 antibody of the present invention is a conformational epitope.

In a further aspect of the invention, an anti-C5 antibody according to any of the above embodiments is a monoclonal antibody, including a chimeric, humanized or human antibody. In one embodiment, an anti-C5 antibody is an antibody fragment, e.g., a Fv, Fab, Fab', scFv, diabody, or F(ab')$_2$ fragment. In another embodiment, the antibody is a full length antibody, e.g., an intact IgG1 or IgG4 antibody or other antibody class or isotype as defined herein.

In a further aspect, an anti-C5 antibody according to any of the above embodiments may incorporate any of the features, singly or in combination, as described in Sections 1-7 below:

1. Antibody Affinity

In certain embodiments, an antibody provided herein has a dissociation constant (Kd) of ≤1 µM, ≤100 nM, ≤10 nM, ≤1 nM, ≤0.1 nM, ≤0.01 nM, or ≤0.001 nM (e.g., $10^{-8}$ M or less, e.g., from $10^{-8}$ M to $10^{-13}$ M, e.g., from $10^{-9}$ M to $10^{-13}$ M).

In one embodiment, Kd is measured by a radiolabeled antigen binding assay (RIA). In one embodiment, an RIA is performed with the Fab version of an antibody of interest and its antigen. For example, solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., *J. Mol. Biol.* 293:865-881(1999), herein incorporated by reference in its entirety). To establish conditions for the assay, MICROTITER® multi-well plates (Thermo Scientific) are coated overnight with 5 µg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23'C). In a non-adsorbent plate (Nunc #269620), 100 pM or 26 pM [$^{125}$I]-antigen are mixed with serial dilutions of a Fab of interest (e.g., consistent with assessment of the anti-VEGF antibody, Fab-12, in Presta et al., *Cancer Res.* 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 µl/well of scintillant (MICROSCINT-20™; Packard) is added, and the plates are counted on a TOP-COUNT™ gamma counter (Packard) for ten minutes. Concentrations of each Fab that give less than or equal to 20% of maximal binding are chosen for use in competitive binding assays.

According to another embodiment, Kd is measured using a BIACORE® surface plasmon resonance assay. For example, an assay using a BIACORE®-2000 or a BIACORE®-3000 (BIACORE®, Inc., Piscataway, N.J.) is performed at 25° C. with immobilized antigen CM5 chips at ~10 response units (RU). In one embodiment, carboxymethylated dextran biosensor chips (CM5, BIACORE®, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 µg/ml (~0.2 µM) before injection at a flow rate of 5 µl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 µl/minute. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio $k_{off}/k_{on}$. See, e.g., Chen et al., *J. Mol. Biol.* 293:865-881 (1999). If the on-rate exceeds $10^6$ $M^{-1}$ $s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-AMINCO™ spectrophotometer (ThermoSpectronic) with a stirred cuvette.

2. Antibody Fragments

In certain embodiments, an antibody provided herein is an antibody fragment Antibody fragments include, but are not limited to, Fab, Fab', Fab'-SH, F(ab')$_2$, Fv, and scFv fragments, and other fragments described below. For a review of certain antibody fragments, see Hudson et al., *Nat. Med.* 9:129-134 (2003). For a review of scFv fragments, see, e.g., Pluckthün, in *The Pharmacology of Monoclonal Antibodies*, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and F(ab')$_2$ fragments comprising salvage receptor binding epitope residues and having increased in vivo half-life, see U.S. Pat. No. 5,869,046. The contents of each of the above publications is herein incorporated by reference in its entirety.

Diabodies are antibody fragments with two antigen-binding sites that may be bivalent or bispecific. See, for example, EP 404,097; WO 1993/01161; Hudson et al., *Nat. Med.* 9:129-134 (2003); and Hollinger et al., *Proc. Natl. Acad. Sc.*

USA 90:6444-6448 (1993). Triabodies and tetrabodies are also described in Hudson et al., *Nat. Med.* 9:129-134(2003).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516).

Antibody fragments can be made by various techniques, including but not limited to proteolytic digestion of an intact antibody as well as production by recombinant host cells (e.g., *E. coli* or phage), as described herein.

3. Chimeric and Humanized Antibodies

In certain embodiments, an antibody provided herein is a chimeric antibody. Certain chimeric antibodies are described, e.g., in U.S. Pat. No. 4,816,567; and Morrison et al., *Proc. Natl. Acad. Sci. USA* 81:6851-6855 (1984), each of which is herein incorporated by reference in its entirety. In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, *Front. Biosci.* 13:1619-1633 (2008), and are further described, e.g., in Riechmann et al., *Nature* 332:323-329 (1988); Queen et al., *Proc. Nat'l Acad. Sci. USA* 86:10029-10033 (1989); U.S. Pat. Nos. 5,821,337, 7,527,791, 6,982,321, and 7,087,409; Kashmiri et al., *Methods* 36:25-34 (2005) (describing specificity determining region (SDR) grafting); Padlan, *Mol. Immunol.* 28:489-498 (1991) (describing "resurfacing"); Dall'Acqua et al., *Methods* 36:43-60 (2005) (describing "FR shuffling"); and Osbourn et al., *Methods* 36:61-68 (2005) and Klimka et al., *Br. J. Cancer* 83:252-260 (2000) (describing the "guided selection" approach to FR shuffling), each of which is herein incorporated by reference in its entirety.

Human framework regions that may be used for humanization include but are not limited to: framework regions selected using the "best-fit" method (see, e.g., Sims et al., *J. Immunol.* 151:2296 (1993)); framework regions derived from the consensus sequence of human antibodies of a particular subgroup of light or heavy chain variable regions (see, e.g., Carter et al., *Proc. Natl. Acad. Sct. USA* 89:4285 (1992); and Presta et al., *J. Immunol.* 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996), each of which is herein incorporated by reference in its entirety).

4. Human Antibodies

In certain embodiments, an antibody provided herein is a human antibody. Human antibodies can be produced using various techniques known in the art. Human antibodies are described generally in van Dijk and van de Winkel, *Curr. Opin. Pharma.* 5:368-74 (2001) and Lonberg, *Curr. Opin. Immunol.* 20:450-459 (2008).

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, *Nat. Biotech.* 23:1117-1125 (2005). See also, e.g., U.S. Pat. Nos. 6,075,181 and 6,150,584 describing XENO-MOUSE™ technology; U.S. Pat. No. 5,770,429 describing HUMAB® technology; U.S. Pat. No. 7,041,870 describing K-M MOUSE® technology, and US Patent Application Publication No. US 2007/0061900, describing VELOCI-MOUSE® technology, each of which is herein incorporated by reference in its entirety). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor, *J. Immunol.* 133:3001 (1984); Brodeur et al., *Monoclonal Antibody Production Techniques and Applications*, pp. 51-63 (Dekker, Inc., New York, 1987); and Boerner et al., *J. Immunol.* 147:86 (1991).) Human antibodies generated via human B-cell hybridoma technology are also described in Li et al., *Proc. Natl. Acad. Sci. USA* 103:3557-3562 (2006). Additional methods include those described, for example, in U.S. Pat. No. 7,189,826 (describing production of monoclonal human IgM antibodies from hybridoma cell lines) and Ni, *Xiandai Mianyixue* 26(4):265-268 (2006) (describing human-human hybridomas). Human hybridoma technology (Trioma technology) is also described in Vollmers, *Histology and Histopathology* 20(3):927-937 (2005) and Vollmers, *Methods and Findings in Experimental and Clinical Pharmacology* 27(3):185-191 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

5. Library-Derived Antibodies

Antibodies of the invention may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al., *Methods in Molecular Biology* 178:1-37 (O'Brien et al., ed., Human Press, Totowa, N. J., 2001) and further described, e.g., in McCafferty et al., *Nature* 348:552-

554; Clackson et al., *Nature* 352:624-628 (1991); Marks et al., *J. Mol. Biol.* 222:581-597 (1992); Marks, *Meth. Mol. Biol.* 248:161-175 (Lo, ed., Human Press, Totowa, N.J., 2003); Sidhu et al., *J. Mol. Biol.* 338(2):299-310 (2004); Lee et al., *J. Mol. Biol.* 340(5):1073-1093 (2004); Fellouse, *Proc. Natl. Acad. Sc. USA* 101(34):12467-12472 (2004); Lee et al., *J. Immunol. Methods* 284(1-2): 119-132 (2004), each of which is herein incorporated by reference in its entirety.

In certain phage display methods, repertoires of VH and VL genes are separately cloned by polymerase chain reaction (PCR) and recombined randomly in phage libraries, which can then be screened for antigen-binding phage as described in Winter et al., *Ann. Rev. Immunol.* 12:433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al., *EMBO J,* 12:725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom, *J. Mol. Biol.* 227:381-388 (1992). Patent publications describing human antibody phage libraries include, for example: U.S. Pat. No. 5,750, 373, and US Publ. Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

6. Multispecific Antibodies

In certain embodiments, an antibody provided herein is a multispecific antibody, e.g., a bispecific antibody. Multispecific antibodies are monoclonal antibodies that have binding specificities for at least two different sites. In certain embodiments, one of the binding specificities is for C5 and the other is for any other antigen. In certain embodiments, bispecific antibodies may bind to two different epitopes of C5. Bispecific antibodies may also be used to localize cytotoxic agents to cells which express C5. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein and Cuello, *Nature* 305:537 (1983)), WO 93/08829, and Traunecker et al., *EMBO J.* 10:3655 (1991)), and "knob-in-hole" engineering (see, e.g., U.S. Pat. No. 5,731,168. Multi-specific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al, *Science* 229:81 (1985)); using leucine zippers to produce bi-specific antibodies (see, e.g., Kostelny et al., *J. Immunol.* 148(5):1547-1553 (1992)); using "diabody" technology for making bispecific antibody fragments (see, e.g., Hollinger et al, *Proc. Natl. Acad. Sci. USA* 90:6444-6448 (1993)); and using single-chain Fv (scFv) dimers (see, e.g., Gruber et al., *J. Immunol.* 152:5368 (1994)); and preparing trispecific antibodies as described, e.g., in Tutt et al., *J. Immunol.* 147:60 (1991). The contents of each of the above publications is herein incorporated by reference in its entirety.

Engineered antibodies with three or more functional antigen binding sites, including "Octopus antibodies," are also included herein (see, e.g., US 2006/0025576).

The antibody or fragment herein also includes a "Dual Acting FAb" or "DAF" comprising an antigen binding site that binds to C5 as well as another, different antigen (see, US 2008/0069820, for example).

7. Antibody Variants

In certain embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

a. Substitution, Insertion, and Deletion Variants

In certain embodiments, antibody variants having one or more amino acid substitutions are provided. Sites of interest for substitutional mutagenesis include the HVRs and FRs. Conservative substitutions are shown in Table 1 under the heading of "preferred substitutions." More substantial changes are provided in Table 1 under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE 1

| Original Residue | Exemplary Substitutions | Preferred Substitutions |
| --- | --- | --- |
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties: (1) hydrophobic: Norleucine, Met, Ala, Val, Leu, lie; (2) neutral hydrophilic: Cys, Ser, Thr, Asn, Gln; (3) acidic: Asp, Glu; (4) basic: His, Lys, Arg; (5) residues that influence chain orientation: Gly, Pro; and (6) aromatic: Trp, Tyr, Phe.

Non-conservative substitutions will entail exchanging a member of one of these classes for another class.

One type of substitutional variant involves substituting one or more hypervariable region residues of a parent antibody (e.g., a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g., binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, *Methods Mol. Biol.* 207:179-196 (2008)), and/or residues that contact antigen, with the resulting variant VH or VL being tested for binding affinity. Affinity maturation by constructing and reselecting from secondary libraries has been described, e.g., in Hoogenboom at al., in *Methods in Molecular Biology* 178:1-37 (O'Brien et al., ed., Human Press, Totowa, N.J., (2001).) In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may, for example, be outside of antigen contacting residues in the HVRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham, *Science* 244:1081-1085 (1989). In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g., for ADEPT) or a polypeptide which increases the serum half-life of the antibody.

b. Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al., *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e. g. complex, hybrid and high mannose structures) as measured by MALDI-TOF mass spectrometry, as described in WO 2008/077546, for example. Asn297 refers to the asparagine residue located at about position 297 in the Fc region (Eu numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO 2005/053742; WO 2002/031140; Okazaki et al., *J. Mol. Biol.* 336:1239-1249 (2004); Yamane-Ohnuki et al., *Biotech. Bioeng.* 87:614 (2004). Examples of cell lines capable of producing defucosylated antibodies include Lec13 CHO cells deficient in protein fucosylation (Ripka et al., *Arch. Biochem. Biophys.* 249: 533-545 (1986); US 2003/0157108, Presta, L; and WO 2004/056312, Adams et al., especially at Example 11), and knockout cell lines, such as alpha-1,6-fucosyltransferase gene, FUT8, knockout CHO cells (see, e.g., Yamane-Ohnuki et al., *Biotech. Bioeng.* 87:614 (2004); Kanda et al., *Bio-* technol. Bioeng. 94(4):680-688 (2006); and WO2003/085107. The contents of each of the above publications is herein incorporated by reference in its entirety.

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

c. Fc Region Variants

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g., a substitution) at one or more amino acid positions.

In certain embodiments, the invention contemplates an antibody variant that possesses some but not all effector functions, which make it a desirable candidate for applications in which the half life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, Annu. Rev. Immunol. 9:457-492 (1991). Non-limiting examples of in vitro assays to assess ADCC activity of a molecule of interest is described in U.S. Pat. No. 5,500,362 (see, e.g., Hellstrom et al., Proc. Nat'l Acad. Sci. USA 83:7059-7063 (1986)) and Hellstrom et al., Proc. Nat'l Acad. Sci. USA 82:1499-1502 (1985); U.S. Pat. No. 5,821,337 (see Bruggemann et al., J. Exp. Med. 166:1351-1361 (1987)). Alternatively, non-radioactive assays methods may be employed (see, for example, ACTI™ non-radioactive cytotoxicity assay for flow cytometry (CellTechnology, Inc. Mountain View, Calif.); and CytoTox 96® non-radioactive cytotoxicity assay (Promega, Madison, Wis.)). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al., Proc. Nat'l Acad. Sc. USA 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., J. Immunol. Methods 202:163 (1996); Cragg et al., Blood 101:1045-1052 (2003); and Cragg et al., Blood 103:2738-2743 (2004)). FcRn binding and in vivo clearance/half life determinations can also be performed using methods known in the art (see, e.g., Petkova et al., Int'l. Immunol. 18(12):1759-1769 (2006)). The contents of each of the above publications is herein incorporated by reference in its entirety.

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields et al., J. Biol. Chem. 9(2):6591-6604 (2001), each of which is herein incorporated by reference in its entirety.)

In certain embodiments, an antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 1999/51642, and Idusogie et al., J. Immunol. 164:4178-4184 (2000), each of which is herein incorporated by reference in its entirety.)

Antibodies with increased half lives and improved binding to the neonatal Fc receptor (FcRn), which is responsible for the transfer of maternal IgGs to the fetus (Guyer et al., J. Immunol. 117:587 (1976) and Kim et al., J. Immunol. 24:249 (1994)), are described in US2005/0014934 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826, herein incorporated by reference in its entirety.)

See also Duncan, Nature 322:738-40 (1988); U.S. Pat. Nos. 5,648,260; 5,624,821; and WO 1994/29351 concerning other examples of Fc region variants.

d. Cysteine Engineered Antibody Variants

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described, e.g., in U.S. Pat. No. 7,521,541.

e. Antibody Derivatives

In certain embodiments, an antibody provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, polypropylene glycol homopolymers, polypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In one embodiment, the nonproteinaceous moiety is a carbon nanotube (Kam et al., *Proc. Natl. Acad. Sci. USA* 102:11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

B. Recombinant Methods and Compositions

Antibodies may be produced using recombinant methods and compositions, e.g., as described in U.S. Pat. No. 4,816,567. In one embodiment, isolated nucleic acid encoding an anti-C5 antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g., a Chinese Hamster Ovary (CHO) cell or lymphoid cell (e.g., Y0, NS0, Sp20 cell). In one embodiment, a method of making an anti-C5 antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an anti-C5 antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, *Methods in Molecular Biology*, Vol. 248 (B. K. C. Lo, ed., Humana Press, Totowa, N. J., 2003), pp. 245-254, describing expression of antibody fragments in *E. coli*.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, *Nat. Biotech.* 22:1409-1414 (2004), and Li et al., *Nat. Biotech.* 24:210-215 (2006).

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al, *J. Gen Virol.* 36:59 (1977)); baby hamster kidney cells (BHK); mouse sertoli cells (TM4 cells as described, e.g., in Mather, *Biol. Reprod.* 23:243-251 (1980)); monkey kidney cells (CV1); African green monkey kidney cells (VERO-76); human cervical carcinoma cells (HELA); canine kidney cells (MDCK); buffalo rat liver cells (BRL 3A); human lung cells (W138); human liver cells (Hep G2); mouse mammary tumor (MMT 060562); TRI cells, as described, e.g., in Mather et al, *Annals N. Y. Acad. Sci.* 383:44-68 (1982); MRC 5 cells; and FS4 cells. Other useful mammalian host cell lines include Chinese hamster ovary (CHO) cells, including DHFR⁻ CHO cells (Urlaub et al., *Proc. Natl. Acad. Set. USA* 77:4216 (1980)); and myeloma cell lines such as Y0, NS0 and Sp2/0. For a review of certain mammalian host cell lines suitable for antibody production, see, e.g., Yazaki and Wu, *Methods in Molecular Biology*, Vol. 248 (B. K. C. Lo, ed., Humana Press, Totowa, N.J.), pp. 255-268 (2003).

Polyclonal antibodies are preferably raised in animals by multiple subcutaneous (sc) or intraperitoneal (ip) injections of the relevant antigen and an adjuvant. It may be useful to conjugate the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups.

Animals (usually non-human mammals) are immunized against the antigen, immunogenic conjugates, or derivatives by combining, e.g., 100 μg or 5 μg of the protein or conjugate (for rabbits or mice, respectively) with 3 volumes of Freund's complete adjuvant and injecting the solution intradermally at multiple sites. One month later the animals are boosted with ⅕ to ⅒ the original amount of peptide or conjugate in Freund's complete adjuvant by subcutaneous injection at multiple sites. Seven to 14 days later the animals are bled and the serum is assayed for antibody titer. Animals are boosted until the titer plateaus. Preferably, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

Monoclonal antibodies are obtained from a population of substantially homogeneous antibodies, i.e., the individual antibodies comprising the population are identical except for possible naturally occurring mutations and/or post-translational modifications (e.g., isomerizations, amidations) that may be present in minor amounts. Thus, the modifier "monoclonal" indicates the character of the antibody as not being a mixture of discrete antibodies.

For example, the monoclonal antibodies may be made using the hybridoma method first described by Kohler et al. *Nature* 256(5517):495-497 (1975). In the hybridoma method, a mouse or other appropriate host animal, such as a hamster, is immunized as hereinabove described to elicit lymphocytes that produce or are capable of producing antibodies that will specifically bind to the protein used for immunization. Alternatively, lymphocytes may be immunized in vitro.

The immunizing agent will typically include the antigenic protein or a fusion variant thereof. Generally either peripheral blood lymphocytes (PBLs) are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, Monoclonal Antibodies: Principles and Practice, Academic Press (1986), pp. 59-103).

Immortalized cell lines are usually transformed mammalian cells, particularly myeloma cells of rodent, bovine and human origin. Usually, rat or mouse myeloma cell lines are employed. The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which are substances that prevent the growth of HGPRT-deficient cells.

Preferred immortalized myeloma cells are those that fuse efficiently, support stable high-level production of antibody by the selected antibody-producing cells, and are sensitive to a medium such as HAT medium. Among these, preferred are murine myeloma lines, such as those derived from MOPC-21 and MPC-11 mouse tumors available from the Salk Institute Cell Distribution Center, San Diego, Calif. USA, and SP-2 cells (and derivatives thereof, e.g., X63-Ag8-653) available from the American Type Culture Collection, Manassas, Va. USA. Human myeloma and mouse-human heteromyeloma cell lines also have been described for the production of human monoclonal antibodies (Kozbor et al., *J Immunol.* 133(6):3001-3005 (1984); Brodeur et al., Monoclonal Antibody Production Techniques and Applications, Marcel Dekker, Inc., New York (1987), pp. 51-63).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunosorbant assay (ELISA). Such techniques and assays are known in the art. For example, binding affinity may be determined by the Scatchard analysis of Munson, *Anal Biochem.* 107(1):220-239 (1980).

After hybridoma cells are identified that produce antibodies of the desired specificity, affinity, and/or activity, the clones may be subcloned by limiting dilution procedures and grown by standard methods (Goding, supra). Suitable culture media for this purpose include, for example, D-MEM or RPMI-1640 medium. In addition, the hybridoma cells may be grown in vivo as tumors in a mammal.

The monoclonal antibodies secreted by the subclones are suitably separated from the culture medium, ascites fluid, or serum by conventional immunoglobulin purification procedures such as, for example, protein A-Sepharose, hydroxyapatite chromatography, gel electrophoresis, dialysis, or affinity chromatography.

Antibodies may be produced by immunizing an appropriate host animal against an antigen. In one embodiment, the antigen is a polypeptide comprising a full-length C5. In one embodiment, the antigen is a polypeptide comprising the β chain (SEQ ID NO: 40) of C5.

In a further embodiment, the invention provides a method of producing an anti-C5 antibody that comprises immunizing an animal against a polypeptide antigen, wherein the polypeptide comprises (a) the MG1-MG2 domain (SEQ ID NO: 43) of the β chain of C5; (b) the region corresponding to amino acids at positions 33 to 124 of the β chain (SEQ ID NO: 40) of C5; (c) at least one fragment selected from amino acids 47-57, 70-76, and 107-110 of the β chain (SEQ ID NO: 40) of C5; or (d) a fragment of the β chain (SEQ ID NO: 40) of C5 which comprises at least one amino acid selected from Glu48, Asp51, His70, His72, Lys109, and His110. In one embodiment, the antigen is a polypeptide comprising the MG1-MG2 domain (SEQ ID NO: 43) of the β chain of C5. In one embodiment, the antigen is a polypeptide comprising the MG1 domain (SEQ ID NO: 41) of the β chain of C5. In one embodiment, the antigen is a polypeptide comprising the region corresponding to the amino acids at positions 19 to 180 of the β chain of C5. In one embodiment, the antigen is a polypeptide comprising the region corresponding to the amino acids at positions 33 to 124 of the β chain of C5. In one embodiment, the antigen is a polypeptide comprising at least one fragment selected from amino acids 47-57, 70-76, and 107-110 of the β chain (SEQ ID NO: 40) of C5. In one embodiment, the antigen is a polypeptide comprising a fragment of the β chain of C5 which comprises at least one amino acid selected from the group consisting of Thr47, Glu48, Ala49, Phe50, Asp51, Ala52, Thr53, Lys57, His70, Val71, His72, Ser74, Glu76, Val107, Ser108, Lys109, and His110. In one embodiment, the antigen is a polypeptide comprising a fragment of the β chain of C5 which comprises at least one amino acid selected from the group consisting of Glu48, Asp51, His70, His72, Lys109, and His110. Also included in the present invention are antibodies produced by immunizing an animal against the antigen. The antibodies may incorporate any of the features, singly or in combination, as described in "Exemplary Anti-C5 Antibodies" above.

C. Assays

Anti-C5 antibodies provided herein may be identified, screened for, or characterized for their physical/chemical properties and/or biological activities by various assays known in the art.

1. Binding Assays and Other Assays

In one aspect, an antibody of the invention is tested for its antigen binding activity, e.g., by known methods such as ELISA, Western blot, BIACORE®, etc.

In another aspect, competition assays may be used to identify an antibody that competes for binding to C5 with an anti-C5 antibody described herein. In certain embodiments, when such a competing antibody is present in excess, it blocks (e.g., reduces) the binding of a reference antibody to C5 by at least 10%, 15%, 20%, 25%, 30%, 35%, 40%, 45%, 50%, 55%, 60%, 65%, 70%, 75%, or more. In some instances, binding is inhibited by at least 80%, 85%, 90%, 95%, or more. In certain embodiments, such a competing antibody binds to the same epitope (e.g., a linear or a conformational epitope) that is bound by an anti-C5 antibody described herein (e.g., an anti-C5 antibody described in Table 2). Detailed exemplary methods for mapping an epitope to which an antibody binds are provided in Morris, "Epitope Mapping Protocols," in *Methods in Molecular Biology vol.* 66 (Humana Press, Totowa, N.J.) (1996).

In an exemplary competition assay, immobilized C5 is incubated in a solution comprising a first labeled (reference) antibody that binds to C5 and a second unlabeled antibody that is being tested for its ability to compete with the first antibody for binding to C5. The second antibody may be present in a hybridoma supernatant. As a control, immobilized C5 is incubated in a solution comprising the first labeled antibody but not the second unlabeled antibody. After incubation under conditions permissive for binding of the first antibody to C5, excess unbound antibody is removed, and the amount of label associated with immobilized C5 is measured. If the amount of label associated with immobilized C5 is substantially reduced in the test sample relative to the control sample, then that indicates that the second antibody is competing with the first antibody for binding to C5. See, Harlow and Lane, Antibodies: *A Laboratory Manual ch.* 14 (Cold Spring Harbor Laboratory, Cold Spring Harbor, N.Y.) (1988).

In another exemplary competition assay, BIACORE® analysis is used to determine the ability of a test anti-C5 antibody to compete with the binding to C5 by a second (reference) anti-C5 antibody. In a further aspect in which a BIACORE® instrument (for example, the BIACORE® 3000) is operated according to the manufacturer's recommendations, C5 protein is captured on a CM5 BIACORE® chip using a standard technique known in the art to generate a C5-coated surface. Typically 200-800 resonance units of C5 would be coupled to the chip (an amount that gives easily measurable levels of binding but that is readily saturable by the concentrations of test antibody being used). The two antibodies (i.e., the test and reference antibody) to be assessed for their ability to compete with each other are mixed at a 1:1 molar ratio of binding sites in a suitable buffer to create a test mixture. When calculating the concentrations on a binding site basis the molecular weight of an a test or reference antibody is assumed to be the total molecular weight of the corresponding antibody divided by the number of C5-binding sites on the antibody. The concentration of each antibody (i.e., test antibody and reference antibody) in the test mixture should be high enough to readily saturate the binding sites for that antibody on the C5 molecules captured on the BIACORE® chip. The test and reference antibodies in the mixture are at the same molar concentration (on a binding basis), typically between 1.00 and 1.5 micromolar (on a binding site basis). Separate solutions containing the test antibody alone and the reference antibody alone are also prepared. Test antibody and reference antibody in these solutions should be in the same buffer and at the same concentration and conditions as in the test mixture. The test mixture containing the test antibody and reference antibody is passed over the C5-coated BIACORE® chip and the total amount of binding is recorded. The chip is then treated in such a way as to remove the bound test or reference antibody without damaging the chip-bound C5. Typically, this is done by treating the chip with 30 mM HCl for 60 seconds. The solution of test antibody alone is then passed over the C5-coated surface and the amount of binding recorded. The chip is again treated to remove all of the bound antibody without damaging the chip-bound C5. The solution of reference antibody alone is then passed over the C5-coated surface and the amount of binding recorded. The maximum theoretical binding of the mixture of test antibody and reference antibody is next calculated, and is the sum of the binding of each antibody (i.e. test and reference) when passed over the C5 surface alone. If the actual recorded binding of the mixture is less than this theoretical maximum then test antibody and reference antibody are competing with each other for binding C5. Thus, in general, a competing test anti-C5 antibody is one which will bind to C5 in the above BIACORE® blocking assay such that during the assay and in the presence of the reference anti-C5 antibody the recorded binding is between 80% and 0.1% (e.g., 80%> to 4%) of the maximum theoretical binding, specifically between 75% and 0.1% (e.g., 75% to 4%) of the maximum theoretical binding, and more specifically between 70% and 0.1% (e.g., 70% to 4%) of maximum theoretical binding (as defined above) of the test antibody and reference antibody in combination.

In certain embodiments, an anti-C5 antibody of the present invention competes for binding C5 with antibody CFA0341 or CFA0330. In some embodiments, an anti-C5 antibody competes for binding C5 with an antibody selected from: CFA0538, CFA0501, CFA0599, CFA0307, CFA0366, CFA0675, and CFA0672. In some embodiments, an anti-C5 antibody competes for binding C5 with antibody CFA0329. In some embodiments, an anti-C5 antibody competes for binding C5 with antibody CFA0666. In some embodiments, an anti-C5 antibody competes for binding C5 with antibody CFA0305.

In certain embodiments, an anti-C5 antibody of the present invention competes for binding C5 with an antibody comprising a VH and VL pair selected from antibody CFA0341 and CFA0330. In some embodiments, an anti-C5 antibody competes for binding C5 with an antibody comprising a VH and VL pair of an antibody selected from: CFA0538, CFA0501, CFA0599, CFA0307, CFA0366, CFA0675, and CFA0672. In some embodiments, an anti-C5 antibody competes for binding C5 with an antibody comprising the VH and VL pair from antibody CFA0329. In some embodiments, an anti-C5 antibody competes for binding C5 with an antibody comprising the VH and VL pair from antibody CFA0666.

In certain embodiments, an anti-C5 antibody of the present invention competes for binding C5 with an antibody comprising a VH and VL pair of antibody CFA0305 or 305LO5.

In further embodiments, the anti-C5 antibody binds to C5 with a higher affinity at neutral pH than at acidic pH. In certain embodiments, an anti-C5 antibody of the present invention competes for binding C5 with an antibody comprising a VH and VL pair selected from: CFA0538, CFA0501, CFA0599, CFA0307, CFA0366, CFA0675, and CFA0672. In some embodiments, an anti-C5 antibody competes for binding C5 with antibody CFA0666. In further embodiments, the anti-C5 antibody binds to C5 with a higher affinity at pH7.4 than at pH5.8.

In further embodiments, the anti-C5 antibody binds to C5 with a higher affinity at neutral pH than at acidic pH. In certain embodiments, an anti-C5 antibody of the present invention competes for binding C5 with an antibody comprising a VH and VL pair of antibody CFA0305 or 305LO5. In further embodiments, the anti-C5 antibody binds to C5 with a higher affinity at pH7.4 than at pH5.8.

In certain embodiments, an anti-C5 antibody of the present invention competes for binding C5 with an antibody comprising a VH and VL pair selected from a VH of SEQ ID NO:22 and a VL of SEQ ID NO:26, or a VH of SEQ ID NO:21 and a VL of SEQ ID NO:25. In some embodiments, an anti-C5 antibody competes for binding C5 with an antibody comprising a VH and VL pair selected from: (a) a VH of SEQ ID NO: 5 and a VL of SEQ ID NO: 15; (b) a VH of SEQ ID NO: 4 and a VL of SEQ ID NO: 14; (c) a VH of SEQ ID NO:6 and a VL of SEQ ID NO:16; (d) aVH of SEQ ID NO:2 and a VL of SEQ ID NO:12; (e) a VH of SEQ ID NO: 3 and a VL of SEQ ID NO: 13; (f) a VH of SEQ ID NO: 1 and a VL of SEQ ID NO: 11; (g) a VH of SEQ ID NO:9 and a VL of SEQ ID NO:19; (h) aVH of SEQ ID NO:7 and a VL of SEQ ID NO:17; and (i) aVH of SEQ ID NO:8 and a VL of SEQ ID NO:18. In some embodiments, an anti-C5 antibody competes for binding C5 with antibody comprising a VH of SEQ ID NO:23 and a VL of SEQ ID NO:27. In some embodiments, an anti-C5 antibody competes for binding C5 with antibody comprising a VH of SEQ ID NO:7 and a VL of SEQ ID NO:17. In further embodiments, the anti-C5 antibody binds to the same epitope as one of the above VH and VL pairs.

In certain embodiments, an anti-C5 antibody of the present invention competes for binding C5 with an antibody comprising a VH and VL pair selected from: (a) a VH of SEQ ID NO:1 and a VL of SEQ ID NO:11; (b) a VH of SEQ ID NO: 22 and a VL of SEQ ID NO:26; (c) a VH of SEQ ID NO:21 and a VL of SEQ ID NO:25; (d) a VH of SEQ ID NO: 5 and a VL of SEQ ID NO:15; (e) a VH of SEQ ID NO:4 and a VL of SEQ ID NO:14; (f) a VH of SEQ ID NO: 6 and a VL of SEQ ID NO: 16; (g) a VH of SEQ ID NO:2 and a VL of SEQ ID NO:12; (h) a VH of SEQ ID NO: 3 and a VL of SEQ ID NO: 13; (i) a VH of SEQ ID NO:9 and a VL of SEQ ID NO:19; (j) a VH of SEQ ID NO:7 and a VL of SEQ ID NO: 17; (k) aVH of SEQ ID NO:8 and a VL of SEQ ID NO:18; (l) a VH of SEQ ID NO: 23 and a VL of SEQ ID NO:27; and (m) a VH of SEQ ID NO:10 and a VL of SEQ ID NO:20. In further embodiments, the anti-C5 antibody binds to the same epitope as one of the above VH and VL pairs.

In certain embodiments, an anti-C5 antibody of the present invention competes for binding C5 with an antibody comprising a VH and VL pair selected from: (a) a VH of SEQ ID NO: 22 and a VL of SEQ ID NO:26; (b) a VH of SEQ ID NO:21 and a VL of SEQ ID NO:25; (c) a VH of SEQ ID NO: 5 and a VL of SEQ ID NO:15; (d) a VH of SEQ ID NO:4 and a VL of SEQ ID NO:14; (e) a VH of SEQ ID NO: 6 and a VL of SEQ ID NO: 16; (f) a VH of SEQ ID NO:2 and a VL of SEQ ID NO:12; (g) a VH of SEQ ID NO: 3 and a VL of SEQ ID NO: 13; (h) a VH of SEQ ID NO:9 and a VL of SEQ ID NO:19; (i) a VH of SEQ ID NO:7 and a VL of SEQ ID NO: 17; (j) aVH of SEQ ID NO:8 and a VL of SEQ ID NO:18; (k) a VH of SEQ ID NO: 23 and a VL of SEQ ID NO:27. In further embodiments, the anti-C5 antibody binds to the same epitope as one of the above VH and VL pairs.

In certain embodiments, an anti-C5 antibody of the present invention competes for binding C5 with an antibody comprising a VH and VL pair selected from a VH of SEQ ID NO:1 and a VL of SEQ ID NO:11, or a VH of SEQ ID NO:10 and a VL of SEQ ID NO:20. In further embodiments, the anti-C5 antibody binds to the same epitope as one of the above VH and VL pairs.

In further embodiments, the anti-C5 antibody binds to C5 with a higher affinity at neutral pH than at acidic pH. In certain embodiments, an anti-C5 antibody binds to C5 with a higher affinity at neutral pH than at acidic pH and competes for binding C5 with an antibody comprising a VH and VL pair selected from: (a) a VH of SEQ ID NO:1 and a VL of SEQ ID NO:11; (b) a VH of SEQ ID NO: 5 and a VL of SEQ ID NO:15; (c) a VH of SEQ ID NO:4 and a VL of SEQ ID NO: 14; (d) a VH of SEQ ID NO: 6 and a VL of SEQ ID NO: 16; (e) a VH of SEQ ID NO:2 and a VL of SEQ ID NO:12; (f) a VH of SEQ ID NO: 3 and a VL of SEQ ID NO: 13; (g) a VH of SEQ ID NO:9 and a VL of SEQ ID NO:19; (h) a VH of SEQ ID NO:7 and a VL of SEQ ID NO: 17; (i) aVH of SEQ ID NO:8 and a VL of SEQ ID NO:18; and (j) a VH of SEQ ID NO:10 and a VL of SEQ ID NO:20. In further embodiments, the anti-C5 antibody binds to C5 with a higher affinity at pH7.4 than at pH5.8. In further embodiments, the anti-C5 antibody binds to the same epitope as one of the above VH and VL pairs.

In some embodiments, the anti-C5 antibody binds to C5 with a higher affinity at neutral pH than at acidic pH and competes for binding C5 with an antibody comprising a VH and VL pair selected from: (a) a VH of SEQ ID NO: 5 and a VL of SEQ ID NO: 15; (b) a VH of SEQ ID NO: 4 and a VL of SEQ ID NO: 14; (c) a VH of SEQ ID NO:6 and a VL of SEQ ID NO:16; (d) aVH of SEQ ID NO:2 and a VL of SEQ ID NO:12; (e) a VH of SEQ ID NO: 3 and a VL of SEQ ID NO: 13; (f) a VH of SEQ ID NO: 1 and a VL of SEQ ID NO: 11; (g) a VH of SEQ ID NO:9 and a VL of SEQ ID NO: 19; (h) aVH of SEQ ID NO:7 and a VL of SEQ ID NO:17; and (i) aVH of SEQ ID NO:8 and a VL of SEQ ID NO: 18. In further embodiments, the anti-C5 antibody binds to C5 with a higher affinity at pH7.4 than at pH5.8. In further embodiments, the anti-C5 antibody binds to the same epitope as one of the above VH and VL pairs.

In some embodiments, the anti-C5 antibody binds to C5 with a higher affinity at neutral pH than at acidic pH and competes for binding C5 with an antibody comprising a VH and VL pair selected from a VH of SEQ ID NO:1 and a VL of SEQ ID NO:11, or a VH of SEQ ID NO:10 and a VL of SEQ ID NO:20. In further embodiments, the anti-C5 antibody binds to C5 with a higher affinity at pH7.4 than at pH5.8. In further embodiments, the anti-C5 antibody binds to the same epitope as one of the above VH and VL pairs.

In certain embodiments, whether an anti-C5 antibody of the present invention binds to a certain epitope can be determined as follows: C5 point mutants in which an amino acid (except for alanine) on C5 is substituted with alanine are expressed in 293 cells, and binding of an anti-C5 antibody to the C5 mutants is tested via ELISA, Western blot or BIACORE®; wherein a substantial reduction or elimination of binding of the anti-C5 antibody to the C5 mutant relative to its binding to wild type C5 indicates that the anti-C5 antibody binds to an epitope comprising that amino acid on C5. In certain embodiments, the amino acid on C5 to be substituted with alanine is selected from the group consisting of Glu48, Asp51, His70, His72, Lys109, and His110 of the β chain of C5 (SEQ ID NO:40). In further embodiments, the amino acid on C5 to be substituted with alanine is Asp51 or Lys109 of the β chain of C5 (SEQ ID NO:40).

In another embodiment, whether an anti-C5 antibody with pH-dependent binding characteristics binds to a certain epitope can be determined as follows: C5 point mutants in which a histidine residue on C5 is substituted with another amino acid (e.g., tyrosine) are expressed in 293 cells, and binding of an anti-C5 antibody to the C5 mutants is tested via ELISA, Western blot or BIACORE®; wherein a substantial reduction of binding of the anti-C5 antibody to wild type C5 at acidic pH relative to its binding to the C5 mutant at acidic pH, indicates that the anti-C5 antibody binds to an epitope comprising that histidine residue on C5. In further embodiments, binding of the anti-C5 antibody to wild type C5 at neutral pH is not substantially reduced relative to its binding to the C5 mutant at neutral pH. In certain embodiments, the histidine residue on C5 to be substituted with another amino acid is selected from the group consisting of His70, His72, and His110 of the β chain of C5 (SEQ ID NO:40). In a further embodiment, the histidine residue His70 is substituted with tyrosine.

2. Activity Assays

In one aspect, assays are provided for identifying anti-C5 antibodies thereof having biological activity. Biological activity may include, e.g., inhibiting the activation of C5, preventing the cleavage of C5 to form C5a and C5b, blocking the access of C5 convertase to the cleavage site on C5, blocking hemolytic activity caused by the activation of C5, etc. Antibodies having such biological activity in vivo and/or in vitro are also provided.

In certain embodiments, an antibody of the invention is tested for such biological activity.

In certain embodiments, whether a test antibody inhibits the cleavage of C5 into C5a and C5b, is determined by methods described in, e.g., Isenman et al., *J Immunol.* 124(1):326-331 (1980). In another embodiment, this is determined by methods for specific detection of cleaved C5a and/or C5b proteins, e.g., ELISAs or Western blots. Where a decreased amount of a cleavage product of C5 (i.e., C5a and/or C5b) is detected in the presence of (or following contact with) the test antibody, the test antibody is identified as an antibody that can inhibit the cleavage of C5. In certain embodiments, the concentration and/or physiologic activity of C5a can be measured by methods, e.g., chemotaxis assays, RIAs, or ELISAs (See, e.g., Ward and Zvaifler *J. Clin. Invest.* 50(3):606-616 (1971)) which is herein incorporated by reference in its entirety.)

In certain embodiments, whether a test antibody blocks the access of C5 convertase to C5 is determined by methods for the detection of protein interactions between the C5 convertase and C5, e.g., ELISAs or BIACORE®. Where the interactions are decreased in the presence of (or following contact with) the test antibody, the test antibody is identified as an antibody that can block the access of C5 convertase to C5.

In certain embodiments, C5 activity can be measured as a function of its cell-lysing ability in a subject's body fluids. The cell-lysing ability, or a reduction thereof; of C5 can be measured by methods well known in the art, for example, a conventional hemolytic assay, such as the hemolysis assay described by Kabat and Mayer (eds), Experimental Immunochemistry, 2nd Edition, 135-240, Springfield, Ill., CC Thomas (1961), pages 135-139, or a conventional variation of that assay, such as the chicken erythrocyte hemolysis method as described in, e.g., Hillmen et al., *N. Engl. J. Med.* 350(6): 552-559 (2004), each of the above publications is herein incorporated by reference in its entirety.

In certain embodiments, C5 activity, or inhibition thereof, is quantified using a CH50eq assay. The CH50eq assay is a method for measuring the total classical complement activity in serum. This test is a lytic assay, which uses antibody-sensitized erythrocytes as the activator of the classical complement pathway, and various dilutions of the test serum to determine the amount required to give 50% lysis (CH50). The percentage of hemolysis can be determined, for example, using a spectrophotometer. The CH50eq assay provides an indirect measure of terminal complement complex (TCC) formation, since the TCC themselves are directly responsible for the hemolysis measured. Inhibition of C5 activation can also be detected and/or measured using the methods set forth and exemplified in the working examples. Using assays of these or other suitable types, candidate antibodies capable of inhibiting the activation of C5 can be screened. In certain embodiments, inhibition of C5 activation includes at least a 5%, 10%, 15%, 20%, 25%, 30%, 35%, or 40% or greater decrease in the C5 activation in an assay as compared to the effect of a negative control under similar conditions. In some embodiments, it refers to inhibition of C5 activation by at least 45%, 50%, 55%, 60%, 65%, 70%, 75%, 80%, 85%, 90%, or 95% or greater.

D. Immunoconjugates

The invention also provides immunoconjugates comprising an anti-C5 antibody herein conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

In one embodiment, an immunoconjugate is an antibody-drug conjugate (ADC) in which an antibody is conjugated to one or more drugs, including but not limited to a maytansinoid (see, U.S. Pat. Nos. 5,208,020, 5,416,064 and European Patent EP 0 425 235 BI); an auristatin such as monomethylauristatin drug moieties DE and DF (MMAE and MMAF) (see, U.S. Pat. Nos. 5,635,483 and 5,780,588, and 7,498, 298); a dolastatin; a calicheamicin or derivative thereof (see, U.S. Pat. Nos. 5,712,374, 5,714,586, 5,739,116, 5,767,285, 5,770,701, 5,770,710, 5,773,001, and 5,877,296; Hinman et al., *Cancer Res.* 53:3336-3342 (1993); and Lode et al., *Cancer Res.* 58:2925-2928 (1998)); an anthracycline such as daunomycin or doxorubicin (see Kratz et al., *Current Mad. Chem.* 13:477-523 (2006); Jeffrey et al., *Bioorganic & Med. Chem. Letters* 16:358-362 (2006); Torgov et al., *Bioconj. Chem.* 16:717-721 (2005); Nagy et al., *Proc. Natl. Acad. Sc. USA* 97:829-834 (2000); Dubowchik et al., *Bioorg. & Med. Chem. Letters* 12:1529-1532 (2002); King et al., *J. Med. Chem.* 45:4336-4343 (2002); and U.S. Pat. No. 6,630,579); methotrexate; vindesine; a taxane such as docetaxel, paclitaxel, larotaxel, tesetaxel, and ortataxel; a trichothecene; and CC1065.

In another embodiment, an immunoconjugate comprises an antibody as described herein conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *sapaonaria*

*officinalis* inhibitor, gelonin, mitogellin, restrictocin, phenomycin, enomycin, and the tricothecenes.

In another embodiment, an immunoconjugate comprises an antibody as described herein conjugated to a radioactive atom to form a radioconjugate. A variety of radioactive isotopes are available for the production of radioconjugates. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the radioconjugate is used for detection, it may comprise a radioactive atom for scintigraphic studies, for example tc99m or I123, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

Conjugates of an antibody and cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(pdiazoniumbenzoyl)-ethyl-enediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., *Science* 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari et al., *Cancer Res.* 52:127-131 (1992); U.S. Pat. No. 5,208,020) may be used.

The immunoconjugates or ADCs herein expressly contemplate, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A).

E. Methods and Compositions for Diagnostics and Detection

In certain embodiments, any of the anti-C5 antibodies provided herein is useful for detecting the presence of C5 in a biological sample. The term "detecting" as used herein encompasses quantitative or qualitative detection. In certain embodiments, a biological sample comprises a cell or tissue, such as serum, whole blood, plasma, biopsy sample, tissue sample, cell suspension, saliva, sputum, oral fluid, cerebrospinal fluid, amniotic fluid, ascites fluid, milk, colostrums, mammary gland secretion, lymph, urine, sweat, lacrimal fluid, gastric fluid, synovial fluid, peritoneal fluid, ocular lens fluid and mucus. In particular embodiments, the biological sample comprises whole blood. In additional embodiments, the biological sample comprises serum or plasma.

In one embodiment, an anti-C5 antibody for use in a method of diagnosis or detection is provided. In a further aspect, a method of detecting the presence of C5 in a biological sample is provided. In certain embodiments, the method comprises contacting the biological sample with an anti-C5 antibody as described herein under conditions permissive for binding of the anti-C5 antibody to C5, and detecting whether a complex is formed between the anti-C5 antibody and C5. Such method may be an in vitro or in vivo method. In one embodiment, an anti-C5 antibody is used to select subjects eligible for therapy with an anti-C5 antibody, e.g., where C5 is a biomarker for selection of patients.

In another embodiment, a method of selecting an individual having a complement-mediated disease or condition which involves excessive or uncontrolled activation of C5 as suitable for a therapy comprising an anti-C5 antibody of the present invention is provided. In certain embodiments, the method comprises (a) detecting a genetic variation in C5 derived from the individual, and (b) selecting the individual as suitable for the therapy comprising an anti-C5 antibody of the present invention when the genetic variation is detected in C5 derived from the individual. In another embodiment, a method of selecting a therapy for an individual having a complement-mediated disease or condition which involves excessive or uncontrolled activation of C5 is provided. In certain embodiments, the method comprises (a) detecting a genetic variation in C5 derived from the individual, and (b) selecting a therapy comprising an anti-C5 antibody of the present invention for the individual when the genetic variation is detected in C5 derived from the individual.

In another embodiment, a method of treating an individual having a complement-mediated disease or condition which involves excessive or uncontrolled activation of C5 is provided. In certain embodiments, the method comprises (a) detecting a genetic variation in C5 derived from the individual, (b) selecting the individual as suitable for the therapy comprising an anti-C5 antibody of the present invention when the genetic variation is detected in C5 derived from the individual, and (c) administering an anti-C5 antibody of the present invention to the individual.

In another embodiment, an anti-C5 antibody of the present invention for use in treating an individual having a complement-mediated disease or condition which involves excessive or uncontrolled activation of C5 is provided. In certain embodiments, the individual is treated with an anti-C5 antibody of the present invention when the genetic variation is detected in C5 derived from the individual.

In another embodiment, in vitro use of a genetic variation in C5 for selecting an individual having a complement-mediated disease or condition which involves excessive or uncontrolled activation of C5 as suitable for a therapy comprising an anti-C5 antibody of the present invention is provided. In certain embodiments, the individual is selected as being suitable for the therapy when the genetic variation is detected in C5 derived from the individual. In another embodiment, in vitro use of a genetic variation in C5 for selecting a therapy for an individual having a complement-mediated disease or condition which involves excessive or uncontrolled activation of C5 is provided. In certain embodiments, a therapy comprising an anti-C5 antibody of the present invention is selected for the individual when the genetic variation is detected in C5 derived from the individual.

It has been reported that some patients who have genetic variation in C5 show poor response to a therapy comprising an existing anti-C5 antibody (Nishimura et al., N. *Engl. J. Med.* 370:632-639 (2014)). It is recommended that such a patient be treated with a therapy comprising an anti-C5 antibody of the present invention, because such an antibody has an inhibitory activity on the activation of C5 variants as well as wild type C5, as demonstrated in the working examples below.

Detection of a genetic variation in C5 can be carried out by using a method known in the prior art. Such a method may include sequencing, PCR, RT-PCR, and a hybridization-based method such as southern blot or northern blot, but is not limited thereto. C5 variants may comprise at least one genetic variation. The genetic variation may be selected from a group consisting of V145I, R449G, V802I, R885H, R928Q, D966Y, S1310N, and E1437D. Herein, R885H, for example, means a genetic variation where arginine at position 885 is substituted by histidine. In certain embodiments, C5 variant has biological activity similar to wild type C5.

Exemplary disorders that may be diagnosed and/or treated using an antibody of the invention include rheumatoid arthritis (RA); systemic lupus erythematosus (SLE); lupus nephritis; ischemia reperfusion injury (IRI); asthma; paroxysmal nocturnal hemoglobinuria (PNH); hemolytic uremic syndrome (HUS) (e.g., atypical hemolytic uremic syndrome (aHUS)); dense deposit disease (DDD); neuromyelitis optica (NMO); multifocal motor neuropathy (MMN); multiple sclerosis (MS); systemic sclerosis; macular degeneration (e.g., age-related macular degeneration (AMD)); hemolysis, elevated liver enzymes, and low platelets (HELLP) syndrome; thrombotic thrombocytopenic purpura (TTP); spontaneous fetal loss; epidermolysis bullosa; recurrent fetal loss; pre-eclampsia; traumatic brain injury; myasthenia gravis; cold agglutinin disease; Sjögren's syndrome; dermatomyositis; bullous pemphigoid; phototoxic reactions; Shiga toxin *E. coli*-related hemolytic uremic syndrome; typical or infectious hemolytic uremic syndrome (tHUS); C3 Glomerulonephritis; Antineutrophil cytoplasmic antibody (ANCA)-associated vasculitis; humoral and vascular transplant rejection; acute antibody mediated rejection (AMR); graft dysfunction; myocardial infarction; an allogenic transplant; sepsis; coronary artery disease; hereditary angioedema; dermatomyositis; Graves' disease; atherosclerosis; Alzheimer's disease (AD); Huntington's disease; Creutzfeld-Jacob disease; Parkinson's disease; cancers; wounds; septic shock; spinal cord injury; uveitis; diabetic ocular diseases; retinopathy of prematurity; glomerulonephritis; membranous nephritis; immunoglobulin A nephropathy; adult respiratory distress syndrome (ARDS); chronic obstructive pulmonary disease (COPD); cystic fibrosis; hemolytic anemia; paroxysmal cold hemoglobinuria; anaphylactic shock; allergy; osteoporosis; osteoarthritis; Hashimoto's thyroiditis; type I diabetes; psoriasis; pemphigus; autoimmune hemolytic anemia (AIHA); idiopathic thrombocytopenic purpura (ITP); Goodpasture syndrome; Degos disease; antiphospholipid syndrome (APS); catastrophic APS (CAPS); a cardiovascular disorder; myocarditis; a cerebrovascular disorder; a peripheral vascular disorder, a renovascular disorder; a mesenteric/enteric vascular disorder, vasculitis; Henoch-SchOnlein purpura nephritis; Takayasu's disease; dilated cardiomyopathy; diabetic angiopathy; Kawasaki's disease (arteritis); venous gas embolus (VGE), restenosis following stent placement; rotational atherectomy; membraneous nephropathy; Guillain-Barré syndrome (GBS); Fisher syndrome; antigen-induced arthritis; synovial inflammation; viral infections; bacterial infections; fungal infections; and injury resulting from myocardial infarction, cardiopulmonary bypass and hemodialysis.

In certain embodiments, labeled anti-C5 antibodies are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}P$, $^{14}C$, $^{125}I$, $^{3}H$, and $^{131}I$, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

F. Pharmaceutical Formulations

Pharmaceutical formulations of an anti-C5 antibody as described herein are prepared by mixing such antibody having the desired degree of purity with one or more optional pharmaceutically acceptable carriers (*Remington's Pharmaceutical Sciences* 16th edition, Osol, A. Ed. (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as polyethylene glycol (PEG). Exemplary pharmaceutically acceptable carriers herein further include interstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Publ. Nos. 2005/0260186 and 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171,586 and WO 2006/044908, the latter formulations including a histidine-acetate buffer.

The formulation herein may also contain more than one active ingredients as necessary for the particular indication being treated, preferably those with complementary activities that do not adversely affect each other. Such active ingredients are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

Sustained-release preparations may be prepared. Suitable examples of sustained-release preparations include semipermeable matrices of solid hydrophobic polymers containing the antibody, which matrices are in the form of shaped articles, e.g., films, or microcapsules.

The formulations to be used for in vivo administration are generally sterile. Sterility may be readily accomplished, e.g., by filtration through sterile filtration membranes.

G. Therapeutic Methods and Compositions

Any of the anti-C5 antibodies provided herein may be used in therapeutic methods. In one aspect, an anti-C5 antibody for use as a medicament is provided. In further aspects, an anti-C5 antibody for use in treating a complement-mediated disease or condition which involves excessive or uncontrolled activation of C5 is provided. In other aspects, the invention provides for the use of an anti-C5 antibody in treating a disease such as paroxysmal nocturnal hemoglobinuria (PNH), age-related macular degeneration, myocardial infarction, rheumatoid arthritis, osteoporosis, osteoarthritis, or inflammation.

In certain embodiments, an anti-C5 antibody for use in a method of treatment is provided. In certain embodiments, the invention provides an anti-C5 antibody for use in a method of treating an individual having a complement-mediated disease or condition which involves excessive or uncontrolled activation of C5, comprising administering to the individual an effective amount of the antiC5 antibody. In one such embodiment, the method further comprises administering to the individual an effective amount of at least one additional therapeutic agent. In certain embodiments, the administered anti-C5 antibody competes for binding C5 with an antibody comprising a VH and VL pair selected from: (a) a VH of SEQ ID NO:1 and a VL of SEQ ID NO: 11; (b) a VH of SEQ ID NO: 22 and a VL of SEQ ID NO:26; (c) a VH of SEQ ID NO:21 and a VL of SEQ ID NO:25; (d) a VH of SEQ ID NO: 5 and a VL of SEQ ID NO: 15; (e) a VH of SEQ ID NO:4 and a VL of SEQ ID NO:14; (f) a VH of SEQ ID NO: 6 and a VL of SEQ ID NO: 16; (g) a VH of SEQ ID NO:2 and a VL of SEQ ID NO:12; (h) a VH of SEQ ID NO: 3 and a VL of SEQ ID NO: 13; (i) a VH of SEQ ID NO:9 and a VL of SEQ ID NO:19; (j) a VH of SEQ ID NO:7 and a VL of SEQ ID NO: 17; (k) aVH of SEQ ID NO:8 and a VL of SEQ ID NO:18; (l) a VH of SEQ ID NO: 23 and a VL of SEQ ID NO:27; and (m) a VH of SEQ ID NO: 10 and a VL of SEQ ID NO:20. In further embodiments, the administered anti-C5 antibody binds to the same epitope as one of the above VH and VL pairs. In certain embodiments, the administered anti-C5 antibody binds C5 and contacts amino acid Asp51 (D51) of SEQ ID NO-39. In additional embodiments, an anti-C5 antibody of the present invention binds C5 and contacts amino acid Lys109 (K109) of SEQ ID NO:39. In a further embodiment, an anti-C5 antibody of the present invention binds C5 and contacts amino acid Asp51 (D51) and amino acid Lys109 (K109) of SEQ ID NO:39.

In another aspect, an anti-C5 antibody is used in a method of treating disease or condition that would be ameliorated by reduced activation of C5, comprising administering to the individual an effective amount of the antiC5 antibody. In one such embodiment, the method further comprises administering to the individual an effective amount of at least one additional therapeutic agent. In certain embodiments, the administered anti-C5 antibody competes for binding C5 with an antibody comprising a VH and VL pair selected from: (a) a VH of SEQ ID NO:1 and a VL of SEQ ID NO:11; (b) a VH of SEQ ID NO: 22 and a VL of SEQ ID NO:26; (c) a VH of SEQ ID NO:21 and a VL of SEQ ID NO:25; (d) a VH of SEQ ID NO: 5 and a VL of SEQ ID NO:15; (e) a VH of SEQ ID NO:4 and a VL of SEQ ID NO:14; (f) a VH of SEQ ID NO: 6 and a VL of SEQ ID NO: 16; (g) a VH of SEQ ID NO:2 and a VL of SEQ ID NO:12; (h) a VH of SEQ ID NO: 3 and a VL of SEQ ID NO: 13; (i) a VH of SEQ ID NO:9 and a VL of SEQ ID NO:19; (j) a VH of SEQ ID NO:7 and a VL of SEQ ID NO: 17; (k) aVH of SEQ ID NO:8 and a VL of SEQ ID NO:18; (l) a VH of SEQ ID NO: 23 and a VL of SEQ ID NO:27; and (m) a VH of SEQ ID NO: 10 and a VL of SEQ ID NO:20. In further embodiments, the administered anti-C5 antibody binds to the same epitope as one of the above VH and VL pairs. In certain embodiments, the administered anti-C5 antibody binds C5 and contacts amino acid Asp51 (D51) of SEQ ID NO:39. In additional embodiments, an anti-C5 antibody of the present invention binds C5 and contacts amino acid Lys109 (K109) of SEQ ID NO:39. In a further embodiment, an anti-C5 antibody of the present invention binds C5 and contacts amino acid Asp51 (D51) and amino acid Lys109 (K109) of SEQ ID NO:39.

In another aspect, an anti-C5 antibody is used in a method of treating an individual determined to have paroxysmal nocturnal hemoglobinuria (PNH), age-related macular degeneration, a myocardial infarction, rheumatoid arthritis, osteoporosis, osteoarthritis, or inflammation, comprising administering to the individual an effective amount of the anti-C5 antibody. In one such embodiment, the method further comprises administering to the individual an effective amount of at least one additional therapeutic agent. In certain embodiments, the administered anti-C5 antibody competes for binding C5 with an antibody comprising a VH and VL pair selected from: (a) a VH of SEQ ID NO:1 and a VL of SEQ ID NO: 11; (b) a VH of SEQ ID NO: 22 and a VL of SEQ ID NO:26; (c) a VH of SEQ ID NO:21 and a VL of SEQ ID NO:25; (d) a VH of SEQ ID NO: 5 and a VL of SEQ ID NO:15; (e) a VH of SEQ ID NO:4 and a VL of SEQ ID NO:14; (l) a VH of SEQ ID NO: 6 and a VL of SEQ ID NO: 16; (g) a VH of SEQ ID NO:2 and a VL of SEQ ID NO:12; (h) a VH of SEQ ID NO: 3 and a VL of SEQ ID NO: 13; (i) a VH of SEQ ID NO:9 and a VL of SEQ ID NO:19; (j) a VH of SEQ ID NO:7 and a VL of SEQ ID NO: 17; (k) aVH of SEQ ID NO:8 and a VL of SEQ ID NO: 18; (l) a VH of SEQ ID NO: 23 and a VL of SEQ ID NO:27; and (m) a VH of SEQ ID NO: 10 and a VL of SEQ ID NO:20. In further embodiments, the administered anti-C5 antibody binds to the same epitope as one of the above VH and VL pairs. In certain embodiments, the administered anti-C5 antibody binds C5 and contacts amino acid Asp51 (D51) of SEQ ID NO:39. In additional embodiments, an anti-C antibody of the present invention binds C5 and contacts amino acid Lys109 (K109) of SEQ ID NO:39. In a further embodiment, an anti-C5 antibody of the present invention binds C5 and contacts amino acid Asp51 (D51) and amino acid Lys109 (K109) of SEQ ID NO:39.

In another aspect, an anti-C5 antibody is used in a method of treating an individual determined to have paroxysmal nocturnal hemoglobinuria (PNH), age-related macular degeneration, a myocardial infarction, rheumatoid arthritis, osteoporosis, osteoarthritis, or inflammation, comprising administering to the individual an effective amount of the anti-C5 antibody. In one such embodiment, the method further comprises administering to the individual an effective amount of at least one additional therapeutic agent.

In certain embodiments, an anti-C5 antibody for use in a method of treatment is provided. In certain embodiments, the invention provides an anti-C5 antibody for use in a method of treating an individual having a complement-mediated disease or condition which involves excessive or uncontrolled activation of C5, comprising administering to the individual an effective amount of the anti-C5 antibody. In one such embodiment, the method further comprises administering to the individual an effective amount of at least one additional therapeutic agent.

When the antigen is a soluble protein, the binding of an antibody to its antigen can result in an extended half-life of the antigen in plasma (i.e., reduced clearance of the antigen from plasma), since the antibody itself has a longer half-life in plasma and serves as a carrier for the antigen. This is due to the recycling of the antigen-antibody complex by FcRn through the endosomal pathway in cell (Roopenian, *Nat. Rev. Immunol.* 7(9):715-725 (2007)). However, an antibody with pH-dependent binding characteristics, which binds to its antigen in neutral extracellular environment while releasing it into acidic endosomal compartments following entry into cells, is expected to have superior properties in terms of antigen neutralization and clearance relative to its counterpart that binds in a pH-independent manner (Igawa et al., *Nat. Biotech.* 28(11): 1203-1207 (2010); Devanaboyina et al., *mAbs* 5(6):851-859 (2013); WO 2009/125825).

In further embodiments, the invention provides an anti-C5 antibody for use in enhancing the clearance of C5 from plasma. In certain embodiments, the invention provides an anti-C5 antibody for use in a method of enhancing the clearance of C5 from plasma in an individual comprising administering to the individual an effective amount of the anti-C5 antibody to enhance the clearance of C5 from plasma. In one embodiment, an anti-C5 antibody enhances the clearance of C5 from plasma, compared to a conventional anti-C5 antibody which does not have pH-dependent binding characteristics. An "individual" according to any of the above embodiments is preferably a human.

In further embodiments, the invention provides an anti-C5 antibody for use in suppressing the accumulation of C5 in plasma. In certain embodiments, the invention provides an anti-C5 antibody for use in a method of suppressing the accumulation of C5 in plasma in an individual, comprising administering to the individual an effective amount of the anti-C5 antibody to suppress the accumulation of C5 in plasma. In one embodiment, the accumulation of C5 in plasma is the result of the formation of an antigen-antibody complex. In another embodiment, an anti-C5 antibody suppresses the accumulation of C5 in plasma, compared to a conventional anti-C5 antibody which does not have pH-dependent binding characteristics. An "individual" according to any of the above embodiments is preferably a human.

An anti-C5 antibody of the present invention may inhibit the activation of C5. In further embodiments, the invention provides an anti-C5 antibody for use in inhibiting the activation of C5. In certain embodiments, the invention provides an anti-C5 antibody for use in a method of inhibiting the activation of C5 in an individual, comprising administering to the individual an effective amount of the anti-C5 antibody to inhibit the activation of C5. In one embodiment, the cytotoxicity mediated by C5 is suppressed by inhibiting the activation of C5. An "individual" according to any of the above embodiments is preferably a human.

In a further aspect, the invention provides the use of an anti-C5 antibody in the manufacture or preparation of a medicament. In one embodiment, the medicament is for treatment of a complement-mediated disease or condition which involves excessive or uncontrolled activation of C5. In a further embodiment, the medicament is for use in a method of treating a complement-mediated disease or condition which involves excessive or uncontrolled activation of C5, comprising administering to an individual having a complement-mediated disease or condition which involves excessive or uncontrolled activation of C5 an effective amount of the medicament. In one such embodiment, the method further comprises administering to the individual an effective amount of at least one additional therapeutic agent. An "individual" according to any of the above embodiments is preferably a human.

In a further embodiment, the medicament is for enhancing the clearance of C5 from plasma. In a further embodiment, the medicament is for use in a method of enhancing the clearance of C5 from plasma in an individual comprising administering to the individual an effective amount of the medicament to enhance the clearance of C5 from plasma. In one embodiment, an anti-C5 antibody enhances the clearance of C5 from plasma, compared to a conventional anti-C5 antibody which does not have pH-dependent binding characteristics. An "individual" according to any of the above embodiments may be a human.

In a further embodiment, the medicament is for suppressing the accumulation of C5 in plasma. In a further embodiment, the medicament is for use in a method of suppressing the accumulation of C5 in plasma in an individual, comprising administering to the individual an effective amount of the medicament to suppress the accumulation of C5 in plasma. In one embodiment, the accumulation of C5 in plasma is a result of the formation of an antigen-antibody complex. In another embodiment, an anti-C5 antibody suppresses the accumulation of C5 in plasma, compared to a conventional anti-C5 antibody which does not have pH-dependent binding characteristics. An "individual" according to any of the above embodiments may be a human.

An anti-C5 antibody of the present invention may inhibit the activation of C5. In a further embodiment, the medicament is for inhibiting the activation of C5. In a further embodiment, the medicament is for use in a method of inhibiting the activation of C5 in an individual, comprising administering to the individual an effective amount of the medicament to inhibit the activation of C5. In one embodiment, the cytotoxicity mediated by C5 is suppressed by inhibiting the activation of C5. An "individual" according to any of the above embodiments may be a human.

In a further aspect, the invention provides a method for treating a complement-mediated disease or condition which involves excessive or uncontrolled activation of C5. In one embodiment, the method comprises administering to an individual having such a complement-mediated disease or condition which involves excessive or uncontrolled activation of C5 an effective amount of an anti-C5 antibody. In one such embodiment, the method further comprises administering to the individual an effective amount of at least one additional therapeutic agent. An "individual" according to any of the above embodiments may be a human.

In a further aspect, the invention provides a method for enhancing the clearance of C5 from plasma in an individual. In one embodiment, the method comprises administering to the individual an effective amount of an anti-C5 antibody to enhance the clearance of C5 from plasma. In one embodiment, an anti-C5 antibody enhances the clearance of C5 from plasma, compared to a conventional anti-C5 antibody which does not have pH-dependent binding characteristics. In one embodiment, an "individual" is a human.

In a further aspect, the invention provides a method for suppressing the accumulation of C5 in plasma in an individual. In one embodiment, the method comprises administering to the individual an effective amount of an anti-C5 antibody to suppress the accumulation of C5 in plasma. In one embodiment, the accumulation of C5 in plasma is a result of the formation of an antigen-antibody complex. In another embodiment, an anti-C5 antibody suppresses the accumulation of C5 in plasma, compared to a conventional anti-C5 antibody which does not have pH-dependent binding characteristics. In one embodiment, an "individual" is a human.

An anti-C5 antibody of the present invention may inhibit the activation of C5. In a further aspect, the invention provides a method for inhibiting the activation of C5 in an individual. In one embodiment, the method comprises administering to the individual an effective amount of an anti-C5 antibody to inhibit the activation of C5. In one embodiment, the cytotoxicity mediated by C5 is suppressed by inhibiting the activation of C5. In one embodiment, an "individual" is a human.

In a further aspect, the invention provides pharmaceutical formulations comprising any of the anti-C5 antibodies provided herein, e.g., for use in any of the above therapeutic methods. In one embodiment, a pharmaceutical formulation comprises any of the anti-C5 antibodies provided herein and a pharmaceutically acceptable carrier. In another embodiment, a pharmaceutical formulation comprises any of the anti-C5 antibodies provided herein and at least one additional therapeutic agent.

In a further aspect, the pharmaceutical formulation is for treatment of a complement-mediated disease or condition which involves excessive or uncontrolled activation of C5. In a further embodiment, the pharmaceutical formulation is for enhancing the clearance of C5 from plasma. In one embodiment, an anti-C5 antibody enhances the clearance of C5 from plasma, compared to a conventional anti-C5 antibody which does not have pH-dependent binding characteristics. In a further embodiment, the pharmaceutical formulation is for suppressing the accumulation of C5 in plasma. In one embodiment, the accumulation of C5 in plasma is a result of the formation of an antigen-antibody complex. In another embodiment, an anti-C5 antibody suppresses the accumulation of C5 in plasma, compared to a conventional anti-C5 antibody which does not have pH-dependent binding characteristics. An anti-C5 antibody of the present invention may inhibit the activation of C5. In a further embodiment, the pharmaceutical formulation is for inhibiting the activation of C5. In one embodiment, the cytotoxicity mediated by C5 is suppressed by inhibiting the activation of C5. In one embodiment, the pharmaceutical formulation is administered to an individual having a complement-mediated disease or condition which involves excessive or uncontrolled activation of C5. An "individual" according to any of the above embodiments is preferably a human.

In one aspect, an individual has wild type C5. In another aspect, an individual has C5 variant. In certain embodiments, C5 variant has biological activity similar to wild type C5. Such C5 variant may comprise at least one variation selected from the group consisting of V145I, R449G, V802I, R885H, R928Q, D966Y, S1310N, and E1437D. Herein, R885H, for example, means a genetic variation where arginine at position 885 is substituted by histidine.

In a further aspect, the invention provides methods for preparing a medicament or a pharmaceutical formulation, comprising mixing any of the anti-C5 antibodies provided herein with a pharmaceutically acceptable carrier, e.g., for use in any of the above therapeutic methods. In one embodiment, the methods for preparing a medicament or a pharmaceutical formulation further comprise adding at least one additional therapeutic agent to the medicament or pharmaceutical formulation.

In certain embodiments, the complement-mediated disease or condition which involves excessive or uncontrolled activation of C5 is selected from the group consisting of rheumatoid arthritis (RA); systemic lupus erythematosus (SLE); lupus nephritis; ischemia reperfusion injury (IRI); asthma; paroxysmal nocturnal hemoglobinuria (PNH); hemolytic uremic syndrome (HUS) (e.g., atypical hemolytic uremic syndrome (aHUS)); dense deposit disease (DDD); neuromyelitis optica (NMO); multifocal motor neuropathy (MMN); multiple sclerosis (MS); systemic sclerosis; macular degeneration (e.g., age-related macular degeneration (AMD)); hemolysis, elevated liver enzymes, and low platelets (HELLP) syndrome; thrombotic thrombocytopenic purpura (TTP); spontaneous fetal loss; epidermolysis bullosa; recurrent fetal loss; pre-eclampsia; traumatic brain injury; myasthenia gravis; cold agglutinin disease; Sjögren's syndrome; dermatomyositis; bullous pemphigoid; phototoxic reactions; Shiga toxin *E. coli*-related hemolytic uremic syndrome; typical or infectious hemolytic uremic syndrome (tHUS); C3 Glomerulonephritis; Antineutrophil cytoplasmic antibody (ANCA)-associated vasculitis; humoral and vascular transplant rejection; acute antibody mediated rejection (AMR); graft dysfunction; myocardial infarction; an allogeneic transplant; sepsis; coronary artery disease; hereditary angioedema; dermatomyositis; Graves' disease; atherosclerosis; Alzheimer's disease (AD); Huntington's disease; Creutzfeld-Jacob disease; Parkinson's disease; cancers; wounds; septic shock; spinal cord injury; uveitis; diabetic ocular diseases; retinopathy of prematurity; glomerulonephritis; membranous nephritis; immunoglobulin A nephropathy; adult respiratory distress syndrome (ARDS); chronic obstructive pulmonary disease (COPD); cystic fibrosis; hemolytic anemia; paroxysmal cold hemoglobinuria; anaphylactic shock; allergy; osteoporosis; osteoarthritis; Hashimoto's thyroiditis; type I diabetes; psoriasis; pemphigus; autoimmune hemolytic anemia (AIHA); idiopathic thrombocytopenic purpura (ITP); Goodpasture syndrome; Degos disease; antiphospholipid syndrome (APS); catastrophic APS (CAPS); a cardiovascular disorder; myocarditis; a cerebrovascular disorder; a peripheral vascular disorder; a renovascular disorder; a mesenteric/enteric vascular disorder, vasculitis; Henoch-Schönlein purpura nephritis; Takayasu's disease; dilated cardiomyopathy; diabetic angiopathy; Kawasaki's disease (arteritis); venous gas embolus (VGE), restenosis following stent placement; rotational atherectomy; membranous nephrnpathy; Guillain-Barré syndrome (GBS); Fisher syndrome; antigen-induced arthritis; synovial inflammation; viral infections; bacterial infections; fungal infections; and injury resulting from myocardial infarction, cardiopulmonary bypass and hemodialysis.

In certain embodiments, the complement-mediated disease or condition is an ocular dissease condition. In further embodiments, the ocular condition is macular degeneration. In further embodiments the macular degeneration is AMD. In further embodiments, the AMD is the dry form of AMD.

In certain embodiments, the complement-mediated disease or condition is paroxysmal nocturnal hemoglobinuria (PNH).

In certain embodiments, the complement-mediated disease or condition is a myocardial infarction.

In certain embodiments, the complement-mediated disease or condition is rheumatoid arthritis (RA).

In certain embodiments, the complement-mediated disease or condition is osteoporosis or osteoarthritis.

In certain embodiments, the complement-mediated disease or condition is inflammation.

In certain embodiments, the complement-mediated disease or condition is cancer.

Antibodies of the invention can be used either alone or in combination with other agents in a therapy. For instance, an antibody of the invention may be co-administered with at least one additional therapeutic agent.

Such combination therapies noted above encompass combined administration (where two or more therapeutic agents are included in the same or separate formulations), and separate administration, in which case, administration of the antibody of the invention can occur prior to, simultaneously, and/or following, administration of the additional therapeutic agent or agents. In one embodiment, administration of the anti-5 antibody and administration of an additional therapeutic agent occur within about one month, or within about one, two or three weeks, or within about one, two, three, four, rive, or six days, of each other.

An antibody of the invention (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g., by injections, such as intravenous or subcutaneous injections, depending in part on whether the administration is brief or chronic. Various dosing schedules including but not limited to single or multiple administrations over various time-points, bolus administration, and pulse infusion are contemplated herein.

Antibodies of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody of the invention (when used alone or in combination with one or more other additional therapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Depending on the type and severity of the disease, about 1 µg/kg to 15 mg/kg (e.g., 0.1 ms/kg-10 mg/kg) of antibody can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g., every week or every three weeks (e.g., such that the patient receives from about two to about twenty, or e.g., about six doses of the antibody). An initial higher loading dose, followed by one or more lower doses may be administered. The progress of this therapy is easily monitored by conventional techniques and assays.

It is understood that any of the above formulations or therapeutic methods may be carried out using an immunoconjugate of the invention in place of or in addition to an anti-C5 antibody.

H. Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is an antibody of the invention. The label or package insert indicates that the composition is used for treating the condition of choice. Moreover, the article of manufacture may comprise (a) a first container with a composition contained therein, wherein the composition comprises an antibody of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

It is understood that any of the above articles of manufacture may include an immunoconjugate of the invention in place of or in addition to an anti-C5 antibody.

EXAMPLES

The following are examples of methods and compositions of the invention. It is understood that various other embodiments may be practiced, given the general description provided above.

Example 1

Preparation of C5

1.1. Expression and Purification of Recombinant Human and Cynomolgus Monkey C5

Recombinant human C5 (NCBI GenBank accession number. NP_001726.2, SEQ ID NO: 39) was expressed transiently using FreeStyle293-F cell line (Thermo Fisher, Carlsbad, Calif., USA). Conditioned media expressing human C5 was diluted with equal volume of milliQ water, then applied to a Q-sepharose FF or Q-sepharose HP anion exchange column (GE healthcare, Uppsala, Sweden), followed by elution with a NaCl gradient. Fractions containing human C5 were pooled, then salt concentration and pH was adjusted to 80 mM NaCl and pH6.4, respectively. The resulting sample was applied to a SP-sepharose HP cation exchange column (GE healthcare, Uppsala, Sweden) and eluted with a NaCl gradient. Fractions containing human C5 were pooled and subjected to CHT ceramic Hydroxyapatite column (Bio-Rad Laboratories, Hercules, Calif., USA). Human C5 eluate was then applied to a Superdex 200 gel filtration column (GE healthcare, Uppsala, Sweden). Fractions containing human C5 were pooled and stored at −150° C.

Expression and purification of recombinant cynomolgus monkey C5 (NCBI GenBank accession number: XP_005580972, SEQ ID NO: 44) was performed the same way as the human counterpart.

1.2. Purification of Cynomolgus Monkey C5 (cynoC5) from Plasma

Plasma sample from cynomolgus monkey was applied to SSL7-agarose (Invivogen, San Diego, Calif., USA) followed by elution with 100 mM NaAcetate, pH3.5. Fractions containing cynoC5 were immediately neutralized and subjected to a Protein A HP column (GE healthcare, Uppsala, Sweden) in tandem to a Peptide M agarose (Invivogen, San Diego, Calif., USA). The flow through fraction was then applied to a Superdex 200 gel filtration column (GE healthcare, Uppsala, Sweden). Fractions containing cynoC5 were pooled and stored at −80° C.

Example 2

Generation of Anti-C5 Antibodies 2.1. Antibody Screening

Anti-C5 antibodies were prepared, selected and assayed as follows:

Twelve to sixteen week old NZW rabbits were immunized intradermally with human C5 and/or monkey C5 (50-100 µg/dose/rabbit). This dose was repeated 4-5 times over a 2 month period. One week after the final immunization, the spleen and blood were collected from the immunized rabbits. Antigen-specific B-cells were stained with labelled antigen, sorted with FCM cell sorter (FACS aria III, BD), and plated in 96-well plates at one cell/well density together with 25,000 cells/well of EL4 cells (European Collection of Cell Cultures) and activated rabbit T-cell conditioned medium diluted 20 times, and were cultured for 7-12 days. EL4 cells were treated with mitomycin C (Sigma, Cat No. M4287) for 2 hours and washed 3 times in advance. The activated rabbit T-cell conditioned medium was prepared by culturing rabbit thymocytes in RPMI-1640 containing Phytohemagglutinin-M (Roche. Cat No. 1 1082132-001), phorbol 12-myristate 13-acetate (Sigma, Cat No. P1585) and 2% FBS. After cultivation, B-cell culture supernatants were collected for further analysis and pellets were cryopreserved.

An ELISA assay was used to test the specificity of antibodies in a B-cell culture supernatant Streptavidin (GeneScript, Cat No. Z02043) was coated onto a 384-well MAXISorp (Nunc, Cat No. 164688) at 50 nM in PBS for 1 hour at room temperature. Plates were then blocked with Blocking One (Nacalai Tesque, Cat No. 03953-95) diluted 5 times. Human or monkey C5 was labelled with NHS-PEG4-Biotin (PIERCE, Cat No. 21329) and was added to the blocked ELISA plates, incubated for 1 hour and washed. B-cell culture supernatants were added to the ELISA plates, incubated for 1 hour and washed. Binding was detected by goat anti-rabbit IgG-Horseradish peroxidase (BETHYL, Cat No. A120-111P) followed by the addition of ABTS (KPL, Cat No. 50-66-06).

An ELISA assay was used to evaluate pH-dependent binding of antibodies against C5. Goat anti-rabbit IgG-Fc (BETHYL, Cat No. A120-111A) diluted to 1 µg/ml with PBS(−) was added to a 384-well MAXISorp (Nunc, Cat No. 164688), incubated for 1 hour at room temperature, and blocked with Blocking One (Nacalai Tesque, Cat No. 03953-95) diluted 5 times. After incubation, plates were washed and B-cell culture supernatants were added. Plates were incubated for 1 hour, washed, and 500 pM of biotinylated human or monkey C5 was added and incubated for 1 hour. After incubation, plates were washed and incubated with either pH7.4 MES buffer (20 mM MES, 150 mM NaCl and 1.2 mM $CaCl_2$) or pH5.8 MES buffer (20 mM MES, 150 mM NaCl and 1 mM EDTA) for 1 hour at room temperature. After incubation, binding of biotinylated C5 was detected by Streptavidin-Horseradish peroxidase conjugate (Thermo Scientific, Cat No. 21132) followed by the addition of ABTS (KPL, Cat No. 50-66-06).

Octet RED384 system (Pall Life Sciences) was used to evaluate affinity and pH-dependent binding of antibodies against C5. Antibodies secreted in the B-cell culture supernatant were loaded onto a Protein A biosensor tip (Pall Life Sciences) and dipped into 50 nM of human or monkey C5 in pH7.4 MES buffer to analyze association kinetics. Dissociation kinetics was analyzed in both pH7.4 MES buffer and pH5.8 MES buffer.

A total of 41,439 B-cell lines were screened for affinity and pH-dependent binding to human or monkey C5 and 677 lines were selected and designated CFA0001-0677. RNA of the selected lines was purified from cryopreserved cell pellets using ZR-96 Quick-RNA kits (ZYMO RESEARCH, Cat No. R1053). DNA encoding antibody heavy chain variable regions in the selected lines was amplified by reverse transcription PCR and recombined with DNA encoding F760G4 (SEQ ID NO: 33) or F939G4 (SEQ ID NO: 34) heavy chain constant region. DNA encoding antibody light chain variable regions was amplified by reverse transcription PCR and recombined with DNA encoding k0MTC light chain constant region (SEQ ID NO: 36). Separately, the heavy and light chain genes of an existing humanized anti-C5 antibody, eculizumab (EcuH-G2G4, SEQ ID NO: 29 and EcuL-k0, SEQ ID NO: 30), were synthesized. DNA encoding VH (EcuH, SEQ ID NO: 31) was fused in-frame to DNA encoding a modified human IgG4 CH (F760G4, SEQ ID NO: 33), and DNA encoding VL (EcuL, SEQ ID NO: 32) was fused in-frame to DNA encoding a k0 light chain constant region (SEQ ID NO: 37). Each of the fused coding sequences was also cloned into an expression vector. The antibodies were expressed in FreeStyle™ 293-F Cells (Invitrogen) and purified from culture supernatant to evaluate functional activity. Neutralizing activities of the antibodies were evaluated by testing inhibition of complement activity using a liposome lysis assay as described in Example 5.1.

2.2. Epitope Binning by Sandwich ELISA

Anti-C5 antibodies with high affinity, pH dependency or neutralizing activity were selected for further analysis. A sandwich ELISA assay was used to group the selected antibodies into different epitope bins binding to the same or overlapping epitopes of the C5 protein. Unlabelled capture antibodies were diluted to 1 µg/ml with PBS (−) and added to 384-well MAXISorp plates (Nunc, Cat No. 164688). Plates were incubated for 1 hour at room temperature and blocked with Blocking One (Nacalai Tesque, Cat No. 03953-95) diluted 5 times. Plates were incubated for 1 hour, washed, and 2 nM of human C5 was added and incubated for 1 hour. After incubation, plates were washed and labelled detection antibodies (1 µg/mL, biotinylated by NHS-PEG4-Biotin) were added. After 1 hour incubation, binding of biotinylated antibody was detected by Streptavidin-Horseradish peroxidase conjugate (Thermo Scientific, Cat No. 21132) followed by the addition of ABTS (KPL, Cat No. 50-66-06).

Figure 1:
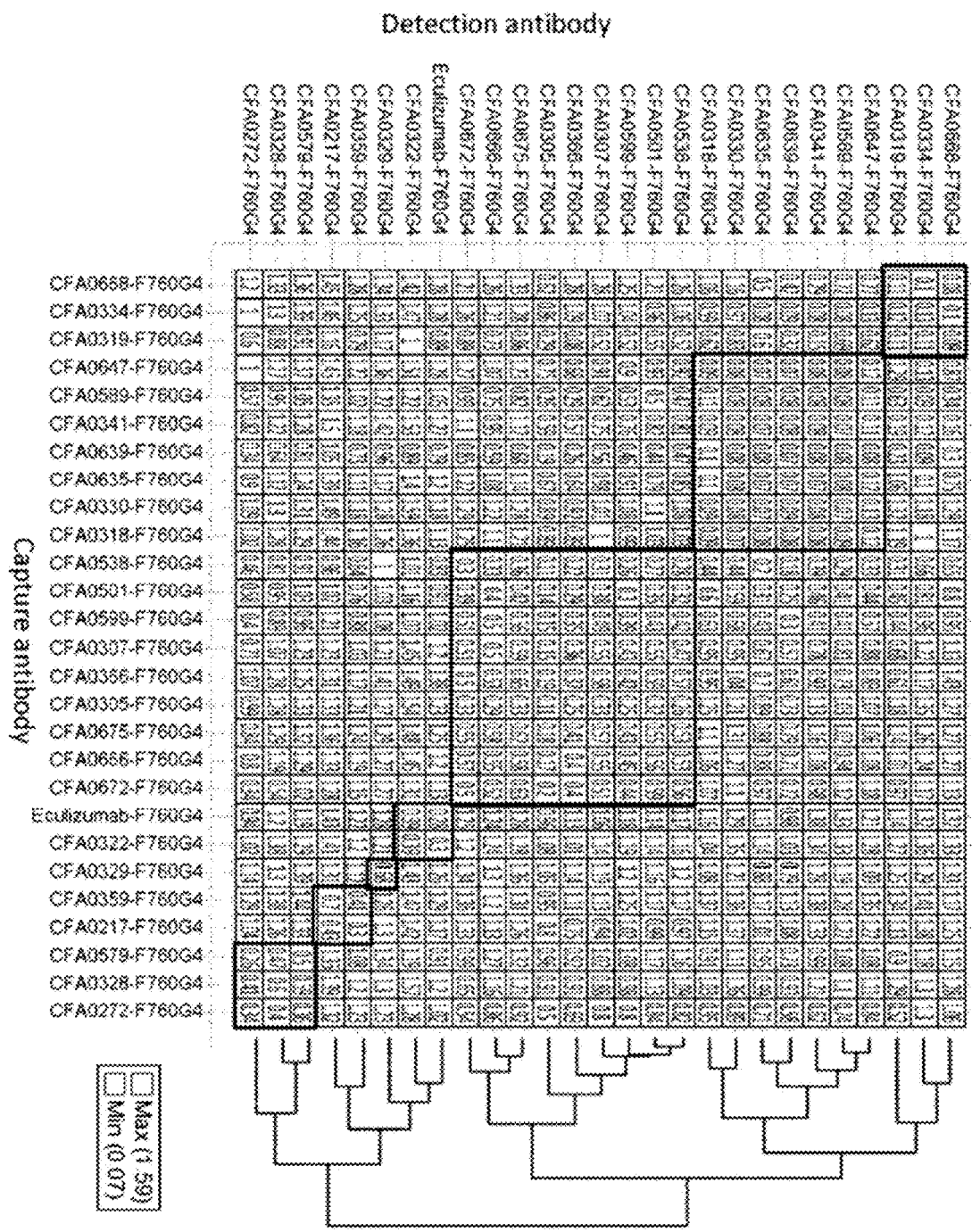
FIG. 1 illustrates epitope binning of anti-C5 antibodies, as described in Example 2.2. Antibodies grouped into the same epitope bin are boxed with a thick line.

All anti-C5 antibodies were used as both a capture antibody and a detection antibody, and paired comprehensively. As shown in FIG. 1, mutually competitive antibodies were grouped into 7 epitope bins: CFA0668, CFA0334 and CFA0319 were grouped into epitope A, CFA0647, CFA0589, CFA0341, CFA0639, CFA0635, CFA0330 and CFA0318 were grouped into epitope B, CFA0538, CFA0501, CFA0599, CFA0307, CFA0366, CFA0305, CFA0675, CFA0666 and CFA0672 were grouped into epitope C, eculizumab and CFA0322 were grouped into epitope D, CFA0329 was grouped into epitope E, CFA0359 and CFA0217 were grouped into epitope F, and CFA0579, CFA0328 and CFA0272 were grouped into epitope G. FIG. 1 shows epitope binning of some of the anti-C5 chimeric antibodies. The sequences of the VH and VL anti-C5 antibodies grouped into epitope C are listed in Table 2.

body were grafted onto homologous human antibody frameworks (FRs) using a conventional CDR grafting approach (Nature 321:522-525 (1986)). The genes encoding the humanized VH and VL were synthesized and combined with a modified human IgG4 CH (SG402, SEQ ID NO: 35) and a human CL (SKI, SEQ ID NO: 38), respectively, and each of the combined sequences was cloned into an expression vector.

A number of mutations and mutation combinations were examined to identify mutations and mutation combinations that improved the binding properties of some of the lead antibodies. Multiple mutations were then introduced to the humanized variable regions to enhance the binding affinity to C5 at a neutral pH or to reduce the binding affinity to C5 at an acidic pH. One of the optimized variants, 305LO5 (VH, SEQ ID NO: 10; VL, SEQ ID NO: 20; HVR-H1, SEQ ID NO: 54; HVR-H2, SEQ ID NO: 64; HVR-H3, SEQ ID NO: 74; HVR-L1, SEQ ID NO: 84; HVR-L2, SEQ ID NO: 94; and HVR-L3, SEQ ID NO: 104), was hence generated from CFA0305.

Antibodies were expressed in HEK293 cells co-transfected with a mixture of heavy and light chain expression vectors and were purified by protein A.

Example 3

Binding Characterization of Anti-C5 Antibodies 3.1. Expression and Purification of Recombinant Antibodies Recombinant antibodies were expressed transiently using FreeStyle293-F cell line (Thermo Fisher, Carlsbad, Calif., USA). Purification from the conditioned media expressing antibodies was performed using a conventional method using protein A. Gel filtration was further conducted if needed.

3.2. Assessment of pH Dependency

The kinetic parameters of anti-C5 antibodies against recombinant human C5 were assessed at pH7.4 and pH5.8, at 37° C. using BIACORE® T200 instrument (GE Healthcare). ProA/G (Pierce) was immobilized onto a CM4 sensorchip using amine coupling kit (GE Healthcare) according to the recommended settings by GE Healthcare. Antibodies and analytes were diluted into the respective running buffers, ACES pH7.4 and pH5.8 (20 mM ACES, 150 mM NaCl, 1.2 mM $CaCl_2$, 0.05% Tween 20, 0.005% $NaN_3$). Each antibody

TABLE 2

Anti-C5 antibodies grouped into epitepe C

| Antibody | SEQ ID NO: | | | | | | | |
|---|---|---|---|---|---|---|---|---|
| | VH | VL | HVR-H1 | HVR-H2 | HVR-H3 | HVR-L1 | HVR-L2 | HVR-L3 |
| CFA0305 | 1 | 11 | 45 | 55 | 65 | 75 | 85 | 95 |
| CFA0307 | 2 | 12 | 46 | 56 | 66 | 76 | 86 | 96 |
| CFA0366 | 3 | 13 | 47 | 57 | 67 | 77 | 87 | 97 |
| CFA0501 | 4 | 14 | 48 | 58 | 68 | 78 | 88 | 98 |
| CFA0538 | 5 | 15 | 49 | 59 | 69 | 79 | 89 | 99 |
| CFA0599 | 6 | 16 | 50 | 60 | 70 | 80 | 90 | 100 |
| CFA0666 | 7 | 17 | 51 | 61 | 71 | 81 | 91 | 101 |
| CFA0672 | 8 | 18 | 52 | 62 | 72 | 82 | 92 | 102 |
| CFA0675 | 9 | 19 | 53 | 63 | 73 | 83 | 93 | 103 |

2.3. Humanization and Optimization

Figure 2A:
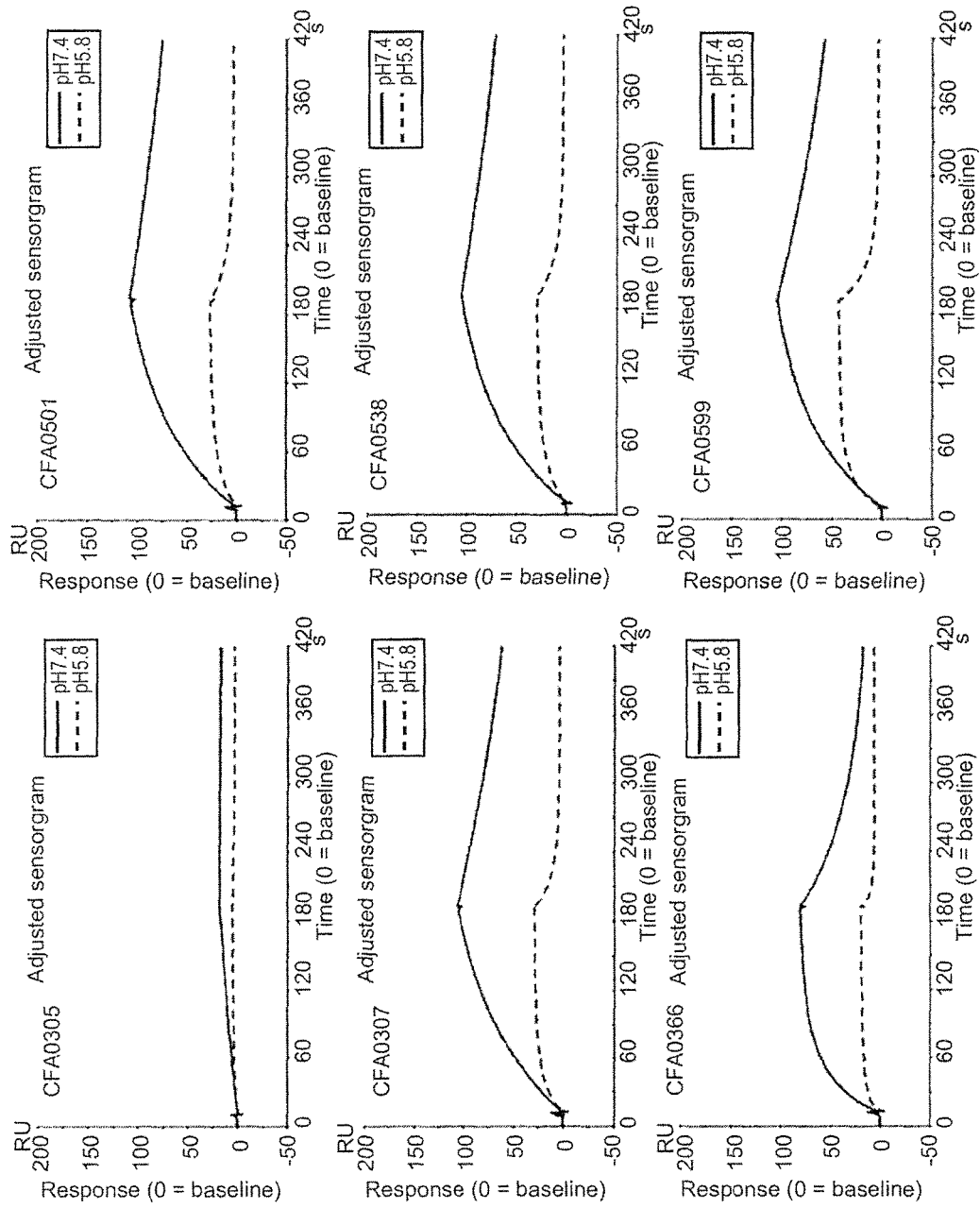
FIG. 2A illustrates BIACORE® sensorgrams of anti-C5 antibodies at pH7.4 (solid line) and pH5.8 (dashed line) to assess pH-dependency, as described in Example 3.2. CFA0305, CFA0307, CFA0366, CFA0501, CFA0538, and CFA0599 are antibodies grouped into epitope C, as described in Example 2.2.
Figure 2B:
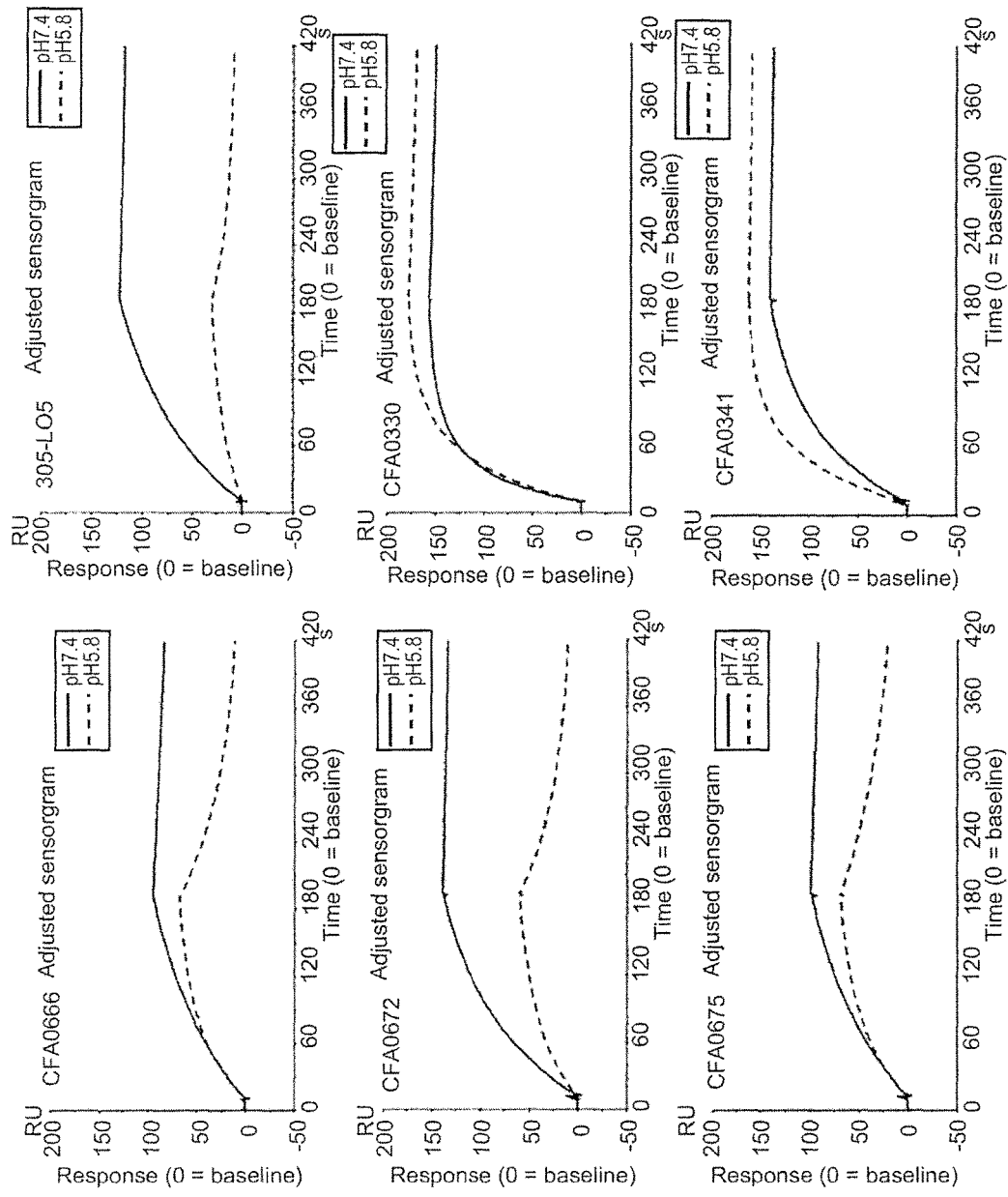
FIG. 2B illustrates BIACORE® sensorgrams of anti-C5 antibodies at pH7.4 (solid line) and pH5.8 (dashed line) to assess pH-dependency, as described in Example 3.2. CFA0666, CFA0672, and CFA0675 are antibodies grouped into epitope C, and CFA0330 and CFA0341 are antibodies grouped into epitope B, as described in Example 2.2. 305LO5 is a humanized antibody of CFA0305, as described in Example 2.3.

Humanization of the variable region of some of the anti-C5 antibodies was performed in order to reduce the potential immunogenicity of the antibodies. Complementarity-determining regions (CDRs) of the anti-C5 rabbit antiwas captured onto the sensor surface by ProA/G. Antibody capture levels were typically 60-90 resonance units (RU). Then, recombinant human C5 was injected at concentrations of 10 and 20 nM or 20 and 40 nM followed by dissociation. The surface was regenerated using 25 mM NaOH. Kinetic parameters at both pH conditions were determined by fitting the sensorgrams with 1:1 binding model using BIACORE® T200 Evaluation software, version 2.0 (GE Healthcare). The sensorgrams of all antibodies are shown in FIGS. 2A and 2B. The association rate (ka), dissociation rate (kd), and binding affinity (KD) of the antibodies are listed in Table 3. All antibodies except CFA0330 (VH, SEQ ID NO: 21 and VL, SEQ ID NO: 25) and CFA0341 (VH, SEQ ID NO: 22 and VL, SEQ ID NO: 26) showed a relatively faster dissociation rate at pH 5.8 than pH7.4.

TABLE 3

Kinetic parameters of anti-C5 antibodies under pH 7.4 and pH 5.8 conditions

| Antibody Name | pH 7.4 | | | pH 5.8 | | |
|---|---|---|---|---|---|---|
| | ka | kd | KD | ka | kd | KD |
| CFA0305 | 3.82E+04 | 5.89E−04 | 1.54E−08 | 4.27E+04 | 1.83E−02 | 4.30E−07 |
| CFA0307 | 3.24E+05 | 2.63E−03 | 8.13E−09 | 2.04E+05 | 3.34E−02 | 1.64E−07 |
| CFA0366 | 1.04E+06 | 9.34E−03 | 8.99E−09 | 9.35E+05 | 7.03E−02 | 7.52E−08 |
| CFA0501 | 4.74E+05 | 1.69E−03 | 3.56E−09 | 1.50E+05 | 2.62E−02 | 1.74E−07 |
| CFA0538 | 4.73E+05 | 1.85E−03 | 3.91E−09 | 1.22E+05 | 3.01E−02 | 2.46E−07 |
| CFA0599 | 4.74E+05 | 2.81E−03 | 5.93E−09 | 4.54E+05 | 3.73E−02 | 8.21E−08 |
| CFA0666 | 3.65E+05 | 6.26E−04 | 1.71E−09 | 2.82E+05 | 9.39E−03 | 3.33E−08 |
| CFA0672 | 5.23E+05 | 1.83E−04 | 3.51E−10 | 7.11E+04 | 9.78E−03 | 1.38E−07 |
| CFA0675 | 3.83E+05 | 4.12E−04 | 1.08E−09 | 3.89E+05 | 6.61E−03 | 1.70E−08 |
| 305-LO5 | 4.48E+05 | 2.11E−04 | 4.71E−10 | 2.03E+06 | 2.85E−02 | 1.40E−08 |
| CFA0330 | 1.66E+06 | 2.02E−04 | 1.22E−10 | 1.22E+06 | 2.24E−04 | 1.84E−10 |
| CFA0341 | 6.28E+05 | 9.77E−05 | 1.55E−10 | 1.24E+06 | 7.39E−05 | 5.95E−11 |

3.3. Cross Reactivity Check

To observe the cross-reactivity of anti-C5 antibodies against human C5 (hC5) and cynomolgus monkey C5 (cynoC5), BIACORE® kinetics analysis was performed. The assay setting was the same as described in Example 3.2, Recombinant cynoC5 was injected at concentrations of 2, 10, and 50 nM. Kinetic parameters were determined by the same data fitting as described in Example 3.2. Binding kinetics and affinity at pH7.4 are listed in Table 4. The kinetic parameters against hC5 presented in Table 4 are the results of Example 3.2. All anti-C5 antibodies except CFA0672 showed comparable KD toward hC5 and cynoC5. KD of CFA0672 toward cynoC5 was 8 times weaker than toward hC5.

Example 4

Epitope Mapping of Anti-C5 Antibodies 4.1. Binding of Anti-C5 MAbs to C5 β-chain-derived Peptides Anti-C5 monoclonal antibodies (MAbs) were tested for binding to C5 β-chain-derived peptides in Western blot analysis. The C5 peptides: 19-180, 161-340, 321-500, and 481-660, fused to GST-tag (pGEX-4T-1, GE Healthcare Life Sciences, 28-9545-49) were expressed in *E. coli* (DH5α, TOYOBO, DNA-903). The *E. coli* samples were harvested after incubation with 1 mM Isopropyl β-D-1-thiogalactopyranoside (IPTG) for 5 hours at 37° C., and centrifuged at 20000×g for 1 min to obtain pellets. The pellets were suspended with a sample buffer solution (2ME+) (Wako, 191-13272), and used for Western blot analysis. Expression of each peptide was confirmed with anti-GST antibody (Abcam, ab9085) (FIG. 3). The arrow indicates GST-fused C5 peptides (46-49 kDa). Anti-C5 MAbs: CFA0305, CFA0307, CFA0366, CFA0501, CFA0538, CFA0599, CFA0666, CFA0672, and CFA0675, bound to 19-180 of C5 (FIG. 3).

4.2. Expression and Purification of MG1-MG2 Domain (1-225) of Human C5

Recombinant MG1-MG2 domain (SEQ ID NO: 43) of human C5 β-chain was expressed transiently using FreeStyle293-F cell line (Thermo Fisher, Carlsbad, Calif., USA).

TABLE 4

Binding kinetics and affinity of anti-C5 antibodies against hC5 and cynoC5 at pH 7.4

| Antibody Name | affinity against hC5 | | | affinity against cynoC5 | | |
|---|---|---|---|---|---|---|
| | ka | kd | KD | ka | kd | KD |
| CFA0305 | 3.82E+04 | 5.89E−04 | 1.54E−08 | 1.21E+04 | 6.70E−04 | 5.54E−09 |
| CFA0307 | 3.24E+05 | 2.63E−03 | 8.13E−09 | 2.90E+05 | 2.23E−03 | 7.68E−09 |
| CFA0366 | 1.04E+06 | 9.34E−03 | 8.99E−09 | 5.04E+05 | 9.04E−03 | 1.79E−08 |
| CFA0501 | 4.74E+05 | 1.69E−03 | 3.56E−09 | 2.66E+05 | 1.56E−03 | 5.88E−09 |
| CFA0538 | 4.73E+05 | 1.85E−03 | 3.91E−09 | 3.05E+05 | 1.66E−03 | 5.44E−09 |
| CFA0599 | 4.74E+05 | 2.81E−03 | 5.93E−09 | 5.42E+05 | 2.35E−03 | 4.33E−09 |
| CFA0666 | 3.65E+05 | 6.26E−04 | 1.71E−09 | 3.14E+05 | 4.93E−04 | 1.57E−09 |
| CFA0672 | 5.23E+05 | 1.83E−04 | 3.51E−10 | 6.41E+05 | 1.85E−03 | 2.88E−09 |
| CFA0675 | 3.83E+05 | 4.12E−04 | 1.08E−09 | 2.94E+05 | 3.78E−04 | 1.29E−09 |

Conditioned media expressing the MG1-MG2 domain was diluted with ½ vol of milliQ water, followed by application to a Q-sepharose FF anion exchange column (GE healthcare, Uppsala, Sweden). The flow through fraction from the anion exchange column was adjusted to pH 5.0 and applied to a SP-sepharose HP cation exchange column (GE healthcare, Uppsala, Sweden) and eluted with a NaCl gradient. Fractions containing the MG1-MG2 domain were collected from the eluent and subsequently subjected to a Superdex 75 gel filtration column (GE healthcare, Uppsala, Sweden) equilibrated with 1×PBS. The fractions containing the MG1-MG2 domain were then pooled and stored at −80° C.

4.3. Binding Ability to MG1-MG2 Domain

The binding ability of anti-C5 antibodies towards the MG1-MG2 domain was measured using the same assay settings as described in Example 3.2, except that measurements were only performed under pH7.4 conditions. The MG1-MG2 domain was injected at concentrations of 20 nM and 40 nM. As shown in FIG. 4, all antibodies except eculizumab-F760G4 showed an increase of the binding response, indicating these antibodies are MG1-MG2 binders. Eculizumab-F760G4, which is a known α-chain binder, did not show binding to MG1-MG2 domain.

4.4. Binding of Anti-C5 MAbs to C5 MG1-MG2 Domain-derived Peptides

The anti-C5 MAbs were tested for binding to MG1-MG2 domain-derived peptides in Western blot analysis. The C5 peptides: 33-124, 45-124, 52-124, 33-111, 33-108, and 45-111 (SEQ ID NO:40), fused to GST-tag, were expressed in E. coli. The E. coli samples were harvested after incubation with 1 mM IPTG for 5 hours at 37° C., and centrifuged at 20000×g for 1 minute to obtain pellets. The pellets were suspended with the sample buffer solution (2ME+), and used for Western blot analysis. Expression of C5-derived peptides was confirmed with anti-GST antibody (FIG. 5A). CFA0305 bound to only the peptide of 33-124 (FIG. 5B). CFA0305 bound to β-chain of recombinant human C5 (rhC5) (approx. 70 kDa), which was used as a control. FIG. 5C summarizes the reaction of anti-C5 MAbs to C5-derived peptides.

4.5. Binding of Anti-C5 MAbs to C5 Mutants

Since three amino acid residues in the C5 β-chain: E48, D51, and K109, were predicted to be involved in the binding between C5 and the anti-C5-MAbs by crystal structure analysis, the anti-C5 MAbs were tested for binding to human C5 point mutants in Western blot analysis. C5 point mutants, in which any one of E48, D51, and K109 was substituted with alanine, were expressed in FS293 cells by lipofection. Culture media was harvested 5 days after lipofection, and thereafter used for Western blot. SDS-PAGE was conducted under reducing conditions. The results are shown in FIG. 6. Eculizumab bound to α-chain of wild type (WT) C5 and three C5 point mutants, whereas CFA0305 bound to the β-chain of WT C5 strongly, the E48A C5 mutant weakly, and did not bind to the β-chain of the D51A and K109A C5 mutants, indicating that these 3 amino acid residues are involved in the antibody/antigen interactions. Table 5 presents a summary of Western blot analysis of the anti-C5 MAbs (CFA0305, CFA0307, CFA0366, CFA0501, CFA0538, CFA0599, CFA0666, CFA0672, and CFA0675). The anti-C5 MAbs are grouped into the same epitope C, but binding patterns are slightly different between the antibodies, suggesting that the binding regions of C5 to the anti-C5 MAbs are close to each other but not identical.

TABLE 5

Summary of anti-C5 MAbs reaction to C5 mutants

| | WT | E48A | D51A | K109A |
|---|---|---|---|---|
| Eculizumab | + | + | + | + |
| CFA0305 | + | + | − | − |
| CFA0307 | + | − | − | − |
| CFA0366 | + | − | − | − |
| CFA0501 | + | − | − | − |
| CFA0538 | + | − | − | − |
| CFA0599 | + | − | − | + |
| CFA0666 | + | − | − | + |
| CFA0672 | + | − | − | + |
| CFA0675 | + | + | − | + |

4.6. BIACORE® Binding Analysis of Anti-C5 Antibodies with C5 Mutants

To test if residues E48, G51, and K109 are indeed involved in antibody/antigen interactions, BIACORE® binding analysis was performed. Three C5 mutants were prepared: E48A, G51A, and K109A, as described in Example 4.5. Culture supernatant samples containing the mutant C5 over-expressed in FS293 cells were prepared at 40 µg/ml of the mutant C5. For BIACORE® binding analysis, the sample was diluted 10× with BIACORE® running buffer (ACES pH7.4, 10 mg/ml BSA, 1 mg/ml carboxymethyl dextran) to a final sample concentration of 4 µg/ml of the mutant C5.

The interactions of the three C5 mutants with anti-C5 antibodies were assessed at 37° C. with BIACORE® T200 instrument (GE Healthcare), using the assay condition described in Example 3.2. ACES pH 7.4 buffer containing 10 mg/ml BSA, 1 mg/ml carboxymethyl dextran was used as running buffer. Eculizumab-F760G4 and 305LO5 were captured on different flow cells by monoclonal mouse anti-human IgG, Fc fragment specific antibody (GE Healthcare). Flow cell 1 was used as the reference surface. Wild type and mutant C5 proteins were injected over sensor surface at 4 µg/ml concentration to interact with the captured antibodies. At the end of each analysis cycle, the sensor surface was regenerated with 3M MgCl$_2$. The results were analyzed with Bia Evaluation software, version 2.0 (GE Healthcare). Curves of reference flow cell (flow cell 1) and blank injections of running buffer were subtracted from curves of the flow cell with captured antibodies.

As shown in FIG. 7, all three C5 mutants could bind to eculizumab with a similar binding profile compared to wild type C5. For the 305LO5, all three mutants showed lower binding response to 305LO5 compared to wild type C5. The D51A and K109A mutants reduced the binding of C5 by 305LO5 to the baseline level.

4.7. Identification of His Residues on C5 that Contribute to pH Dependent Interactions Between Anti-C5 Antibody and C5

The crystal structure analysis revealed that 3 histidine residues on human C5 are located at the antibody/antigen interface. A histidine residue with a typical pKa of approximately 6.0 is known to contribute to pH dependent protein-protein interactions (Igawa et al., *Biochim Biophys Acta* 1844(11):1943-1950 (2014)). To investigate which of the His residues on the antibody/antigen interface contribute to pH dependent interactions between anti-C5 antibody and C5, BIACORE® binding analysis was performed. Three human C5 mutants with a single His mutation (H70Y, H72Y, and H110Y) and a mutant with a double-His mutation (H70Y+H110Y) were prepared as follows: single His mutants in which any one of H70, H72, and H110 is substituted with tyrosine, and a double His mutant in which both H70 and H110 are substituted with tyrosine, were expressed in FS293 cells by lipofection. The antigen binding properties of the C5 His mutants to 305LO5, a pH-dependent anti-C5 antibody, were determined by a modified BIACORE® assay as described in Example 4.6. Briefly, an additional dissociation phase at pH5.8 was integrated into the BIACORE® assay immediately after the dissociation phase at pH7.4 to assess the pH-dependent dissociation between the antibody and the antigen from the complexes formed at pH7.4. The dissociation rate at pH5.8 was determined by processing and fitting data using Scrubber 2.0 (BioLogic Software) curve fitting software.

As shown in FIG. 8, the C5 single His mutation at H70 or H110 and the double His mutation (H70+H110) did not affect the binding of C5 to the 305LO5 at neutral pH. Meanwhile, the single His mutation at H72 exhibited a significant impairment of binding of C5 to 305LO5. The dissociation rates at pH5.8 for the C5 His mutants and the C5-wt protein are shown in Table 6. As shown in Table 6, the C5-wt showed fastest dissociation from 305LO5 at pH5.8 among the C5 antigens tested. The single His mutation at H70 exhibited an almost two-fold slower dissociation rate at pH5.8 and the single His mutation at H110 resulted in a slightly slower dissociation rate at pH5.8 compared to C5-wt. The double His mutation at both H70 and H110 resulted in larger effect on pH-dependent binding with a dissociation rate at pH5.8 almost three fold slower than C5-wt.

TABLE 6 pH 5.8 dissociation rate value for C5 His mutants binding to 305LO5

| Antigens | kd (1/s) |
|---|---|
| C5-wt | 1.1E−2 |
| C5-H70Y | 5.3E−3 |
| C5-H110Y | 9.3E−3 |
| C5-H70Y, H110Y | 3.9E−3 |

Example 5

Inhibitory Activity of Anti-C5 Antibodies on C5 Activation 5.1. Inhibition of Complement-activated Liposome Lysis by Anti-C5 MAbs The anti-C5 MAbs were tested for inhibition of complement activity by a liposome lysis assay. Thirty microliters of normal human serum (6.7%) (Biopredic, SER018) was mixed with 20 μL of the diluted MAb in a 96-well plate and incubated on a shaker for 30 minutes at 25° C. Liposomes sensitized with the antibodies against dinitrophenyl (Autokit CH50, Wako, 995-40801) were transferred into each well and the plate was placed on a shaker for 2 minutes at 25° C. Fifty microliters of substrate solution (Autokit CH50) was added to each well and mixed by shaking for 2 minutes at 25° C. The final mixture was incubated at 37° C. for 40 minutes, and thereafter OD at 340 nm of the mixture was measured. The percent of liposome lysis was defined as $100\times[(OD_{MAb}-OD_{serum\ and\ liposome\ background})]/[(OD_{without\ MAb}-OD_{serum\ and\ liposome\ background})]$. FIG. 9A shows that anti-C5 Mabs: CFA0305, 0307, 0366, 0501, 0538, 0599, 0666, 0672, and 0675, inhibited the liposome lysis. Two non-pH-dependent antibodies: CFA0330 and 0341, also inhibited the lysis (FIG. 9B).

5.2. Inhibition of C5a Generation by Anti-C5 MAbs

The anti-C5 MAbs were tested for C5a generation during liposome lysis to confirm that the anti-C5 MAbs inhibit cleavage of C5 into C5a and C5b. The C5a level in the supernatants from liposome lysis assay was quantified using a C5a ELISA kit (R&D systems, DY2037). All MAbs inhibited C5a generation in the supernatants dose-dependently (FIGS. 10A and 10B).

5.3. Inhibition of Complement-activated Hemolysis by Anti-C5 MAbs

The anti-C5 MAbs were tested for inhibition of the classical complement activity in a hemolytic assay. Chicken red blood cells (cRBCs) (Innovative research, IC05-0810) were washed with gelatin/veronal-buffered saline containing 0.5 mM $MgCl_2$ and 0.15 mM $CaCl_2$(GVB++) (Boston BioProducts, IBB-300X), and thereafter sensitized with anti-chicken RBC antibody (Rockland 103-4139) at 1 μg/ml for 15 minutes at 4° C. The cells were then washed with GVB++ and suspended in the same buffer at $5\times10^7$ cells/ml. In a separate round-bottom 96-well microtest plate, 50 μl of normal human serum (20%) (Biopredic, SER019) was mixed with 50 μl of diluted Mab and incubated on a shaker at 37° C. for 30 minutes. Sixty microliters of the sensitized cRBCs suspension was then added to the wells containing the serum, and the antibody mixture was incubated at 37° C. for 30 minutes. After the incubation, the plate was centrifuged at 1000×g for 2 minutes at 4° C. Supernatants (100 μl) were transferred to wells on a flat-bottom 96-well microtest plate for measurement of OD at 415 nm with a reference wavelength at 630 nm. The percent of hemolysis was defined as $100\times[(OD_{MAb}-OD_{serum\ and\ cRBCs})]/[(OD_{without\ MAb}-OD_{serum\ and\ cRBCs\ background})]$. FIG. 11 shows that anti-C5 Mabs: CFA0305 and 305LO5, inhibited the hemolysis of cRBCs.

5.4. Inhibition of Alternative Complement Pathway by Anti-C5 MAbs

A hemolytic assay for the alternative pathway was performed in a similar way to the classical pathway haemolytic assay. Blood collected from a New Zealand White rabbit (InVivos) was mixed with the same volume of Alsever's solution (Sigma, A3551), and the mixture was used as rabbit RBCs (rRBCs). rRBCs were washed with GVB supplemented with 2 mM $MgCl_2$ and 10 mM EGTA and suspended in the same buffer at $7\times10^8$ cells/ml. In a round-bottom 96-well microtest plate, 40 μl of normal human serum (25%) (Biopredic, SER019) was mixed with 40 μl of diluted Mab and incubated on a shaker at 37° C. for 30 minutes. Twenty microliters of the rRBCs suspension was then added to the wells containing the serum, and the antibody mixture was incubated at 37° C. for 60 minutes. After the incubation, the plate was centrifuged at 1000×g for 2 minutes at 4° C. Supernatants (70 μl) were transferred to wells on a flat-bottom 96-well microtest plate for measurement of OD at 415 nm with a reference wavelength at 630 nm. FIG. 12 shows that anti-C5 Mabs: CFA0305 and CFA0672, inhibited the hemolysis of rRBCs, indicating that these antibodies inhibit the alternative complement pathways.

Example 6

Pharmacokinetic Study of Anti-C5 Monoclonal Antibodies with Human C5 in Mice 6.1. In Vivo Test Using C57BL/6 Mice The in vivo kinetics of human C5 (Calbiochem) and anti-human C5 antibody was assessed after administering human C5 alone or human C5 and anti-human C5 antibody to C57BL/6 mice (In Vivos or Biological Resource Centre, Singapore). A human C5 solution (0.01 mg/ml) or a solution of mixture containing human C5 and anti-human C5 antibody (0.01 mg/ml and 2 mg/ml (CFA0305-F760G4, CFA0307-F760G4, CFA0366-F760G4, CFA0501-F760G4, CFA0538-F760G4, CFA0599-F760G4, CFA0666-F760G4, CFA0672-F760G4, and CFA0675-F760G4) or 0.2 mg/ml (CFA0330-F760G4, and CFA0341-F760G4), respectively) was administered once at a dose of 10 ml/kg into the caudal vein. In this case, the anti-human C5 antibody is present in excess over human C5, and therefore almost every human C5 is assumed to be bound to the antibody. Blood was collected 5 minutes, seven hours, one day, two days, three days, and seven days after administration. The collected blood was immediately centrifuged at 14,000 rpm and 4° C. for 10 minutes to separate the plasma. The separated plasma was stored in a refrigerator at −80° C. before assay. The anti-human C5 antibodies used are: above-described CFA0305-F760G4, CFA0307-F760G4, CFA0330-F760G4, CFA0341-F760G4, CFA0366-F760G4, CFA0501-F760G4, CFA0538-F760G4, CFA0599-F760G4, CFA0666-F760G4, CFA0672-F760G4, and CFA0675-F760G4.

6.2. Measurement of Total Human C5 Plasma Concentration by Electrochemiluminescence (ECL) Assay The concentration of total human C5 in mouse plasma was measured by ECL.

In the presence of CFA0330-F760G4, CFA0341-F760G4, or human C5 alone in the plasma sample, the following method was used. Anti-human C5 antibody (Santa Cruz) was dispensed onto a MULTI-ARRAY 96-well bare plate (Meso Scale Discovery) and allowed to stand overnight at 4° C. to prepare anti-human C5-immobilized plates. Calibration curve samples and mouse plasma samples diluted 100-fold or more with 1 μ/ml injected antibody (CFA0330-F760G4 or CFA0341-F760G4) were prepared and incubated for 30 minutes at 37° C. Subsequently, the samples were dispensed onto the anti-human C5-immobilized plates, and allowed to stand for one hour at room temperature. Then, SULFO-TAG labelled anti-human IgG antibody (Meso Scale Discovery) was added to react for one hour at room temperature, and washing was performed. Immediately thereafter, Read Buffer T (×4) (Meso Scale Discovery) was dispensed and measurement was performed using a Sector Imager 2400 (Meso Scale Discovery).

In the presence of CFA0305-F760G4, CFA0307-F760G4, CFA0366-F760G4, CFA0501-F760G4, CFA0538-F760G4, CFA0599-F760G4, CFA0666-F760G4, CFA0672-F760G4, or CFA0675-F760G4 in the plasma sample, the following method was used. Anti-human C5 antibody (CFA0329-F939G4; VH, SEQ ID NO: 23 and VL, SEQ ID NO: 27) was dispensed onto a MULTI-ARRAY 96-well bare plate (Meso Scale Discovery) and allowed to stand overnight at 4° C. to prepare anti-human C5-immobilized plates. Calibration curve samples and mouse plasma samples diluted 100-fold or more with acidic solution (pH 5.5) were prepared and incubated for 30 minutes at 37° C. Subsequently, the samples were dispensed onto the anti-human C5-immobilized plates, and allowed to stand for one hour at room temperature. Then, SULFO-TAG labelled anti-human C5 antibody (CFA0300-F939G4; VH, SEQ ID NO: 24 and VL, SEQ ID NO: 28) was added to react for one hour at room temperature, and washing was performed. Immediately thereafter, Read Buffer T (×4) (Meso Scale Discovery) was dispensed and measurement was performed using a Sector Imager 2400 (Meso Scale Discovery).

The human C5 concentration was calculated based on the response of the calibration curve using the analytical software SOFTmax PRO (Molecular Devices). The time course of plasma human C5 concentration after intravenous administration as measured by this method is shown in FIG. 13. Data are plotted as the percentage remaining compared to the plasma human C5 concentration at 5 minutes.

6.3. Measurement of Anti-human C5 Antibody Plasma Concentration by ECL Assay

The concentration of anti-human C5 antibody in mouse plasma was measured by ECL. Anti-human IgG (γ-chain specific) F(ab')2 antibody fragment (Sigma) or anti-human IgG κ chain antibody (Antibody Solutions) was dispensed onto a MULTI-ARRAY 96-well bare plate (Meso Scale Discovery) and allowed to stand overnight at 4° C. to prepare anti-human IgG-immobilized plates. Calibration curve samples and mouse plasma samples diluted 100-fold or more were prepared. Subsequently, the samples were dispensed onto the anti-human IgG-immobilized plates, and allowed to stand for one hour at room temperature. Then, biotinylated Anti-Human IgG Antibody (Southernbiotech) or SULFO-TAG labelled anti-human IgG Fc antibody (Southernbiotech) was added to react for one hour at room temperature, and washing was performed. Subsequently, only when biotinylated Anti-Human IgG Antibody was used, SULFO-TAG labelled streptavidin (Meso Scale Discovery) was added to react for one hour at room temperature, and washing was performed. Immediately thereafter, Read Buffer T (×4) (Meso Scale Discovery) was dispensed and measurement was performed using a Sector Imager 2400 (Meso Scale Discovery). The anti-human C5 antibody concentration was calculated based on the response of the calibration curve using the analytical software SOFTmax PRO (Molecular Devices). The time course of plasma anti-human C5 antibody concentration after intravenous administration as measured by this method is shown in FIG. 14. Data are plotted as the percentage remaining compared to the plasma anti-human C5 antibody concentration at 5 minutes.

6.4. Effect of pH Dependent Anti-Human C5 Antibody Binding Upon Clearance of Human C5 In Vivo The pH dependent anti-human C5 antibodies (CFA0305-F760G4, CFA0307-F760G4, CFA0366-F760G4, CFA0501-F760G4, CFA0538-F760G4, CFA0599-F760G4, CFA0666-F760G4, CFA0672-F760G4, and CFA0675-F760G4) and non pH dependent anti-human C5 antibodies (CFA0330-F760G4, and CFA0341-F760G4) were tested in vivo and the resulting plasma anti-human C5 antibody concentration and plasma human C5 concentration were compared. As shown in FIG. 14, the antibody exposure was comparable. Meanwhile, the clearance of human C5 simultaneously administered with the pH dependent anti-human C5 antibodies was accelerated compared to that with the non pH dependent anti-human C5 antibodies (FIG. 13).

Example 7

Optimization of Anti-C5 Monoclonal Antibodies (305 Variants)

A number of mutations were introduced to the optimized variable region of the anti-C5 antibody 305L05 to further improve its properties, and the optimized variable regions 305LO15, 305LO16, 305LO18, 305LO19, 305LO20, 305LO22, and 305LO23 were generated. Amino acid sequences of VH and VL of the 305 variants are listed in Tables 7 and 8, respectively. The genes encoding the humanized VH were combined with a modified human IgG1 CH variant SG115 (SEQ ID NO: 114), and modified human IgG4 CH variants SG422 (SEQ ID NO: 115) or SG429 (SEQ ID NO: 116). The genes encoding the humanized VL were combined with a human CL (SKl, SEQ ID NO: 38). Separately, heavy and light chain genes encoding a humanized anti-C5 antibody, BNJ441 (BNJ441H, SEQ ID NO: 149; BNJ441L, SEQ ID NO: 150), were synthesized and each was cloned into an expression vector.

Antibodies were expressed in HEK293 cells co-transfected with a combination of heavy and light chain expression vectors, and were purified by protein A.

Antibodies and analytes for condition (1) and (3) were diluted in ACES pH7.4 buffer (20 mM ACES, 150 mM NaCl, 1.2 mM CaCl$_2$, 0.05% Tween 20, 0.005% NaN$_3$) and for condition (2) they were diluted in ACES pH5.8 buffer (20 mM ACES, 150 mM NaCl, 1.2 mM CaCl$_2$, 0.05% Tween 20, 0.005% NaN$_3$). Each antibody was captured onto the sensor surface by ProA/G. Antibody capture levels were typically 60-90 resonance units (RU). Then, recombinant human C5 was injected at 3 to 27 nM or 13.3 to 120 nM prepared by three-fold serial dilution, followed by dissocia-

TABLE 7

VH amino acid sequences of the 305 variants

| Antibody | VH | HVR-H1 | HVR-H2 | HVR-H3 |
|---|---|---|---|---|
| 305LO5 | SEQ ID NO: 10 | SEQ ID NO: 54 SSYYVA | SEQ ID NO: 64 AIYTGSGATYKASWAKG | SEQ ID NO: 74 DGGYDYPTHAMHY |
| 305LO15 | SEQ ID NO: 106 | SEQ ID NO: 117 SSYYMA | SEQ ID NO: 118 AIFTGSGAEYKAEWAKG | SEQ ID NO: 121 DAGYDYPTHAMHY |
| 305LO16 | SEQ ID NO: 107 | SEQ ID NO: 117 SSYYMA | SEQ ID NO: 119 AIFTGSGAEYKAEWVKG | SEQ ID NO: 121 DAGYDYPTHAMHY |
| 305LO18 | SEQ ID NO: 108 | SEQ ID NO: 117 SSYYMA | SEQ ID NO: 118 AIFTGSGAEYKAEWAKG | SEQ ID NO: 121 DAGYDYPTHAMHY |
| 305LO19 | SEQ ID NO: 109 | SEQ ID NO: 117 SSYYMA | SEQ ID NO: 118 AIFTGSGAEYKAEWAKG | SEQ ID NO: 121 DAGYDYPTHAMHY |
| 305LO20 | SEQ ID NO: 109 | SEQ ID NO: 117 SSYYMA | SEQ ID NO: 118 AIFTGSGAEYKAEWAKG | SEQ ID NO: 121 DAGYDYPTHAMHY |
| 305LO22 | SEQ ID NO: 109 | SEQ ID NO: 117 SSYYMA | SEQ ID NO: 118 AIFTGSGAEYKAEWAKG | SEQ ID NO: 121 DAGYDYPTHAMHY |
| 305LO23 | SEQ ID NO: 110 | SEQ ID NO: 117 SSYYMA | SEQ ID NO: 120 GIFTGSGATYKAEWAKG | SEQ ID NO: 121 DAGYDYPTHAMHY |

TABLE 8

VL amino acid sequences of the 305 variants

| Antibody | VL | HVR-L1 | HVR-L2 | HVR-L3 |
|---|---|---|---|---|
| 305LO5 | SEQ ID NO: 20 | SEQ ID NO: 84 QASQNIGSSLA | SEQ ID NO: 94 GASKTHS | SEQ ID NO: 104 QSTKVGSSYGNH |
| 305LO15 | SEQ ID NO: 111 | SEQ ID NO: 122 RASQGISSSLA | SEQ ID NO: 123 GASETES | SEQ ID NO: 125 QNTKVGSSYGNT |
| 305LO16 | SEQ ID NO: 111 | SEQ ID NO: 122 RASQGISSSLA | SEQ ID NO: 123 GASETES | SEQ ID NO: 125 QNTKVGSSYGNT |
| 305LO18 | SEQ ID NO: 111 | SEQ ID NO: 122 RASQGISSSLA | SEQ ID NO: 123 GASETES | SEQ ID NO: 125 QNTKVGSSYGNT |
| 305LO19 | SEQ ID NO: 111 | SEQ ID NO: 122 RASQGISSSLA | SEQ ID NO: 123 GASETES | SEQ ID NO: 125 QNTKVGSSYGNT |
| 305LO20 | SEQ ID NO: 112 | SEQ ID NO: 122 RASQGISSSLA | SEQ ID NO: 123 GASETES | SEQ ID NO: 125 QNTKVGSSYGNT |
| 305LO22 | SEQ ID NO: 113 | SEQ ID NO: 122 RASQGISSSLA | SEQ ID NO: 124 GASTTQS | SEQ ID NO: 125 QNTKVGSSYGNT |
| 305LO23 | SEQ ID NO: 113 | SEQ ID NO: 122 RASQGISSSLA | SEQ ID NO: 124 GASTTQS | SEQ ID NO: 125 QNTKVGSSYGNT |

Example 8

Binding Characterization of Anti-C5 Antibodies (305 Variants)

The kinetic parameters of anti-C5 antibodies against recombinant human C5 were assessed at 37° C. using BIACORE® T200 instrument (GE Healthcare) at three different conditions; (1) both association and dissociation were at pH7.4, (2) both association and dissociation were at pH5.8, and (3) association was at pH7.4 but dissociation was at pH5.8. ProA/G (Pierce) was immobilized onto a CM1 sensorchip using amine coupling kit (GE Healthcare) according to the recommended settings by GE Healthcare.

tion. The surface was regenerated using 25 mM NaOH. Kinetic parameters at condition (1) and (2) were determined by fitting the sensorgrams with a 1:1 binding model and the dissociation rate at condition (3) was determined by fitting the sensorgrams with a 1:1 dissociation for MCK model using BIACORE® T200 Evaluation software, version 2.0 (GE Healthcare). pH dependency of all antibodies were shown as ratio of dissociation rate of condition (2) and (1).

Association rate (ka), dissociation rate (kd), binding affinity (KD), and pH dependency are listed in Table 9. All antibodies showed a faster dissociation rate at pH 5.8 than pH7.4 and their pH dependency was around 20 fold.

TABLE 9

Kinetics parameters of anti-C5 antibody variants under pH 7.4 and pH 5.8 conditions

| | 7.4 7.4 | | | 5.8 5.8 | | | 7.4_5.8 | pH |
|---|---|---|---|---|---|---|---|---|
| | ka (1/Ms) | kd (1/s) | KD (M) | ka (1/Ms) | kd (1/s) | KD (M) | kd (1/s) | dependency |
| LO15-SG422 | 1.40E+06 | 4.19E−04 | 3.00E−10 | 1.34E+05 | 8.79E−03 | 6.57E−08 | 1.61E−02 | 21.0 |
| LO15-SG115 | 1.31E+06 | 3.54E−04 | 2.70E−10 | 9.49E+04 | 8.27E−03 | 8.72E−08 | 1.67E−02 | 23.4 |
| LO16-SG422 | 1.28E+06 | 4.12E−04 | 3.21E−10 | 1.09E+05 | 8.69E−03 | 7.95E−08 | 1.61E−02 | 21.1 |
| LO18-SG422 | 1.36E+06 | 4.26E−04 | 3.14E−10 | 1.39E+05 | 8.65E−03 | 6.24E−08 | 1.69E−02 | 20.3 |
| LO19-SG422 | 1.37E+06 | 4.76E−04 | 3.46E−10 | 1.38E+05 | 8.30E−03 | 6.00E−08 | 1.61E−02 | 17.4 |
| LO20-SG115 | 1.44E+06 | 4.67E−04 | 3.24E−10 | 1.41E+05 | 8.18E−03 | 5.81E−08 | 1.61E−02 | 17.5 |
| LO20-SG422 | 1.35E+06 | 4.70E−04 | 3.49E−10 | 1.36E+05 | 8.15E−03 | 5.99E−08 | 1.55E−02 | 17.3 |
| LO22-SG115 | 1.46E+06 | 3.82E−04 | 2.62E−10 | 1.71E+05 | 9.30E−03 | 5.45E−08 | 1.46E−02 | 24.3 |
| LO23-SG115 | 1.53E+06 | 4.23E−04 | 2.77E−10 | 1.33E+05 | 8.55E−03 | 6.41E−08 | 1.73E−02 | 20.2 |

The binding affinity of anti-C5 antibodies (BNJ441, eculizumab, and a 305 variant) to recombinant human C5 at pH7.4 and pH5.8 were determined at 37° C. using a BIACORE® T200 instrument (GE Healthcare) to assess the effect of pH upon antigen binding. Goat anti-human IgG (Fc) polyclonal antibody (KPL #01-10-20) was immobilized onto a CM4 sensorchip using an amine coupling kit (GE Healthcare) according to the recommended settings by manufacturer. Antibodies and analytes were diluted either in ACES pH7.4 buffer or ACES pH5.8 buffer containing 20 mM ACES, 150 mM NaCl, 1.2 mM $CaCl_2$, 0.05% Tween 20, and 0.005% $NaN_3$. Antibodies were captured on the sensor surface using the anti-Fc method, capture levels were typically 50-80 resonance units (RU). Recombinant human C5 was prepared by three-fold serial dilution starting from 27 nM for pH7.4 assay conditions, or 135 nM for pH 5.8 assay conditions. The surface was regenerated using 20 mM HCl, 0.01% Tween 20. The data were processed and fit with a 1:1 binding model using BiaEvaluation 2.0 software (GE Healthcare).

The binding affinity (KD) of BNJ441, eculizumab, and the 305 variant to recombinant human C5 at pH7.4 and pH5.8 is shown in Table 10. The 305 variant showed a ratio of (KD at pH 5.8)/(KD at pH 7.4) of almost 800, 8 fold higher than BNJ441 which only showed a ratio of (KD at pH 5.8)/(KD at pH 7.4) of 93.

TABLE 10

| | KD (M) | | ratio of KD at |
|---|---|---|---|
| Antibody | pH 7.4 | pH 5.8 | pH 5.8/pH 7.4 |
| 305LO5 variant | 1.66E−10 | 1.32E−07 | 795 |
| Eculizumab | 1.42E−10 | 2.64E−09 | 19 |
| BNJ441 | 1.38E−09 | 1.28E−07 | 93 |

Example 9

Inhibitory Activity of Anti-C5 Antibodies (305 Variants) on C5 Activation 9.1. Inhibition of Complement-activated Liposome Lysis by Anti-C5 MAbs The anti-C5 MAbs were tested for inhibition of complement activity by a liposome lysis assay. Thirty microliters of normal human serum (6.7%) (Biopredic, SER019) was mixed with 20 μL of diluted MAb in a 96-well plate and incubated on a shaker for 30 min at room temperature. Liposome solution sensitized with antibodies against dinitrophenyl (Autokit CH50, Wako, 9953-40801) was transferred into each well and placed on a shaker for 2 min at 37° C. Fifty microliters of substrate solution (Autokit CH50) was added to each well and mixed by shaking for 2 min at 37° C. The final mixture was incubated at 37° C. for 40 minutes, and thereafter OD at 340 nm was measured. The percent of liposome lysis was defined as $100 \times [(OD_{MAb} - OD_{serum\ and\ liposome\ background})]/[(OD_{without\ MAb} - OD_{serum\ and\ liposome\ background})]$. FIG. 15 shows that the anti-C5 Mabs: 305LO15-SG422, 305LO16-SG422, 305LO18-SG422, 305LO19-SG422, 305LO20-SG422, and 305LO20-SG115, inhibited liposome lysis. Two antibodies with Fc variants: 305LO15-SG115 and 305LO23-SG429, also inhibited liposome lysis (FIG. 16).

The anti-C5 MAbs were tested for inhibition of recombinant human C5 (SEQ ID NO: 39). Ten microliters of C5-deficient human serum (Sigma, C1163) was mixed with 20 μL of diluted MAb and 20 μL of recombinant C5 (0.1 μg/mL) in a 96-well plate and incubated on a shaker for 1 hour at 37° C. Liposomes (Autokit CH50) were transferred into each well and placed on a shaker for 2 min at 37° C. Fifty microliters of substrate solution (Autokit CH50) was added to each well and mixed by shaking for 2 min at 37° C. The final mixture was incubated at 37° C. for 180 minutes, and thereafter OD at 340 nm was measured. The percent of liposome lysis was defined as above. FIG. 17 shows that anti-C5 Mabs: 305LO22-SG115, 305LO22-SG422, 305LO23-SG115, and 305LO23-SG422, inhibited liposome lysis.

9.2. Inhibition of C5a Generation by Anti-C5 MAbs

Anti-C5 MAbs were tested for C5a generation during liposome lysis to confirm that anti-C5 MAbs inhibit cleavage of C5 into C5a and C5b. C5a levels in the supernatants from a liposome lysis assay were quantified using a C5a ELISA kit (R&D systems, DY2037). All MAbs inhibited C5a generation in the supernatants in a dose-dependent manner (FIGS. 18 and 19).

9.3. Measurement of Complement Activity in Cynomolgus Monkey Plasma

Anti-C5 MAbs were tested for inhibition of complement activity in cynomolgus monkey plasma. The anti-C5 Mabs were intra administered to the monkeys (20 mg/kg), and plasma samples were collected periodically until day 56. Chicken red blood cells (cRBCs) (Innovative research, IC05-0810) were washed with gelatin/veronal-buffered saline containing 0.5 mM $MgCl_2$ and 0.15 mM $CaCl_2$ (GVB++) (Boston BioProducts, IBB-300X), and thereafter sensitized with anti-chicken RBC antibody (Rockland 103-4139) at 1 μg/ml for 15 minutes at 4° C. The cells were then washed with GVB++ and suspended in the same buffer at $1 \times 10^8$ cells/ml. In a separate round-bottom 96-well microtest plate, monkey plasma was incubated with the sensitized cRBCs at 37° C. for 20 minutes. After the incubation, the plate was centrifuged at 1000×g for 2 minutes at 4° C. Supernatants were transferred to wells on a flat-bottom 96-well microtest plates for measurement of OD at 415 nm with a reference wavelength at 630 nm. The percent of hemolysis was defined as 100×[($OD_{Post\ administration}$−$OD_{plasma\ and\ cRBCs\ background}$)]/[($OD_{Pre\ administration}$−$OD_{plasma\ and\ cRBCs\ background}$)]. FIG. 20 shows that anti-C5 MAbs: 305LO15-SG422, 305L15-SG115, 305LO16-SG422, 305LO18-SG422, 305LO19-SG422, 305LO20-SG422, 305LO20-SG115, and 305LO23-SG15, inhibited the complement activity in the plasma.

9.4. Inhibition of Biological Activity of C5 Variants by Anti-C5 MAbs

Anti-C5 MAbs were tested for the inhibition of recombinant human C5 variants: V145I, R449G, V802I, R885H, R928Q, D966Y, S1310N, and E1437D. It has been reported that PNH patients who have a R885H mutation in C5 show poor response to eculizumab (see, e.g., Nishimura et al., *New Engl. J. Med.* 370:632-639 (2014)). Each of the human C5 variants was expressed in FS293 cells, and the supernatants were used for the following study. Ten microliters of C5-deficient human serum (Sigma, C1163) was mixed with 20 μL of diluted MAb and 20 μL of cell culture media containing a recombinant C5 variant (2-3 μg/mL) in a 96-well plate and incubated on a shaker for 0.5 hour at 37° C. Liposomes (Autokit CH50) were transferred into each well and placed on a shaker for 2 min at 37° C. Fifty microliters of substrate solution (Autokit CH50) was added to each well and mixed by shaking for 2 min at 37° C. The final mixture was incubated at 37° C. for 90 minutes, and thereafter OD at 340 nm was measured. The percent of liposome lysis was defined as above. FIG. 21 shows that an anti-C5 MAb (eculizumab) did not inhibit the R885H C5 variant, but inhibited the other variants tested. FIG. 22 shows that the anti-C5 MAb (a 305 variant) inhibited all variants of C5 tested.

9.5. Inhibition of Complement-activated Liposome Lysis by Anti-C5 MAbs

Anti-C5 MAbs were tested for inhibition of complement activity by a liposome lysis assay. Thirty microliters of normal human serum (6.7%) (Biopredic, SER019) was mixed with 20 μL of diluted MAb in a 96-well plate and incubated on a shaker for 30 min at room temperature. Liposome solution sensitized with antibodies against dinitrophenyl (Autokit CH50, Wako, 995-40801) was transferred into each well and placed on a shaker for 2 minutes at 25° C. Fifty microliters of substrate solution (Autokit CH50) was added to each well and mixed by shaking for 2 minutes at 25° C. The final mixture was incubated at 37° C. for 45 minutes, and thereafter OD at 340 nm was measured. The percent inhibition of liposome lysis was defined as 100×[($OD_{MAb}$−$OD_{serum\ and\ liposome\ background}$)]/[($OD_{without\ MAb}$−$OD_{serum\ and\ liposome\ background}$)]. FIG. 23 shows that the anti-C5 MAbs, BNJ441 and the 305 variant inhibited liposome lysis, and that the 305 variant has stronger inhibitory activity than BNJ441.

Example 10

Pharmacokinetic Study of Anti-C5 Monoclonal Antibodies (305 Variants) in Cynomolgus Monkey 10.1. In Vivo Test Using Cynomolgus Monkey The in vivo kinetics of anti-human C5 antibody was assessed after administering anti-human C5 antibody in cynomolgus monkey (Shin Nippon Biomedical Laboratories, Ltd., Japan). A solution of anti-human C5 antibody (2.5 mg/ml) was administered once at a dose of approximately 8 ml/kg into the cephalic vein of the forearm by 30 minutes infusion. Blood was collected at pre-administration and 5 minutes, seven hours, one day, two days, three days, seven days, fourteen days, twenty one days, twenty eight days, thirty five days, forty two days, forty nine days, and fifty six days alter administration. The collected blood was immediately centrifuged at 1,700×g and 4° C. for 10 minutes to separate the plasma. The separated plasma was stored in a refrigerator at −70° C. or below before assay. The anti-human C5 antibodies were prepared as described in Example 7.

10.2. Measurement of Total Cynomolgus Monkey C5 Plasma Concentration by ELISA Assay The concentration of total cynomolgus monkey C5 in cynomolgus monkey plasma was measured by ELISA. Anti-human C5 antibody (in-house antibody generated using the method described in Example 2) was dispensed onto Nunc-ImmunoPlate MaxiSorp (Nalgc Nunc International) and allowed to stand overnight at 4° C. to prepare anti-cynomolgus monkey C5-immobilized plates. Calibration curve samples and cynomolgus monkey plasma samples diluted 20000-fold with 0.4 μg/ml injected antibody were prepared and incubated for 60 minutes at 37° C. Subsequently, the samples were dispensed onto the anti-cynomolgus monkey C5-immobilized plates, and allowed to stand for one hour at room temperature. Then, HRP-labelled anti-human IgG Antibody (SouthernBiotech) was added to react for thirty minutes at room temperature, and washing was performed. Subsequently, ABTS ELISA HRP Substrate (KPL) was added. The signal was measured by a plate reader at a wavelength of 405 nm. The cynomolgus monkey C5 concentration was calculated based on the response of the calibration curve using the analytical software SOFTmax PRO (Molecular Devices). The time course of plasma cynomolgus monkey C5 concentration after intravenous administration as measured by this method is shown in FIG. 24. Data are plotted as the percentage remaining compared to plasma cynomolgus monkey C5 concentration at pre-administration. The pH dependent anti-human C5 antibodies (305LO15-SG422, 305LO15-SG115, 305LO6-SG422, 305LO18-SG422, 305L19-SG422, 305LO20-SG422, 305L20-SG115, 305LO22-SG422, 305LO23-SG422, and 305LO23-SG115) showed lower accumulation of plasma C5 compared to non pH dependent anti-human C5 antibodies.

10.3. Measurement of Anti-human C5 Antibody Plasma Concentration by ELISA Assay

The concentration of anti-human C5 antibody in cynomolgus monkey plasma was measured by ELISA. Anti-human IgG κ chain antibody (Antibody Solutions) was dispensed onto Nunc-ImmunoPlate MaxiSorp (Nalge Nunc International) and allowed to stand overnight at 4° C. to prepare anti-human IgG-immobilized plates. Calibration curve samples and cynomolgus monkey plasma samples diluted 100-fold or more were prepared. Subsequently, the samples were dispensed onto the anti-human IgG-immobilized plates, and allowed to stand for one hour at room temperature. Then, HRP-labelled anti-human IgG antibody (SouthernBiotech) was added to react for thirty minutes at room temperature, and washing was performed. Subsequently, ABTS ELISA HRP Substrate (KPL) was added. The signal was measured by a plate reader at a wavelength of 405 nm. The anti-human C5 antibody concentration was calculated based on the response of the calibration curve using the analytical software SOFTmax PRO (Molecular Devices).

The time course of plasma anti-human C5 antibody concentration after intravenous administration as measured by this method is shown in FIG. 25. The pH dependent anti-human C5 antibodies (305LO15-SG422, 305LO15-SG115, 305LO16-SG422, 305LO18-SG422, 305LO19-SG422, 305LO20-SG422, 305LO20-SG115, 305LO22-SG422, 305LO23-SG422, and 305LO23-SG115) displayed longer half-life compared to non pH dependent anti-human C5 antibodies.

Example 11

X-Ray Crystal Structure Analysis of a 305 Variant Fab and Human C5-MG1 Domain Complex 11.1. Expression and Purification of the MG1 Domain (20-124) of Human C5

The MG1 domain (amino acid residues 20-124 of SEQ ID NO:39) fused to a GST-tag via thrombin cleavable linker (GST-MG1) was expressed in the *E. coli* strain BL21 DE3 pLysS (Promega) using a pGEX-4T-1 vector (GE healthcare). Protein expression was induced with 0.1 mM Isopropyl β-D-1-thiogalactopyranoside (IPTG) at 25° C. for 5 hours. The bacterial cell pellet was lysed with Bugbuster (Merck) supplemented with lysonase (Merck) and complete protease inhibitor cocktail (Roche), followed by the purification of GST-MG1 from the soluble fraction using a GSTrap column (GE healthcare) according to the manufacturer's instruction. The GST tag was cleaved with thrombin (Sigma), and the resulting MG1 domain was further purified with a Superdex 75 gel filtration column (GE healthcare). Fractions containing MG1 domain were pooled and stored at −80° C.

11.2. Preparation of Fab Fragment of a 305 Variant

Fab fragments of one of the optimized variants from 305 were prepared by the conventional method using limited digestion with papain (Roche Diagnostics, Cat No. 1047825), followed by loading onto a protein A column (MabSlect SuRe, GE Healthcare) to remove Fc fragments, a cation exchange column (HiTrap SP HP, GE Healthcare), and a gel filtration column (Superdex200 16/60, GE Healthcare). Fractions containing Fab fragment were pooled and stored at −80° C.

11.3. Preparation of a 305 Variant Fab and Human C5-MG1 Domain Complex

Purified recombinant human C5-MG1 domain was mixed with a purified 305 variant Fab fragment in a 1:1 molar ratio. The complex was purified by gel filtration chromatography (Superdex200 10/300 increase, GE Healthcare) using a column equilibrated with 25 mM HEPES pH 7.5, 100 mM NaCl.

11.4. Crystallization

The purified complexes were concentrated to about 10 mg/mL, and crystallization was carried out by the sitting drop vapor diffusion method in combination with the seeding method at 4° C. The reservoir solution consisted of 0.2 M magnesium formate dehydrate, 15.0% w/v polyethylene glycol 3350. This succeeded in yielding plate-like crystals in a few days. The crystal was soaked in a solution of 0.2 M magnesium formate dehydrate, 25.0% w/v polyethylene glycol 3350, and 20% glycerol.

11.5. Data Collection and Structure Determination

X-ray diffraction data were measured by BL32XU at SPring-8. During the measurement, the crystal was constantly placed in a nitrogen stream at −178° C. to maintain a frozen state, and a total of 180 X-ray diffraction images were collected using an MX-225HS CCD detector (RAY-ONIX) attached to a beam line, while rotating the crystal 1.0° at a time. Determination of the cell parameters, indexing the diffraction spots, and processing the diffraction data obtained from the diffraction images were performed using the Xia2 program (Winter, *J. Appl. Cryst.* 43:186-190 (2010), XDS Package (*Acta. Cryst.* D66:125-132 (2010)), and Scala (*Acta. Cryst.* D62:72-82 (2006)), and finally the diffraction intensity data up to 2.11 Å resolution was obtained. The crystallography data statistics are shown in Table 11.

TABLE 11

X-ray data collection and refinement statistics

| Data collection | |
|---|---|
| Space group | P1 |
| Unit Cell | |
| a, b, c (Å) | 39.79, 55.10, 127.76 |
| α, β, γ (°) | 89.18, 86.24, 78.20 |
| Resolution (Å) | 49.49-2.11 |
| Total reflections | 112,102 |
| Unique reflections | 56,154 |
| Completeness (highest resolution shell) (%) | 92.1 (95.8) |
| $R_{merge}$ [a] (highest resolution shell) (%) | 7.2 (31.7) |
| Refinement | |
| Resolution (Å) | 25.00-2.11 |
| Reflections | 53,398 |
| R factor [b] ($R_{free}$ [c]) (%) | 20.42 (26.44) |
| rms deviation from ideal | |
| Bond lengths (Å) | 0.0088 |
| Bond angles (°) | 1.3441 |

[a] $R_{merge} = \Sigma hkl \Sigma j |Ij (hkl) - <I (hkl)>| / \Sigma hkl \Sigma j |Ij (hkl)|$, where Ij (hkl) and <I (hkl)> are the intensity of measurement j and the mean intensity for the reflection with indices hkl, respectively.
[b] R factor = $\Sigma hkl ||F_{calc}(hkl)| - |F_{obs}(hkl)|| / \Sigma hkl |F_{obs}(hkl)|$, where $F_{obs}$ and $F_{calc}$ are the observed and calculated structure factor amplitudes, respectively.
[c] $R_{free}$ is calculated with 5% of the reflection randomly set aside.

The structure was determined by molecular replacement with the program Phaser (McCoy et al., *J. Appl. Cryst.* 40:658-674 (2007)). The search model of the Fab domain was derived from the published human IgG4 Fab crystal structure (PDB code: 1BBJ), and the search model of the MG1 domain was from the published human C5 crystal structure (PDB code: 3CU7, Fredslund et al., *Nat. Immunol.* 9:753-760 (2008)). A model was built with the Coot program (Emsley et al., *Acta Cyst.* D66:486-501 (2008)) and refined with the program Refmac5 (Murshudov et al., *Acta Cyst.* D67:355-367 (2011)). The crystallographic reliability factor (R) for the diffraction intensity data from 25-2.11 Å was 20.42%, with a Free R value of 26.44%. The structure refinement statistics are shown in Table 11.

11.6. Overall Structure of a 305 Variant Fab and C5-MG1 Domain Complex

The Fab fragment of an optimized variant from 305 ("305 Fab") bound to the human C5-MG1 domain ("MG1") in a 1:1 ratio, and the asymmetric unit of the crystal structure contained two complexes, Molecules 1 and 2, as depicted in FIG. 26A. Molecules 1 and 2 can be aligned well at 0.717 Å RMSD with the Cα atom position in all the residues, as shown in FIG. 26B. The figures discussed below were prepared using Molecule 1.

In FIGS. 27A and 27B, the epitope of the 305 Fab contact region is mapped in the MG1 amino acid sequence and in the crystal structure, respectively. The epitope includes the amino acid residues of MG1 that contain one or more atoms located within 4.5 Å distance from any part of the 305 Fab in the crystal structure. In addition, the epitope within 3.0 Å is highlighted in FIG. 27A.

11.7. Interactions of E48, D51, and K109

As described in Examples 4.5 and 4.6, the anti-C5 Mabs that include the 305 antibody series were tested for binding to three human C5 point mutants, E48A, D51A, and K109A, by Western blot and BIACORE® binding analyses. While the 305 variants bound WT C5 strongly, they bound the E48A C5 mutant only weakly and did not bind to the D51A and K109A mutants. The crystal structure of the 305 Fab and MG1 complex revealed that the three amino acids E48, D51, and K109, are all within 3.0 Å distance from the 305 Fab, forming a number of hydrogen bonds with the Fab, as shown in FIG. 28A. On more detailed examination, the K109 residue of MG1 is buried in a groove formed at the interface of the heavy chain of the Fab and tightly interacts with the Fab by three hydrogen bonds with H-CDR3_G97, H-CDR3_Y100, and H-CDR3_T100b, and by a salt bridge with H-CDR3_D95 (FIG. 28D). D51 is located between MG1 and the heavy chain of the 305 Fab and makes two hydrogen bonds with H-CDR1_Ser32 and H-CDR2_Ser54 to fill the space (FIG. 28C). These indicate that K109 and D51 of C5 are both critical residues for binding of the 305 antibody series. On the other hand, E48 is located closer to the surface and forms only one hydrogen bond with the Fab, suggesting that its contribution to the antibody binding would be less than those of K109 and E51 (FIG. 28B). These relationships are consistent with the results of the Western blot and BIACORE® binding analyses of human C5 mutants (Examples 4.5 and 4.6). The residue numbering for the Fab amino acids is based on the Kabat numbering scheme. (Kabat et al., Sequences of Proteins of Immunological Interest, 5th Ed. Public Health Service, NIH, Bethesda, Md., 1991)

11.8. Interactions of H70, H72, and H110 of Human C5 and 305 Antibody Series

The crystal structure analysis revealed that three histidine residues on human C5, namely, H70, H72, and H110, are included in the epitope of the 305 variant Fab, as shown in FIG. 27A and FIG. 29A. A BIACORE® binding analysis was performed to investigate the contribution of these histidine residues to the pH-dependent protein-protein interaction between human C5 and the 305 variant Fab using the human C5 mutants H70Y, H72Y, H110Y, and H70Y+H10Y (Example 4.7). H72Y resulted in the complete loss of the binding of the 305 variant Fab to C5. This residue of C5 is located in the pocket formed by the CDR2 loop of the heavy chain of the 305 Fab and the loop of MG1 (L73, S74, and E76) and fills this space tightly, as shown in FIG. 29C. In addition, the H72 residue of C5 makes a hydrogen bond with H-CDR2_Y58. The H72Y mutation would not be expected to be tolerated as there is not enough space to accommodate the bulkier side chain of tyrosine. Also a hydrogen bond with H-CDR2_Y58 cannot be maintained. With regards to the contribution of H70 and H110 to pH dependency, H70Y and H110Y mutations resulted in slower dissociation of the 305 variant Fab from C5 at pH 5.8. H70 forms an intra-molecular hydrogen bond with T53 of MG1, which is believed to be disrupted at pH 5.8 when protonation of H70 of C5 causes a conformational change in the corresponding part of the interaction interface of MG1 (FIG. 29B). For H110, protonation of this C5 residue would be expected to cause a charge repulsion to the 305 Fab, which may be augmented by the protonation of the neighboring histidine residue, H-CDR3_H100c (FIG. 29D).

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

---

What is claimed is:

1. An isolated antibody that binds to C5, wherein the antibody comprises:
   (a) a HVR-H1 comprising the amino acid sequence SSYYX$_1$X$_2$, wherein X$_1$ is M or V, X$_2$ is C or A (SEQ ID NO: 126);
   (b) a HVR-H2 comprising the amino acid sequence X$_1$IX$_2$TGSGAX$_3$YX$_4$AX$_5$WX$_6$KG, wherein X$_1$ is C, A or G, X$_2$ is Y or F, X$_3$ is T, D or E, X$_4$ is Y, K or Q, X$_5$ is S, D or E, X$_6$ is A or V (SEQ ID NO: 127); and
   (c) a HVR-H3 comprising the amino acid sequence DX$_1$GYX$_2$X$_3$PTHAMX$_4$X$_5$, wherein X$_1$ is G or A, X$_2$ is V, Q or D, X$_3$ is T or Y, X$_4$ is Y or H, X$_5$ is L or Y (SEQ ID NO: 128);
   (d) a HVR-L1 comprising the amino acid sequence X$_1$ASQX$_2$IX$_3$SX$_4$LA, wherein X$_1$ is Q or R, X$_2$ is N, Q or G, X$_3$ is G or S, X$_4$ is D, K or S (SEQ ID N: 129);
   (e) a HVR-L2 comprising the amino acid sequence GASX$_1$X$_2$X$_3$S, wherein X$_1$ is K, E or T, X$_2$ is L or T, X$_3$ is A, H, E or Q (SEQ ID NO: 130); and
   (f) a HVR-L3 comprising the amino acid sequence QX$_1$TX$_2$VGSSYGNX$_3$, wherein X$_1$ is S, C, N or T, X$_2$ is F or K, X$_3$ is A, T or H (SEQ ID NO: 131).

2. The antibody of claim 1, further comprising a heavy chain variable domain framework FR1 comprising the amino acid sequence of SEQ ID NO: 132, 133, or 134; a FR2 comprising the amino acid sequence of SEQ ID NO: 135 or 136; a FR3 comprising the amino acid sequence of SEQ ID NO: 137, 138, or 139; and a FR4 comprising the amino acid sequence of SEQ ID NO: 140 or 141.

3. The antibody of claim 1, further comprising a light chain variable domain framework FR1 comprising the amino acid sequence of SEQ ID NO: 142, or 143; a FR2 comprising the amino acid sequence of SEQ ID NO: 144 or 145; a FR3 comprising the amino acid sequence of SEQ ID NO: 146 or 147; and a FR4 comprising the amino acid sequence of SEQ ID NO: 148.

4. An isolated antibody that binds to C5 and comprises a VH sequence of SEQ ID NO: 10, 106, 107, 108, 109, or 110, and a VL sequence of SEQ ID NO: 20, 111, 112, or 113.

5. An antibody that binds to C5 and comprises a VH and VL pair selected from:
   (a) a VH of SEQ ID NO:10 and a VL of SEQ ID NO:20;
   (b) a VH of SEQ ID NO:107 and a VL of SEQ ID NO:111;
   (c) a VH of SEQ ID NO:108 and a VL of SEQ ID NO:111;
   (d) a VH of SEQ ID NO:109 and a VL of SEQ ID NO:111;
   (e) a VH of SEQ ID NO:109 and a VL of SEQ ID NO:112;
   (f) a VH of SEQ ID NO:109 and a VL of SEQ ID NO:113; and
   (g) a VH of SEQ ID NO:110 and a VL of SEQ ID NO:113.

6. The antibody of claim 5, which is a full length IgG1 or IgG4 antibody.

7. An antibody that binds to C5 and comprises a VH of SEQ ID NO:106 and a VL, of SEQ ID NO:111.

8. The antibody of claim 7, which is a full length IgG1 or IgG4 antibody.

9. An isolated antibody that binds to C5, wherein the antibody comprises:
- (a) (i) a HVR-H1 comprising the amino acid sequence of SEQ ID NO: 117;
  - (ii) a HVR-H2 comprising the amino acid sequence of SEQ ID NO: 119;
  - (iii) a HVR-H3 comprising the amino acid sequence of SEQ ID NO: 121;
  - (iv) a HVR-L1 comprising the amino acid sequence of SEQ ID NO: 122;
  - (v) a HVR-L2 comprising the amino acid sequence of SEQ ID NO: 123; and
  - (vi) a HVR-L3 comprising the amino acid sequence of SEQ ID NO: 125;
- (b) (i) a HVR-H1 comprising the amino acid sequence of SEQ ID NO: 117;
  - (ii) a HVR-H2 comprising the amino acid sequence of SEQ ID NO: 118;
  - (iii) a HVR-H3 comprising the amino acid sequence of SEQ ID NO: 121;
  - (iv) a HVR-L1 comprising the amino acid sequence of SEQ ID NO: 122;
  - (v) a HVR-L2 comprising the amino acid sequence of SEQ ID NO: 124; and
  - (vi) a HVR-L3 comprising the amino acid sequence of SEQ ID NO: 125;
- (c) (i) a HVR-H1 comprising the amino acid sequence of SEQ ID NO: 117;
  - (ii) a HVR-H2 comprising the amino acid sequence of SEQ ID NO: 120;
  - (iii) a HVR-H3 comprising the amino acid sequence of SEQ ID NO: 121;
  - (iv) a HVR-L1 comprising the amino acid sequence of SEQ ID NO: 122;
  - (v) a HVR-L2 comprising the amino acid sequence of SEQ ID NO: 124; and
  - (vi) a HVR-L3 comprising the amino acid sequence of SEQ ID NO: 125; and
- (d) (i) a HVR-H1 comprising the amino acid sequence of SEQ ID NO: 54;
  - (ii) a HVR-H2 comprising the amino acid sequence of SEQ ID NO: 64;
  - (iii) a HVR-H3 comprising the amino acid sequence of SEQ ID NO: 74;
  - (iv) a HVR-L1 comprising the amino acid sequence of SEQ ID NO: 84;
  - (v) a HVR-L2 comprising the amino acid sequence of SEQ ID NO: 94; and
  - (vi) a HVR-L3 comprising the amino acid sequence of SEQ ID NO: 104.

10. The antibody of claim 9, further comprising a heavy chain variable domain framework FR1 comprising the amino acid sequence of SEQ ID NO: 132, 133, or 134; a FR2 comprising the amino acid sequence of SEQ ID NO: 135 or 136; a FR3 comprising the amino acid sequence of SEQ ID NO: 137, 138, or 139; and a FR4 comprising the amino acid sequence of SEQ ID NO: 140 or 141.

11. The antibody of claim 9, further comprising a light chain variable domain framework FR1 comprising the amino acid sequence of SEQ ID NO: 142, or 143; a FR2 comprising the amino acid sequence of SEQ ID NO: 144 or 145; a FR3 comprising the amino acid sequence of SEQ ID NO: 146 or 147; and a FR4 comprising the amino acid sequence of SEQ ID NO: 148.

12. The antibody of claim 9, which comprises a VH selected from the group consisting of SEQ ID NO: 10, 106, 107, 108, 109, and 110.

13. The antibody of claim 9, which comprises a VL selected from the group consisting of SEQ ID NO: 20, 111, 112, and 113.

14. The antibody of claim 9, which is a full length IgG1 or IgG4 antibody.

15. The antibody of claim 9, which is a full length antibody and comprises a IgG1 CH variant sequence of SEQ ID NO: 114.

16. The antibody of claim 9, which is a full length antibody and comprises a IgG4 CH sequence of SEQ ID NO: 35, 115, or 116.

17. The antibody of claim 15, which further comprises a CL of SEQ ID NO: 38.

18. The antibody of claim 16, which further comprises a CL of SEQ ID NO: 38.

19. The antibody of claim 18, which comprises a IgG4 CH sequence of SEQ ID NO: 115 and a CL of SEQ ID NO: 38.

20. The antibody of claim 18, which comprises a IgG4 CH sequence of SEQ ID NO: 116 and a CL of SEQ ID NO: 38.

21. A pharmaceutical formulation comprising the antibody of claim 9 and a pharmaceutically acceptable carrier.

22. An isolated antibody that binds to C5, wherein the antibody comprises:
- (a) a HVR-H1 comprising the amino acid sequence of SEQ ID NO: 117;
- (b) a HVR-H2 comprising the amino acid sequence of SEQ ID NO: 118;
- (c) a HTV-H3 comprising the amino acid sequence of SEQ ID NO: 121;
- (d) a HVR-L1 comprising the amino acid sequence of SEQ ID NO): 122;
- (e) a HVR-L2 comprising the amino acid sequence of SEQ ID NO: 123; and
- (f) a HVR-L3 comprising the amino acid sequence of SEQ ID NO: 125.

23. The antibody of claim 22, further comprising a heavy chain variable domain framework FR1 comprising the amino acid sequence of SEQ ID NO: 132, 133, or 134; a FR2 comprising the amino acid sequence of SEQ ID NO: 135 or 136; a FR3 comprising the amino acid sequence of SEQ ID NO: 137, 138, or 139; and a FR4 comprising the amino acid sequence of SEQ ID NO: 140 or 141.

24. The antibody of claim 22, further comprising a light chain variable domain framework FR1 comprising the amino acid sequence of SEQ ID NO: 142, or 143; a FR2 comprising the amino acid sequence of SEQ ID NO: 144 or 145; a FR3 comprising the amino acid sequence of SEQ ID NO: 146 or 147; and a FR4 comprising the amino acid sequence of SEQ ID NO: 148.

25. The antibody claim 22, which comprises a VH of SEQ ID NO: 108 or 109.

26. The antibody of claim 22, which comprises a VH of SEQ ID NO: 106.

27. The antibody of claim 22, which comprises a VL of SEQ ID NO: 111.

28. The antibody of claim 22, which comprises a VL of SEQ ID NO: 112.

29. The antibody of claim 22, which is a full length IgG1 or IgG4 antibody.

30. The antibody of claim 22, which is a length antibody and comprises a IgG1 CH variant sequence of SEQ ID NO: 114.

31. The antibody of claim 22, which is a full length antibody and comprises a IgG4 CH sequence of SEQ ID NO: 35, 115, or 116.

32. The antibody of claim 30, which further comprises a CL of SEQ ID NO: 38.

33. The antibody of claim 31, which further comprises a CL of SEQ ID NO: 38.

34. The antibody of claim 33, which comprises a IgG4 CH sequence of SEQ ID NO: 115 and a CL of SEQ ID NO: 38.

35. The antibody of claim 33, which comprises a IgG4 CH sequence of SEQ ID NO: 116 and a CL of SEQ ID NO: 38.

36. A pharmaceutical formulation comprising the antibody of claim 22 and a pharmaceutically acceptable carrier.

37. The antibody of claim 1, which is a full length IgG1 or IgG4 antibody.

38. The antibody of claim 1, which is a full length antibody and comprises a IgG1 CH variant sequence of SEQ ID NO: 114.

39. The antibody of claim 1, which is a full length antibody and comprises a IgG4 CH sequence of SEQ ID NO: 35, 115, or 116.

40. The antibody of claim 38, which further comprises a CL of SEQ ID NO: 38.

41. The antibody of claim 39, which further comprises a CL, of SEQ ID NO: 38.

42. The antibody of claim 41, which comprises a IgG4 CH sequence of SEQ ID NO: 115 and a CL of SEQ ID NO: 38.

43. The antibody of claim 41, which comprises a IgG4 CH sequence of SEQ ID NO:116 and a CL of SEQ ID NO: 38.

44. A pharmaceutical formulation comprising the antibody of claim 1 and a pharmaceutically acceptable carrier.

45. The antibody of claim 4, which is a full length IgG1 or IgG4 antibody.

46. The antibody of claim 4, which is a full length antibody and comprises a IgG1 CH variant sequence of SEQ ID NO: 114.

47. The antibody of claim 4, which is a full length antibody and comprises a IgG4 CH sequence of SEQ ID NO: 35, 115, or 116.

48. The antibody of claim 46, which further comprises a CL of SEQ ID NO: 38.

49. The antibody of claim 47, which further comprises a CL of SEQ ID NO: 38.

50. The antibody of claim 49, which comprises a IgG4 CH sequence of SEQ ID NO:115 and a CL of SEQ ID NO: 38.

51. The antibody of claim 49, which comprises a IgG4 CH sequence of SEQ ID NO: 116 and a CL of SEQ ID NO: 38.

52. A pharmaceutical formulation comprising the antibody of claim 4 and a pharmaceutically acceptable carrier.

53. The antibody of claim 5, which is a full length antibody and comprises a IgG1 CH variant sequence of SEQ ID NO:114.

54. The antibody of claim 5, which is a full length antibody and comprises a IgG4 CH sequence of SEQ ID NO: 35, 115, or 116.

55. The antibody of claim 53, which further comprises a CL of SEQ ID NO:38.

56. The antibody of claim 54, which further comprises a CL of SEQ ID NO:38.

57. The antibody of claim 56, which comprises a IgG4 CH sequence of SEQ ID NO:115 and a CL of SEQ ID NO:38.

58. The antibody of claim 56, which comprises a IgG4 CH sequence of SEQ ID NO:116 and a CL of SEQ ID NO: 38.

59. A pharmaceutical formulation comprising the antibody of claim 5 and a pharmaceutically acceptable carrier.

60. The antibody of claim 7, which is a full length antibody and comprises a IgG1 CH variant sequence of SEQ ID NO:114.

61. The antibody of claim 7, which is a full length antibody and comprises a IgG4 CH sequence of SEQ ID NO: 35, 115, or 116.

62. The antibody of claim 60, which further comprises a CL of SEQ ID NO: 38.

63. The antibody of claim 61, which further comprises a CL of SEQ ID NO: 38.

64. The antibody of claim 63, which comprises a IgG4 CH sequence of SEQ ID NO:115 and a CL of SEQ ID NO: 38.

65. The antibody of claim 63, which comprises a IgG4 CH sequence of SEQ ID NO:116 and a CL of SEQ ID NO: 38.

66. A pharmaceutical formulation comprising the antibody of claim 7 and a pharmaceutically acceptable carrier.

* * * * *

UNITED STATES PATENT AND TRADEMARK OFFICE
CERTIFICATE OF CORRECTION

PATENT NO. : 9,765,135 B2  
APPLICATION NO. : 14/974350  
DATED : September 19, 2017  
INVENTOR(S) : Ruike et al.

Page 1 of 1

It is certified that error appears in the above-identified patent and that said Letters Patent is hereby corrected as shown below:

In the Claims

In Column 203, Claim 1, at Line 58, please replace "(SEQ ID N: 129)" with -- (SEQ ID NO: 129) --.

In Column 205, Claim 7, at Line 2, please replace "VL, of SEQ ID NO:111" with -- VL of SEQ ID NO:111 --.

In Column 206, Claim 22, at Line 33, please replace "(c) a HTV-H3" with -- (c) a HVR-H3 --.

In Column 206, Claim 22, at Line 36, please replace "SEQ ID NO): 122" with -- SEQ ID NO: 122 --.

In Column 206, Claim 25, at Line 55, please replace "The antibody claim 22" with -- The antibody of claim 22 --.

In Column 207, Claim 41, at Line 25, please replace "CL, of SEQ ID NO: 38" with -- CL of SEQ ID NO: 38 --.

Signed and Sealed this  
First Day of May, 2018

Andrei Iancu  
*Director of the United States Patent and Trademark Office*